US012698492B2

(12) United States Patent
Liang et al.

(10) Patent No.: US 12,698,492 B2
(45) Date of Patent: Aug. 4, 2026

(54) ISOLATED CAS13 PROTEIN AND USE THEREOF

(71) Applicants: GUANGZHOU REFORGENE MEDICINE CO., LTD., Guangzhou (CN); ZHEJIANG SYNSORBIO TECHNOLOGY CO., LTD, Shaoxing (CN)

(72) Inventors: Junbin Liang, Guangzhou (CN); Xingxiang Liang, Guangzhou (CN); Yang Sun, Shaoxing (CN); Hui Xu, Guangzhou (CN); Zhiqin Peng, Guangzhou (CN); Kaiwei Si, Guangzhou (CN); Desheng Huangfu, Guangzhou (CN)

(73) Assignees: GUANGZHOU REFORGENE MEDICINE CO., LTD., Guangzhou (CN); ZHEJIANG SYNSORBIO TECHNOLOGY CO., LTD, Shaoxing (CN)

( * ) Notice: Subject to any disclaimer, the term of this patent is extended or adjusted under 35 U.S.C. 154(b) by 0 days.

(21) Appl. No.: 18/652,819

(22) Filed: May 2, 2024

(65) Prior Publication Data

US 2024/0279630 A1     Aug. 22, 2024

Related U.S. Application Data

(63) Continuation of application No. PCT/CN2022/129825, filed on Nov. 4, 2022.

(30) Foreign Application Priority Data

Nov. 5, 2021     (CN) .......................... 202111306149.9
May 13, 2022     (CN) .......................... 202210518826.1

(51) Int. Cl.
| | |
|---|---|
| *C12N 9/22* | (2006.01) |
| *C12N 15/11* | (2006.01) |
| *C12N 15/90* | (2006.01) |
| *C12Q 1/6816* | (2018.01) |

(52) U.S. Cl.
CPC ................ *C12N 9/22* (2013.01); *C12N 15/11* (2013.01); *C12N 15/907* (2013.01); *C12Q 1/6816* (2013.01); *C12N 2310/20* (2017.05); *C12N 2320/10* (2013.01)

(58) Field of Classification Search
CPC ........ C12N 9/22; C12N 15/11; C12N 15/907; C12N 2310/20; C12N 2320/10; C12N 5/10; C12N 15/113; C12N 15/85; C12Q 1/6816
See application file for complete search history.

(56) References Cited

U.S. PATENT DOCUMENTS

| | | |
|---|---|---|
| 2021/0009974 A1 | 1/2021 | Harrington et al. |
| 2021/0269795 A1 | 9/2021 | Yang et al. |
| 2022/0364071 A1 | 11/2022 | Zhang et al. |
| 2024/0110165 A1 | 4/2024 | Zhang et al. |

FOREIGN PATENT DOCUMENTS

| | | |
|---|---|---|
| CA | 3064601 A1 | 1/2019 |
| CN | 110799645 A | 2/2020 |
| CN | 112410377 A | 2/2021 |
| CN | 112522271 A | 3/2021 |
| CN | 113337488 A | 9/2021 |
| CN | 113348245 A | 9/2021 |
| WO | 2021055874 A1 | 3/2021 |
| WO | 2021175230 A1 | 9/2021 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Zhang et al., Nature Communications 10:2544, pp. 1-11. 2019.*
Cox et al., Science 358:1019-1027, 2017.*
Jan. 19, 2023 International Search Report issued in International Patent Application No. PCT/CN2022/129825.
Jan. 19, 2023 Written Opinion of the International Searching Authority issued in International Patent Application No. PCT/CN2022/129825.
Ian M. Slaymaker et al., High-resolution structure of Cas13b and biochemical characterization of RNA targeting and cleavage, Cell reports, Mar. 26, 2019.
Eugene V. Koonin and Kira S. Makarova, Evolutionary plasticity and functional versatility of CRISPR systems, PLoS biology, Jan. 5, 2022.
M. Richter and R. Rosselló-Móra, Shifting the genomic gold standard for the prokaryotic species definition, Proc Natl Acad Sci, Nov. 10, 2009, vol. 106, No. 45, pp. 19126-19131.
Fahreddin Palaz et al., CRISPR-Cas13 System as a Promising and Versatile Tool for Cancer Diagnosis, Therapy, and Research, ACS Synthetic Biology, May 26, 2021.
Lijun Peng et al., New tools for nucleic acid detection and gene editing: CRISPR/Cas13 system*, Chin J Clin Lab Sci, May 7, 2019, vol. 37, No. 5.

(Continued)

*Primary Examiner* — Delia M Ramirez

(57)     ABSTRACT

The present disclosure relates to an isolated Cas13 protein and use thereof. The amino acid sequence of the isolated Cas13 protein comprises a sequence having ≥50% sequence identity with the sequence as shown in any one of SEQ ID NO: 1-SEQ ID NO: 7, and SEQ ID NO: 60. The Cas13 protein is a Cas13 enzyme with an endonuclease activity, which can be used in a CRISPR/Cas system to achieve targeting and modification of a target nucleic acid, enriching the enzymes and systems available in a CRISPR-C as editing system.

2 Claims, 12 Drawing Sheets

Specification includes a Sequence Listing.

(56)           References Cited

OTHER PUBLICATIONS

Aug. 17, 2023 The First Office Action and Search Report issued in
Chinese Patent Application No. 202210518826.1.
Oct. 13, 2025 Partial Supplementary European search report issued
in European Patent Application No. 22889405.1.
Jan. 5, 2026 Extended European search report issued in European
Patent Application No. 22889405.1.

* cited by examiner

Stem 1

Bulge

Stem 2

Loop

A (SEQ ID NO: 15)
B (SEQ ID NO: 16)
C (SEQ ID NO: 17)
D (SEQ ID NO: 18)
E (SEQ ID NO: 19)
F (SEQ ID NO: 62)
G (SEQ ID NO: 20)
H (SEQ ID NO: 21)
I

Figure 9B:
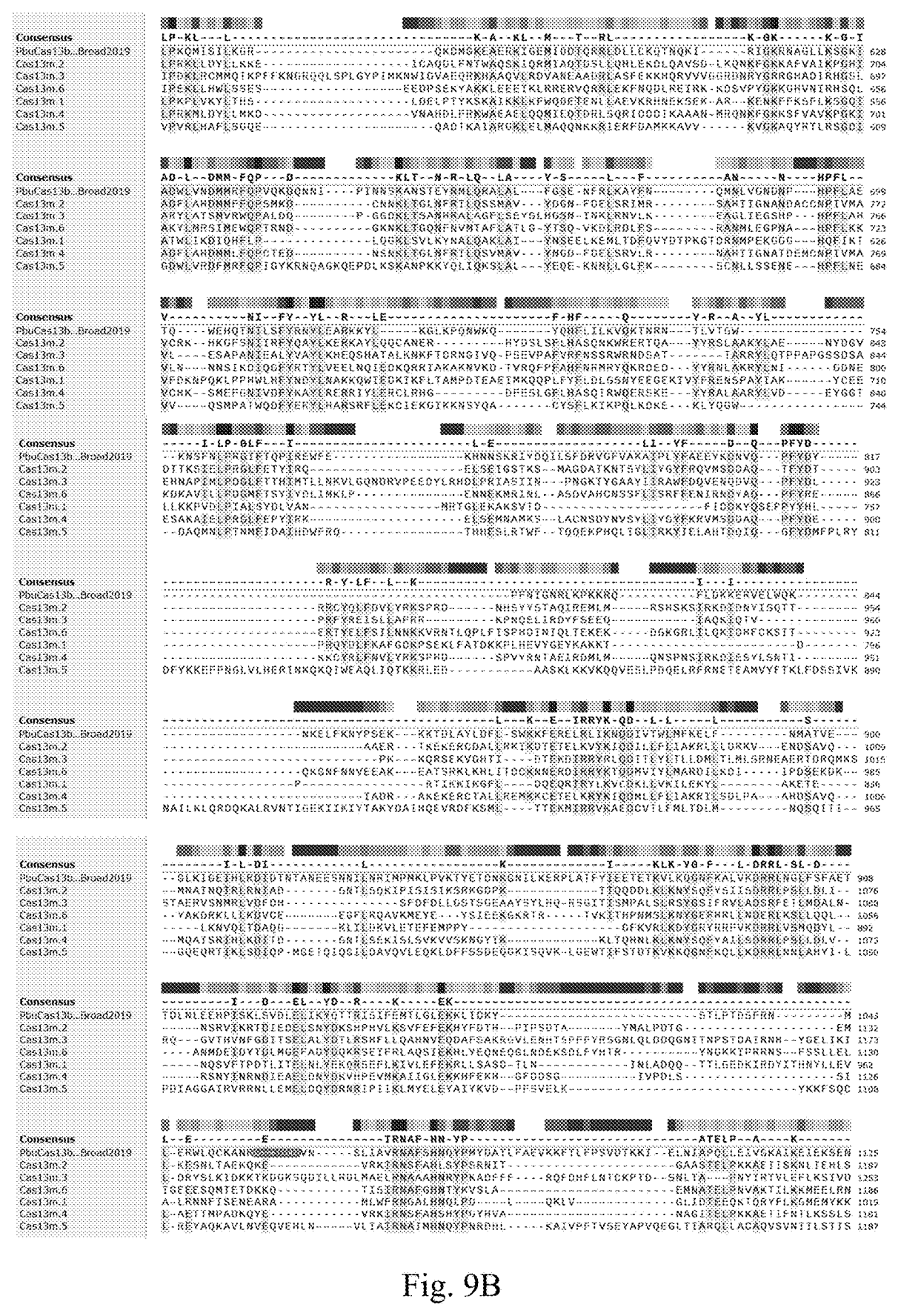

| Consensus | | |
|---|---|---|
| PbuCas13b...Broad2019 | KN - - - - - - - - - - - - - - - - | 1127 |
| Cas13m.2 | NAE - - - - - - - - - - - - - IK | 1192 |
| Cas13m.3 | NNFTPLLHEESPENESKSE | 1272 |
| Cas13m.6 | KL - - - - - - - - - - - - - - - - | 1188 |
| Cas13m.1 | GIE - - - - - - - - - - - - KIS | 1025 |
| Cas13m.4 | DE - - - - - - - - - - - - - - - - | 1183 |
| Cas13m.5 | KFE - - - - - - - - - - - - - - - | 1190 |

Fig. 9C

SEQUENCE LISTING

```
Sequence total quantity: 105
SEQ ID NO: 1          moltype = AA  length = 1025
FEATURE               Location/Qualifiers
source                1..1025
                      mol_type = protein
                      organism = synthetic construct
SEQUENCE: 1
MNPQARTRKP ETPLKPVGNE HFAVFINIAR HNAFIAITEL SKIYGMTPPN EDELATSRFI   60
AAFDSTTIDV RKLKQRLKRL SSLMPFLKSL QDKTDAEIIG ILKDLLSLVN QFRNYYSHYN  120
TSDFLTINSN EFITSDKVSI LENIFEKAVL SLTNSEKAYD RFEIISLLKS EKRADKPYFY  180
EFIENNKISE KAIAFFFCLF LDKPNAMKFL KRLKGFKGAD TKQFRATLEA YTTYCIQLPE  240
PKFLSDRPNL AIILDGIEHL KRCPIEVHKT LSFRDKQKFE RKVMREDLNG DLQEENIELL  300
RYDDRFAEFA MRYLDDFDIL SDAKKQNTYR FEIQLGKKVV ESKKLAEETT EAQDKIPVRF  360
KPVKAFGKLA DIPRKKDEAV IDWQQDLEEL YAYEPHYKIE NHSIGIKKIA TEDTFRLNNP  420
EELPDAYLSE YQLRNIIFLS LESSNKEEFF MACQIRIGKI KSLYKALSAP THYKESIKQK  480
YNELINNNLL PKPLVKYLTH SLDELPTYKS KAIKKLKFWQ DETENLLAEV KRHNEKSEKA  540
RKENKFFKSF LKSGQIATWL IKDIQHFLPL QGKLSVLKYN ALQAKLAIYN SEELKEMLTD  600
FQVYDTPKGT DRNMPEKGGG HQFIKTVFDK NPQKLPPHWL HFYNDYLNAK KQWIEDKIKF  660
LTAMPDTEAE IMKQQPLFYF LDLGSNYEEG EKIVYFRENS PAYIAKYCEE LLKKPVDLPI  720
ALSYDLVANM RTGLEKAKSV TDFIDDKYQS EPPYYHLPRQ YDLFKAFGDK PSEKLFATDK  780
KPLHEVYGEY KAKKTDPRTI KKIKGFLDQE QRIRYLKVCD KLLVKILEKY LAKETELKNV  840
QLTDAQGKLI LDKVLETEFE MPPYGFKVRL KDYGRYRRFV KDRRLVSMQD YLNQSVFTPD  900
TLITELNLYE KQRSEFLKIV LEFEKRLLSA SDTLNINLAD QQTTLGEDKI RDYITHNYLL  960
EVALRNNFIS ENEARAMLWF RNGALHNQLP DLQKLVGLID TEEQKTQRYF LKGMEMYKKG 1020
IEKIS                                                            1025

SEQ ID NO: 2          moltype = AA  length = 1192
```

-continued

```
FEATURE                 Location/Qualifiers
source                  1..1192
                        mol_type = protein
                        organism = synthetic construct
SEQUENCE: 2
MTILEKYMPL NEMGKIKSLV DELKGIPGAM NATLRQEIFQ NIKKTKLQVK FLEEYPETLF   60
TDSGNLIPII GNNDNSSSGT PSKQEVSDID ANQASRINYL PHETMGEIKS VYGTYIEMAF  120
HNFYLTMHHI YAVVFGEDIM EEAKKEFDKN NTNSTKYFTF DFANERTIWK PMFDRAERAK  180
PEQKEHFEKL VVKHFPFLKA IDALEDRKRK TKIQALCVFS LVLRELRNVY SHYLFYPFKN  240
QVDKYKENIP FVLDMMEILY TGAQREVKGR FGFDDKKMQC AKKYERNKDH SQRDHQGKII  300
KAVPKKNFRY NLYKKEDSEA IITPFGLVFL TSLFLEKKYA KILSDKTHCI KYTDQEVLCE  360
IISVYRIRLH IQKLSVTKDT DALALDIINE LQRCPKRLFE MLSPDDQQKF RIKPTDSQYA  420
DDVLMIRHQD RFAHLLLKYI DDAHLFNCIR FQVSLGRYFF RFYDKSCIDS TGDKRVRSIS  480
KNVNGFGRIT DIEDYRKEVY GDMIREYEDV HANTSMEKPY ITDHHAKYLI SNNRIGLYIR  540
KEEDTQCLLP ELTPDGARNF APTCWLSIYE LPALAFLLHL YNGDGSRVEE IIQTKVANYQ  600
RLFADVRDGK VCPVKDEAEL TTILQTYGNI EPSQLPRKLL DYLLKKEICA QDLFNTWAQS  660
KIQRMIAQTD SLLQHLEKDL QAVSDLKQNK FGKKAFVAIK PGHIADFLAH DMMFFQPSMK  720
DCNNKLTGLN FRILQSSMAV YDGNFDELSR IMRSAHIIGN ANDACCNPIV MAVCRKHKGF  780
SNIIRFYQAY LKERKAYLQQ CANERHYDSL SFLHASQNKW RERTQAYYRS LAAKYLAENY  840
DGVDTTKSIE LPRGLFETYI RQELSEIGST KSMAGDATKN TSYLIYGYFR QVMSDDAQTF  900
YDTRRCYQLF DVLYRKSPRD NHSYYSTAQI REMLMRSHSK SIRKDIDNYI SQTTAAERTK  960
EKERCDALLR KIKDTETELK VYKIQDILLF LIAKRLLLDR KVENDSAVQM NAINQIRLRN 1020
IADGNTLSQK IPISISIKSR KGDPKIIQQD DLKLKNYSQF YSIISDRRLP SLLDLINSRV 1080
IKRTDIEDEL SNYDKSHPHV LKSVFEFEKH YFDTHPIPSD TAYMALPDTG EMLKESNLTA 1140
EKQKEVRKIR NSFAHLSYPS RNITGAASTE LPKKAEIISK NLIEHLSNAE IK         1192

SEQ ID NO: 3           moltype = AA   length = 1272
FEATURE                Location/Qualifiers
source                 1..1272
                       mol_type = protein
                       organism = synthetic construct
SEQUENCE: 3
MYHLSDANHG KHIAGTYYEM AMGNFIHTLS HMLVRAGIKV NKLEDNYSIE REIMNLTAPG   60
AYDAQRAALS RLLYRHFPFF GPIMADHTDH ILSSKRKKVQ SASDDGNLDL GQELKDEVAG  120
ASACQMIRYL ATIAGALVYY RNMYSHKNHY DNAQDIAAQQ EREQKLALWL DVVFRGARDI  180
LLTRKSHPQP DTDFLTQNGT INYYIEKNGK SAYNPNFYFK PGLKTDNGWV MTDFGKFFFC  240
SLFLRRADAE RFAAETDLYV GSPFKITAQE RARLQEAENK RAADEQARAS SAGFPHIVNP  300
RTIGPSESPQ NNIIREMLNM HRARIPRERR IDADMSEGIL AMDIMNELRR CPLSLYNTLS  360
PEAKASFEKT GVTPEGGIVS NLLVRHSDRY PELALRAIDQ MELLPTIRFH VRLGSLRFRF  420
YEKKLIDGSH TLRTVQKAVN GFGRWQEVEP RRVEKYTAIQ ARCQNDKGID QFLPDSPTTT  480
PYITDWRTTY NIHANRIGLA WNLPQMSDGI YLPNLDTDKG DNLHRKALID MPAPMCYLSI  540
FDLPALLFYC HIYTHYHGTK YHLPSAESII QAKYDALHKF FSFAAAQNHS AEQLREKQLE  600
LNLADNEIPD KLRCMMQTKP FFKNGRQQLS PLGYPIMKNW IGVAEQRKHA AQVLRDVANE  660
AADRLASFEK KHQRVVVGGR DNRYGRRGHA DIRHGSLARY LATSMVRWQP ALDQPGGDKL  720
TSANHRALAG FLSEYGLHGS NINKLRNVLK EAGLIEGSHP HPPLAHVLES APANIEALYV  780
AYLKHEQSHA TALKNKFTDR NGIVQPSEVP AFVRFNSSRW RNDSATTARR YLQTPPAPGS  840
SDSAEHNAPI MLPDGLFTTH IMTLLNKVLG QNDRVPEEDY LHDLPRIAS IINPNGKTYG  900
AAYIIRAWFD QVENQDVQPF YDLPRFYREI SLLAPRRKPN QELIRDYFSE EQIAQKIQTV  960
PKKQRSEKVG HTIDTEKDIR RYRLQDITLY LTLLDMLTLM LSRNEAERTD RQMKSSTAER 1020
VSNMRLVDFD HSFDFDLLGS TSGEAAYSYL HQRSGITISM PALSLRSYGS IFRVLADSRF 1080
ETLMDALNRQ GVTHVNFGDI TSELALYDTL RSHFLLQAHN VEQDAFSAKR GVLENHTSPF 1140
FYRSGNLQLD DQGNITNPST DAIRNHYGEL IKILDRYSLK IDKKTKDGKS QDILLRDLMA 1200
ELRNAAAHNR YPKADFFFRQ FDHFLNTCKP TDSNLTAPNY IRTVLEFLKS IVDNNFTPLL 1260
HEESPENESK SE                                                    1272

SEQ ID NO: 4           moltype = AA   length = 1183
FEATURE                Location/Qualifiers
source                 1..1183
                       mol_type = protein
                       organism = synthetic construct
SEQUENCE: 4
MPMSTIIDKY MPLNDWNRIE SLIGELRAIS GAMNCAVRRA VFENIKKAKL QIKFNDQYPE   60
SIFTDKNGSI PIVGTTEANN PENGGNNECE QSNNYLSIDY LPRVTQEDKK SVYGTYFEMA  120
FHNFFITLHH IYSLIFGEDI MEVAKSEYSQ TQTDSFQDDF ANKYTVWNPL FTRLRRAKAE  180
QKERFEELAI KHFPFLKALD ALKGENRVSK VDALERFSVV VRELRNIYLH YCIIPSDKQK  240
KEYSDNISFI FDLMDLLFTG AKREVKTRFA LSDDQMSCAD KYEPNSDRSL RDIHGKTLRI  300
VPKKNFRYHL YKVGDDAKII SPFGLVFLAS LFLEKKYAKI LSDKAHVVRL NDKGVICEMI  360
SVYRIRLHIN RLSISKSTDT LALDIINELQ RCPKKVFELL PPVAQQRFRV KPESSHAPEV  420
LMVRHNDRFV HLLLKYIDDA KLFEHIRFQV SLGRYFFRFY DKICIDTSSE KRVRSICKDV  480
HGFGRISEIE ELRREKWKDI LREYDEVHAN TADEKPYITD HRANYLIGNN KVGIYLLKEG  540
DEQCIMPELL PNGARNHAPT CWLSTYELPA LAFLLHLYNA DGARVEEIIE KQVAGYRRLF  600
ADVRDGSVAP VASVEELDEL LKGYGDMQAC NLPRKMLDYL LMKDVNAHDL FRKWAEAELQ  660
QMIEQTDRLS QRIDDDIKAA ANMRQNKFGK KSFVAVKPGK IADFLAHDMM LFQPCTEDNS  720
NKLTGLNFRI LQSVMAVYNG DFDELSRVLK NAHIIGNATD EMCNPIVMAV CHKSMEFGNI  780
VDFYKAYLRE RRIYLERCLR HGDFESLGFL HASQIRWQER SKEYYRALAA RYLVDEYGGT  840
ESAKAIELPR GLFEPYIRKE LSEMNAMKSL ACNSDYNVSY LIYGYFKRVM SDDAQPFYDE  900
KKCYRLFNVL YRKSPHDSPV YRNTAEIRDM LMQNSPNSIR KDIESYLSNT IIADRAKEKE  960
RCTALLREMK KCETELRYK IQDMLLFLIA KRILSDLPAA HDSAVQMQAI SRIHLKDITD 1020
GNTLSEKISL SVKVVSKNGY IKKLTQHNLK LKNYSQFYAI LSDRRLPSLL DLVRSNYINR 1080
```

```
NDIEAELDNY DKVHPEVMKA IIGLEKKHFE KHGFDDSGIV PDLSSILAET TMPADKQYEV   1140
RKIRNSFAHS HYPGYHVANA GITELPKKAE TIFNTLKSSL SDE                      1183

SEQ ID NO: 5          moltype = AA  length = 1190
FEATURE               Location/Qualifiers
source                1..1190
                      mol_type = protein
                      organism = synthetic construct
SEQUENCE: 5
METTINNRIG KGEYYTEESK EFLAAYFNQA IHNVFIVLNH IAKRFGMDEL SSDEELKNWL     60
IGRQREKKRN AIDRQRFLEL IDRHFPFLRI ANADKKDAKR ENDLEDNLAL LITLLNDLTE    120
RRNKYSHAIT HASIESNDRE LVWRLYSIYD ANINLVKRDY FESNVHTEIN EDPYEKQVEH    180
LRRFCMNNDR TKVDEKGKKK PAMPNPRFRT PFLNAETNQL SIYGLVFFVS LFLEKKYAIQ    240
MQKNVYGLKD ARDTKFKMTN EVFCRSRIIM PRVRLHSDKS TDALVLDMLN ELAKAPEVLF    300
DQLTDPFKEK FYIESIDSLE ESDIITPVRA IRKQNRFMYF ALRYLDESNA FSKLRFQIDL    360
GNYHYHLYES KINDQTESRH LTRKLFGFGK LIAFEQEFAP EEWKMKSKDL DYYEGATQPF    420
IAKTYPHYHL EENKIGILFN GQAEVQWPHL DVEEHESFPK YKRRANEKAD AFLSGNELLA    480
AAFCHHLYAS IGKPNTVEKI IRDKYHALRQ LFSDLKSGNL QNLLGDNTSN EAISQLLFEK    540
YRLTLSEVPV RLHAFLSGQE QADTKAIARG KLELMAQQNK KRIERFDAMK KAVVKVGKAQ    600
YRTLRSGDIG DWLVRDFMRF QPIGYKRNQA GKQEPDLKSK ANPKKYQLIQ KSLALYEQEK    660
NNLLGLFKSC NLLSSENEHP FLNEVVQSMP ATWQDFYERY LHARSRFLEK CIEKGIKKNS    720
YQACYSFLKI KPQLKDKEKL YQGWDAQMNL PTNMFIDAIH DWFRQTHHES LRTWFTQQEK    780
PHQLIGLIRK YIELAHTDQI QGFYDMFPLR YDFYKKEFPN GLVLHERINK QKQIWEAQLI    840
QTKKRLEDAA SKLKKVKQQV ESLPDQELRF RNETEAMVYF TKLFDSSIVK NAILKLQRDQ    900
KALRVNTIGE KIKIYTAKY DAIHQEVRDF KSMLTTEKMI RRVKAEDCVT LFMLTDLMNQ     960
SQITIGQEQR TIKLSDIQPM GETQIQGILD AVQVLEQKLD FFSSDEQGKI SQVKLGEWTI   1020
FSTDTKVKKQ GNFKQLLKDR RLNNLAHYIL PDIAGGAIRV RRNLLEMELD QYDRNRIPII   1080
KLMYELEYAI YKVDPFSVEL KYKKFSQCLR EYAQKAVLNV EQVEHLNVLI AIRNAIMHNQ   1140
YPNRDHLKAI VPFTVSEYAP VQEGLTIARQ LLACAQVSVN IILSTISKFE             1190

SEQ ID NO: 6          moltype = AA  length = 1158
FEATURE               Location/Qualifiers
source                1..1158
                      mol_type = protein
                      organism = synthetic construct
SEQUENCE: 6
MKEKIKNKSS IIRIIMSNYD DKGLKEFKVL YNKQGGVDTF TCKTDIVDGT IIFLEIEKHL     60
RDFGDDFSWD ISSDGKSVEI TKLINGKETR KYKVSIKNSS TKDKKNLVEL EVEDLKESAI    120
DRRRTKSSTK RVLLSKDVME RYAEIAFSKK ERWEEIDSQK IYKVKRFLDY RSNMLIYFQF    180
INDFLTKGIP DELDKNGEIK QLELWKLIDD DETISDKNLN QVSKNLYTYI SQEIKDSQTR    240
AENNREKNKE KEHFKEFYAF NDISEESIRE DVKKFIYLYA NLRHNLMHYN YSFFENLFEG    300
KDLVIEKTKS LLSSTLDLNI FKELSNIVEL REENKTNYLD DETTIRVLGK EKKAKTLHKI    360
YSILCSRKNG FNKFINSFFS TDGIEEEFLK SEIKKDFLER LNWVEKSLIE KINNPPSDTK    420
LKYKNDKTIE NMTKEKEEKL ELISLLNPQV SDYKTENFTP YYWDIHQSPS YKKLYNDRKV    480
LVSELSKLIA IGINSDTKKR ITDLNAELLK IKIKMEKITK LNSKIRLQYK LQMAFGFIYA    540
NYSKVYKEKR VLNINGFVQN FDPTKLNKEK ELESRLIYLK APYNIFEDNK SLDFNMKIVE    600
NIPVSEKSIF RIKPENNLSK FYILSYLLLP VELRGDFLGY VKHHYYGIKN VDFEEIPDIK    660
EDKPNENSDS FFHNLRLFEK NSKKFELIKY RLVEFGNLKD HLPRIYEKFG IKPDVLEYIE    720
NSGNKDSKLF DRNILLPIMK YYQHIFKLLN DIEVHALLRF SEKDSISLDE SIKECSKGKF    780
LNFGKLLFLS RYGLEAKKDN KFKDIFNREN GLSITKDDAK TERKKYFEIF ETRNKIAHLN    840
YKQLFHDLLF DSNININKEL EGIIQETKTI GLNAQTLGVK LNDFYMRKE MFISNQKKSS     900
MTLINNPLSK DKDTKEIGLL KLYGLSKSQP KDLILAKYKE LMNLIEKTED SILKKKDFLP    960
VKEVSITVKK STPNKKGIMV ELPEILQIKD LNEMDLLAYA SNIRGKLHKD SSDLFGIYKK   1020
LTIKELKKKL INLFIKGEKR YLNLELVNKT GYMAIYESTG LYPKSYEILN HEISFSEISM   1080
KNWYEHDFKP IFQIDGSLPN NTDYKNGVFI YTSPYEFRDK ELMKKQRTVH KRDIEKTFYN   1140
ENDMDYTGIY NQKIKALY                                                 1158

SEQ ID NO: 7          moltype = AA  length = 931
FEATURE               Location/Qualifiers
source                1..931
                      mol_type = protein
                      organism = synthetic construct
SEQUENCE: 7
MMGNKKSVAK ANGLKSTFVL GENTAYMTSF GRGNAAQPEK HIRDATVTDI QHTFRAKTDG     60
GRTVHIEGRV GASDVLLPDA ANQLHAKDAV EQMYFGKAFS DNIHIQIAYN IMDIKKIFGV    120
YANIIVHTVN NLCCDGDKQD DFLGMFKTQN RYQVAAWAHK IVSLHLVKNE LRGGGFFMDQ    180
EVWRAHVRTD FKSLNLAVNA FMKKYPQKYP YWSVKIVSDF IVQEMGIKNK VILEKAAESY    240
AEFETVAKRL EKSAYYFSDI FAGKDGKFDE QKAFDLLRVL GMMRQEAFHE KNSSASWLYN    300
LDAEADEDIK AALRTVVDTK VNGINTNFAK QNKVNLLVLQ EIYPQKSKAD LVREYYDFSV    360
RKAFKNLGFS VKTLRETMCA FDAASVITDK QYDTVRGKLY SLFDFVIYNY CLENEAVCNA    420
FVEELRANLD PENKTALYQT LAEKVWAEIG DIVLQRILPQ MHAKKIQERS KETDAETVEM    480
QGYVQAPKDL SLFSKAVYCI SMFLDGKEIN SFLSALINKF ENISSLCAVL AYNGLEPEFV    540
APFTFFADSQ AIAEDLRYIK SIARMSKGKK ATKDSPVTVK EMQYFDAAAV LGETDTEKVK    600
AAFHLGDKSA STADKAFRNF VVNNVINSNR FVYVVRFINP KNAREIMQNR ALIAFVLKDI    660
PQSQLVRYCG TAGIACNADE PNTEAMVNAL ADMLLQVRFD AFSNVQQKVK ADSAEAVQKE    720
KYKAIIGLYL TVLYLLVKTL VKINMNYAIA FGILERDCQI MNQKHGKNPK RDRDAFYMRE    780
QQNKQYVYNA RAITELFIEN GWLNKRVQKS VENNAALYSD EAFYKYRNLV AHLNVISALP    840
KYAKNITKVK SLFDVYHYIL FLSLCEDKYS NLPEAVTKSL CKNGKTMLEN AREYQTVCKD    900
FLYGLNTPFA YNAARYINLS NREKFLAGFG K                                   931
```

```
SEQ ID NO: 8            moltype = DNA  length = 3078
FEATURE                 Location/Qualifiers
source                  1..3078
                        mol_type = other DNA
                        organism = synthetic construct
SEQUENCE: 8
atgaatccac aagcacgtac acgtaaacct gaaacaccac ttaaacccgt aggaaatgaa    60
cattttgctg tatttatcaa tatcgcacgc cacaatgctt ttattgctat cactgagcta   120
agtaaaatct acggtatgac tcctcccaat gaagatgaat tagctacatc tcgtttttata  180
gccgcctttg actccacaac aattgatgta cgtaagctaa aacagcgatt gaaaagactt   240
tcaagtttga tgcctttttt gaaatcttta caggataaaa ccgatgctga aattatcgga   300
atccttaaag acctcctctc tcttgttaat caatttagaa actactattc tcactataat   360
acttccgatt ttctcacaat caatagtaac gaatttatta cttctgataa agtttcaatc   420
ttagaaaata tttttgaaaa ggctgtctta tcattaacca attcagaaaa ggcttatgat   480
agatttgaaa ttatttcttt actgaaaagt gaaaaacgag cggataagcc ttatttctat   540
gaatttatcg aaaacaacaa aatctctgaa aaagctattg ctttcttctt ctgtttgttt   600
ttggataaac ccaacgccat gaagttctta aaaaggctca aaggatttaa aggggctgat   660
actaagcaat ttagagcaac tttggaagcc tatacgactt actgtattca gttacctgaa   720
cctaaatttc tatctgaccg accaaatctt gccataatct tagacggaat cgaacatcta   780
aaaaggtgtc caattgaagt tcataaaacc cttagtttca gagacaaaca aaaatttgaa   840
cgaaaagtaa tgagggaaga cctcaatggg gacttgcagg aggaaaatat tgaattactc   900
agatatgatg atagattcgc tgagtttgcc atgcgttatt tggatgattt tgatattttg   960
tccgatgcca aaaaacagaa cacataccgt tttgaaattc aattaggaaa gaaggtggta  1020
gaatctaaaa aattggcaga agaaactacc gaggcacagg ataaaatccc tgtcaggttc  1080
aagcctgtga aggcatttgg caaattggca gatattcctc gtaagaaaga tgaagccgtt  1140
attgactggc aacaagattt ggaagaacta tacgcttacg aacctcatta caagattgaa  1200
aatcactcta ttggtatcaa gaaaattgca accgaagata cttttcgttt gaacaatccc  1260
gaagaattac ctgatgctta tctgagtgaa tatcagttgc gtaacattat ttttctgagt  1320
ttagaatcaa gcaacaaaga agaatttttc atggcttgcc aaatacggat tggtaaaatc  1380
aaaagcctat acaaagctct ctcagcacct acacactaca aagaaagcat aaagcaaaaa  1440
tataatgagc tgattaacaa taatttacta cctaagccat tggtcaaata cttaacgcat  1500
agtttagacg aattgccaac ttacaaatca aaagccatca aaaaattgaa gttttggcaa  1560
gacgaaacag aaaatttatt ggcggaagtc aaaagacata atgagaaatc ggagaaggct  1620
cgaaaggaaa ataaattctt taagtccttc ttgaaatcag ggcaaatagc tacttggttg  1680
ataaaagata ttcagcactt tttgcctttg caaggtaaac tttctgtgct aaaatataat  1740
gcacttcaag ctaaattggc gatttacaat tcggaagaat tgaaagagat gctcactgat  1800
tttcaagtct atgataccccc aaaaggaacg gacagaaata tgcctgaaaa aggcggaggg  1860
catcaattta tcaagactgt ttttgataaa aatccccaaa aattacctcc tcattggttg  1920
catttttata atgattacct caatgctaaa aagcaatgga ttgaagacaa aatcaagttt  1980
ctgacagcca tgccagacac tgaggctgaa attatgaagc aacagccact tttctacttt  2040
ttggatttag gttcaaatta tgaagagggt gagaaaatag tctatttccg tgagaactcg  2100
cccgcataca tagccaagta ttgcgaagag ttactcaaag agcccgttga tttaccgatt  2160
gccctgagct atgaccttgt ggctaatatg cgtacaggct tagaaaaagc taaatctgtt  2220
accgatttta ttgacgataa atatcaatca gaacctccat attatcatct cccaagacaa  2280
tacgatttat tcaaagcatt tggcgataaa ccttctgaaa aactgtttgc tactgacaaa  2340
aagcccctgc atgaagtgta tggagagtat aaagccaaga aacagatcc aagaacgatt  2400
aaaaagataa agggattttt agaccaagaa caacgcatcc gatacctgaa agtttgtgat  2460
aaaactcttg tgaaaatatt agaaaaatac cttgccaaag aaacggagct taaaaacgtt  2520
caattgacgg acgcacaagg aaaattgatt ttggataaag tgttagagac agaatttgaa  2580
atgcctccct atggtttcaa ggtgcgtttg aaggactatg gacgttatcg ccgtttttcg  2640
aaagaccgcc gattggtttc tatgcaagac tatctcaatc aaagtgtctt tacgcccgac  2700
acgctcatta cagaattaaa tctttacgaa aaacagcgaa gtgagttttt gaaaatagtg  2760
cttgaattgg aaaaacgact tttgtctgcc tcagacacat tgaacattaa cttagctgac  2820
caacaacaa cattaggtga ggataaaata cgagactaca taacccacaa ctaccttttg  2880
gaagtggctt tacgaaataa ttttatctca gaaaatgaag caagagccat gttgtgtttt  2940
agaaatggag cattgcataa ccaattgccc gacctacaaa aattagtagg tttgattgat  3000
accgaagaac aaaaaacaca aagatacttt ctgaaaggaa tggaaatgta taaaaaagga  3060
attgagaaaa tatcataa                                               3078

SEQ ID NO: 9            moltype = DNA  length = 3579
FEATURE                 Location/Qualifiers
source                  1..3579
                        mol_type = other DNA
                        organism = synthetic construct
SEQUENCE: 9
atgacaatcc tggaaaaata tatgcccttg aatgaaatgg gcaaaatcaa atcgttggtc    60
gatgaactta aaggcatccc tggggcaatg aacgccaccc tacggcagga aatctttcag   120
aacatcaaaa aaacaaaact acaggtaaag tttttgaaag aatatcctga gacgcttttt   180
acggattcgg gaaatctcat tcctatcatt ggcaataatg ataactcatc ctcgggaacg   240
ccctcaaaac aagaggtctc tgacatagac gccaatcaag caagccgaat aaactatctg   300
ccccatgaaa caatgggaga gataaaatct gtgtacggca cgtacattga gatggctttc   360
cataactttt acctgacaat gcatcatatc tatgcggtcg tctttggaga agacatcatg   420
gaagagtgaaa aaaagaatt tgacaagaac aacaccaaat ctacaaaata cttcaccttc   480
gactttgcca atgaacgaac catatgtgaag cctatgttcg atcgagctga agagcaaaa   540
cctgaacaaa aagaacactt cgagaaattg gtcgtcaaac atttcccatt tctcaaagca   600
atagatgccc ttgaagacag aaagagaaag acaaaaatac aggcattatg tgtattctcg   660
ttagttttgc gggaattgag aaacgtctat tcacactatc ttttctatcc ctttaagaat   720
caagtagaca aatacaaaga gaacatcccc tttgtacttg atatgatgga gattctatat   780
```

```
accggtgccc aaagagaagt caaagggcgc tttggttttg atgacaagaa gatgcaatgc   840
gccaaaaaat atgaacgcaa caaagatcat tcacagcgag accaccaagg aaaaatcatc   900
aaagctgtac caaagaaaaa ctttagatac aatctgtata aaaaggaaga tagcgaggca   960
ataataactc cctttggctt ggtgtttctc accagccttt tcctcgaaaa gaaatatgcc  1020
aagatcctat ctgacaagac acattgcata aaatatacgg atcaagaggt tttatgtgag  1080
attatctcag tatatcgcat tcgcctgcac attcagaaac tcagtgtcac gaaagatacg  1140
gatgcgttag cccttgatat tatcaacgag ttgcagcgtt gtccgaaaag gcttttcgaa  1200
atgctatcac cagatgacca acagaaattt cggatcaagc ctaccgattc gcaatacgct  1260
gatgatgttt tgatgattcg tcatcaagac cgtttcgcac acctcctgtt aaaatatata  1320
gacgatgccc acctctttaa ttgtattcgg ttccaagtct ctttgggccg gtatttcttc  1380
cgtttctatg acaagagttg cattgattcc accggcgaca aacgggtgcg ctccattagt  1440
aagaatgtaa acggatttgg aagaatcact gacatagaag attacaggaa agaagtgtat  1500
ggagatatga tacgcgaata tgaggatgtc catgcaaaca cttctatgga aaagccttat  1560
attacagacc accatgcgaa atatctgatt agcaacaaca ggattggcct ctatatcagg  1620
aaagaggaag atacgcaatg cctttttgcca gagctgacgc ctgatggcgc acgtaacttc  1680
gcaccgacgt gttggttgag tatttatgaa ctgcctgccc ttgcttttct acttcacctt  1740
tacaacggag acggatcaag ggtagaagaa attattcaaa cgaaagttgc caactaccaa  1800
cgcctgtttg cagatgtccg agacggcaag gtctgtccag tgaaagacga agcagagttg  1860
actacgatac tccagaccta cggaaatata gaaccatccc agcttcctcg caaattgctt  1920
gattatctat taaagaaaga gatatgcgca caggatttgt tcaacacatg ggcacaatcc  1980
aaaatacaac ggatgatagc ccagaccgac agcctgctgc aacaccttga aaaagacctt  2040
caagctgttt ctgacctcaa acagaataaa ttcggaaaga aagccttcgt tgccatcaag  2100
ccggggcata tcgcagactt tctggcacac gacatgatgt tctttcagcc ctccatgaag  2160
gattgcaaca caaactcac agggctgaac tttcgcatct tgcagtcatc catggctgtc  2220
tacgatggga atttcgatga actgtcacgt atcatgcgga gtgcacacat cataggcaat  2280
gcaaatgatg cgtgttgcaa tccaattgta atggcggtat gccgcaagca taaaggattc  2340
agtaatatca tccggttcta tcaggcatac ctgaaggagc gcaaggcata cctacagcaa  2400
tgcgccaatg agaggcatta cgactccttg agtttcctgc atgcatcaca aaacaaatgg  2460
agagaaagga cccaggctta ctaccggtca ttagcagcga aatacttggc agaaaattat  2520
gacggtgtgg ataccaccaa atccatcgaa ctgcccagg gtttgtttga aacatatatc  2580
cggcaagaac tctccgagat aggtagcacg aagtccatgg ccggcgatgc caccaaaaac  2640
acatcctacc tcatatacgg ctatttcagg caagttatga gcgatgacgc ccagaccttc  2700
tatgataccc gcagatgcta tcagctgttt gatgtgcttt atcgcaaatc accacgcgac  2760
aaccattcct actatagcac ggcacaaatc cgcgaaatgc ttatgcgcag tcactccaaa  2820
tccattcgca aggacataga caactatata tcccaaacaa cggcagcaga aagaacaaaa  2880
gaaaaagaac gctgcgatgc cctgcttagg aaaataaaag ataccgaaac tgaactgaag  2940
gtctacaaaa ttcaggacat attgcttttc cttattgcca agcgcttgct gctggacaga  3000
aaagtggaaa atgactcggc ggtgcagatg aacgcaatca accaaattcg gttgaggaac  3060
atcgcagacg gcaatacact ctctcagaaa atacctatta gcatcagcat aaagtcaagg  3120
aaaggagatc ccaagattat tcaacaggat gacctaaaac taaagaatta ctctcagttc  3180
tactcgatta tcagcgaccg ccgtttacca tcgttgcttg atctgattaa ctctcgagtt  3240
attaagagaa cggacatcga agacgaattg agcaactacg acaagtcaca tccccatgta  3300
ctgaaatccg tctttgagtt tgaaaagcac tattttgata ctcaccgat accatcagat  3360
accgcctaca tggcattacc tgacacaggc gaaatgctga aagagagcaa cttgactgct  3420
gaaaagcaga aagaggttcg caagatacgt aattcctttg cccaccttc atatccgagc  3480
agaaatatca ccggtgcagc atccacgaa ttgcccaaaa aagcagaaat catatcaaaa  3540
aacctgatcg agcacctaag caatgcagaa atcaagtaa                          3579
```

```
SEQ ID NO: 10           moltype = DNA   length = 3819
FEATURE                 Location/Qualifiers
source                  1..3819
                        mol_type = other DNA
                        organism = synthetic construct
SEQUENCE: 10
atgtatcatc tttcggacgc aaaccacggc aaacacatcg ctggcaccta ttacgaaatg   60
gcgatgggaa atttcataca cactctttca cacatgctgg ttcgtgctgg catcaaagtg  120
aataagctgg aagacaacta ctccatcgag cgcgaaatca tgaatctgac cgcccctggg  180
gcgtacgatg cccagcgtgc ggctctgtct cgcctccttt accgccactt cccccttcttc  240
ggccccataa tggccgacca caccgaccac atactttcct ccaagcgcaa gaaggtgcaa  300
tctgccagtg atgatggcaa tctgtgatttg ggccaagagt taaaagatga agttgcagga  360
gcttcggcct gccaaatgat ccgctatctt gccaccatcg ctggggcatt ggtctactat  420
cgcaatatgt actcgcacaa gaatcactac gacaacgcgc aggatatcgc agcacaacaa  480
gaacgcgaac agaaactggc cctatggttg gatgtcgtct tccgcggcgc acgcgacatt  540
cttctcacac gcaagtctca tccccagccc gacaccgact tcctcaccca aaatggcacc  600
atcaattatt acatcgaaaa aaacggcaag tcggcctaca atcccaactt ctatttcaaa  660
cccggactga aaccgacaa cggctggtt atgaccgact tcggcaaatt tttctttttgc  720
tcgctttttct tgcgcaggc cgatgccgaa cggttcgccg cagaaaccga cctctatgtt  780
ggcagcccgt tcaagattac cgcacaggaa cgtgctcgcc ttcaggaggc cgaaaacaag  840
cgtgccgccg acgagcaggc tcgcgcgaggc agcgctggat ttccccacat cgtcaaccca  900
cgcaccatcg gcccgagcga gtcgcctcaa aacaatatca ttcgcgaaat gctcaatatg  960
caccgtgctc gcatccctcg cgaacgccgc atcgatgccg acatgtcgga aggtattctg 1020
gcaatggaca ttatgaatga gctgcgccgg tgcccattgt cgctctacaa cacactctcc 1080
cctgaggcca aagcctcctt cgaaaaaacg ggcgtcaccc ccgaggggg gattgtgtcc 1140
aacctactcg tccgccattc cgaccggtac ccggagctcg catccgtgc catcgaccaa 1200
atggaactcc tccctaccat cagatttcat gtccgcctcg gctccctccg attccgcttc 1260
tacgaaaaga aactcatcga cgggtcgcac accctccgca ccgtccaaaa ggcagtcaat 1320
ggcttcggac gttggcagga ggtggaaccc cgacgcgttg aaaatacac cgccatccag 1380
gcccgctgcc agaacgacaa aggcatcgac cagttcctcc cagacagccc caccaccacc 1440
ccatacatca ccgactggcg caccacctac aatatccacg ccaaccgcat cggtctggct 1500
```

```
tggaacctgc cgcaaatgtc cgatggcatc taccttccca atcttgatac cgacaagggc   1560
gacaatctac accgaaaagc gctaatcgac atgccggctc cgatgtgcta cctcagcatc   1620
ttcgacctcc ctgcactgct cttctactgc catatctaca cgcactacca tggcaccaaa   1680
taccatctgc cctccgccga gagcattata caggccaaat acgacgcact gcataagttc   1740
ttttccttcg ccgcagcgca gaaccactcc gccgaacagc tgcgggaaaa acaactcgaa   1800
ctcaatctcg ccgacaacga aatcccagac aaactccgat gcatgatgca gacaaagccg   1860
ttcttcaaaa atggacgaca acagctttct cctttaggct atcccatcat gaaaaattgg   1920
atcggtgtgg ccgaacagcg caaacatgcg gcccaggtgc tccgcgatgt ggcgaacgag   1980
gccgctgacc gtcttgctag cttcgaaaaa aaacaccagc gcgttgtcgt aggcggacgc   2040
gacaaccgct acggccggcg tggccatgcc gacatacgcc acggctccct ggctcgctac   2100
ctggcaacaa gcatggtccg atggcaaccc gccttggacc agcccggcgg cgacaaactg   2160
acctccgcca accaccgcgc cctggcgggc ttcctgtccg aatacggact gcacggctcc   2220
aacatcaaca aactccgtaa tgtgctgaaa gaagccggcc tcatcgaagg ctcccatcca   2280
cacccctcc tcgctcatgt ccttgaatcc gcccccgcca acatcgaagc gctctacgtc   2340
gcctacctca aacacgagca gtcccacgcc accgcgctga aaaataaatt caccgaccgc   2400
aacggtattg tgcagccgtc cgaggtaccc gcattcgtca ggttcaattc ctcgcgttgg   2460
cgcaacgact ccgccaccac cgcccgccgc taccttcaga ctccaccgc acctggcagt   2520
tccgactctg ccgaacacaa cgcacccatc atgctccctg acggcctctt cacaacccac   2580
atcatgacac tcctcaataa agttctgggc caaaacgata gggttcccga ggaagactac   2640
ctgcgacacg acctcccccg catcgcctcc atcatcaatc ccaacggcaa aacctacggc   2700
gcagcctaca tcatccgcgc atggttcgat caagtggaaa accaagacgt ccagcctttc   2760
tacgacctcc cgcgcttcta ccgcgaaatt tctctgctcg caccgcggcg aaaacccaat   2820
caggaactca ttcgcgacta cttctccgaa gagcagatcg cacagaaaat acaaaccgtc   2880
cccaaaaaac aacgctccga aaagtggggc cacaccatcg acacagaaaa ggacatacga   2940
cgctaccgcc tccaagacat cacgctttac ctcaccctgc tcgacatgct taccctgatg   3000
ctttcacgca acgaggccga aagaaccgac cgccaaatga aatcttcaac tgcagaacgt   3060
gtctccaata tgcgcctcgt cgacttcgac cacagcttcg acttcgacct ccttggcagc   3120
acctccggcg aggccgccta ctcctacctc caccaacgca gtggcatcac catctccatg   3180
cctgccctct ccctccgcag ctatggctcc atcttccgcg tcttggccga cagccgcttc   3240
gaaaccctca tggacgctct gaatcgccag ggggtgacac acgtcaactt cggccgatatc   3300
acctccgaac tcgcactcta cgacaccctc cgctcccact tcctcctcca ggcacacaac   3360
gtcgaacagg acgcattctc cgccaaacgc ggcgtcctcg aaaaccacac ctcaccattc   3420
ttctaccgca gcggcaatct gcagctcgac gaccaaggaa acatcaccaa cccttcgacc   3480
gacgccatcc gcaaccacta cggcgaacta atcaaaatac tggaccgcta ctccctcaaa   3540
atcgacaaaa aaacaaaaga tggaaagtcg caagatatcc tgctccgcga cctgatggcc   3600
gaactgcgca acgccgccgc tcacaaccga taccccaagg ccgacttctt cttcaggcag   3660
ttcgatcact tcctcaacac ctgtaaaccg acagactcaa acctcactgc accaaaactac   3720
attcggactg tactcgaatt cttgaaaagc attgtggaca acaacttcac cccctgcta   3780
cacgaagaat ctccggaaaa tgaaagcaaa agtgaataa                          3819
```

SEQ ID NO: 11            moltype = DNA   length = 3552
FEATURE                  Location/Qualifiers
source                   1..3552
                         mol_type = other DNA
                         organism = synthetic construct
SEQUENCE: 11

```
atgcctatgt cgacgattat tgacaaatat atgccactta atgactggaa cagaatagag   60
tcattgatag gtgagttaag ggcaatttcc ggggcgatga attgtgcggt gcgcagagct   120
gtttttgaga atatcaagaa agcaaaactt caaatcaagt tcaatgacca ataccctgaa   180
tccatttta ccgacaaaaa tggatctata cccatagttg gcactaccga agcaaataat   240
ccggaaaatg gtgggaataa cgaatgtgag caatcaaata attatttgag tatagattat   300
ctgccacgag tgacccagga agataaaaag tcggtctatg ggacttattt tgaaatggcg   360
tttcacaact tttttatcac attgcaccat atctactccc tcattttcgg tgaagacatt   420
atggaagtgg caaaaagtga atactcccaa acacaaaccg attcttttca agatgatttt   480
gccaataaat atactgtgtg gaatcctctg ttcacaagat taaggcgagc caaagctgag   540
cagaaagagc gttttgaaga gcttgcaata aagcattttc ctttcctaaa agcactcgat   600
gcgctcaaag gtgagaatcg ggtttctaag gttgatgcgc ttgagcggtt ttctgtagtc   660
gttcgtgaat tgagaaacat ttatctgcac tactgcatca tcccgagcga caagcagaag   720
aaggaataca gcgacaaatat ctctttcatc ttcgatttaa tggatctact gttcactggc   780
gcaaagaggg aggtgaagac caggtttgct ttaagcgacg accaaatgag ctgtgccgac   840
aagtatgagc caaatagcga ccgctcccta cgcgacattc acggcaaaac gttaagaata   900
gttcccaaga aaaatttccg gtatcatcta tataaggttg gtgacgacgc gaagataatc   960
tcgccatttg gccttgtgtt tcttgccagt ctgtttcttg aaaaaaaata tgccaaaata   1020
ttgtccgaca aggcacacgt cgttcgcctt aatgacaagg gtgtgatttg tgaagatgatt   1080
tcggtatatc gcattcgcct gcatatcaat agactaagca tctcaaaaag cacagatacc   1140
ttggcattgg acattatcaa cgaactgcaa cgctgcccga aaaagtgtct tgagctgctg   1200
ccgccagtcg cacagcagcg attcagggtg aagcctgaat catcacacgc ccccgaagtg   1260
ctcatggttc gccacaacga ccgttttgtt catcttttgc tgaaatatat tgatgatgct   1320
aagctgtttg agcacattcg atttcaagta tctttaggcg gttacttctt ccggttctac   1380
gacaagattt gcatcgacac ctcaagtgaa aagagggtgc gctccatctg caaagatgtg   1440
cacggattcg gacgtatttc tgagattgaa gagcttcgca gggaaaaatg gaaagatatt   1500
ctgcgggaat atgatgaggt gcacgccaat actgccgacg agaagcccta tatcaccgac   1560
caccgagcca actacttgat tggtaacaac aaggtgggaa tctatctgct gaaggagggc   1620
gacgaacagt gcattatgcc tgaactgttg cccaatggtg cccggaatca tgccgccaact   1680
tgctggctca gcacctacga gctgccggct cttgctttct tgctgcatct ctacaatgca   1740
gatggagcaa gggttgagga gattattgag aagcaggttg ccggctaccg acgtctgttt   1800
gccgatgtgc gcgatggcag tgtcgcccct gtggcaagtg tggaggagct tgatgagttg   1860
ctgaagggct acggtgatat gcaggcgtgc aatctgccgc gtaagatgct cgactatctg   1920
cttatgaaag atgtcaatgc acacgatttg ttccgcaaat gggccgaagc ggaattgcag   1980
```

-continued

```
cagatgattg agcagacaga ccggctgtcg cagcgcatcg acgacgacat taaagccgca   2040
gccaatatga ggcaaaacaa attcggaaag aagtcttttg tggcagtgaa gccgggtaaa   2100
atcgccgatt tccttgcgca cgacatgatg ctgtttcagc cttgcaccga ggacaacagc   2160
aacaagctga ctggccttaa tttccgcatc ttgcagtcgg ttatggctgt ctacaatggt   2220
gacttcgatg aactgtcgag agtgctccgc aatgcccaca tcattggcaa cgcaaccgat   2280
gagatgtgca atcccattgt aatggctgta tgcacaaga gcatggaatt tggcaatatt   2340
gtagatttct acaaggcata tctccgtgag cgacgcatct atcttgagcg gtgcttgcgg   2400
cacggcgatt ttgagtctct tggatttctt catgcctctc agatccgatg gcaggaaaga   2460
agcaaggaat actatcgtgc tttggctgca cgatacctcg tagatgaata cggcggaaca   2520
gagtcggcaa aagccatcga acttccgcga ggtttgtttg agccatatat ccgcaaggaa   2580
ctatcggaga tgaatgctat gaaatcattg gcatgcaact ccgactacaa tgtttcatac   2640
ctaatctatg gctatttcaa gagagttatg tccgatgatg ctcagccttt ctacgacgaa   2700
aagaaatgct atcgactctt caatgtgctc tatcgcaaat cgcctcacga ctcgccggtc   2760
tatcgcaata cggctgaaat acgcgatatg ttgatgcaga atagcccgaa ctctatccga   2820
aaggatattg aatcgtatct cagcaacacc attatagccg atagagccaa ggagaaaagag   2880
cgttgcacgg cattgctcag ggaaatgaag aagtgtgaaa ccgagctgaa acgctacaag   2940
attcaggata tgctgctatt tctgattgca aagcgcattc tgtctgacct accggctgca   3000
catgattcgg ctgttcaaat gcaggcaata agcaggattc atcttaagga cattaccgac   3060
ggcaacactt tgtcggagaa gatttccactg agcgtgaaag tagtatcaaa aaacggatat   3120
attaagaagt tgacacagca taacttgaaa ctgaagaact attctcagtt ttatgccatt   3180
ctcagcgacc gacgactgcc gtcgttgctc gacttggttc gctctaatta catcaatcgg   3240
aacgacatcg aagccgaact cgacaattac gacaaagttc acccggaagt gatgaaggca   3300
attatcgggc tcgagaagaa acacttcgaa aagcacggct ttgacgattc tggcatagtt   3360
cctgatttaa gcagcatcct tgccgaaacg acaatgcccg cagacaaaca atatgaagta   3420
cgcaagattc gcaacagttt tgctcattct cattatcctg gttatcatgt cgcaaatgct   3480
ggcataacag agttgcccaa aaaggctgaa accatattta acacattaaa aagtagcttg   3540
agcgatgaat aa                                                       3552
```

```
SEQ ID NO: 12        moltype = DNA  length = 3573
FEATURE              Location/Qualifiers
source               1..3573
                     mol_type = other DNA
                     organism = synthetic construct
SEQUENCE: 12
atggaaacaa cgataaacaa cagaatcggg aaaggtgaat actatacaga ggaaagcaag   60
gagtttcttg ctgcctactt taatcaggcc atacacaatg ttttcattgt actaaatcat   120
attgcgaaac gctttgggat ggatgaattg tcttcggacg aagaactaaa aaactggtta   180
attggacgac aacgtgaaaa gaaacgaaat gcgattgatc gtcaacgctt cttagaattg   240
attgatcggc attttccttt tttacgcatt gctaatgctg acaaaaaaga cgcgaaaaga   300
gaaaacgatt tagaagataa tcttgcctta ctcataacgc tattaaatga cttaactgaa   360
agacgcaata agtatagtca tgcaattact cacgcaagca tagaaagtaa tgatcgcgaa   420
ttagtttggc gtttgtacag catttatgat gccaatatca acctcgttaa acgagattat   480
tttgaatcca atgtgcatac agaaatcaat gaagaccctt atgaaaaaca agttgaacac   540
ttgcgccgat tctgtatgaa caacgacaga accaaagttg atgaaaaagg gaaaaagaaa   600
cctgctatgc cgaatccaag atttaggaca cccttttaa atgcgaaaac caatcaactg   660
agtatttacg gtttggtgtt ttttgtgtcg ctttttttgg aaaagaagta tgcaattcag   720
atgcagaaaa atgtatatgg tttaaaagat gctcgcgata caaagtttaa aatgaccaat   780
gaggtatttt gcagaagtcg gatcatcatg cctcgtgttc gcttgcacag cgataaatca   840
acggatgctc ttgtattgga tatgctcaat gaattggcca aagcaccaga ggtgctattc   900
gatcaactga cagacccttt taaagagaaa ttctatatcg agtcgataga tagccttgaa   960
gaatcagaca ttattactcc tgtcagagcg attcgcaaac aaaataggtt tatgtatttc   1020
gcacttcggt atttagatga aagcaatgcc ttttctaaac tacgcttcca aatagatctt   1080
ggcaattatc attatcacct ttatgaatct aaaatacag atcaaactga aagccgacat   1140
ctaacgcgca aactatttgg ttttgggaaa ctgatagcct ttgaacaaga atttgcgccc   1200
gaagaatgga aaatgaaaag caaagattta gattattatg aaggagcaac acagcccttt   1260
attgcaaaaa cgtacccaca ttatcatctc gaagaaaata aaatcggtat tttatttaac   1320
ggacaagcag aagtacaatg gccacactta gatgtggaag aacatgaaag tttcccaaaa   1380
tacaaacgtc gtgctaacga aaaagcagat gcgtttctaa gtgggaatga attgttggca   1440
gcggcattct gtcatcattt gtatgcctcc attggaaagc ccaataccgt agaaaaaata   1500
atccgcgaca agtatcatgc cttgcggcaa ttattttccg atttaaaatc aggaaactta   1560
caaaacttgt taggcgataa tacgagtaat gaagccattt ctcaactgct ttttgaaaaa   1620
tataggctta cactatcaga agttcccgtt cgactacatg ctttttttgag tggacaagaa   1680
caagccgata caaaagcaat agctagaggg aaactagaac taatggccca acaaaacaaa   1740
aaaagaattg aacggtttga tgcaatgaag aaagccgtta ttaaggtagg caaggctcaa   1800
tatcgaacac tccgttcagg ggatattggg gattggcttg tgcgtgattt tatgcgtttt   1860
caaccaattg gctataaacg caatcaagca ggtaaacaag aaccagactt aaaaagcaaa   1920
gcaaatccca agaaatatca gttaatccaa aaaagtttag ccctttacga acaagagaaa   1980
aataacctct tgggtttatt taaaagttgc aacttattgt catcagaaaa cgaacatcca   2040
tttcttaatg aagttgtgca gtcaatgcca gcgacatggc aagatttcta tgaacgttat   2100
ctccatgccc gttctcgttt tttgaaaaa tgtatcgaaa aaggtattaa gaaaaattcc   2160
taccaagcgt gttactcatt tctaaaaata aaaccccaat taaaggataa ggaaaaacta   2220
tatcagggtt gggatgctca aatgaactta ccaacgaata tgtttattga tgccattcac   2280
gactggtttg ccaaacaca ccatgaatca ttacggacat ggtttacaca acaagaaaaa   2340
ccacatcaac tcattcggact tattcgcaaa tacattgaact tagcacacac cgaccagata   2400
caaggctttt atgatatgtt tccgttgcgt tacgactttt acaaaaaaga atttccaaat   2460
gggcttgttc ttcacgagcg gattaacaag caaaaacaaa tctgggaagc tcaactcata   2520
caaaccaaaa aacggttaga agatgcagca agcaaattaa aaaaagtgaa acagcaagtc   2580
gaatcgttgc ccgaccaaga gcttcgattt cgcaatgaaa cagaggcgat ggtctatttt   2640
accaagttat ttgactcaag cattgtcaag aatgcaattc tcaaactgca aagagatcag   2700
```

```
aaagcacttc gtgtaaatac aattggagaa aaaattatca agatttatac agcaaaatac  2760
gatgccattc atcaagaggt acgagacttt aaatccatgc tgacaactga aaaaatgatt  2820
cgtcggggtta aggcagagga ttgtgtaacg ctatttatgc tgaccgattt gatgaatcaa  2880
agtcaaatca cgattggaca agaacagcga actattaaac tcagcgatat tcaacctatg  2940
ggcgaaacgc aaattcaagg cattcttgat gcagttcagg tattggagca aaaattagat  3000
ttttttttcca gtgatgaaca aggaaaaata agtcaggtta agctgggcga atggacgatt  3060
ttttcaactg atacaaaagt aaagaagcaa ggaaatttta aacaattgtt aaaagatcgc  3120
cgcctcaaca acctagcaca ctatattttg ccagatatag caggaggagc gattcgagta  3180
cgacgcaatt tgttggagat ggagttagat caatacgacc gtaatcgcat tcctattatt  3240
aaactgatgt atgaactcga atatgcgatc tataaggttg atccattttc agtagaacta  3300
aaatataaaa agtttagcca atgcttgcgt gaatatgctc aaaaagcagt tttgaatgtt  3360
gaacaagtgg aacatttgaa tgtgttgatt gccatacgca atgccattat gcacaaccaa  3420
tatcccaatc gagaccattt aaaagctatc gtgccattta cggtaagcga atatgcgcca  3480
gttcaagaag gattaaccat tgcgcgggcag cttctagcat gtgcgcaagt gagcgtcaac  3540
attattttat ccaccatctc aaaatttgaa taa                                3573

SEQ ID NO: 13            moltype = DNA  length = 3477
FEATURE                  Location/Qualifiers
source                   1..3477
                         mol_type = other DNA
                         organism = synthetic construct
SEQUENCE: 13
atgaaagaga aaatcaaaaa taaaagttcc ataatcagaa taataatgtc aaactatgat  60
gacaaaggct tgaaagaatt caaagtttta tataataagc aaggtggagt agatactttt  120
acttgcaaaa ctgatattgt tgatggaact attatttttt tagaaattga aaaacattta  180
agagattttg gagacgattt ttcgtgggat atttcaagtg agttgaaatc agttgagatt  240
acaaaactta taaatggaaa agaaacaaga aagtacaaag taagtattaa aaattcaagt  300
acaaaagata aaaagaattt agttgaatta gaggtcgagg acttaaaaga aagtgcaata  360
gatagaagga ggactaaaag tagtacaaaa agagtttgc tttctaaaga tgtaatggaa  420
agatatgcag aaattgcttt tagtaaaaaa gaacgttggg aagagataga ttctcaaaaa  480
atttataaag tcaaaagatt tttagattat cgttctaata tgcttatata ttttcagttt  540
attaatgatt ttttgactaa agggatacct gatgaattag ataaaaatgg agaaataaaa  600
cagttggaac tttggaaact tatagatgat gatgaaacta tatctgataa aaacttaaat  660
caagtctcca agaatttata tacttatatt tctcaagaaa ttaaagatag tcaaactaga  720
gctgaaaata acagagaaaa aaataaagaa aaagagcatt ttaaagaatt ttatgcattt  780
aatgatattt ctgaagaaag cataagagag gacgttaaaa aattcatata tttatacgct  840
aatttaagac ataatttaat gcattataat tactctttt ttgaaaatct ttttgaggggt  900
aaagatcttg ttattgaaaa aactaaaagt ctgttgagtt ctactttaga tttaaatatt  960
tttaaggaac tttcaaacat agtagagttg agagaagaga ataaacaaa ctatcttgat  1020
gatgaaacaa ctataagagt tcttggaaaa gaaaaaaaag caaaaacttt gcataaaatt  1080
tatagtattc tttgtagtag aaaaaatggt tttaacaagt ttattaactc attttttttct  1140
acagatggta tagaggaaga gttttttaaaa tcagagtaa aaaaagattt tttagaaagg  1200
ttaaattggg ttgaaaagtc attaattgaa aaaataacaa atccaccaag tgatacaaag  1260
ttaaaatata aaaatgacaa aactatagaa aatatgacca aagaaaagga ggaaaaatta  1320
gagttaatct ctctttttgaa tccacaagtt agcgattata agaccgagaa ttttactcca  1380
tattattggg acatacatca gagcccttca tacaagaaac tatataatga tagaaaagtt  1440
ttagtttcgg aactttcaaa actaatagcc attggtataa atagtgatac caagaaaaga  1500
ataactgatt taaatgctga acttttaaag attaagataa aaatggaaaa aattactaag  1560
cttaactcaa aaataagact tcaatataag ttacaaatgg catttggttt catttatgcc  1620
aattattcaa aagtatacaa agaaaaaaga gtacttaata taaatggatt tgtgcaaaac  1680
tttgacccga caaaactaaa taaagagaaa gaattagaat caaggttaat ttatttaaaa  1740
gctcctttata atatatttga agacaataag tctttagatt tcaatatgaa aattgtagaa  1800
aacattccag tttcagaaaa atcaatctttt agaataaaac cagagaataa tctttccaag  1860
ttttatattc tatcttattt acttctacct gtagaactta ggggagattt tttaggatat  1920
gttaaacatc attactatgg gataaaaaat gtagattttg atgaaaatac tgatattaaa  1980
gaagataagc ctaatgaaaa ttctgatagc tttttttccata atttgagact ttttgaaaaa  2040
aatagtaaaa aatttgaatt aataaaaatat agattagtgg aatttggtaa tttgaaagac  2100
catcttccaa gaatttatga aaaatttgga atcaaaccag atgtttttaga atatatcgaa  2160
aattcaggga ataaggattc caaacttttt gatagaaaca tactgttgcc tattatgaag  2220
tattatcaac atattttaa acttcttaat gatattgagg ttcatgcttt gttaagattt  2280
tcggagaaag attctatatc tcttgatgaa agcataaaag aatgtagtaa ggggaaattc  2340
ctaaattttg gaaagcttct gttttttatct agatatggat tagaagcgaa aaaagataat  2400
aagtttaaag atatttttaa tcgagagaat ggattatcaa taacaaaaga tgatgctaaa  2460
actgaaagaa agaaatattt tgaaatattt gaaacaagaa acaaaatagc tcacttaaac  2520
tacaaacagc ttttccatga cttattattt gatagtaata tcaatataaa caaggaatta  2580
gaaggaatta ttcaagaaac taaaactatc gggcttaatg ctcaaacttt aggttacaac  2640
ttcttaaatg acttttatat gagaaaagag atgtttatta gtaatcagaa aaagtcctca  2700
atgactctaa taaataaccc tttatctaaa gataaagata ccaaagaaat aggactctta  2760
aaattatatg gtttatcaaa gtctcaacct aaagattaa ttttagctaa atataaagaa  2820
cttatgaatt taattgaaaa aacagaggat tctattcttta agaaaaaaga ttttttttacct  2880
gtgaaagaag tttctattac agttaaaaaa tccacgccaa ataaaaaagg aataatggtt  2940
gaacttccag aaatacttca aataaaggat ttaaatgaaa tggatttact tgcttatgct  3000
tcaaatatta gaggtaaact tcataaagat tcttccgacc ttttttggaat ctataaaaaa  3060
ttaactaaa aagagttgaa aaagaaactt ataaatcttt ttataaaagg agaaaaaaagg  3120
tatctcaacc tagaacttgt aaacaagact ggttatatgg caatatatga atctacaggt  3180
ttatatccta aatcttatga aatattaaat cacgaaatct cttttagtga aattagtatg  3240
aaaaattggt atgaacatga ttttaaacct atattccaaa ttgatggaag tctaccaaat  3300
aatacagatt ataaaaatgg tgtgtttatt tacacaagtc cctacgaatt tagagataaa  3360
gagcttatga aaaaacagag aactgtacac aaaaagagata tagaaaaaaac atttttataat  3420
```

-continued

```
gaaaacgata tggattacac aggtatctac aatcaaaaaa taaaagctct ctattga       3477

SEQ ID NO: 14          moltype = DNA   length = 2796
FEATURE                Location/Qualifiers
source                 1..2796
                       mol_type = other DNA
                       organism = synthetic construct
SEQUENCE: 14
atgatgggga ataaaaagtc ggttgcaaaa gccaacggct taaaatctac tttcgttttg       60
ggcgaaaata cggcgtatat gacttcgttc ggcaggggaa atgcggcaca gccggaaaaa      120
catatccgcg acgctacggt gacggatatt caacatactt tccgtgcaaa aaccgacggg      180
ggcagaacgg tgcatatcga aggcagagtc ggggcgtccg atgtgttgct gccggatgcc      240
gctaaccaac tgcacgccaa agatgccgtt gagcaaatgt atttcggcaa agcgtttcg       300
gacaatatcc acatccaaat cgcctacaac attatggaca ttaaaaagat tttcggtggt      360
tatgccaata tcatagtgca taccgtcaac aatctttgct gtgacggaga caagcaggac      420
gatttcctcg gtatgtttaa aacgcaaaat cggtatcaag ttgcggcgtg ggcacataaa      480
attgtttcgt tgcatttggt gaaaaacgag ttgcgcggcg gcggattttt tatggaccaa      540
gaggtttggc gtgcacatgt cagaacggat ttcaagtcct tgaatcttgc ggtgaatgct      600
tttatgaaaa agtatcccca aaaatatccg tattggagtg tgaaaattgt atctgacttt      660
atcgtgcagg aaatgggcat aaagaataaa gtcattttgg aaaaagcggc cgagagttat      720
gcggaatttg aaactgtcgc caaacgcctt gaaaaatccg cttattattt ttcggacata      780
tttgccggca aagacggtaa atttgatgaa caaaaggcct ttgatttatt gcgcgttttg      840
ggtatgatgc ggcaagaagc cttccacgaa aaaaacagtt ctgcttcttg gctgtacaat      900
ttggacgcgg aagccgacga ggacatcaaa gccgcgctga gaaccgttgt cgataccaaa      960
gtaaacggta tcaatacgaa ttttgccaaa caaaataagg taaaccttct tgttttgcag     1020
gaaatttacc cgcaaaaaag caaggcggac ttggtgcgcg agtattatga cttttcggtg     1080
cgcaaggcgt ttaaaaatct cggttttttcc gtgaaaactt tacgcgaaac gatgtgtgca     1140
tttgatgcgg cttctgtaat caccgacaag caatatgaca ctgtgcgcgg aaaactgtat     1200
agtttgtttg atttttgtgat ttacaattat tgcttggaaa acgaggcggt ttgcaatgcc     1260
tttgttgaag aattgcgcgc caatttggac ccggaaaaca aaacggcttt gtaccaaacc     1320
cttgccgaga aagtttgggc ggaaatcggc gacattgtgc tgcagcgaat tttgccgcag     1380
atgcatgcga aaaaaattca agagagatcc aaagaaaccg atgccgaaac ggttgaaatg     1440
caagggtatg tgcaggcgcc gaaggacttg tcgctgtttt caaaggcggt gtattgtatt     1500
tccatgtttt tggacggcaa ggaaatcaac agttttttaa gcgcgttgat taacaagttt     1560
gaaaatattt cttccttgtg tgcagtactg gcgtataacg gattggaacc ggaatttgtc     1620
gcgcccttta cattttttgc cgacagtcaa gccattgccg aggatttgcg gtatatcaaa     1680
tccattgccc gtatgagcaa aggcaaaaaa gcaacgaaag acagcccgt taccgtgaaa      1740
gaaatgcaat atttcgatgc tgccgccgtg ttgggcgaaa cggacacgga aaaagtgaaa     1800
gcggcattc acttgggtga caagtcggct tccacggcg acaaggcgtt ccgaaatttc      1860
gtggtgaata atgtaatcaa ttccaaccgt tttgtgtatg tggttcgctt tattaacccg     1920
aaaaatgcac gcgaaattat gcaaaaccgt gcgctgattg cgtttgtgtt gaaagatatt     1980
ccgcaaagcc agttggtgcg ctattgcggt acggcgggga ttgcctgtaa cgcggacgag     2040
ccgaataccg aagccatggt aaatgcgctt gcagatatgc tgttgcaggt gcgggtttgat    2100
gctttcagta atgtgcaaca aaaggtcaag gcggattctg cagaggctgt gcaaaaggaa     2160
aaatacaaag cgattatcgg gttgtatttg actgtgctgt atttactggt aaaaacactt     2220
gtaaaaatca atatgaatta tgccattgca ttcgggattt tggagcgtga ctgtcaaatt     2280
atgaaccaaa agcacggcaa aaatccgaaa cgcgaccgcg acgcatttta tatgcgcgaa     2340
cagcaaaaca agcagtatgt ttataacgca cgcgccatta cagaattgtt tatagaaaac     2400
ggatggctga ataagcgcgt gcaaaaaagc gtggaaaata acgccgcact gtattcggac     2460
gaagcgtttt ataaatacag aaatcttgtg gcgcatttga atgtgatttc cgcacttccg     2520
aaatacgcaa aaaacattac caaggtgaaa tctttgttcg atgtgtatca ttacattttg     2580
ttcttgtcgc tttgcgagga taaatacagc aatctgcccg aagcggtgac gaaatccttt     2640
tgcaaaaacg gtaaaacgat gttggaaaac gcgcgggaat accaaacggt ttgcaaagat     2700
tttctgtatg ggttgaacac gccgtttgcg tataacgccg cgcggtatat caacctttcc     2760
aaccgtgaaa agttcctggc ggggtttggg aagtaa                              2796

SEQ ID NO: 15          moltype = RNA   length = 36
FEATURE                Location/Qualifiers
source                 1..36
                       mol_type = other RNA
                       organism = synthetic construct
SEQUENCE: 15
gttgttacag cccttagttt gtagggtaat gacaac                               36

SEQ ID NO: 16          moltype = RNA   length = 36
FEATURE                Location/Qualifiers
source                 1..36
                       mol_type = other RNA
                       organism = synthetic construct
SEQUENCE: 16
gttgtagatg acctcgtttt ggaggggaaa cacaac                               36

SEQ ID NO: 17          moltype = RNA   length = 36
FEATURE                Location/Qualifiers
source                 1..36
                       mol_type = other RNA
                       organism = synthetic construct
SEQUENCE: 17
gttgtagaag ccgttcattc gggacggtat gacaac                               36
```

```
SEQ ID NO: 18            moltype = RNA   length = 36
FEATURE                  Location/Qualifiers
source                   1..36
                         mol_type = other RNA
                         organism = synthetic construct
SEQUENCE: 18
gttgtaaata cccacgtttt ggtgggctaa tacaac                              36

SEQ ID NO: 19            moltype = RNA   length = 36
FEATURE                  Location/Qualifiers
source                   1..36
                         mol_type = other RNA
                         organism = synthetic construct
SEQUENCE: 19
gttgtgtgtg cctttcaaat tgaaggcgtt cccaac                              36

SEQ ID NO: 20            moltype = RNA   length = 31
FEATURE                  Location/Qualifiers
source                   1..31
                         mol_type = other RNA
                         organism = synthetic construct
SEQUENCE: 20
atgactatac cagcaatggc tggattaaaa c                                   31

SEQ ID NO: 21            moltype = RNA   length = 37
FEATURE                  Location/Qualifiers
source                   1..37
                         mol_type = other RNA
                         organism = synthetic construct
SEQUENCE: 21
ggttttacac ccgtgtaaaa ctacacagtt ctaaaac                             37

SEQ ID NO: 22            moltype = AA   length = 1114
FEATURE                  Location/Qualifiers
source                   1..1114
                         mol_type = protein
                         organism = synthetic construct
SEQUENCE: 22
MGSSHHHHHH SSGLVPRGSH MASMTGGQQM GRGSPAAKKK KLDGSVDMNP QARTRKPETP     60
LKPVGNEHFA VFINIARHNA FIAITELSKI YGMTPPNEDE LATSRFIAAF DSTTIDVRKL    120
KQRLKRLSSL MPFLKSLQDK TDAEIIGILK DLLSLVNQFR NYYSHYNTSD FLTINSNEFI    180
TSDKVSILEN IFEKAVLSLT NSEKAYDRFE IISLLKSEKR ADKPYFYEFI ENNKISEKAI    240
AFFFCLFLDK PNAMKFLKRL KGFKGADTKQ FRATLEAYTT YCIQLPEPKF LSDRPNLAII    300
LDGIEHLKRC PIEVHKTLSF RDKQKFERKV MREDLNGDLQ EENIELLRYD DRFAEFAMRY    360
LDDFDILSDA KKQNTYRFEI QLGKKVVESK KLAEETTEAQ DKIPVRFKPV KAFGKLADIP    420
RKKDEAVIDW QQDLEELYAY EPHYKIENHS IGIKKIATED TFRLNNPEEL PDAYLSEYQL    480
RNIIFLSLES SNKEEFFMAC QIRIGKIKSL YKALSAPTHY KESIKQKYNE LINNNLLPKP    540
LVKYLTHSLD ELPTYKSKAI KKLKFWQDET ENLLAEVKRH NEKSEKARKE NKFFKSFLKS    600
GQIATWLIKD IQHFLPLQGK LSVLKYNALQ AKLAIYNSEE LKEMLTDFQV YDTPKGTDRN    660
MPEKGGGHQF IKTVFDKNPQ KLPPHWLHFY NDYLNAKKQW IEDKIKFLTA MPDTEAEIMK    720
QQPLFYFLDL GSNYEEGEKI VYFRENSPAY IAKYCEELLK KPVDLPIALS YDLVANMRTG    780
LEKAKSVTDF IDDKYQSEPP YYHLPRQYDL FKAFGDKPSE KLFATDKKPL HEVYGEYKAK    840
KTDPRTIKKI KGFLDQEQRI RYLKVCDKLL VKILEKYLAK ETELKNVQLT DAQGKLILDK    900
VLETEFEMPP YGFKVRLKDY GRYRRFVKDR RLVSMQDYLN QSVFTPDTLI TELNLYEKQR    960
SEFLKIVLEF EKRLLSASDT LNINLADQQT TLGEDKIRDY ITHNYLLEVA LRNNFISENE   1020
ARAMLWFRNG ALHNQLPDLQ KLVGLIDTEE QKTQRYFLKG MEMYKKGIEK ISTGGGPGGG   1080
AAAGSGSPKK KRKVGSGSKR PAATKKAGQA KKKK                               1114

SEQ ID NO: 23            moltype = AA   length = 1281
FEATURE                  Location/Qualifiers
source                   1..1281
                         mol_type = protein
                         organism = synthetic construct
SEQUENCE: 23
MGSSHHHHHH SSGLVPRGSH MASMTGGQQM GRGSPAAKKK KLDGSVDMTI LEKYMPLNEM     60
GKIKSLVDEL KGIPGAMNAT LRQEIFQNIK KTKLQVKFLE EYPETLFTDS GNLIPIIGNN    120
DNSSSGTPSK QEVSDIDANQ ASRINYLPHE TMGEIKSVYG TYIEMAFHNF YLTMHHIYAV    180
VFGEDIMEEA KKEFDKNNTN STKYFTFDFA NERTIWKPMF DRAERAKPEQ KEHFEKLVVK    240
HFPFLKAIDA LEDRKRKTKI QALCVFSLVL RELRNVYSHY LFYPFKNQVD KYKENIPFVL    300
DMMEILYTGA QREVKGRFGF DDKKMQCAKK YERNKDHSQR DHQGKIIKAV PKKNFRYNLY    360
KKEDSEAIIT PFGLVFLTSL FLEKKYAKIL SDKTHCIKYT DQEVLCEIIS VYRIRLHIQK    420
LSVTKDTDAL ALDIINELQR CPKRLFEMLS PDDQQKFRIK PTDSQYADDV LMIRHQDRFA    480
HLLLKYIDDA HLFNCIRFQV SLGRYFFRFY DKSCIDSTGD KRVRSISKNV NGFGRITDIE    540
DYRKEVYGDM IREYDVHAN TSMEKPYITD HHAKYLISNN RIGLYIRKEE DTQCLLPELT    600
PDGARNFAPT CWLSIYELPA LAFLLHLYNG DGSRVEEIIQ TKVANYQRLF ADVRDGKVCP    660
VKDEAELTTI LQTYGNIEPS QLPRKLLDYL LKKEICAQDL FNTWAQSKIQ RMIAQTDSLL    720
QHLEKDLQAV SDLKQNKFGK KAFVAIKPGH IADFLAHDMM FFQPSMKDCN NKLTGLNFRI    780
LQSSMAVYDG NFDELSRIMR SAHIIGNAND ACCNPIVMAV CRKHKGFSNI IRFYQAYLKE    840
```

```
RKAYLQQCAN ERHYDSLSFL HASQNKWRER TQAYYRSLAA KYLAENYDGV DTTKSIELPR    900
GLFETYIRQE LSEIGSTKSM AGDATKNTSY LIYGYFRQVM SDDAQTFYDT RRCYQLFDVL    960
YRKSPRDNHS YYSTAQIREM LMRSHSKSIR KDIDNYISQT TAAERTKEKE RCDALLRKIK   1020
DTETELKVYK IQDILLFLIA KRLLLDRKVE NDSAVQMNAI NQIRLRNIAD GNTLSQKIPI   1080
SISIKSRKGD PKIIQQDDLK LKNYSQFYSI ISDRRLPSLL DLINSRVIKR TDIEDELSNY   1140
DKSHPHVLKS VFEFEKHYFD THPIPSDTAY MALPDTGEML KESNLTAEKQ KEVRKIRNSF   1200
AHLSYPSRNI TGAASTELPK KAEIISKNLI EHLSNAEIKT GGGPGGGAAA GSGSPKKKRK   1260
VGSGSKRPAA TKKAGQAKKK K                                            1281

SEQ ID NO: 24          moltype = AA  length = 1361
FEATURE                Location/Qualifiers
source                 1..1361
                       mol_type = protein
                       organism = synthetic construct
SEQUENCE: 24
MGSSHHHHHH SSGLVPRGSH MASMTGGQQM GRGSPAAKKK KLDGSVDMYH LSDANHGKHI    60
AGTYYEMAMG NFIHTLSHML VRAGIKVNKL EDNYSIEREI MNLTAPGAYD AQRAALSRLL   120
YRHFPFFGPI MADHTDHILS SKRKKVQSAS DDGNLDLGQE LKDEVAGASA CQMIRYLATI   180
AGALVYYRNM YSHKNHYDNA QDIAAQQERE QKLALWLDVV FRGARDILLT RKSHPQPDTD   240
FLTQNGTINY YIEKNGKSAY NPNFYFKPGL KTDNGWVMTD FGKFFFCSLF LRRADAERFA   300
AETDLYVGSP FKITAQERAR LQEAENKRAA DEQARASSAG FPHIVNPRTI GPSESPQNNI   360
IREMLNMHRA RIPRERRIDA DMSEGILAMD IMNELRRCPL SLYNTLSPEA KASFEKTGVT   420
PEGGIVSNLL VRHSDRYPEL ALRAIDQMEL LPTIRFHVRL GSLRFRFYEK KLIDGSHTLR   480
TVQKAVNGFG RWQEVEPRRV EKYTAIQARC QNDKGIDQFL PDSPTTTPYI TDWRTTYNIH   540
ANRIGLAWNL PQMSDGIYLP NLDTDKGDNL HRKALIDMPA PMCYLSIFDL PALLFYCHIY   600
THYHGTKYHL PSAESIIQAK YDALHKFFSF AAAQNHSAEQ LREKQLELNL ADNEIPDKLR   660
CMMQTKPFFK NGRQQLSPLG YPIMKNWIGV AEQRKHAAQV LRDVANEAAD RLASFEKKHQ   720
RVVVGGRDNR YGRRGHADIR HGSLARYLAT SMVRWQPALD QPGGDKLTSA NHRALAGFLS   780
EYGLHGSNIN KLRNVLKEAG LIEGSHPHPF LAHVLESAPA NIEALYVAYL KHEQSHATAL   840
KNKFTDRNGI VQPSEVPAFV RFNSSRWRND SATTARRYLQ TPPAPGSSDS AEHNAPIMLP   900
DGLFTTHIMT LLNKVLGQND RVPEEDYLRH DLPRIASIIN PNGKTYGAAY IIRAWFDQVE   960
NQDVQPFYDL PRFYREISLL APRRKPNQEL IRDYFSEEQI AQKIQTVPKK QRSEKVGHTI  1020
DTEKDIRRYR LQDITLYLTL LDMLTLMLSR NEAERTDRQM KSSTAERVSN MRLVDFDHSF  1080
DFDLLGSTSG EAAYSYLHQR SGITISMPAL SLRSYGSIPR VLADSRFETL MDALNRQGVT  1140
HVNFGDITSE LALYDTLRSH FLLQAHNVEQ DAFSAKRGVL ENHTSPFFYR SGNLQLDDQG  1200
NITNPSTDAI RNHYGELIKI LDRYSLKIDK KTKDGKSQDI LLRDLMAELR NAAAHNRYPK  1260
ADFFFRQFDH FLNTCKPTDS NLTAPNYIRT VLEFLKSIVD NNFTPLLHEE SPENESKSET  1320
GGGPGGGAAA GSGSPKKKRK VGSGSKRPAA TKKAGQAKKK K                      1361

SEQ ID NO: 25          moltype = AA  length = 1272
FEATURE                Location/Qualifiers
source                 1..1272
                       mol_type = protein
                       organism = synthetic construct
SEQUENCE: 25
MGSSHHHHHH SSGLVPRGSH MASMTGGQQM GRGSPAAKKK KLDGSVDMPM STIIDKYMPL    60
NDWNRIESLI GELRAISGAM NCAVRRAVFE NIKKAKLQIK FNDQYPESIF TDKNGSIPIV   120
GTTEANNPEN GGNNECEQSN NYLSIDYLPR VTQEDKKSVY GTYFEMAFHN FFITLHHIYS   180
LIFGEDIMEV AKSEYSQTQT DSFQDDFANK YTVWNPLFTR LRRAKAEQKE RFEELAIKHF   240
PFLKALDALK GENRVSKVDA LERFSVVVRE LRNIYLHYCI IPSDKQKKEY SDNISFIFDL   300
MDLLFTGAKR EVKTRFALSD DQMSCADKYE PNSDRSLRDI HGKTLRIVPK KNFRYHLYKV   360
GDDAKIISPF GLVFLASLFL EKKYAKILSD KAHVVRLNDK GVICEMISVY RIRLHINRLS   420
ISKSTDTLAL DIINELQRCP KKVFELLPPV AQQRFRVKPE SSHAPEVLMV RHNDRFVHLL   480
LKYIDDAKLF EHIRFQVSLG RYFFRFYDKI CIDTSSEKRV RSICKDVHGF GRISEIEELR   540
REKWKDILRE YDEVHANTAD EKPYITDHRA NYLIGNNKVG IYLLKEGDEQ CIMPELLPNG   600
ARNHAPTCWL STYELPALAF LLHLYNADGA RVEEIIEKQV AGYRRLFADV RDGSVAPVAS   660
VEELDELLKG YGDMQACNLP RKMLDYLLMK DVNAHDLFRK WAEAELQQMI EQTDRLSQRI   720
DDDIKAAANM RQNKFGKKSF VAVKPGKIAD FLAHDMMLFQ PCTEDNSNKL TGLNFRILQS   780
VMAVYNGDFD ELSRVLRNAH IIGNATDEMC NPIVMAVCHK SMEFGNIVDF YKAYLRERRI   840
YLERCLRHGD FESLGFLHAS QIRWQERSKE YYRALAARYL VDEYGGTESA KAIELPRGLF   900
EPYIRKELSE MNAMKSLACN SDYNVSYLIY GYFKRVMSDD AQPFYDEKKC YRLFNVLYRK   960
SPHDSPVYRN TAEIRDMLMQ NSPNSIRKDI ESYLSNTIIA DRAKEKERCT ALLREMKKCE  1020
TELKRYKIQD MLLFLIAKRI LSDLPAAHDS AVQMQAISRI LSEKISLSVK            1080
VVSKNGYIKK LTQHNLKLKN YSQFYAILSD RRLPSLLDLV RSNYINRNDI EAELDNYDKV  1140
HPEVMKAIIG LEKKHFEKHG FDDSGIVPDL SSILAETTMP ADKQYEVRKI RNSFAHSHYP  1200
GYHVANAGIT ELPKKAETIF NTLKSSLSDE TGGGPGGGAA AGSGSPKKKR KVGSGSKRPA  1260
ATKKAGQAKK KK                                                     1272

SEQ ID NO: 26          moltype = AA  length = 1279
FEATURE                Location/Qualifiers
source                 1..1279
                       mol_type = protein
                       organism = synthetic construct
SEQUENCE: 26
MGSSHHHHHH SSGLVPRGSH MASMTGGQQM GRGSPAAKKK KLDGSVDMET TINNRIGKGE    60
YYTEESKEFL AAYFNQAIHN VFIVLNHIAK RFGMDELSSD EELKNWLIGR QREKKRNAID   120
RQRFLELIDR HFPFLRIANA DKKDAKREND LEDNLALLIT LLNDLTERRN KYSHAITHAS   180
IESNDRELVW RLYSIYDANI NLVKRDYFES NVHTEINEDP YEKQVEHLRR FCMNNDRTKV   240
DEKGKKKPAM PNPRFRTPFL NAETNQLSIY GLVFFVSLFL EKKYAIQMQK NVYGLKDARD   300
```

```
TKFKMTNEVF CRSRIIMPRV RLHSDKSTDA LVLDMLNELA KAPEVLFDQL TDPFKEKFYI   360
ESIDSLEESD IITPVRAIRK QNRFMYFALR YLDESNAFSK LRFQIDLGNY HYHLYESKIN   420
DQTESRHLTR KLFGFGKLIA FEQEFAPEEW KMKSKDLDYY EGATQPFIAK TYPHYHLEEN   480
KIGILFNGQA EVQWPHLDVE EHESFPKYKR RANEKADAFL SGNELLAAAF CHHLYASIGK   540
PNTVEKIIRD KYHALRQLFS DLKSGNLQNL LGDNTSNEAI SQLLFEKYRL TLSEVPVRLH   600
AFLSGQEQAD TKAIARGKLE LMAQQNKKRI ERFDAMKKAV VKVGKAQYRT LRSGDIGDWL   660
VRDFMRFQPI GYKRNQAGKQ EPDLKSKANP KKYQLIQKSL ALYEQEKNNL LGLFKSCNLL   720
SSENEHPFLN EVVQSMPATW QDFYERYLHA RSRFLEKCIE KGIKKNSYQA CYSFLKIKPQ   780
LKDKEKLYQG WDAQMNLPTN MFIDAIHDWF RQTHHESLRT WFTQQEKPHQ LIGLIRKYIE   840
LAHTDQIQGF YDMFPLRYDF YKKEFPNGLV LHERINKQKQ IWEAQLIQTK KRLEDAASKL   900
KKVKQQVESL PDQELRFRNE TEAMVYFTKL FDSSIVKNAI LKLQRDQKAL RVNTIGEKII   960
KIYTAKYDAI HQEVRDFKSM LTTEKMIRRV KAEDCVTLFM LTDLMNQSQI TIGQEQRTIK  1020
LSDIQPMGET QIQGILDAVQ VLEQKLDFFS SDEQGKISQV KLGEWTIFST DTKVKKQGNF  1080
KQLLKDRRLN NLAHYILPDI AGGAIRVRRN LLEMELDQYD RNRIPIIKLM YELEYAIYKV  1140
DPFSVELKYK KFSQCLREYA QKAVLNVEQV EHLNVLIAIR NAIMHNQYPN RDHLKAIVPF  1200
TVSEYAPVQE GLTIARQLLA CAQVSVNIIL STISKFETGG GPGGGAAAGS GSPKKKRKVG  1260
SGSKRPAATK KAGQAKKKK                                              1279

SEQ ID NO: 27           moltype = AA  length = 1247
FEATURE                 Location/Qualifiers
source                  1..1247
                        mol_type = protein
                        organism = synthetic construct
SEQUENCE: 27
MGSSHHHHHH SSGLVPRGSH MASMTGGQQM GRGSPAAKKK KLDGSVDMKE KIKNKSSIIR   60
IIMSNYDDKG LKEFKVLYNK QGGVDTFTCK TDIVDGTIIF LEIEKHLRDF GDDFSWDISS   120
DGKSVEITKL INGKETRKYK VSIKNSSTKD KKNLVELEVE DLKESAIDRR RTKSSTKRVL   180
LSKDVMERYA EIAFSKKERW EEIDSQKIYK VKRFLDYRSN MLIYFQFIND FLTKGIPDEL   240
DKNGEIKQLE LWKLIDDDET ISDKNLNQVS KNLYTYISQE IKDSQTRAEN NREKNKEKEH   300
FKEFYAFNDI SEESIREDVK KFIYLYANLR HNLMHYNYSF FENLFEGKDL VIEKTKSLLS   360
STLDLNIFKE LSNIVELREE NKTNYLDDET TIRVLGKEKK AKTLHKIYSI LCSRKNGFNK   420
FINSFFSTDG IEEEFLKSEI KKDFLERLNW VEKSLIEKIN NPPSDTKLKY KNDKTIENMT   480
KEKEEKLELI SLLNPQVSDY KTENFTPYYW DIHQSPSYKK LYNDRKVLVS ELSKLIAIGI   540
NSDTKKRITD LNAELLKIKI KMEKITKLNS KIRLQYKLQM AFGFIYANYS KVYKEKRVLN   600
INGFVQNFDP TKLNKEKELE SRLIYLKAPY NIFEDNKSLD FNMKIVENIP VSEKSIFRIK   660
PENNLSKFYI LSYLLLPVEL RGDFLGYVKH HYYGIKNVDF EEIPDIKEDK PNENSDSFFH   720
NLRLFEKNSK KFELIKYRLV EFGNLKDHLP RIYEKFGIKP DVLEYIENSG NKDSKLFDRN   780
ILLPIMKYYQ HIFKLLNDIE VHALLRFSEK DSISLDESIK ECSKGKFLNF GKLLFLSRYG   840
LEAKKDNKFK DIFNRENGLS ITKDDAKTER KKYFEIFETR NKIAHLNYKQ LFHDLLFDSN   900
ININKELEGI IQETKTIGLN AQTLGYNFLN DFYMRKEMFI SNQKKSSMTL INNPLSKDKD   960
TKEIGLLKLY GLSKSQPKDL ILAKYKELMN LIEKTEDSIL KKKDFLPVKE VSITVKKSTP  1020
NKKGIMVELP EILQIKDLNE MDLLAYASNI RGKLHKDSSD LFGIYKKLTI KELKKKLINL  1080
FIKGEKRYLN LELVNKTGYM AIYESTGLYP KSYEILNHEI SFSEISMKNW YEHDFKPIFQ  1140
IDGSLPNNTD YKNGVFIYTS PYEFRDKELM KKQRTVHKRD IEKTFYNEND MDYTGIYNQK  1200
IKALYTGGGP GGGAAAGSGS PKKKRKVGSG SKRPAATKKA GQAKKKK             1247

SEQ ID NO: 28           moltype = AA  length = 1020
FEATURE                 Location/Qualifiers
source                  1..1020
                        mol_type = protein
                        organism = synthetic construct
SEQUENCE: 28
MGSSHHHHHH SSGLVPRGSH MASMTGGQQM GRGSPAAKKK KLDGSVDMMG NKKSVAKANG   60
LKSTFVLGEN TAYMTSFGRG NAAQPEKHIR DATVTDIQHT FRAKTDGGRT VHIEGRVGAS   120
DVLLPDAANQ LHAKDAVEQM YFGKAFSDNI HIQIAYNIMD IKKIFGVYAN IIVHTVNNLC   180
CDGDKQDDFL GMFKTQNRYQ VAAWAHKIVS LHLVKNELRG GGFFMDQEVW RAHVRTDFKS   240
LNLAVNAFMK KYPQKYPYWS VKIVSDFIVQ EMGIKNKVIL EKAAESYAEF ETVAKRLEKS   300
AYYFSDIFAG KDGKFDEQKA FDLLRVLGMM RQEAFHEKNS SASWLYNLDA EADEDIKAAL   360
RTVVDTKVNG INTNFAKQNK VNLLVLQEIY PQKSKADLVR YGFDFSVRKA FKNLGFSVKT   420
LRETMCAFDA ASVITDKQYD TVRGKLYSLF DFVIYNYCLE NEAVCNAFVE ELRANLDPEN   480
KTALYQTLAE KVWAEIGDIV LQRILPQMHA KKIQERSKET DAETVEMQGY VQAPKDLSLF   540
SKAVYCISMF LDGKEINSFL SALINKFENI SSLCAVLAYN GLEPEFVAPF TFFADSQAIA   600
EDLRYIKSIA RMSKGKKATK DSPVTVKEMQ YFDAAAVLGE TDTEKVKAAF HLGDKSASTA   660
DKAFRNFVVN NVINSNRFVY VVRFINPKNA REIMQNRALI AFVLKDIPQS QLVRYCGTAG   720
IACNADEPNT EAMVNALADM LLQVRFDAFS NVQQKVKADS AEAVQKEKYK AIIGLYLTVL   780
YLLVKTLVKI NMNYAIAFGI LERDCQIMNQ KHGKNPKRDR DAFYMREQQN KQYVYNARAI   840
TELFIENGWL NKRVQKSVEN NAALYSDEAF YKYRNLVAHL NVISALPKYA KNITKVKSLF   900
DVYHILFLS LCEDKYSNLP EAVTKSLCKN GKTMLENARE YQTVCKDFLY GLNTPFAYNA   960
ARYINLSNRE KFLAGFGKTG GGPGGGAAAG SGSPKKKRKV GSGSKRPAAT KKAGQAKKKK  1020

SEQ ID NO: 29           moltype = DNA  length = 720
FEATURE                 Location/Qualifiers
source                  1..720
                        mol_type = other DNA
                        organism = synthetic construct
SEQUENCE: 29
atggtgagca aggcgagga gctgttcacc ggggtggtgc ccatcctggt cgagctggac   60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
```

-continued

```
ctcgtgacca ccctgaccta cggcgtgcag tgcttcagcc gctacccga ccacatgaag  240
cagcacgact tcttcaagtc cgccatgccc gaaggctacg tccaggagcg caccatcttc  300
ttcaaggacg acggcaacta caagacccgc gccgaggtga agttcgaggg cgacaccctg  360
gtgaaccgca tcgagctgaa gggcatcgac ttcaaggagg acggcaacat cctggggcac  420
aagctggagt acaactacaa cagccacaac gtctatatca tggccgacaa gcagaagaac  480
ggcatcaagg tgaacttcaa gatccgccac aacatcgagg acggcagcgt gcagctcgcc  540
gaccactacc agcagaacac ccccatcggc gacggccccg tgctgctgcc cgacaaccac  600
tacctgagca cccagtccgc cctgagcaaa gacccccaacg agaagcgcga tcacatggtc  660
ctgctggagt tcgtgaccgc cgccgggatc actctcggca tggacgagct gtacaagtaa  720
```

SEQ ID NO: 30                     moltype = DNA   length = 30
FEATURE                          Location/Qualifiers
source                           1..30
                                 mol_type = other DNA
                                 organism = synthetic construct
SEQUENCE: 30
```
tgccgttctt ctgcttgtcg gccatgatat                                    30
```

SEQ ID NO: 31                     moltype = DNA   length = 4828
FEATURE                          Location/Qualifiers
source                           1..4828
                                 mol_type = other DNA
                                 organism = synthetic construct
SEQUENCE: 31
```
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact  120
aggggttcct gcggcctcta gactcgaggc gttgacattg attattgact agttattaat  180
agtaatcaat tacggggtca ttagttcata gcccatatat ggagttccgc gttacataac  240
ttacggtaaa tggcccgcct ggctgaccgc ccaacgaccc ccgcccattg acgtcaataa  300
tgacgtatgt tcccatagta acgccaatag ggactttcca ttgacgtcaa tgggtggagt  360
atttacggta aactgcccac ttggcagtac atcaagtgta tcatatgcca agtacgcccc  420
ctattgacgt caatgacggt aaatggcccg cctggcatta tgcccagtac atgaccttat  480
gggactttcc tacttggcag tacatctacg tattagtcat cgctattacc atggtgatgc  540
ggttttggca gtacatcaat gggcgtggat agcggtttga ctcacgggga tttccaagtc  600
tccaccccat tgacgtcaat gggagtttgt tttggcacca aaatcaacgg gactttccaa  660
aatgtcgtaa caactccgcc ccattgacgc aaatgggcgg taggcgtgta cggtgggagg  720
tctatataag cagagctctc tggctaacta ccggtgccac catggtgagc aagggcgagg  780
agctgttcac cggggtggtg cccatcctgg tcgagctgga cggcgacgta aacggccaca  840
agttcagcgt gtccggcgag ggcgagggcg atgccaccta cggcaagctg accctgaagt  900
tcatctgcac caccggcaag ctgcccgtgc cctggcccac cctcgtgacc accctgacct  960
acggcgtgca gtgcttcagc cgctaccccg accacatgaa gcagcacgac ttcttcaagt 1020
ccgccatgcc cgaaggctac gtccaggagc gcaccatctt cttcaaggac gacggcaact 1080
acaagacccg cgccgaggtg aagttcgagg gcgacaccct ggtgaaccgc atcgagctga 1140
agggcatcga cttcaaggag gacggcaaca tcctggggca caagctggag tacaactaca 1200
acagccacaa cgtctatatc atggccgaca gcagaagaa cggcatcaag gtgaacttca 1260
agatccgcca acatcgag gacggcagcg tgcagctcgc cgaccactac cagcagaaca 1320
cccccatcgg cgacggcccc gtgctgctgc ccgacaacca ctacctgagc acccagtccg 1380
ccctgagcaa agaccccaac gagaagcgcg atcacatggt cctgctggag ttcgtgaccg 1440
ccgccgggat cactctcggc atggacgagc tgtacaagta aagcggccga attcctagag 1500
ctcgctgatc agcctcgact gtgccttcta gttgccagcc atctgttgtt tgcccctccc 1560
ccgtgcctc cttgacctg gaaggtgcca ctcccactgt cctttcctaa taaaatgagg 1620
aaattgcatc gcattgtctg agtaggtgtc attctattct ggggggtggg gtggggcagg 1680
acagcaaggg ggaggattgg gaagagaata gcaggcatgc tggggaggta ccgagggcct 1740
atttcccatg attccttcat atttgcatat acgatacaag gctgttagag agataattgg 1800
aattaatttg actgtaaaca caaagatatt agtacaaaat agtgctttaa gaaagtaata 1860
atttcttggg tagtttgcag ttttaaaatt atgttttaaa atggactatc atatgcttac 1920
cgtaacttga agtatttcg atttcttggc tttatatatc ttgtggaaag gacgaaacac 1980
cggagaccac ggcaggtctc agttttagta ctctggaaac agaatctact aaaacaaggc 2040
aaaatgccgt gtttatctcg tcaacttgtt ggcgagattt ttgctgccgg aggaacccct 2100
agtgatggag ttggccactc cctctctgcg cgctcgctcg ctcactgagg ccgggcgacc 2160
aaaggtcgcc cgacgcccgg gctttgcccg ggcggcctca gtgagcgagc gagcgcgcag 2220
ctgcctgcag gggcgcctga tgcggtattt tctccttacg catctgtgcg gtatttcaca 2280
ccgcatacgt caaagcaacc atagtacgcg ccctgtagcg cgcattaag cgcggcgggt 2340
gtggtggtta cgcgcagcgt gaccgctaca cttgccagcg ccctagcgcc cgctcctttc 2400
gctttcttcc cttcctttct cgccacgttc gccggctttc cccgtcaagc tctaaatcgg 2460
gggctccctt tagggttccg atttagtgct ttacggcacc tcgaccccaa aaaacttgat 2520
ttgggtgatg gttcacgtag tgggccatcg ccctgataga cggttttttcg ccctttgacg 2580
ttggagtcca cgttctttaa tagtggactc ttgttccaaa ctggaacaac actcaaccct 2640
atctcgggct attcttttga tttataaggg attttgccga tttcggccta ttggttaaaa 2700
aatgagctga tttaacaaaa atttaacgcg aatttttaaca aaatattaac gtttacaatt 2760
ttatggtgca ctctcagtac aatctgctct gatgccgcat agttaagcca gccccgacac 2820
ccgccaacac ccgctgacgc gccctgacgg gcttgtctgc tcccggcatc cgcttacaga 2880
caagctgtga ccgtctccgg gagctgcatg tgtcagaggt tttcaccgtc atcaccgaaa 2940
cgcgcgagac gaaagggcct cgtgatacgc ctatttttat aggttaatgt catgataata 3000
atggtttctt agacgtcagg tggcactttt cggggaaatg tgcgcggaac ccctatttgt 3060
ttatttttct aaatacattc aaatatgtat ccgctcatga caataaacc ctgataaatg 3120
cttcaataat attgaaaaag gaagagtatg agtattcaac atttccgtgt cgcccttatt 3180
cccttttttg cggcattttg ccttcctgtt tttgctcacc cagaaacgct ggtgaaagta 3240
aaagatgctg aagatcagtt gggtgcacga gtgggttaca tcgaactgga tctcaacagc 3300
```

-continued

```
ggtaagatcc ttgagagttt tcgccccgaa gaacgttttc caatgatgag cacttttaaa   3360
gttctgctat gtggcgcggt attatccgt attgacgccg ggcaagagca actcggtcgc    3420
cgcatacact attctcagaa tgacttggtt gagtactcac cagtcacaga aaagcatctt   3480
acggatggca tgacagtaag agaattatgc agtgctgcca taaccatgag tgataacact   3540
gcggccaact tacttctgac aacgatcgga ggaccgaagg agctaaccgc ttttttgcac   3600
aacatggggg atcatgtaac tcgccttgat cgttgggaac cggagctgaa tgaagccata   3660
ccaaacgacg agcgtgacac cacgatgcct gtagcaatgg caacaacgtt gcgcaaacta   3720
ttaactggcg aactacttac tctagcttcc cggcaacaat aatagactg gatggaggcg     3780
gataaagttg caggaccact tctgcgctcg gcccttccgg ctggctggtt tattgctgat    3840
aaatctggag ccggtgagcg tggaagccgc ggtatcattg cagcactggg gccagatggt   3900
aagccctccc gtatcgtagt tatctcacacg acggggagtc aggcaactat ggatgaacga   3960
aatagacaga tcgctgagat aggtgcctca ctgattaagc attggtaact gtcagaccaa   4020
gtttactcat atatacttta gattgattta aaacttcatt tttaatttaa aaggatctag   4080
gtgaagatcc ttttgataa tctcatgacc aaaatccctt aacgtgagtt ttcgttccac   4140
tgagcgtcag accccgtaga aaagatcaaa ggatcttctt gagatccttt ttttctgcgc   4200
gtaatctgct gcttgcaaac aaaaaaacca ccgctaccag cggtggtttg tttgccggat   4260
caagagctac caactctttt tccgaaggta actggcttca gcagagcgca gataccaaat   4320
actgtccttc tagtgtagcc gtagttaggc caccacttca agaactctgt agcaccgcct   4380
acatacctcg ctctgctaat cctgttacca gtggctgctg ccagtggcga taagtcgtgt   4440
cttaccgggt tggactcaag acgatagtta ccggataagg cgcagcggtc gggctgaacg   4500
gggggttcgt gcacacagcc cagcttggag cgaacgacct acaccgaact gagataccta   4560
cagcgtgagc tatgagaaag cgccacgctt cccgaagggg aaaggcggac aggtatccgg   4620
gtaagcggca gggtcggaac aggagagcgc acgagggagc ttccaggggg aaacgcctgg   4680
tatctttata gtcctgtcgg gtttcgccac ctctgacttg agcgtcgatt tttgtgatgc   4740
tcgtcagggg ggcggagcct atggaaaaac gccagcaacg cggcctttt acggttcctg    4800
gccttttgct ggccttttgc tcacatgt                                       4828
```

```
SEQ ID NO: 32        moltype = DNA  length = 7701
FEATURE              Location/Qualifiers
source               1..7701
                     mol_type = other DNA
                     organism = synthetic construct
SEQUENCE: 32
cctgcaggca gctgcgcgct cgctcgctca ctgaggccgc ccgggcgtcg ggcgaccttt   60
ggtcgcccgg cctcagtgag cgagcgagcg cgcagagagg gagtgagcaa ctccatcact   120
aggggttcct cgcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc ccgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggtttggat agcggtttga ctcacgggga tttccaagtc   600
tccaccccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catgccggca gctaagaaaa   780
agaaactgga tggcagcgtc gacatgacca tcctggagaa gtacatgccc ctgaacgaga   840
tgggcaagat caagagcctg gtggacgagc tgaaggcgt ccccggcgcc atgaacgcca   900
ccctgagaca ggagatcttc cagaacatca agaaaccaa gctgcaggtg aagttcctgg   960
aggagtaccc cgagacactg ttcaccgaca gcggcaacct gatccccatc atcggcaaca   1020
acgacaacag cagcagcggc accccagca agcaggaggt gagcgacatc gacgccaacc   1080
aggccagcag aatcaactac ctgccccacg agacaatggg cgagatcaag agcgtgtacg   1140
gcacctacat cgagatggcc ttccacaact tctacctgac catgcaccac atctacgccg   1200
tggtgttcgg cgaggacatc atggaggagg ccaagaagga gttcgacaag aacaacacca   1260
acagcaccaa gtacttcacc ttcgacttcg caacgagga aacatctgga aagcccatgt   1320
tcgacagagc cgagagagcc aagcccgagc agaaggagca cttcgagaag ctggtggtga   1380
agcacttccc cttcctgaag gccatcgacg ccctggagga cagaaagaga aagaccaaga   1440
tccaggccct gtgcgtgttc agcctggtgc tgagagagct gagaaacgtg tacagccact   1500
acctgttcta cccccttcaag aaccaggtgg acaagtacaa ggagaacatc cccttcgtgc   1560
tggacatgat ggagatcctg tacaccggcg cccagagaga ggtgaagggc agattcggct   1620
tcgacgacaa gaagatgcag tgcgccaaga gtacgagag aaacaaggac cacagccaga   1680
gagatcacca gggcaagatc atcaaggccg tgcccaagaa gaacttcaga tacaacctgt   1740
acaagaagga ggacagcgag gccatcatca ccccccttcgg cctggtgttc ctgaccagcc   1800
tgttcctgga gaagaagtac gccaagatcc tgagcgacaa gacccactgc atcaagtaca   1860
ccgaccagga ggtgctgtgc gagatcatca gcgtgtacag aatcagactg cacatccaga   1920
agctgagcgt gaccaaggac accgacgccc tggccctgga catcatcaac gagctgcaga   1980
gatgccccaa gagactgttc gagatgctga gccccgacga ccagcagaag ttcagaatca   2040
agcccaccga cagccagtac gccgacgacg tgctgatgat cagacaccag gacagattcg   2100
cccacctgct gctgaagtac atcgacgacg cccacctgtt caactgcatc agattccagg   2160
tgagcctggg cagatacttc ttcagattct acgacaagag ctgcatcgac agcaccggcg   2220
acaagagagt gagaagcatc agcaagaacg tgaacggctt cggcagaatc accgacatcg   2280
aggactacaa aaaggaggtg tacggcgaca tgatcagaga gtacgaggac gtgcacgcca   2340
acaccagcat ggagaagccc tacatcaccg accaccacgc caagtacctg atcagcaaca   2400
acagaatcgg cctgtacatc agaaaggagg aggacaccgc ctgcgtgctg cccgagctga   2460
ccccccgacgg cgccagaaac ttcgcccca cctgctggct gagcatctac gagctgcccg   2520
ccctggcctt cctgctgcac ctgtacaacg cgacggcag cagagtggag gagatcatcc   2580
agaccaaggt ggccaactac cagagactgt cgccgacgt gagagacggc aaggtgtgcc   2640
ccgtgaagga cgaggccgag ctgaccacca tcctgcagac ctacgccaac atcgagccca   2700
gccagctgcc cagaaagctg ctggactacc tgctgaagaa ggagatctgc gcccaggacc   2760
```

-continued

```
tgttcaacac ctgggcccag agcaagatcc agagaatgat cgcccagacc gacagcctgc  2820
tgcagcacct ggagaaggac ctgcaggccg tgagcgacct gaagcagaac aagttcggca  2880
agaaggcctt cgtggccatc aagcccggcc acatcgccga cttcctggcc cacgacatga  2940
tgttcttcca gcccagcatg aaggactgca acaacaagct gaccggcctg aacttcagaa  3000
tcctgcagag cagcatggcc gtgtacgacg gcaacttcga cgagctgagc agaatcatga  3060
gaagcgccca catcatcggc aacgccaacg acgcctgctg caaccccatc gtgatggccg  3120
tgtgcagaaa gcacaagggc ttcagcaaca tcatcagatt ctaccaggcc tacctgaagg  3180
agagaaaggc ctacctgcag cagtgcgcca acgagagaca ctacgacagc ctgagcttcc  3240
tgcacgccag ccagaacaag tggagagaga gaacccaggc ctactacaga agcctggccg  3300
ccaagtacct ggccgagaac tacgacggcg tggacaccac caagagcatc gagctgccca  3360
gaggcctgtt cgagacatac atcagacagg agctgagcga gatcggcagc accaagagca  3420
tggccggcga cgccaccaag aacaccagct acctgatcta cggctacttc agacaggtga  3480
tgagcgacga cgcccagacc ttctacgaca ccagaagatg ctaccagctg ttcgacgtgc  3540
tgtacagaaa gagccccaga gacaaccaca gctactacag caccgcccag atcagagaga  3600
tgctgatgag aagccacagc aagagcatca gaaaggacat cgacaactac atcagccaga  3660
ccaccgccgc cgagagaacc aaggagaagg agagatgcga cgccctgctg agaaagatca  3720
aggacaccga gacagagctg aaggtgtaca agatccagga catcctgctg ttcctgatcg  3780
ccaagagact gctgctggac agaaaggtgg agaacgacag cgccgtgcag atgaacgcca  3840
tcaaccagat cagactgaga aacatcgccg acgcgaacac cctgagccag aagatcccca  3900
tcagcatcag catcaagagc agaaagggcg accccaagat catccagcag gacgacctga  3960
agctgaagaa ctacagccag ttctacagca tcatcagcga cagaagattg cccagcctgc  4020
tggacctgat caacagcagg gtgatcaaga gaaccgacat cgaggacgag ctgagcaact  4080
acgacaagag ccacccccac gtgctgaaga gcgtgttcga gttcgagaag cactacttcg  4140
acacccaccc catccccagc gacaccgcct acatggccct gcccgacacc ggcgagatgc  4200
tgaaggagag caacctgacc gccgagaagc agaaggaggt gagaaagatc agaaacagct  4260
tcgcccacct gagctacccc agcagaaaca tcaccggcgc cgccgacacc gagctgccca  4320
agaaggccga gatcatcagc aagaacctga tcgagcacct gagcaacgcc gagatcaaga  4380
caggcggcgg ccccggcggc ggcgccgccg ccggcagcgg cagccctaag aaaaaacgaa  4440
aagttggcag cggaagcaaa aggccggcgg ccacgaaaaa ggccggccag gcaaaaaaga  4500
aaaagctcga gtacccatac gatgttccag attacgcttg agaattcccc ttgagcatct  4560
gacttctggc taataaagga aatttatttt cattgcaata gtgtgttgga atttttgtg   4620
tctctcaggt accgagggcc tatttcccat gattccttca tatttgcata tacgatacaa  4680
ggctgttaga gagataattg gaattaattt gactgtaaac acaagatat tagtacaaaa   4740
tacgtgacgt agaaagtaat aatttcttgg gtagtttgca gttttaaaat tatgttttaa  4800
aatggactat catatgctta ccgtaacttg aaagtatttc gatttcttgg ctttatatat  4860
cttgtggaaa ggacgaaaca ccgtgccgtt cttctgcttg tcggccatga tatgtgtag   4920
atgacctcgt tttggagggg aaacacaact ttttgcggc cgcaggaacc cctagtgatg   4980
gagttggcca ctccctctct gcgcgctcgc tcgctcactg aggccgggcg accaaaggtc  5040
gcccgacgcc cgggctttgc ccgggcggcc tcagtgagcg agcgagcgcg cagctgcctg  5100
caggggcgcc tgatgcggta ttttctcctt acgcatctgt gcggtatttc acaccgcata  5160
cgtcaaagca accatagtac gcgccctgta gcggcgcatt aagcgcggcg ggtgtggtgg  5220
ttacgcgcag cgtgaccgct acacttgcca gcgccttagc gcccgctcct ttcgctttct  5280
tcccttcctt tctcgccacg ttcgccggct ttccccgtca agctctaaat cggggggtcc  5340
ctttagggtt ccgatttagt gctttacggc acctcgaccc caaaaaactt gatttgggtg  5400
atggttcacg tagtgggcca tcgccctgat agacggtttt tcgccctttg acgttggagt  5460
ccacgttctt taatagtgga ctcttgttcc aaactggaac aacactcaac tctatctcgg  5520
gctattcttt tgatttataa gggattttgc cgatttcggt ctattggtta aaaaatgagc  5580
tgatttaaca aaaatttaac gcgaatttta acaaaatatt aacgtttaca ttttatggt   5640
gcactctcag tacaatctgc tctgatgccg catagttaag ccagccccga cacccgccaa  5700
cacccgctga cgcgccctga cgggcttgtc tgctcccggc atccgcttac agacaagctg  5760
tgaccgtctc cgggagctgc atgtgtcaga ggttttcacc gtcatcaccg aaacgcgcga  5820
gacgaaaggg cctcgtgata cgcctatttt tataggttaa tgtcatgata ataatggttt  5880
cttagacgtc aggtggcact tttcgggaa atgtgcgcgg aacccctatt tgtttatttt   5940
tctaaataca ttcaaatatg tatccgctca tgagacaata accctgataa atgcttcaat  6000
aatattgaaa aaggaagagt atgagtattc aacatttccg tgtcgccctt attccctttt  6060
ttgcggcatt ttgccttcct gttttttgctc acccagaaac gctggtgaaa gtaaaagatg  6120
ctgaagatca gttgggtgca cgagtgggtt acatcgaact ggatctcaac agcggtaaga  6180
tccttgagag ttttcgcccc gaagaacgtt ttccaatgat gagcactttt aaagttctgc  6240
tatgtggcgc ggtattatcc cgtattgacg ccgggcaaga gcaactcggt cgccgcatac  6300
actattctca gaatgacttg gttgagtact caccagtcac agaaaagcat cttacggatg  6360
gcatgacagt aagagaatta tgcagtgctg ccataaccat gagtgataac actgcggcca  6420
acttacttct gacaacgatc ggaggaccga aggagctaac cgcttttttg cacaacatgg  6480
gggatcatgt aactcgcctt gatcgttggg aaccggagct gaatgaagcc ataccaaacg  6540
acgagcgtga ccacgatg cctgtagcaa tggcaacaac gttgcgcaaa ctattaactg   6600
gcgaactact tactctagct tcccggcaac aattaataga ctggatggag gcggataaag  6660
ttgcaggacc acttctgcgc tcggcccttc cggctggctg gtttattgct gataaatctg  6720
gagccggtga gcgtggaagc cgcggtatca ttgcagcact ggggccagat ggtaagccct  6780
cccgtatcgt agttatctac acgacgggga gtcaggcaac tatggatgaa cgaaatagac  6840
agatcgctga gataggtgcc tcactgatta agcattggta actgtcagac caagtttact  6900
catatatact ttagattgat ttaaaacttc atttttaatt taaaaggatc taggtgaaga  6960
tcctttttga taatctcatg accaaaatcc cttaacgtga gttttcgttc cactgagcgt  7020
cagacccccg agaaaagatc aaaggatctt cttgagatcc tttttttctg cgcgtaatct  7080
gctgcttgca aacaaaaaaa ccaccgctac cagcggtggt ttgtttgccg gatcaagagc  7140
taccaactct ttttccgaag gtaactggct tcagcagagc gcagatacca aatactgttc  7200
ttctagtgta gccgtagtta ggccaccact tcaagaactc tgtagcaccg cctacatacc  7260
tcgctctgct aatcctgtta ccagtggctg ctgccagtgg cgataagtcg tgtcttaccg  7320
ggttggactc aagacgatag ttaccggata aggcgcagcg tcgggctga acggggggt    7380
cgtgcacaca gcccagcttg gagcgaacga cctacaccga actgagatac ctacagcgtg  7440
agctatgaga aagcgccacg cttcccgaag ggagaaaggc ggacaggtat ccggtaagcg  7500
```

```
gcagggtcgg aacaggagag cgcacgaggg agcttccagg gggaaacgcc tggtatcttt   7560
atagtcctgt cgggtttcgc cacctctgac ttgagcgtcg attttttgtga tgctcgtcag   7620
gggggcggag cctatggaaa aacgccagca acgcggcctt tttacggttc ctggcctttt   7680
gctggccttt tgctcacatg t                                             7701
```

SEQ ID NO: 33          moltype = DNA  length = 7941
FEATURE                Location/Qualifiers
source                 1..7941
                       mol_type = other DNA
                       organism = synthetic construct
SEQUENCE: 33

```
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact   120
aggggttcct gcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc ccgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccaccccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catgccggca gctaagaaaa   780
agaaactgga tggcagcgtc gacatgtacc acctgagcga cgccaaccac ggcaagcaca   840
tcgccggcac ctactacgag atggccatgg gcaacttcat ccacaccctg agccacatgc   900
tggtgagagc cggcatcaag gtgaacaagc tggaggacaa ctacagcatc gagagagaga   960
tcatgaacct gaccgccccc ggcgcctacg acgcccagag agccgccctg agcagactgc   1020
tgtacagaca cttcccccttc ttcggcccca tcatggccga ccacaccgac cacatcctga   1080
gcagcagag aaagaaggtg cagagcgcca gcgacgaccg caacctggac ctgggccccg   1140
agctgaagga cgaggtggcc ggcgccagcg cctgccagat gatcagatac ctggccacca   1200
tcgccggcgc cctggtgtac tacagaaaca tgtacagcca caagaaccac tacgacaacg   1260
cccaggacat cgccgcccag caggagagag agcagaagct ggccctgtgg ctggacgtgg   1320
tgttcagagg cgccagagac atcctgctga ccagaaagag ccacccccag cccgacaccg   1380
acttcctgac ccagaacggc accatcaact actacatcga gaagaacggc aagagcgcct   1440
acaaccccaa cttctacttc aagcccggcc tgaaaaccga caacggctgg gtgatgaccg   1500
acttcggcaa gttcttcttc tgcagcctgt tcctgagaag agccgacgcc gagagattcg   1560
ccgccgagac agacctgtac gtgggcagcc ccttcaagat caccgcccag gagagagcca   1620
gactgcagga ggccgagaac aagagagccg ccgacgagcg gccagagcc agcagcgccg   1680
gcttcccccca catcgtgaac cccagaacca tcgcccccag cgagagcccc cagaacaaca   1740
tcatcagaga gatgctgaac atgcacagag ccagaatccc cagagagaga agaatcgacg   1800
ccgacatgag cgagggcatc ctggccatgg acatcatgaa cgagctgaga agatgccccc   1860
tgagcctgta caacaccctg agcccccgagg gcaaggccag cttcgagaaa accgccgtga   1920
cccccgaggg cggcatcgtg agcaacctgc tggtgagaca cagcgacaga taccccccgagc   1980
tggccctgag agccatcgac cagatggagc tgctgcccac catcagattc cacgtgagac   2040
tgggcagcct gagattcaga ttctacgaga agaagctgat cgacggcagc cacacccctga   2100
gaaccgtgca gaaggccgtg aacggcttcg gcagatggca ggaggtggag cccagaaagg   2160
tggagaagta caccgccatc caggccagat gccagaacga caagggcatc gaccagttcc   2220
tgcccgacag ccccaccacc accccctaca tcaccgactg gagaaccacc tacaacatcc   2280
acgccaacag aatcggcctg gcctggaacc tgccccagat gagcgacggc atctacctgc   2340
ccaactggga caccgacaag ggcgacaacc tgcacagaaa ggccctgatc gacatgcccg   2400
cccccatgtg ctacctgagc atcttcgacc tgcccgccct gctgttctac tgccacatct   2460
acacccacta ccacggcacc aagtaccacc tgcccagcgc cgagagcatc atccaggcca   2520
agtacgacgc cctgcacaag ttcttcagct tcgccgccgc ccagaaccac agcgccgagc   2580
agctgagaga gaagcagctg gagctgaacc tggccgacaa cgagatcccc gacaagctga   2640
gatgcatgat gcagaccaag cccttcttca agaacggcag acagcagctg agccccctgc   2700
gctaccccat catgaagaac tggatcggcg tggccgagca gagaaagcac gccgcccagg   2760
tgctgagaga cgtggccaac gaggccgccg acagactggc cagcttcgag aagaagcacc   2820
agagagtggt ggtgggcggc agagacaaca gatacggcag aaggaggccg gccgacatca   2880
gacaccggcag cctggccaga tacctggcca ccagcatggt ggatgagcag cccgccctgg   2940
accagcccgg cggcgacaag ctgaccagcg ccaaccacag agccctggcc ggcttcctga   3000
gcgagtacgg cctgcacggc agcaacatca caagctgag aaacgtgctg aaggaggccg   3060
gcctgatcga gggccagccac ccccaccctc tcctggccca cgtgctggag agcgcccccg   3120
ccaacatcga ggcctgtac gtggccacc tgaagcagca gcagagccac gccaagagcc   3180
tgaagaacaa gttcaccgac agaaaccggca tcgtgcagcc cagcgaggtg cccgccttcg   3240
tgagattcaa cagcagcaga tggagaaacg acagcgccac caccgccaga agatacctgc   3300
agaccccccc cgcccccggc agcagcgaca cgccgagca caacgccccc atcatgctgc   3360
ccgacggcct gttcaccacc cacatcatga ccctgctgaa caagtgctg ggccagaacc   3420
acagagtgcc cgaggaggac tacctgacgac acgacctgcc cgaatcgcc agcatcatca   3480
accccaacgg caagacctac ggcgccgcct acatcatcag agcctggttc gaccaggtgg   3540
agaaccagga cgtgcagccc ttctacgacc tgcccagatt ctacagagag atcagcctgc   3600
tggccccccag aagaaagccc aaccaggagc tgatcagaga ctacttcagc gaggagcaga   3660
tcgcccagaa gatccagacc gtgcccaaga gcagagagaag cgagaggtgg gccaacca   3720
tcgacaccga gaaggacatc agaagatca gactgcagaa catcaccctg tacctgaccc   3780
tgctggacat gctgaccctg atgctgagca gaaacgagc cgagagaacc gacagacaga   3840
tgaagagcag caccgccgag agagtgagca acatggact ggtggacttc gaccacagct   3900
tcgacttcga cctgctgggc agcaccacgc gcgaggccgc ctacagctac ctgcaccaga   3960
gaagcggcat caccatcagc atgcccgccc tgagcctgag aagctacggc agcatcttca   4020
gagtgctggc cgacagcaga ttcgagacac tgatggacgc cctgaacaga cagggcgtga   4080
```

```
cccacgtgaa cttcggcgac atcaccagcg agctggccct gtacgacacc ctgagaagcc   4140
acttcctgct gcaggcccac aacgtggagc aggacgcctt cagcgccaag agaggcgtgc   4200
tggagaacca caccagcccc ttcttctaca gaagcggcaa cctgcagctg gacgaccagg   4260
gcaacatcac caacccagc accgacgcca tcagaaacca ctacggcgag ctgatcaaga   4320
tcctggacag atacagcctg aagatcgaca agaaaaccaa ggagtggcca agccaggaca   4380
tcctgctgag agacttgatg gccgagctga gaaacgccgc cgcccacaac agatacccca   4440
aggccgactt cttcttcaga cagttcgacc acttcctgaa cacctgcaag cccaccgaca   4500
gcaacctgac cgcccccaac tacatcagaa ccgtgctgga gttcctgaag agcatcgtgg   4560
acaacaactt cacccccctg ctgcacgagg agagccccga gaacgagagc aagagcgaga   4620
caggcggcgg ccccggcggc ggcgccgccg ccggcagcgg cagccctaag aaaaaacgaa   4680
aagttggcag cggaagcaaa aggccggcgg ccacgaaaaa ggccggccag gcaaaaaaga   4740
aaaagctcga gtacccatac gatgttccag attacgcttg agaattcccc ttgagcatct   4800
gacttctggc taataaagga aatttatttt cattgcaata gtgtgttgga attttttgtg   4860
tctctcaggt accgagggcc tatttcccat gattccttca tatttgcata tacgatacaa   4920
ggctgttaga gagataattg gaattaattt gactgtaaac acaaagatat tagtacaaaa   4980
tacgtgacgt agaaagtaat aatttcttgg gtagtttgca gttttaaaat tatgttttaa   5040
aatggactat catatgctta ccgtaacttg aaagtatttc gatttcttgg ctttatatat   5100
cttgtggaaa ggacgaaaca ccgtgccgtt cttctgcttg tcggccatga tatgttgtag   5160
aagccgttca ttcgggacgg tatgacaact tttttgcggc cgcaggaacc cctagtgatg   5220
gagttggcca ctccctctct gcgcgctcgc tcgctcactg aggccgggcg accaaaggtc   5280
gcccgacgcc cgggctttgc ccgggcggcc tcagtgagcg agcgagcgcg cagctgcctg   5340
cagggcgccc tgatgcggta tttttctctt acgcatctgt gcggtatttc acaccgcata   5400
cgtcaaagca accatagtac gcgccctgta gcggcgcatt aagcgcggcg ggtgtggtgg   5460
ttacgcgcag cgtgaccgct acacttgcca gcgccttagc gcccgctcct ttcgctttct   5520
tcccttcctt tctcgccacg ttcgccggct ttccccgtca agctctaaat cggggggctcc   5580
ctttagggtt ccgatttagt gctttacggc acctcgaccc caaaaaactt gatttgggtg   5640
atggttcacg tagtgggcca tcgccctgat agacggtttt tcgccctttg acgttggagt   5700
ccacgttctt taatagtgga ctcttgttcc aaactggaac aacactcaac tctatctcgg   5760
gctattcttt tgatttataa gggattttgc cgatttcggt ctattggtta aaaaatgagc   5820
tgatttaaca aaaatttaac gcgaattta acaaaatatt aacgtttaca attttatggt   5880
gcactctcag tacaatctgc tctgatgccg catagttaag ccagccccga cacccgccaa   5940
cacccgctga cgcgccctga cgggcttgtc tgctcccggc atccgcttac agacaagctg   6000
tgaccgtctc cgggagctgc atgtgtcaga ggttttcacc gtcatcaccg aaacgcgcga   6060
gacgaaaggg cctcgtgata cgcctatttt tataggttaa tgtcatgata ataatggttt   6120
cttagacgtc aggtggcact tttcggggaa atgtgcgcgg aacccctatt tgtttatttt   6180
tctaaataca ttcaaatatg tatccgctca tgagacaata accctgataa atgcttcaat   6240
aatattgaaa aaggaagagt atgagtattc aacatttccg tgtcgccctt attccctttt   6300
ttgcggcatt ttgccttcct gttttttgctc acccagaaac gctggtgaaa gtaaaagatg   6360
ctgaagatca gttgggtgca cgagtgggtt acatcgaact ggatctcaac agcggtaaga   6420
tccttgagag ttttcgcccc gaagaacgtt ttccaatgat gagcactttt aaagttctgc   6480
tatgtggcgc ggtattatcc cgtattgacg ccgggcaaga gcaactcggt cgccgcatac   6540
actattctca gaatgacttg gttgagtact caccagtcac agaaaagcat cttacggatg   6600
gcatgacagt aagagaatta tgcagtgctg ccataaccat gagtgataac actgcggcca   6660
acttacttct gacaacgatc ggaggaccga aggagctaac cgcttttttg cacaacatgg   6720
gggatcatgt aactcgcctt gatcgttggg aaccggagct gaatgaagcc ataccaaacg   6780
acgagcgtga caccacgatg cctgtagcaa tggcaacaac gttgcgcaaa ctattaactg   6840
gcgaactact tactctagct tcccggcaac aattaataga ctggatggag gcggataaag   6900
ttgcaggacc acttctgcgc tcggcccttc cggctggctg gtttattgct gataaatctg   6960
gagccggtga gcgtggaagc cgcggtatca ttgcagcact ggggccagat ggtaagccct   7020
cccgtatcgt agttatctac acgacgggga gtcaggcaac tatggatgaa cgaaatagac   7080
agatcgctga taggtgcc tcactgatta gcattggta actgtcagac caagtttact   7140
catatatact ttagattgat ttaaaacttc atttttaatt taaaaggatc taggtgaaga   7200
tcctttttga taatctcatg accaaaatcc cttaacgtga gttttcgttc cactgagcgt   7260
cagacccgt agaaaagatc aaaggatctt cttgagatcc ttttttttctg cgcgtaatct   7320
gctgcttgca aacaaaaaaa ccaccgctac cagcggtggt ttgtttgccg gatcaagagc   7380
taccaactct ttttccgaag gtaactggct tcagcagagc gcagatacca aatactgttc   7440
ttctagtgta gccgtagtta ggccaccact tcaagaactc tgtagcaccg cctacatacc   7500
tcgctctgct aatcctgtta ccagtggctg ctgccagtgg cgataagtcg tgtcttaccg   7560
ggttggactc aagacgatag ttaccggata aggcgcagcg gtcgggctga acggggggtt   7620
cgtgcacaca gcccagcttg gagcgaacga cctacaccga actgagatac ctacagcgtg   7680
agctatgaga aagcgccacg cttcccgaag ggagaaaggc ggacaggtat ccggtaagcg   7740
gcagggtcgg aacaggagag cgcacgaggg agcttccagg gggaaacgcc tggtatcttt   7800
atagtcctgt cgggtttcgc cacctctgac ttgagcgtcg atttttgtga tgctcgtcag   7860
gggggcggag cctatggaaa aacgccagca acgcggcctt tttacggttc ctggcctttt   7920
gctggccttt tgctcacatg t                                            7941
```

```
SEQ ID NO: 34          moltype = DNA   length = 7695
FEATURE                Location/Qualifiers
source                 1..7695
                       mol_type = other DNA
                       organism = synthetic construct
SEQUENCE: 34
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact   120
aggggttcct gcggcctcta gactcgagc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc ccgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcccc   420
```

-continued

```
ctattgacgt caatgacggt aaatggcccg cctggcatta tgcccagtac atgaccttat   480
gggactttcc tacttggcag tacatctacg tattagtcat cgctattacc atggtgatgc   540
ggtttttggca gtacatcaat gggcgtggat agcggtttga ctcacgggga tttccaagtc   600
tccacccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catgccggca gctaagaaaa   780
agaaactgga tggcagcgtc gacatggaga ccaccatcaa caacagaatc ggcaagggcg   840
agtactacac cgaggagagc aaggagttcc tggccgccta cttcaaccag gccatccaca   900
acgtgttcat cgtgctgaac cacatcgcca agagattcga catggacgag ctgagcagcg   960
acgaggagct gaagaactgg ctgatcggca gacagagaga gaagaagaga aacgccatcg   1020
acagacagag attcctggag ctgatcgaca gacacttccc cttcctgaga atcgccaacg   1080
ccgacaagaa ggacgccaag agagagaacg acctggagga caacctggcc ctgctgatca   1140
ccctgctgaa cgacctgacc gagagaagaa acaagtacag ccacgccatc acccacgcca   1200
gcatcgagag caacgacaga gagctggtgt ggagactgta cagcatctac gacgccaaca   1260
tcaacctggt gaagagagac tacttcgaga gcaacgtgca caccgagatc aacgaggacc   1320
cctacgagaa gcaggtggag cacctgagaa gattctgcat gaacaacgac agaaccaagg   1380
tggacgaga gggcaagaag aagcccgcca tgcccaaccc cagattcaga accccccttcc   1440
tgaacgccga gacaaaccag ctgagcatct acggcctggt gttcttcgtg agcctgttcc   1500
tggagaagaa gtacgccatc cagatgcaga agaacgtgta cggcctgaag gacgccagag   1560
acaccaagtt caagatgacc aacgaggtgt tctgcagaag cagaatcatc atgcccagag   1620
tgagactgca cagcgacaag agcaccgacg ccctggtgct ggacatgctg aacgagctgg   1680
ccaaggcccc cgaggtgctg ttcgaccagc tgaccgaccc cttcaaggag aagttctaca   1740
tcgagagcat cgacagcctg gaggagagcg acatcatcac ccccgtgaga gccatcagaa   1800
agcagaacag attcatgtac ttcgccctga gataacctgga cgagagcaac gccttcagca   1860
agctgagatt ccagatcgac ctgggcaact accactacca cctgtacgag agcaagatca   1920
acgaccagac cgagagcaga cacctgacca gaaagctgtt cggcttcggc aagctgatcg   1980
ccttcgagca ggagttcgcc cccgaggagt ggaagatgaa gagcaaggac ctggactact   2040
acgagggcgc cacccagccc ttcatcgcca agacctaccc ccactaccac ctggaggaga   2100
acaagatcgg catcctgttc aacggccagg ccgaggtgca gtggcccac ctggacgtgg   2160
aggagcagga gagcttcccc aagtacaaga gaagagccaa cgagaaggcc gacgccttcca   2220
tgagcggcaa cgagctgctg ccgccgcct tctgccacca cctgtacgcc agcatcggca   2280
agcccaacac cgtggagaag atcatcgaga caagtacca cgccctgaga cagctgttca   2340
gcgacctgaa gagcggcaac ctgcagaacc tgctgggcga caacaccagc aacgaggcca   2400
tcagccagct gctgttcgag aagtacgac tgaccctgag cgaggtgccc gtgagactgc   2460
acgccttcct gagcggccag gagcaggccg acaccaagcc catcgccaga ggcaagctgg   2520
agctgatggc ccagcagaac aagaagagaa tcgagagatt cgacgccatg aagaaggccg   2580
tggtgaaggt gggcaaggcc cagtacgaaa ccctgagaag cggcgacatc ggcgactggc   2640
tggtgagaga cttcatgaga ttccagccca tcggctacaa gagaaaccag gccggcaagc   2700
aggagcccga cctgaagagc aaggccaacc ccaagaagta ccagctgatc cagaagagcc   2760
tggccctgta cgagcaggag aagaacaacc tgctgggcct gttcaagagc tgcaacctgc   2820
tgagcagcga gaacgagcac cccttcctga acgaggtggt gcagagcatg cccgccacct   2880
ggcaggactt ctacgagaga tacctgcacg ccagaagcag attcctggag aagtgcatcg   2940
agaaggcat caagaagaac agctaccagg cctgctacaa cttcctgaag atcaagcccc   3000
agctgaagga caaggagaag ctgtaccagg ctgggacgc ccagatgaac ctgcccacca   3060
acatgttcat cgacgccatc cacgactggt tcagacagac ccaccacgag agcctgagaa   3120
cctggttcac ccagcaggag aagcccacc agctgatcgg cctgatcaga aagtacatcg   3180
agctgcccca ccgaccag atccagggct tctacgacat gttccccctg agatacgact   3240
tctacaagaa ggagttcccc aacggcctgg tgctgcacga gagaatcaac aagcagaagc   3300
agatctggga ggcccagctg atccagacca agaagagact ggaggacgcc gccagcaagc   3360
tgaagaaggt gaagcagcag gtggagagcc tgcccgacca ggagctgaga ttcagaaacg   3420
agacagagac catggtgtac ttcaccaagc tgttcgacag cagcatcgtg aagaacgcca   3480
tcctgaagct gcagagagat cagaaggccc tgagagtgaa caccatcggc gagaagatca   3540
tcaagatcta caccgccaag tacgacgcca tccaccagga ggtgagagac ttcaagagca   3600
tgctgaccac cgagaagatg atcagaagag tgaaggccga ggactgcgtg accctgttca   3660
tgctgaccga cctgatgaac cagagccgag ccaggagcag agaaccatca   3720
agctgagcga catccagccc atgggcgaga cacagatcca gggcatcctg acgccgtgc   3780
aggtgctgga gcagaagctg gacttcttca gcagcgacga gcagggcaag atcagccagg   3840
tgaagctggg cgagtggacc atcttcagca ccgacaccaa ggtgaagaag cagggcaact   3900
tcaagcagct gctgaaggac agaagattga acaacctggc ccactacatc ctgcccgaca   3960
tcgccggcgg cgccatcaga gtgagaagaa acctgctgga gatggagctg gaccagtacg   4020
acagaaacag aatccccatc atcaagctga tgtacgagct ggagtacgcc atctacaagg   4080
tggacccctt cagcgtggag ctgaagtaca agaagttcag ccagtgcctg agagagtacg   4140
cccagaaggc cgtgctgaac gtggagcagg tggagcacct gaacgtgctg atcgccatca   4200
gaaaccgcat catgcacaac cagtaccca acagagatca cctgaaggcc acgtggccct   4260
tcaccgtgag cgagtacgcc cccgtgcagg agggcctgac catcgccaga cagctgtgga   4320
cctgcgccca ggtgagcgtg aacatcatcc tgacgcacat cagcaagttc gagacaggcg   4380
gcggcccgg cggcggcgcc gccgccggca gcggcagccc taagaaaaaa cgaaaagttg   4440
gcagcggaag caaaaggccg gcggccacga aaaaggccgg ccaggcaaaa aagaaaaagc   4500
tcgagtaccc atacgatgtt ccagattacg cttgagaatt cccttgagc atctgacttc   4560
tggctaataa aggaaattta ttttcattgc aatagtgtgt tggaattttt tgtgtctctc   4620
aggtaccgag ggcctatttc ccatgattcc ttcatatttg catatacgat acaaggctgt   4680
tagagagata attggaatta atttgactgt aaacacaaag atattagtac aaaatacgtg   4740
acgtagaaag taataatttc ttgggtagtt tgcagtttta aaattatgtt ttaaaatgga   4800
ctatcatatg cttaccgtaa cttgaaagta tttcgatttc ttggctttat atatcttgtg   4860
gaaaggacga aacaccgtgc cgttcttctg cttgtcggcc atgatatgtt gtgtgtgcct   4920
ttcaaattga aggcgttccc aacttttttg cggccgcagg aacccctagt gatggagttg   4980
gccactccct ctctgcgcgc tcgctcgctc actgaggccg ggcgaccaaa ggtcgcccga   5040
cgcccgggct ttgcccgggc ggcctcagtg agcgagcgag cgcgcagctg cctgcagggg   5100
cgcctgatgc ggtattttct ccttacgcat ctgtgcggta tttcacaccg catacgtcaa   5160
```

-continued

```
agcaaccata gtacgcgccc tgtagcggcg cattaagcgc ggcgggtgtg gtggttacgc   5220
gcagcgtgac cgctacactt gccagcgcct tagcgcccgc tcctttcgct ttcttccctt   5280
cctttctcgc cacgttcgcc ggctttcccc gtcaagctct aaatcggggg ctccctttag   5340
ggttccgatt tagtgcttta cggcacctcg accccaaaaa acttgatttg ggtgatggtt   5400
cacgtagtgg gccatcgccc tgatagacgg tttttcgccg tttgacgttg gagtccacgt   5460
tctttaatag tggactcttg ttccaaactg gaacaacact caactctatc tcgggctatt   5520
cttttgattt ataagggatt ttgccgattt cggtctattg gttaaaaaat gagctgattt   5580
aacaaaaatt taacgcgaat tttaacaaaa tattaacgtt tacaatttta tggtgcactc   5640
tcagtacaat ctgctctgat gccgcatagt taagccagcc ccgacacccg ccaacacccg   5700
ctgacgcgcc ctgacgggct tgtctgctcc cggcatccgc ttacagacaa gctgtgaccg   5760
tctccgggag ctgcatgtgt cagaggtttt caccgtcatc accgaaacgc gcgagacgaa   5820
agggcctcgt gatacgccta ttttttatagg ttaatgtcat gataataatg gtttcttaga   5880
cgtcaggtgg cacttttcgg ggaaatgtgc gcggaacccc tatttgttta tttttctaaa   5940
tacattcaaa tatgtatccg ctcatgagac aataaccctg ataaatgctt caataatatt   6000
gaaaaaggaa gagtatgagt attcaacatt tccgtgtcgc ccttattccc ttttttgcgg   6060
catttttgcct tcctgttttt gctcacccag aaacgctggt gaaagtaaaa gatgctgaag   6120
atcagttggg tgcacgagtg ggttacatcg aactggatct caacagcggt aagatccttg   6180
agagttttcg ccccgaagaa cgttttccaa tgatgagcac tttaaagtt ctgctatgtg   6240
gcgcggtatt atcccgtatt gacgccgggc aagagcaact cggtcgccgc atacactatt   6300
ctcagaatga cttggttgag tactcaccag tcacagaaaa gcatcttacg gatggcatga   6360
cagtaagaga attatgcagt gctgccataa ccatgagtga taacactgcg gccaacttac   6420
ttctgacaac gatcggagga ccgaaggagc taaccgcttt tttgcacaac atgggggatc   6480
atgtaactcg ccttgatcgt tgggaaccgg agctgaatga agccatacca aacgacgagc   6540
gtgacaccac gatgcctgta gcaatggcaa caacgttgcg caaactatta actggcgaac   6600
tacttactct agcttcccgg caacaattaa tagactggat ggaggcggat aaagttgcag   6660
gaccacttct gcgctcggcc cttccggctg gctggtttat tgctgataaa tctggagccg   6720
gtgagcgtgg aagccgcggt atcattgcag cactgggggcc agatggtaag ccctcccgta   6780
tcgtagttat ctacacgacg gggagtcagg caactatgga tgaacgaaat agacagatcg   6840
ctgagatagg tgcctcactg attaagcatt ggtaactgtc agaccaagtt tactcatata   6900
tactttagat tgatttaaaa cttcatttttt aatttaaaag gatctaggtg aagatccttt   6960
ttgataatct catgaccaaa atcccttaac gtgagttttc gttccactga gcgtcagacc   7020
ccgtagaaaa gatcaaagga tcttcttgag atcctttttt tctgcgcgta atctgctgct   7080
tgcaaacaaa aaaaccaccg ctaccagcgg tggtttgttt gccggatcaa gagctaccaa   7140
ctctttttcc gaaggtaact ggcttcagca gagcgcagat accaaatact gttcttctag   7200
tgtagccgta gttaggccac cacttcaaga actctgtagc accgcctaca tacctcgctc   7260
tgctaatcct gttaccagtg gctgctgcca gtggcgataa gtcgtgtctt accgggttgg   7320
actcaagacg atagttaccg gataaggcgc agcggtcggg ctgaacgggg ggttcgtgca   7380
cacagcccag cttggagcga acgacctaca ccgaactgag atacctacag cgtgagctat   7440
gagaaagcgc cacgcttccc gaagggagaa aggcggacag gtatccggta agcggcaggg   7500
tcggaacagg agagcgcacg aggggagcttc caggggggaaa cgcctggtat ctttatagtc   7560
ctgtcgggtt tcgccacctc tgacttgagc gtcgatttttt gtgatgctcg tcaggggggc   7620
ggagcctatg gaaaaacgcc agcaacgcgg cctttttacg gttcctggcc ttttgctggc   7680
cttttgctca catgt                                                     7695
```

```
SEQ ID NO: 35          moltype = DNA   length = 6919
FEATURE                Location/Qualifiers
source                 1..6919
                       mol_type = other DNA
                       organism = synthetic construct
SEQUENCE: 35
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact   120
aggggttcct gcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc cgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca gtacgccccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccaccccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catgccggca gctaagaaaa   780
agaaactgga tggcagcgtc gacatgatgg gcaacaagaa gacgtggcc aaggccaacg   840
gcctgaagag caccttcgtg ctgggcgaga acaccgccta catgaccagc ttcggcagag   900
gcaacgccgc ccagcccgag aagcacatca gagacgccac cgtgaccgac atccagcaca   960
ccttcagagc caagaccgac ggcggcagaa ccgtgcacat cgagggcaga gtgggcgcca   1020
gcgacgtgct gctgcccgac gccgccaacc agctgcacgc caaggacgcc gtggagcaga   1080
tgtacttcgg caaggccttc agcgacaaca tcccacatcca aacatcatgg   1140
acatcaagaa gatcttcggc gtgtacgcca acatcatcgt gcacaccgtg aacaacctgt   1200
gctcgacgg cgacaagcag gacgacttcc tgggcatgtt caagacccag aacagatacc   1260
aggtggccgc ctgggcccac aagatcgtga gcctgcacct ggtgaagaac gagctgagag   1320
gcggcggctt cttcatggac caggaggtgt ggagagccca cgtgagaacc gacttcaaga   1380
gcctgaagag gcccgtgaac gccttcatga gaagtacc ccagaagtac ccctactgga   1440
gcgtgaagat cgtgagcgac ttcatcgtgc aggagatggg catcaagaac aaggtgatcc   1500
tggagaaggc cgccgagagc tacgccgagt cgagacagt ggccaagaga ctggagaaga   1560
gcgcctacta cttcagcgac atcttcgccg gcaaggacgg caagttcgac gagcagaagg   1620
ccttcgacct gctgagagtg ctgggcatga tgagacagga ggccttccac gagaagaaca   1680
gcagcgccag ctggctgtac aacctggacg ccgaggccga cgaggacatc aaggccgccc   1740
```

```
tgagaaccgt ggtggacacc aaggtgaacg gcatcaacac caacttcgcc aagcagaaca  1800
aggtgaacct gctggtgctg caggagatct accccagaa gagcaaggcc gacctggtga   1860
gagagtacta cgacttcagc gtgagaaagg ccttcaagaa cctgggcttc agcgtgaaaa   1920
ccctgagaga gacaatgtgc gccttcgacg ccgccagcgt gatcaccgac aagcagtacg   1980
acaccgtgag aggcaagctg tacagcctgt tcgacttcgt gatctacaac tactgcctgg   2040
agaacgaggc cgtgtgcaac gccttcgtgg aggagctgag agccaacctg gaccccgaga   2100
acaagaccgc cctgtaccag accctggccg agaaggtgtg ggccgagatc ggcgacatcg   2160
tgctgcagag aatcctgccc cagatgcacg ccaagaagat ccaggagaga agcaaggaga   2220
cagacgccga gacagtggag atgcagggct acgtgcaggc ccccaaggac ctgagcctgt   2280
tcagcaaggc cgtgtactgc atcagcatgt tcctggacag caaggagatc aacagcttcc   2340
tgagcgccct gatcaacaag ttcgagaaca tcagcagcct gtgcgccgtg ctggcctaca   2400
acggcctgga gcccgagttc gtggccccct tcaccttctt cgccgacagc caggccatcg   2460
ccgaggacct gagatacatc aagagcatcg ccagaatgag caagggcaag aaggccacca   2520
aggacagccc cgtgaccgtg aaggagatgc agtacttcga cgccgccgcc gtgctgggcg   2580
agacagacac cgagaaggtg aaggccgcct tccacctggg cgacaagagc gccagcaccg   2640
ccgacaaggc cttcagaaac ttcgtggtga acaacgtgat caacagcaac agattcgtgt   2700
acgtggtgag attcatcaac cccaagaacg ccagagagat catgcagaac agagccctga   2760
tcgccttcgt gctgaaggac atcccccaga gccagctggt gagatactgc ggcaccgccg   2820
gcatcgcctg caacgccgac gagcccaaca ccgaggccat ggtgaacgcc ctggccgaca   2880
tgctgctgca ggtgagattc gacgccttca gcaacgtgca gcagaaggtg aaggccgaca   2940
gcgccgaggc cgtgcagaag gagaagtaca aggccatcat cggcctgtac ctgaccgtgc   3000
tgtacctgct ggtgaaaacc ctggtgaaga tcaacatgaa ctacgccatc gccttcggca   3060
tcctggagag agactgccag atcatgaacc agaagcacgc caagaacccc aagagagaca   3120
gagacgcctt ctacatgaga gagcagcaga acaagcagta cgtgtacaac gccagagcca   3180
tcaccgagct gttcatcgag aacggctggc tgaacaagag agtgcagaag agcgtggaga   3240
acaacgccgc cctgtacagc gacgaggcct tctacaagta cagaaacctg gtggcccacc   3300
tgaacgtgat cagcgccctg cccaagtacg ccaagaacat caccaaggtg aagagcctgt   3360
tcgacgtgta ccactacatc ctgttcctga gcctgtgcga ggacaagtac agcaacctgc   3420
ccgaggccgt gaccaagagc ctgtgcaaga acggcaagac catgctggag aacgccagag   3480
agtaccagac cgtgtgcaag gacttcctgt acggcctgaa cacccccttc gcctacaacg   3540
ccgccagata catcaacctg agcaacagag agaagttcct ggccggcttc ggcaagacag   3600
gcggcggccc cggcggcggc gccgccgccg gcagcggcag ccctaagaaa aaacgaaaag   3660
ttggcagcgg aagcaaaagg ccggcggcca cgaaaaaggc cggccaggca aaaaagaaaa   3720
agctcgagta cccatacgat gttccagatt acgcttgaga attccccttg agcatctgac   3780
ttctggctaa taaaggaaat ttattttcat tgcaatagtg tgttggaatt ttttgtgtct   3840
ctcaggtacc gagggcctat ttcccatgat tccttcatat ttgcatatac gatacaaggc   3900
tgttagagag ataattggaa ttaatttgac tgtaaacaca aagatattag tacaaaatac   3960
gtgacgtaga aagtaataat ttcttgggta gtttgcagtt ttaaaattat gttttaaaat   4020
ggactatcat atgcttaccg taacttgaaa gtatttcgat ttcttggctt tatatatctt   4080
gtggaaagga cgaaacaccg ggttttacac ccgtgtaaaa ctacacagtt ctaaaactgc   4140
cgttcttctg cttgtcggcc atgatatttt tttgcggccg caggaacccc tagtgatgga   4200
gttggccact ccctctctgc gcgctcgctc gctcactgag gccgggcgac caaaggtcgc   4260
ccgacgcccg ggctttgccc gggcggcctc agtgagcgag cgagcgcgca gctgcctgca   4320
ggggcgcctg atgcggtatt ttctccttac gcatctgtgc ggtatttcac accgcatacg   4380
tcaaagcaac catagtacgc gccctgtagc ggcgcattaa gcgcggcggg tgtggtggtt   4440
acgcgcagcg tgaccgctac acttgccagc gccttagcgc ccgctccttt cgctttcttc   4500
ccttcctttc tcgccacgtt cgccggcttt ccccgtcaag ctctaaatcg gggctccctt   4560
ttagggttcc gatttagtgc tttacggcac ctcgacccca aaaaacttga tttgggtgat   4620
ggttcacgta gtgggccatc gccctgatag acggtttttc gccctttgac gttggagtcc   4680
acgttcttta atagtggact cttgttccaa actggaacaa cactcaactc tatctcgggc   4740
tattcttttg atttataagg gattttgccg atttcggtct attggttaaa aaatgagctg   4800
atttaacaaa aatttaacgc gaattttaac aaaatattaa cgtttacaat tttatggtac   4860
actctcagta caatctgctc tgatgccgca tagttaagcc agccccgaca cccgccaaca   4920
cccgctgacg cgccctgacg ggcttgtctg ctcccggcat ccgcttacag acaagctgtg   4980
accgtctccg ggagctgcat gtgtcagagg ttttcaccgt catcaccgaa acgcgcgaga   5040
cgaaagggcc tcgtgatacg cctatttttta taggttaatg tcatgataat aatggtttct   5100
tagacgtcag gtggcacttt tcggggaaat gtgcgcggaa cccctatttg tttattttc   5160
taaatacatt caaatatgta tccgctcatg agacaataac cctgataaat gcttcaataa   5220
tattgaaaaa ggaagagtat gagtattcaa catttccgtg tcgcccttat tcccttttt   5280
gcggcatttt gccttcctgt ttttgctcac ccagaaacgc tggtgaaagt aaaagatgct   5340
gaagatcagt tgggtgcacg agtgggttac atcgaactgg atctcaacag cggtaagatc   5400
cttgagagtt ttcgccccga agaacgtttt ccaatgatga gcacttttaa agttctgcta   5460
tgtggcgcgg tattatcccg tattgacgcc gggcaagagc aactcggtcg ccgcatacac   5520
tattctcaga atgacttggt tgagtactca ccagtcacag aaaagcatct tacggatggc   5580
atgacagtaa gagaattatg cagtgctgcc ataaccatga gtgataacac tgcggccaac   5640
ttacttctga caacgatcgg aggaccgaag gagctaaccg cttttttgca caacatgggg   5700
gatcatgtaa ctcgccttga tcgttgggaa ccggagctga atgaagccat accaaacgac   5760
gagcgtgaca ccacgatgcc tgtagcaatg gcaacaacgt tgcgcaaact attaactggc   5820
gaactactta ctctagcttc ccggcaacaa ttaatagact ggatggaggc ggataaagtt   5880
gcaggaccac ttctgcgctc ggcccttccg gctggctggt ttattgctga taaatctgga   5940
gccggtgagc gtgaagccg cggtatcatt gcagcactgg ggcagatgg taagccctcc   6000
cgtatcgtag ttatctacac gacggggagt caggcaacta tggatgaacg aaatagacag   6060
atcgctgaga taggtgcctc actgattaag cattggtaac tgtcagacca gtttactca    6120
tatatacttt agattgattt aaaacttcat ttttaattta aaaggatcta ggtgaagatc    6180
ctttttgata atctcatgac caaaatccct taacgtgagt tttcgttcca ctgagcgtca    6240
gaccccgtag aaaagatcaa aggatcttct tgagatcctt tttttctgcg cgtaatctgc    6300
tgcttgcaaa caaaaaaacc accgctacca gcggtggttt gtttgccgga tcaagagcta    6360
ccaactcttt ttccgaaggt aactggcttc agcagagcga gataccaaa tactgttctt     6420
ctagtgtagc cgtagttagg ccaccacttc aagaactctg tagcaccgcc tacataccte    6480
```

```
gctctgctaa tcctgttacc agtggctgct gccagtggcg ataagtcgtg tcttaccggg   6540
ttggactcaa gacgatagtt accggataag gcgcagcggt cgggctgaac ggggggttcg   6600
tgcacacagc ccagcttgga gcgaacgacc tacaccgaac tgagatacct acagcgtgag   6660
ctatgagaaa gcgccacgct tcccgaaggg agaaaggcgg acaggtatcc ggtaagcggc   6720
agggtcggaa caggagagcg cacgagggag cttccagggg gaaacgcctg gtatctttat   6780
agtcctgtcg ggtttcgcca cctctgactt gagcgtcgat ttttgtgatg ctcgtcaggg   6840
gggcggagcc tatggaaaaa cgccagcaac gcggccttt tacggttcct ggccttttgc      6900
tggcctttg ctcacatgt                                               6919

SEQ ID NO: 36          moltype = DNA   length = 7690
FEATURE                Location/Qualifiers
source                 1..7690
                       mol_type = other DNA
                       organism = synthetic construct
SEQUENCE: 36
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc ccgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccaccccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catgccggca gctaagaaaa   780
agaaactgga tggcagcgtc gacatgacca tcctggagaa gtacatgccc ctgaacgaga   840
tgggcaagat caagagcctg gtggacgagc tgaagggcct cccgcgcgcc atgaacgcca   900
ccctgagaca ggagatcttc cagaacatca agaaaaccaa gctgcaggtg aagttcctga   960
aggagtaccc cgagacactg ttcaccgaca gcggcaacct gatccccatc atcggcaaca  1020
acgacaacag cagcagcggc accccccagca agcaggaggt gagcgacatc gacgccaacc  1080
aggccagcag aatcaactac ctgccccacg agacaatggg cgagatcaag agcgtgtacg  1140
gcacctacat cgagatggcc ttccacaact tctacctgac catgcaccac atctacgccg  1200
tggtgttcgg cgaggacatc atggaggagg ccaagaagga gttcgacaag aacaacacca  1260
acagcaccaa gtacttcacc ttcgacttcg ccaacgagag aaccatctgg aagcccatgt  1320
tcgacagagc cgagagagcc aagcccgagc agaaggagca cttcgagaag ctggtggtga  1380
agcacttccc cttcctgaag gccatcgacg ccctggagga cagaaagaa aagaccaaga  1440
tccaggccct gtgcgtgttc agcctggtgc tgagagagct gagaaacgtg tacagccact  1500
acctgttcta cccccttcaag aaccaggtgg acaagtacaa ggagaacatc cccttcgtgc  1560
tggacatgat ggagatcctg tacaccggcg cccagagaga ggtgaagggc agattcggct  1620
tcgacgacaa gaagatgcag tgcgccaaga agtacggag aaacaaggac cacagccaga  1680
gagatcacca gggcaagatc atcaaggccg tgcccaagaa gaacttcaga tacaacctgt  1740
acaagaagga ggacagcgag gccatcatca ccccttcgg cctggtgttc ctgaccagcc  1800
tgttcctgga gaagaagtac gccaagatcc tgagcgacaa gacccactgc atcaagtaca  1860
ccgaccagga ggtgctgtgc gagatcatca gcgtgtacag aatcagactg cacatccaga  1920
agctgagcgt gaccaaggac accgacgccc tggccctgga catcatcaac gagctgcaga  1980
gatgccccaa gagactgttc gagatgctga gcccccgacga ccagcagaag ttcagaatca  2040
agcccaccga cagccagtac gccgacgacg tgctgatgat cagacaccag gacagattcg  2100
cccacctgct gctgaagtac atcgacgacg cccacctgtt caactgcatc agattccagg  2160
tgagcctggg cagatacttc ttcagattct acgacaagag ctgcatcgac agcaccggcg  2220
acaagagagt gagaagcatc agcaagaacg tgaacggctt cggcagaatc accgacatcg  2280
aggactacag aaaggaggtg tacggcgaca tgatcagaga gtacgaggac gtgcacgcca  2340
acaccagcat ggagaagccc tacatcaccg accaccaccg caagtacctg atcagcaaca  2400
acagaatcgg cctgtacatc agaaaggagg aggacaccca gtgcctgctg cccgagctga  2460
cccccgacgg cgccagaaac ttcgcccca cctgctggct gagcatctac gagctgcccg  2520
ccctggcctt cctgctgcac ctgtacaacg gcgacgcgcag cagagtggag gagatcatcc  2580
agaccaaggt ggccaactac cagagactgt tcgccgacgt gagagacgac aaggtgtgcc  2640
ccgtgaagga cgaggccgag ctgaccacca tcctgcacag ctacggcaac atcgagcgca  2700
gccagctgcc cagaaagctg ctggactacc tgctgaagaa ggagatctgc gcccaggacc  2760
tgttcaacac ctgggcccag agcaagatcc agagaatgat cgcccagacc gacagcctgc  2820
tgcagcacct ggagaaggac ctgcaggccg tgagcgacct gaagcagaac aagttcggca  2880
agaaggcctt cgtggccatc aagcccggcc acatcgccgg cttcctgcca cacacatga  2940
tgttcttcca gcccagcatg aaggactgca caacaagct gaccggcctg aacttcagaa  3000
tcctgcagag cagcatggcc gtgtacgacg gcaacttcga cgagctgagc agaatcatga  3060
gaagcgccca tcatcggc aacgccacg acgcctgctg caaccccatc gtgatggccg  3120
tgtgtcagaaa gcacaagggc ttcagcaaca tcatcagatt ctaccaggcc tacctgaagg  3180
agagaaaggc ctacctgcag cagtgccca acagagacagc ctacgacagc ctgagcttcc  3240
tgcacgccag ccagaacaag tggagagaga gaacccaggc ctactacaga gcctggccg  3300
ccaagtacct ggccgagaac tacgacgcg tggacaccac caagagcatc gagctgccca  3360
gaggcctgtt cgagacatac atcagacagg agctgagcga gatcggcagc accaagagca  3420
tggccggcga cgccaccaag aacaccagct acctgatcta cggctacttc agacaggtga  3480
tgagcggga gcgcccagacc ttctacgaca ccagaagatg ctaccagatg ttcgacgtgc  3540
tgtacagaaa gagccccaga gacaaccaca gctactacag caccgcccag atcagagaga  3600
tgctgatgag aagccacagc aagagcatca gaaaggacat cgacaactac atcagccaga  3660
ccaccgccgc cgagagaacc aaggagaagg agagatgcga cgccctgctg agaaagatca  3720
aggacaccga gacagagctg aaggtgtaca agatccagga catcctgctg ttcctgatcg  3780
ccaagagact gctgctggac agaaaggtgg agaacgacag cgccgtgcag atgaacgcca  3840
```

```
tcaaccagat cagactgaga aacatcgccg acggcaacac cctgagccag aagatcccca   3900
tcagcatcag catcaagagc agaaaggggc accccaagat catccagcag gacgacctga   3960
agctgaagaa ctacagccag ttctacagca tcatcagcga cagaagattg cccagcctgc   4020
tggacctgat caacagcaga gtgatcaaga gaaccgacat cgaggacgag ctgagcaact   4080
acgacaagag ccacccccac gtgctgaaga gcgtgttcga gttcgagaag cactacttcg   4140
acacccaccc catccccagc gacaccgcct acatggccct gcccgacacc ggcgagatgc   4200
tgaaggagag caacctgacc gccgagaagc agaaggaggt gagaaagatc agaaacagct   4260
tcgcccacct gagctacccc agcagaaaca tcaccggcgc cgccagcacc gagctgccca   4320
agaaggccga gatcatcagc aagaacctga tcgagcacct gagcaacgcc gagatcaaga   4380
caggcggcgg ccccggccgc ggcgccgccg ccggcagcgg cagccctaag aaaaaacgaa   4440
aagttggcag cggaagcaaa aggccggcgg ccacgaaaaa ggccggccag gcaaaaaaga   4500
aaaagctcga gtacccatac gatgttccag attacgcttg agaattcccc ttgagcatct   4560
gacttctggc taataaagga aatttatttt cattgcaata gtgtgttgga attttttgtg   4620
tctctcaggt accgagggcc tatttcccat gattccttca tatttgcata tacgatacaa   4680
ggctgttaga gagataattg gaattaattt gactgtaaac acaaagatat tagtacaaaa   4740
tacgtgacgt agaaagtaat aatttcttgg gtagtttgca gttttaaaat tatgttttaa   4800
aatggactat catatgctta ccgtaacttg aaagtatttc gatttcttgg cttttatatat   4860
cttgtggaaa ggacgaaaca ccggagacca cggcaggtct cagttgtaga tgacctcgtt   4920
ttggagggga aacacaactt ttttgcggcc gcaggaaccc ctagtgatgg agttggccac   4980
tccctctctg cgcgctcgct cgctcactga ggccgggcga ccaaaggtcg cccgacgccc   5040
gggctttgcc cgggcggcct cagtgagcga gcgagcgcgc agctgcctgc aggggcgcct   5100
gatgcggtat tttctcctta cgcatctgtg cggtatttca caccgcatac gtcaaagcaa   5160
ccatagtacg cgccctgtag cggcgcatta agcgcggcgg gtgtggtggt tacgcgcagc   5220
gtgaccgcta cacttgccag cgccttagcg cccgctcctt tcgctttctt cccttccttt   5280
ctcgccacgt tcgccggctt tccccgtcaa gctctaaatc gggggctccc tttagggttc   5340
cgatttagtg ctttacggca cctcgacccc aaaaaacttg atttgggtga tggttcacgt   5400
agtgggccat cgccctgata gacggttttt cgccctttga cgttggagtc cacgttcttt   5460
aatagtggac tcttgttcca aactggaaca acactcaact ctatctcggg ctattctttt   5520
gatttataag ggattttgcc gatttcggtc tattggttaa aaaatgagct gatttaacaa   5580
aaatttaacg cgaattttaa caaaatatta acgtttacaa ttttatggtg cactctcagt   5640
acaatctgct ctgatgccgc atagttaagc cagccccgac acccgccaac acccgctgac   5700
gcgccctgac gggcttgtct gctcccggca tccgcttaca gacaagctgt gaccgtctcc   5760
gggagctgca tgtgtcagag gttttcaccg tcatcaccga aacgcgcgag acgaaagggc   5820
ctcgtgatac gcctattttt ataggttaat gtcatgataa ttttatggtttc ttagacgtca   5880
ggtggcactt ttcggggaaa tgtgcgcgga acccctattt gtttattttt ctaaatacat   5940
tcaaatatgt atccgctcat gagacaataa ccctgataaa tgcttcaata atattgaaaa   6000
aggaagagta tgagtattca acatttccgt gtcgccctta ttcccttttt tgcggcattt   6060
tgccttcctg ttttttgctca cccagaaacg ctggtgaaag taaaagatgc tgaagatcag   6120
ttgggtgcac gagtgggtta catcgaactg gatctcaaca gcggtaagat ccttgagagt   6180
tttcgccccg aagaacgttt tccaatgatg agcacttttta aagttctgct atgtggcgcg   6240
gtattatccc gtattgacgc cgggcaagag caactcggtc gccgcataca ctattctcag   6300
aatgacttgg ttgagtactc accagtcaca gaaaagcatc ttacggatgg catgacagta   6360
agagaattat gcagtgctgc cataaccatg agtgataaca ctgcggccaa cttacttctg   6420
acaacgatcg gaggaccgaa ggagctaacc gcttttttgc acaacatggg gatcatgta   6480
actcgccttg atcgttggga accggagctg aatgaagcca taccaaacga cgagcgtgac   6540
accacgatgc ctgtagcaat ggcaacaacg ttgcgcaaac tattaactgg cgaactactt   6600
actctagctt cccggcaaca attaatagac tggatggagg cggataaagt tgcaggacca   6660
cttctgcgct cggcccttcc ggctggctgg tttattgctg ataaatctgg agccggtgag   6720
cgtggaagcc gcggtatcat tgcagcactg gggccagatg gtaagccctc ccgtatcgta   6780
gttatctaca cgacggggag tcaggcaact atggatgaac gaaatagaca gatcgctgag   6840
ataggtgcct cactgattaa gcattggtaa ctgtcagacc aagtttactc atatatactt   6900
tagattgatt taaaacttca ttttttaattt aaaaggatct aggtgaagat cctttttgat   6960
aatctcatga ccaaaatccc ttaacgtgag ttttcgttcc actgagcgtc agaccccgta   7020
gaaaagatca aaggatcttc ttgagatcct tttttttctgc gcgtaatctg ctgcttgcaa   7080
acaaaaaaac caccgctacc agcggtggtt tgtttgccgg atcaagagct accaactctt   7140
tttccgaagg taactggctt cagcagagcg cagataccaa atactgttct tctagtgtag   7200
ccgtagttag gccaccactt caagaactct gtagcaccgc ctacatacct cgctctgcta   7260
atcctgttac cagtggctgc tgccagtggc gataagtcgt gtcttaccgg gttggactca   7320
agacgatagt taccggataa ggcgcagcgg tcgggctgaa cggggggttc gtgcacacag   7380
cccagcttgg agcgaacgac ctacaccgaa ctgagatacc tacagcgtga gctatgagaa   7440
agcgccacgc ttcccgaagg gagaaaggcg gacaggtatc cggtaagcgg cagggtcgga   7500
acaggagagc gcacgaggga gcttccaggg gaaacgcct ggtatcttta tagtcctgtc   7560
gggtttcgcc acctctgact tgagcgtcga ttttgtgat gctcgtcagg ggggcggagc   7620
ctatggaaaa acgccagcaa cgcggccttt ttacggttcc tggcctttg ctggcctttt   7680
gctcacatgt                                                          7690
```

SEQ ID NO: 37          moltype = DNA  length = 7930
FEATURE                Location/Qualifiers
source                 1..7930
                       mol_type = other DNA
                       organism = synthetic construct
SEQUENCE: 37

```
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact   120
aggggttcct gcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc ccgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcccc   420
```

-continued

```
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccacccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catgccggca gctaagaaaa   780
agaaactgga tggcagcgtc gacatgtacc acctgagcga cgccaaccac ggcaagcaca   840
tcgccggcac ctactacgag atggccatgg gcaacttcat ccacaccctg agccacatgc   900
tggtgagagc cggcatcaag gtgaacaagc tggaggacaa ctacagcatc gagagagaga   960
tcatgaacct gaccgcccc ggcgcctacg acgcccagag agccgccctg agcagactgc  1020
tgtacagaca cttccccttc ttcggcccca tcatggccga ccacaccgac cacatcctga  1080
gcagcaagag aaagaaggtg cagagcgcca gcgacgacgg caacctggac ctgggccagg  1140
agctgaagga cgaggtggcc ggcgccagcg cctgccagat gatcagatac ctggccacca  1200
tcgccggcgc cctggtgtac tacagaaaca tgtacagcca caagaaccac tacgacaacg  1260
cccaggacat cgccgcccag caggagagag agcagaagct ggccctgtgg ctggacgtgg  1320
tgttcagagg cgccagagac atcctgctga ccagaaagac ccaccccag cccgacaccg  1380
acttcctgac ccagaacggc accatcaact actacatcga gaagaacggc aagagcgcct  1440
acaaccccaa cttctacttc aagcccggcc tgaaaaccga caggcctggc gtgatgaccg  1500
acttcggcaa gttcttcttc tgcagcctgt tcctgagaag agccgacgcc gagagattcc  1560
ccgccgagac agacctgtac gtgggcagcc ccttcaagat caccgcccag gagagagcca  1620
gactgcagga ggccgagaac aagagagccg ccgacgagca ggccagagcc agcagcgccg  1680
gcttccccca catcgtgaac cccagaacca tcggccccac tcggccccag cagaacaaca  1740
tcatcagaga gatgctgaac atgcacagag ccagaatccc cagagagaga agaatcgacg  1800
ccgacatgag cgagggcatc ctggccatgg acatcatgaa cgagctgaga agtgccccc   1860
tgagcctgta caacaccctg agcccgagg ccaaggccag cttcgagaaa accggcgtga   1920
ccccgaggg cggcatcgtg agcaacctgc tggtgagaca cagcgacaga taccccgagg  1980
tggccctgag agccatcgac cagatggagc tgctgcccac catcagattc cacgtgagac  2040
tgggcagcct gagattcaga ttctacgaga agaagctgat cgacggcagc cacaccctga  2100
gaaccgtgca gaaggccgtg aacggcttcg gcagatggca ggaggtggag cccagaagag  2160
tggagaagta caccgccatc caggccagat gccagaacga caagggcatc gaccagttcc  2220
tgcccgacag ccccaccacc acccctaca tcaccgactg gagaaccacc tacaacatcc   2280
acgccaacag aatcggcctg gcctggaacc tgcccagat gagcgacggc atctacctgc  2340
ccaacctgga caccgacaag ggcgacaacc tgcacagaaa ggccctgatc gacatgcccg  2400
cccccatgtg ctacctgagc atcttcgacc tgcccgccct gctgttctac tgccacatct  2460
acacccacta ccacggcacc aagtaccacc tgcccagcgc cgagagcatc atccaggcca  2520
agtacgacgc cctgcacaag ttcttcagct tcgccgccgc ccagaaccac agcgccgagc  2580
agctgagaga gaagcagctg gagctgaacc tggccgacaa cgagatcccc gacaagctga  2640
gatgcatgat gcagaccaag cccttcttca agaacgcag acagcagctg agcccctgg   2700
gctaccccat catgaagaac tggatcggcg tggccgagca gagaaagcac gccgcccagg  2760
tgctgagaga cgtggccaac gaggccgccg cacagactgg cagcttcgag aagaagcacc  2820
agagagtggt ggtgggcggc agagacaaca gatacggcag aagaggccac gccgacatca  2880
gacacggcag cctggccaga tacctggcca ccagcatggt gagatggcag cccgccctgg  2940
accagcccg cggcgacaag ctgaccagcg ccaaccacag accctggcc ggcttcctgg  3000
gcgagtacgg cctgcacggc agcaacatca acaagctgag aaacgtgctg aaggaggccg  3060
gcctgatcga gggcagccac ccccaccct tcctggccca cgtgctggag agcgccccg   3120
ccaacatcga ggcctgtac gtggcctacc tgaagcacga gcagagccac gccaccgccc  3180
tgaagaacaa gttcaccgac agaaacggcca tcgtgcaac cagcgaggtg ccgcccttcg  3240
tgagattcaa cagcagcaga tggagaaacg acagcgccac caccgccaga agatacctgc  3300
agaccccccc cgccccggc agcagcgaca gcgccgagca caacgccccc atcatgctgc  3360
ccgacggcct gttcaccacc cacatcatga ccctgctgaa caaggtgctg ggccagaacg  3420
acagagtgcc cgaggaggac tacctgagac acgacctgcc cagaatcgcc agcatcatca  3480
accccaacgg caagacctac ggcgccgcct acatcatcag agcctggttc gaccaggtgg  3540
agaaccagga cgtgcagccc ttctacgacc tgcccagatt ctacagagag atcagcctgc  3600
tggccccag aagaaagccc aaccaggagc tgatcagaga ctacttcagc gaggagcaga  3660
tcgcccagaa gatccagacc gtgcccaaga agcagagaag cgagaaggtg ggccacacca  3720
tcgacaccga gaaggacatc agaagataca gactgcagga catcaccctg tacctgaccc  3780
tgctggacat gctgacctg atgctgagca gaaacgaggc cgagagaacc gacagacaga  3840
tgaagagcag caccgccgag agagtgagca acatgagact ggtggacttc gaccacagct  3900
tcgacttcga cctgctgggc agcaccagcg cgaggccgc ctacagctac ctgcaccaga  3960
gaagcggcat caccatcagc atgcccgccc tgagcctgag aagctacgac agcatcttca  4020
gagtgctggc cgacagcaga ttcgagcaca tgatgacgac cctgaacaga cagggcgtga  4080
cccacgtgaa cttcggcgac atcaccacgc agctggcccc tgtacgacacc ctgagaagcc  4140
acttcctgct gcaggcccac aacgtggagc aggacgcctt cagcgccaag agaggcgtgc  4200
tggagaacca caccagcccc ttcttctaca gaagcgccaa cctgcagctg gacgaccagg  4260
gcaacatcac caaccccagc accgacgcca tcagaaacca ctacggcgag ctgatcaaga  4320
tcctggacag atacagcctg aagatcgaca agaaaccaa ggacggcaag agccaggaca  4380
tcctgctgag agacttgatg gccgagctga gaaacgccgc cgcccacaac agatacccca  4440
aggccgactt cttcttcaga cagttcgacc acttcctgaa cacctgcaag cccaccgaca  4500
gcaacctgac cgcccccaac tacatcagaa ccgtgctgga gttcctgaag agcatcgtgg  4560
acaacaactt caccccctg ctgcacgagg agagccccga gaacgagagc aagagcgaga  4620
caggcggcg ccccggcggc ggcgccgccg ccggcagcgg cagccctaag aaaaaacgaa  4680
aagttggcag cggaagcaaa aggccggcgg ccacgaaaaa ggccggcagg caaaaaagga  4740
aaagctcga gtacccatac gatgttccag attacgcttg agaattcccc ttgagcatct  4800
gacttctggc taataaagga aatttatttt cattgcaata gtgtgttgga attttttgtg  4860
tctctcaggt accgagggcc tatttcccat gattccttca tatttgcata tacgatacaa  4920
ggctgttaga gagataattg gaattaattt gactgtaaac acaaagatat tagtacaaaa  4980
tacgtgacgt agaaagtaat aatttcttgg gtagtttgca gttttaaaat tatgttttaa  5040
aatggactat catatgctta ccgtaacttg aaagtatttc gatttcttgg ctttatatat  5100
cttgtggaaa ggacgaaaca ccggagacca cggcaggtct cagttgtaga agccgttcat  5160
```

-continued

```
tcgggacggt atgacaactt ttttgcggcc gcaggaaccc ctagtgatgg agttggccac   5220
tccctctctg cgcgctcgct cgctcactga ggccggggcga ccaaaggtcg cccgacgccc   5280
gggctttgcc cgggcggcct cagtgagcga gcgagcgcgc agctgcctgc aggggcgcct   5340
gatgcggtat tttctcctta cgcatctgtg cggtatttca caccgcatac gtcaaagcaa   5400
ccatagtacg cgccctgtag cggcgcatta agcgcggcgg gtgtggtggt tacgcgcagc   5460
gtgaccgcta cacttgccag cgccttagcg cccgctcctt cgctttctt ccttccttt    5520
ctcgccacgt tcgccggctt tccccgtcaa gctctaaatc gggggctccc tttagggttc   5580
cgatttagtg ctttacggca cctcgacccc aaaaaacttg atttgggtga tggttcacgt   5640
agtgggccat cgccctgata gacggttttt cgccctttga cgttggagtc cacgttcttt   5700
aatagtggac tcttgttcca aactggaaca acactcaact ctatctcggg ctattctttt   5760
gatttataag ggattttgcc gatttcggtc tattggttaa aaaatgagct gatttaacaa   5820
aaatttaacg cgaattttaa caaaatatta acgtttacaa ttttatggtg cactctcagt   5880
acaatctgct ctgatgccgc atagttaagc cagccccgac acccgccaac acccgctgac   5940
gcgccctgac gggcttgtct gctcccggca tccgcttaca gacaagctgt gaccgtctcc   6000
gggagctgca tgtgtcagag gttttcaccg tcatcaccga aacgcgcgag acgaaagggc   6060
ctcgtgatac gcctattttt ataggttaat gtcatgataa taatggtttc ttagacgtca   6120
ggtggcactt ttcgggggaaa tgtgcgcgga accccctattt gtttattttt ctaaatacat   6180
tcaaatatgt atccgctcat gagacaataa ccctgataaa tgcttcaata atattgaaaa   6240
aggaagagta tgagtattca acatttccgt gtcgcccttat ttcccttttt tgcggcattt   6300
tgccttcctg tttttgctca cccagaaacg ctggtgaaag taaaagatgc tgaagatcag   6360
ttgggtgcac gagtgggtta catcgaactg gatctcaaca gcggtaagat ccttgagagt   6420
tttcgccccg aagaacgttt tccaatgatg agcacttttta aagttctgct atgtggcgcg   6480
gtattatccc gtattgacgc cgggcaagag caactcggtc gccgcataca ctattctcag   6540
aatgacttgg ttgagtactc accagtcaca gaaaagcatc ttacggatgg catgacagta   6600
agagaattat gcagtgctgc cataaccatg agtgataaca ctgcggccaa cttacttctg   6660
acaacgatcg gaggaccgaa ggagctaacc gcttttttgc acaacatggg ggatcatgta   6720
actcgccttg atcgttggga accggagctg aatgaagcca taccaaacga cgagcgtgac   6780
accacgatgc ctgtagcaat ggcaacaacg ttgcgcaaac tattaactgg cgaactactt   6840
actctagctt cccggcaaca attaatagac tggatggagg cggataaagt tgcaggacca   6900
cttctgcgct cggcccttcc ggctggctgg tttattggtg ataaatctgg agccggtgag   6960
cgtggaagcc gcggtatcat tgcagcactg gggccagatg gtaagccctc ccgtatcgta   7020
gttatctaca cgacggggag tcaggcaact atggatgaac gaaatagaca gatcgctgag   7080
ataggtgcct cactgattaa gcattggtaa ctgtcagacc aagtttactc atatatactt   7140
tagattgatt taaaacttca tttttaattt aaaaggatct aggtgaagat cctttttgat   7200
aatctcatga ccaaaatccc ttaacgtgag ttttcgttcc actgagcgtc agaccccgta   7260
gaaaagatca aaggatcttc ttgagatcct tttttctgc gcgtaatctg ctgcttgcaa   7320
acaaaaaaac caccgctacc agcggtggtt tgtttgccgg atcaagagct accaactctt   7380
tttccgaagg taactggctt cagcagagcg cagataccaa atactgttct tctagtgtag   7440
ccgtagttag gccaccactt caagaactct gtagcaccgc ctacatacct cgctctgcta   7500
atcctgttac cagtggctgc tgccagtggc gataagtcgt gtcttaccgg gttggactca   7560
agacgatagt taccggataa ggcgcagcgg tcgggctgaa cggggggttc gtgcacacag   7620
cccagcttgg agcgaacgac ctacaccgaa ctgagatacc tacagcgtga gctatgagaa   7680
agcgccacgc ttcccgaagg gagaaaggcg gacaggtatc cggtaagcgg cagggtcgga   7740
acaggagagc gcacgaggga gcttccaggg ggaaacgcct ggtatcttta tagtcctgtc   7800
gggtttcgcc acctctgact tgagcgtcga ttttgtgat gctcgtcagg ggggcggagc    7860
ctatggaaaa acgccagcaa cgcggccttt ttacggttcc tggcctttg ctggcctttt    7920
gctcacatgt                                                          7930
```

```
SEQ ID NO: 38        moltype = DNA   length = 7684
FEATURE              Location/Qualifiers
source               1..7684
                     mol_type = other DNA
                     organism = synthetic construct
SEQUENCE: 38
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact   120
aggggttcct cgcggcctcta gactcgaggc gttgacattg attattgact agttattaat   180
agtaatcaat tacggggtca ttagttcata gcccatatat ggagttccgc gttacataac   240
ttacggtaaa tggcccgcct ggctgaccgc ccaacgaccc cgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccaccccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catgccggca gctaagaaaa   780
agaaactgga tggcagcgtc gacatggaga ccaccatcaa caacagaatc ggcaagggc    840
agtactacac cgaggagagc aaggagttcc tggccgccta cttcaaccag gccatccaca   900
acgtgttcat cgtgctgaac cacatcgcca agagattcgg catggacgag ctgagcagcg   960
acgaggagct gaagaactgg ctgatcggca gacagagaga gaagaagaga aacgccatcg   1020
acagacagag attcctggag ctgatcgaca gacacttccc cttcctgaga atcgccaacg   1080
ccgacaagaa ggacgccaag agagagaacg acctggagga caacctggcc ctgctgatca   1140
ccctgctgaa cgacctgacc gagagaagaa acaagtacag cacgccatc acccacgcca   1200
gcatcgagag caacgacaga gagctggtgt ggagactgta cagcatctac gacgccaaca   1260
tcaacctggt gaagagagac tacttcgaga gcaacgtgca caccgagatc aacgaggacc   1320
cctacgagaa gcaggtggag cacctgagaa gattctgcat gaacaacgac agaaccaagg   1380
tggacgagaa gggcaagaag aagcccgcca tgcccaaccc cagattcaga accccttcc    1440
tgaacgccga gacaaaccag ctgagcatct acggcctggt gttcttcgtg agcctgttcc   1500
```

-continued

```
tggagaagaa gtacgccatc cagatgcaga agaacgtgta cggcctgaag gacgccagag   1560
acaccaagtt caagatgacc aacgaggtgt tctgcagaag cagaatcatc atgcccagag   1620
tgagactgca cagcgacaag agcaccgacg ccctggtgct ggacatgctg aacgagctgg   1680
ccaaggcccc cgaggtgctg ttcgaccagc tgaccgaccc cttcaaggag aagttctaca   1740
tcgcagagcat cgacagcctg gaggagagcg acatcatcac ccccgtgaga gccatcagaa   1800
agcagaacag attcatgtac ttcgccctga gatacctgga cgagagcaac gccttcagca   1860
agctgagatt ccagatcgac ctgggcaact accactacca cctgtacgag agcaagatca   1920
acgaccagac cgagagcaga cacctgacca gaaagctgtt cggcttcggc aagctgatcg   1980
ccttcgagca ggagttcgcc cccgaggagt ggaagatgaa gagcaaggac ctggactact   2040
acgagggcgc cacccagccc ttcatcgcca agacctaccc ccactaccac ctggaggaga   2100
acaagatcgg catcctgttc aacggccagg ccgaggtgca gtggccccac ctggacgtgg   2160
aggagcacga gagcttcccc aagtacaaga gaagagccaa cgagaaggcc gacgccttcc   2220
tgagcggcaa cgagctgctg gccgccgcct tctgccacca cctgtacgcc agcatcggca   2280
agcccaacac cgtggagaag atcatcagag acaagtacca cgccctgaga cagctgttca   2340
gcgacctgaa gagcggcaac ctgcagaacc tgctgggcga caacaccagc aacgaggcca   2400
tcagccagct gctgttcgag aagtacgac tgacccctgag cgaggtgccc gtgagactgc   2460
acgccttcct gagcggccag gagcaggccg acaccaaggc catcgccaga ggcaagctgg   2520
agctgatggc ccagcagaac aagaagagaa tcgagagatt cggcgccatg aagaaggccg   2580
tggtgaaggt gggcaaggcc cagtacagaa ccctgagaag cggcgacatc ggcgactggc   2640
tggtgagaga cttcatgaga ttccagccca tcggctacaa gagaaaccag gccggcaagc   2700
aggagcccga cctgaagagc aaggccaacc ccaagaagta ccagctgatc cagaagagcc   2760
tggccctgta cgagcaggag aagaacaacc tgctcaagag cttcaagagc tgcaacctgc   2820
tgagcagcga gaacgagcac cccttcctga acgaggtggt gcagagcatg cccgccacct   2880
ggcaggactt ctacgagaga tacctgcacg ccagaagcag attcctggag aagtgcatcg   2940
agaagggcat caagaagaac agctaccagg cctgctacga cttcctgaag atcaagcccc   3000
agctgaagga caaggagaag ctgtaccagg gctgggcgc ccagatgaac ctgcccacca   3060
acatgttcat cgacgccatc cacgactggt tcagacagac ccaccacgag agcctgagaa   3120
cctggttcac ccagcaggag aagcccacc agctgatcgg cctgatcaga aagtacatcg   3180
agctggccca caccgaccag atccagggct tctacgacat gttcccctg agatacgact   3240
tctacaagaa ggagttcccc aacggcctgg tgctgcacga gagaatcaac aagcagaagc   3300
agatctggga ggcccagctg atccagacca agaagagact ggaggacgcc gccagcaagc   3360
tgaagaaggt gaagcagcag gtggagagcc tgcccgacca ggagctgaga ttcagaaacg   3420
agacagaggc catggtgtac ttcaccaagc tgttcgacag cagcatcgtg aagaacgcca   3480
tcctgaagct gcagagagat cagaaggccc tgagagtgaa caccatcggc gagaagatca   3540
tcaagatcta caccgccaag tacgacgcca tccaccagga ggtgagagac ttcaagagca   3600
tgctgaccac cgagaagatg atcagaagag tgaaggccga ggactgcgtg accctgttca   3660
tgctgaccga cctgatgaac cagagccaga tcaccatcgg ccaggagcag agaaccatca   3720
agctgagcga catccagccc atgggcgaga cacagatcca gggcatcctg gacgccgtgc   3780
aggtgctgga gcagaagctg gacttcttca gcagcgacga gcagggcaag atcagccagg   3840
tgaagctggg cgagtggacc atcttcagca ccgacaccaa ggtgaagaag cagggcaact   3900
tcaagcagct gctgaaggac agaagattga acaacctggc ccactacatc ctgcccgaca   3960
tcgccggcgg cgccatcaga gtgagaagaa acctgctgga gatggagctg gaccagtacg   4020
acagaaacag aatccccatc atcaagctga tgtacgagct ggacaagagcc atctacaagg   4080
tggacccctt cagcgtggag ctgaagtaca agaagttcag ccagtgcctg agagagtacg   4140
cccagaaggc cgtgctggaa cgtggagcagg tggagcacct gaacgtgctg atcgccatca   4200
gaaacgccat catgcacaac cagtacccca acagagatca cctgaaggcc atcgtgccct   4260
tcaccgtgag cgagtacgcc cccgtgcagg agggcctgac catcgccaga cagctgtgga   4320
cctgcgccca ggtgagcgtg aacatcatcc tgagcaccat cagcaagttc gagacaggcg   4380
gcggcccccgg cggcggcgcc gccgccggca gcggcagccc taagaaaaaa cgaaaagttg   4440
gcagcggaag caaaaggccg gcggccacga aaaaggccgg ccaggcaaaa aagaaaaagc   4500
tcgagtaccc atacgatgtt ccagattacg cttgagaatt cccttgagc atctgacttc   4560
tggctaataa aggaaattta ttttcattgc aatagtgtgt tggaatttt tgtgtctctc   4620
aggtaccgag ggcctatttc ccatgattcc ttcatatttg catatacgat acaaggctgt   4680
tagagagata attggaatta atttgactgt aaacacaaag atattagtac aaaatacgtg   4740
acgtagaaag taataatttc ttgggtagtt tgcagtttta aaattatgtt ttaaaatgga   4800
ctatcatatg cttaccgtaa cttgaaagta tttcgatttc ttggctttat atatcttgtg   4860
gaaaggacga aacaccggag accacggcag gtctcagttg tgtgtgcctt tcaaattgaa   4920
ggcgttccca acttttttgc ggccgcagga acccctagtg atggagttgg ccactccctc   4980
tctgcgcgct cgctcgctca ctgaggccgg gcgaccaaag gtcgcccgac gcccgggctt   5040
tgcccgggcg gcctcagtga gcgagcgagc gcgcagctgc ctgcaggggc gcctgatgcg   5100
gtattttctc cttacgcatc tgtgcggtat ttcacaccgc atacgtcaaa gcaaccatag   5160
tacgcgccct gtagcggcgc attaagcgcg gcgggtgtgg tggttacgcg cagcgtgacc   5220
gctacacttg ccagcgccctt agcgcccgct cctttcgctt tcttcccttc ctttctcgcc   5280
acgttcgccg gctttccccg tcaagctcta aatcggggc tccctttagg gttccgattt   5340
agtgctttac ggcacctcga ccccaaaaaa cttgattTgg gtgatggttc acgtagtggg   5400
ccatcgccct gatagacggt ttttcgccct ttgacgttgg agtccacgtt ctttaatagt   5460
ggactcttgt tccaaactgg aacaacactc aactctatct cgggctattc ttttgattta   5520
taagggattt tgccgatttc ggtctattgg ttaaaaaatg agctgattta acaaaaattt   5580
aacgcgaatt ttaacaaaat attaacgttt acaatttgc ggtgcactct cagtacaatc   5640
tgctctgatg ccgcatagtt aagccagccc cgacacccgc caacacccgc tgacgcgccc   5700
tgacgggctt gtctgctccc ggcatccgct tacagacaag ctgtgaccgt ctccgggagc   5760
tgcatgtgtc agaggttttc accgtcatca ccgaaacgcg cgagacgaaa gggcctcgtg   5820
atacgcctat ttttataggt taatgtcatg ataataatgg tttcttagac gtcaggtggc   5880
acttttcggg gaaatgtgcg cggaacccct atttgtttat ttttctaaat acattcaaat   5940
atgtatccgc tcatgagaca ataaccctga taaatgcttc aataatattg aaaaaggaag   6000
agtatgagta ttcaacattt ccgtgtcgcc cttattccct tttttgcggc attttgcctt   6060
cctgtttttg ctcacccaga aacgctggtg aaagtaaaag atgctgaaga tcagttgggt   6120
gcacgagtgg gttacatcga actggatctc aacagcggta agatccttga gttttcgc   6180
cccgaagaac gttttccaat gatgagcact tttaaagttc tgctatgtgg cgcggtatta   6240
```

```
tcccgtattg acgccgggca agagcaactc ggtcgccgca tacactattc tcagaatgac 6300
ttggttgagt actcaccagt cacagaaaag catcttacgg atggcatgac agtaagagaa 6360
ttatgcagtg ctgccataac catgagtgat aacactgcgg ccaacttact tctgacaacg 6420
atcggaggac cgaaggagct aaccgctttt ttgcacaaca tgggggatca tgtaactcgc 6480
cttgatcgtt gggaaccgga gctgaatgaa gccataccaa acgacgagcg tgacaccacg 6540
atgcctgtag caatggcaac aacgttgcgc aaactattaa ctggcgaact acttactcta 6600
gcttcccggc aacaattaat agactggatg gaggcggata aagttgcagg accacttctg 6660
cgctcggccc ttccggctgg ctggtttatt gctgataaat ctggagccgg tgagcgtgga 6720
agccgcggta tcattgcagc actggggcca gatggtaagc cctcccgtat cgtagttatc 6780
tacacgacgg ggagtcaggc aactatggat gaacgaaata gacagatcgc tgagataggt 6840
gcctcactga ttaagcattg gtaactgtca gaccaagttt actcatatat actttagatt 6900
gatttaaaac ttcattttta atttaaaagg atctaggtga agatcctttt tgataatctc 6960
atgaccaaaa tcccttaacg tgagttttcg ttccactgag cgtcagaccc cgtagaaaag 7020
atcaaaggat cttcttgaga tccttttttt ctgcgcgtaa tctgctgctt gcaaacaaaa 7080
aaaccaccgc taccagcggt ggtttgtttg ccggatcaag agctaccaac tctttttccg 7140
aaggtaactg gcttcagcag agcgcagata ccaaatactg ttcttctagt gtagccgtag 7200
ttaggccacc acttcaagaa ctctgtagca ccgcctacat acctcgctct gctaatcctg 7260
ttaccagtgg ctgctgccag tggcgataag tcgtgtctta ccgggttgga ctcaagacga 7320
tagttaccgg ataaggcgca gcggtcgggc tgaacggggg gttcgtgcac acagcccagc 7380
ttggagcgaa cgacctacac cgaactgaga tacctacagc gtgagctatg agaaagcgcc 7440
acgcttcccg aagggagaaa ggcggacagg tatccggtaa gcggcagggt cggaacagga 7500
gagcgcacga gggagcttcc agggggaaac gcctggtatc tttatagtcc tgtcgggttt 7560
cgccacctct gacttgagcg tcgatttttg tgatgctcgt caggggggcg gagcctatgg 7620
aaaaacgcca gcaacgcggc cttttttacgg ttcctggcct tttgctggcc ttttgctcac 7680
atgt 7684
```

```
SEQ ID NO: 39              moltype = DNA   length = 6909
FEATURE                    Location/Qualifiers
source                     1..6909
                           mol_type = other DNA
                           organism = synthetic construct
SEQUENCE: 39
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggcctcta gactcgaggc gttgacattg attattgact agttattaat 180
agtaatcaat tacggggtca ttagttcata gcccatatat ggagttccgc gttacataac 240
ttacggtaaa tggcccgcct ggctgaccgc ccaacgaccc ccgcccattg acgtcaataa 300
tgacgtatgt tcccatagta acgccaatag ggactttcca ttgacgtcaa tgggtggagt 360
atttacggta aactgcccac ttggcagtac atcaagtgta tcatatgcca agtacgcccc 420
ctattgacgt caatgacggt aaatggcccg cctggcatta tgcccagtac atgaccttat 480
gggactttcc tacttggcag tacatctacg tattagtcat cgctattacc atggtgatgc 540
ggttttggca gtacatcaat gggcgtggat agcggtttga ctcacgggga tttccaagtc 600
tccaccccat tgacgtcaat gggagtttgt tttggcacca aaatcaacgg gactttccaa 660
aatgtcgtaa caactccgcc ccattgacgc aaatgggcgg taggcgtgta cggtgggagg 720
tctatataag cagagctctc tggctaacta ccggtgccac catgccggca gctaagaaaa 780
agaaactgga tggcagcgtc gacatgatgg gcaacaagaa gagcgtggcc aaggccaacg 840
gcctgaagag caccttcgtg ctgggcgaga acaccgccta catgaccagc ttcggcagag 900
gcaacgccgc ccagcccgag aagcacatca gagacgccac cgtgaccgac atccagcaca 960
ccttcagagc caagaccgac ggcggcagaa ccgtgcacat cgagggcaga gtgggcgcca 1020
gcgacgtgct gctgcccgac gccgccaacc agctgcacgc caaggacgcc gtggagcaga 1080
tgtacttcgg caaggccttc agcgacaaca tccacatcca gatcgcctac aacatcatgg 1140
acatcaagaa gatcttcggc gtgtacgcca acatcatcgt gcacaccgtg aacaacctgt 1200
gctgcgacgg cgacaagcag gacgacttcc tgggcatgtt caagacccag aacagatacc 1260
aggtggccgc ctgggcccac aagatcgtga gcctgcacct ggtgaagaac gagctgagag 1320
gcggcggctt cttcatggac caggaggtgt ggagagccca cgtgagaacc gacttcaaga 1380
gcctgaacct ggccgtgaac gccttcatga gaagtaccc ccagaagtac ccctactgga 1440
gcgtgaagat cgtgagcgac ttcatcgtgc aggagatggg catcaagaac aaggtgatcc 1500
tggagaaggc cgccgagagc tacgccgagt tcgagacagt ggccaagaga ctggagaaga 1560
gcgcctacta cttcagcgac atcttcgccg gcaaggacgg caagttcgac gagcagaagg 1620
ccttcgacct gctgagagtg ctgggcatga tgagacaaga ggccttccac gagaagaaca 1680
gcagcgccag ctggctgtac aacctggacg ccgaggccga cgaggacatc aaggccgccc 1740
tgagaacgt ggtggacacc aaggtgaacg gcatcaacac caacttcgcc aagcagaaca 1800
aggtgaacct gctggtgctg caggagatct accccccaga gagcaaggcc gacctggtga 1860
gagagtacta cgacttcagc gtgagaaagg ccttcaagaa cctgggcttc agcgtgaaca 1920
ccctgagaga cacaatgtgc gccttcgacg ccgccagcgt gatcaccgac aagcagtacg 1980
acaccgtgag aggcaagctg tacagcctgt tcgacttcgt gatctacaac tactgcctgg 2040
agaacgaggc cgtgtgcaac gccttcgtgg aggagctgag agccaacctg accccgaga 2100
acaagaccgc cctgtaccag accctggccg agaaggtgtg gggcgagatc ggcgacatcg 2160
tgctgcagag aatcctgccc cagatgcacg ccaagaagat ccaggagaga agcaaggagg 2220
cagacgccga gacagtggag atgcagggct acgtgcaggc ccccaaggac ctgagcctgt 2280
tcagcaaggc cgtgtactgc atcagcatgt cctggacgg caaggagatc aacagcttcc 2340
tgagcgccct gatcaacaag ttcgagaaca tcagcagcct gtgcgccgtg ctggcctaca 2400
acggcctgga gcccgagttc gtggccccct tcaccttctt cgccgacagc caggccatcg 2460
ccgaggacct gagatacatc aagagcatca cagagatcga caaggcaagg gacaggccacca 2520
aggacagccc cgtgaccgtg aaggagatgc agtacttcga cgccgccgcc gtgctgggcg 2580
agacagacac cgagaaggtg aaggccgcct tccacctggg cgacaagagc gccagcaccg 2640
ccgacaaggc cttcagaaac ttcgtggtga caacgtgat caacagcaac agattcgtgt 2700
acgtggtgag attcatcaac cccaagaacg ccagagagat catgcagaac agagccctga 2760
tcgccttcgt gctgaaggac atcccccaga gccagctggt gagatactgc ggcaccgccg 2820
```

-continued

```
gcatcgcctg caacgccgac gagcccaaca ccgaggccat ggtgaacgcc ctggccgaca   2880
tgctgctgca ggtgagattc gacgccttca gcaacgtgca gcagaaggtg aaggccgaca   2940
gcgccgaggc cgtgcagaag gagaagtaca aggccatcat cggcctgtac ctgaccgtgc   3000
tgtacctgct ggtgaaaacc ctggtgaaga tcaacatgaa ctacgccatc gccttcggca   3060
tcctggagag agactgccag atcatgaacc agaagcaccg caagaacccc aagagagaca   3120
gagacgcctt ctacatgaga gagcagcaga acaagcagta cgtgtacaac gccagagcca   3180
tcaccgagct gttcatcgag aacggctggc tgaacaagag agtgcagaag agcgtggaga   3240
acaacgccgc cctgtacagc gacgaggcct tctacaagta cagaaacctg gtggcccacc   3300
tgaacgtgat cagcgccctg cccaagtacg ccaagaacat caccaaggtg aagagcctgt   3360
tcgacgtgta ccactacatc ctgttcctga gcctgtgcga ggacaagtac agcaacctgc   3420
ccgaggccgt gaccaagagc ctgtgcaaga acggcaagac catgctggag aacgccagag   3480
agtaccagac cgtgtgcaag gacttcctgt acggcctgaa cacccccttc gcctacaacg   3540
ccgccagata catcaacctg agcaacagag agaagttcct ggccggcttc ggcaagacag   3600
gcggcggccc cggcggcggc gccgccgccg gcagcggcag ccctaagaaa aaacgaaaag   3660
ttggcagcgg aagcaaaagg ccggcggcca cgaaaaaggc cggccaggca aaaaagaaaa   3720
agctcgagta cccatacgat gttccagatt acgcttgaga attcccccttg agcatctgac   3780
ttctggctaa taaaggaaat ttattttcat tgcaatagtg tgttggaatt ttttgtgtct   3840
ctcaggtacc gagggcctat ttcccatgat tccttcatat ttgcatatac gatacaaggc   3900
tgttagagag ataattggaa ttaatttgac tgtaaacaca aagatattag tacaaaatac   3960
gtgacgtaga aagtaataat ttcttgggta gtttgcagtt ttaaaattat gttttaaaat   4020
ggactatcat atgcttaccg taacttgaaa gtatttcgat ttcttggctt tatatatctt   4080
gtggaaagga cgaaacaccg ggtttacac ccgtgtaaaa ctacacagtt ctaaaacgga   4140
gaccacggca ggtctcattt tttgcggccg caggaacccc tagtgatgga gttggccact   4200
ccctctctgc gcgctcgctc gctcactgag gccgggcgac caaaggtcgc ccgacgcccg   4260
ggctttgccc gggcggcctc agtgagcgag cgagcgcgca gctgcctgca ggggcgcctg   4320
atgcggtatt ttctccttac gcatctgtgc ggtatttcac accgcatacg tcaaagcaac   4380
catagtacgc gccctgtagc ggcgcattaa gcgcggcggg tgtggtggtt acgcgcagcg   4440
tgaccgctac acttgccagc gccttagcgc ccgctccttt cgctttcttc ccttcctttc   4500
tcgccacgtt cgccggcttt ccccgtcaag ctctaaatcg gggctccct ttagggttcc   4560
gatttagtgc tttacggcac ctcgacccca aaaaacttga tttgggtgat ggttcacgta   4620
gtgggccatc gccctgatag acggtttttc gccctttgac gttggagtcc acgttcttta   4680
atagtggact cttgttccaa actggaacaa cactcaactc tatctcgggc tattcttttg   4740
atttataagg gattttgccg atttcggtct attggttaaa aaatgagctg atttaacaaa   4800
aatttaacgc gaattttaac aaaatattaa cgtttacaat tttatggtgc actctcagta   4860
caatctgctc tgatgccgca tagttaagcc agccccgaca cccgccaaca cccgctgacg   4920
cgccctgacg ggcttgtctg ctcccggcat ccgcttacag acaagctgtg accgtctccg   4980
ggagctgcat gtgtcagagg ttttcaccgt catcaccgaa acgcgcgaga cgaaagggcc   5040
tcgtgatacg cctatttta taggttaatg tcatgataat aatggtttct tagacgtcag   5100
gtggcactt tcggggaaat gtgcgcggaa ccctatttg tttattttc taaatacatt   5160
caaatatgta tccgctcatg agacaataac cctgataaat gcttcaataa tattgaaaaa   5220
ggaagagtat gagtattcaa catttccgtg tcgcccttat tccctttttt gcggcatttt   5280
gccttcctgt ttttgctcac ccagaaacgc tggtgaaagt aaaagatgct gaagatcagt   5340
tgggtgcacg agtgggttac atcgaactgg atctcaacag cggtaagatc cttgagagtt   5400
ttcgccccga agaacgtttt ccaatgatga gcacttttaa agttctgcta tgtggcgcgg   5460
tattatcccg tattgacgcc gggcaagagc aactcggtcg ccgcatacac tattctcaga   5520
atgacttggt tgagtactca ccagtcacag aaaagcatct tacggatggc atgacagtaa   5580
gagaattatg cagtgctgcc ataaccatga gtgataacac tgcggccaac ttacttctga   5640
caacgatcgg aggaccgaag gagctaaccg cttttttgca caacatgggg gatcatgtaa   5700
ctcgccttga tcgttgggaa ccggagctga atgaagccat accaaacgac gagcgtgaca   5760
ccacgatgcc tgtagcaatg gcaacaacgt tgcgcaaact attaactggc gaactactta   5820
ctctagcttc ccggcaacaa ttaatagact ggatggaggc ggataaagtt gcaggaccac   5880
ttctgcgctc ggcccttccg gctggctggt ttattgctga taaatctgga gccggtgagc   5940
gtggaagccg cggtatcatt gcagcactgg ggccagatgg taagccctcc cgtatcgtag   6000
ttatctacac gacggggagt caggcaacta tggatgaacg aaatagacag atcgctgaga   6060
taggtgcctc actgattaag cattggtaac tgtcagacca agtttactca tatatacttt   6120
agattgattt aaaacttcat ttttaattta aaaggatcta ggtgaagatc ctttttgata   6180
atctcatgac caaaatccct taacgtgagt tttcgttcca ctgagcgtca gaccccgtag   6240
aaaagatcaa aggatcttct tgagatcctt ttttctgcg cgtaatctgc tgcttgcaaa   6300
caaaaaaacc accgctacca gcggtggttt gtttgccgga tcaagagcta ccaactcttt   6360
ttccgaaggt aactggcttc agcagagcgc agataccaaa tactgttctt ctagtgtagc   6420
cgtagttagg ccaccacttc aagaactctg tagcaccgcc tacatacctc gctctgctaa   6480
tcctgttacc agtggctgct gccagtggcg ataagtcgtg tcttaccggg ttggactcaa   6540
gacgatagtt accggataag gcgcagcggt cgggctgaac ggggggttcg tgcacacagc   6600
ccagcttgga gcgaacgacc tacaccgaac tgagatacct acagcgtgag ctatgagaaa   6660
gcgccacgct tcccgaaggg agaaaggcgg acaggtatcc ggtaagcggc agggtcggaa   6720
caggagagcg cacgagggag cttccagggg gaaacgcctg gtatctttat agtcctgtcg   6780
ggtttcgcca cctctgactt gagcgtcgat ttttgtgatg ctcgtcaggg gggcggagcc   6840
tatggaaaaa cgccagcaac gcggcctttt tacggttcct ggccttttgc tggccttttg   6900
ctcacatgt                                                           6909
```

```
SEQ ID NO: 40          moltype = DNA  length = 7102
FEATURE                Location/Qualifiers
source                 1..7102
                       mol_type = other DNA
                       organism = synthetic construct
SEQUENCE: 40
cctgcaggca gctgcgcgct cgctcgctca ctgaggccgc ccgggcgtcg ggcgaccttt   60
ggtcgcccgg cctcagtgag cgagcagcg cgcagagagg gagtggccaa ctccatcact   120
aggggttcct gcggcctcta gactcgaggc gttgacattg attattgact agttattaat   180
```

-continued

```
agtaatcaat tacggggtca ttagttcata gcccatatat ggagttccgc gttacataac   240
ttacggtaaa tggcccgcct ggctgaccgc ccaacgaccc ccgcccattg acgtcaataa   300
tgacgtatgt tcccatagta acgccaatag ggactttcca ttgacgtcaa tgggtggagt   360
atttacggta aactgcccac ttggcagtac atcaagtgta tcatatgcca agtacgcccc   420
ctattgacgt caatgacggt aaatggcccg cctggcatta tgcccagtac atgaccttat   480
gggactttcc tacttggcag tacatctacg tattagtcat cgctattacc atggtgatgc   540
ggttttggca gtacatcaat gggcgtggat agcggtttga ctcacgggga tttccaagtc   600
tccacccccat tgacgtcaat gggagtttgt tttggcacca aaatcaacgg gactttccaa   660
aatgtcgtaa caactccgcc ccattgacgc aaatgggcgg taggcgtgta cggtgggagg   720
tctatataag cagagctctc tggctaacta ccggtgccac catgagcccc aagaagaaga   780
gaaaggtgga ggccagcatc gaaaaaaaaa agtccttcgc caagggcatg ggcgtgaagt   840
ccacactcgt gtccggctcc aaagtgtaca tgacaacctt cgccgaaggc agcgacgcca   900
ggctggaaaa gatcgtggag ggcgacagca tcaggagcgt gaatgagggc gaggccttca   960
gcgctgaaat ggccgataaa aacgccggct ataagatcgg caacgccaaa ttcagccatc   1020
ctaagggcta cgccgtggtg gctaacaacc ctctgtatac aggacccgtc cagcaggata   1080
tgctcggcct gaaggaaact ctggaaaaga ggtacttcgg cgagagcgct gatggcaatg   1140
acaatatttg tatccaggtg atccataaca tcctggacat tgaaaaaatc ctcgccgaat   1200
acattaccaa cgccgcctac gccgtcaaca atatctccgg cctggataag gacattattg   1260
gattcggcaa gttctccaca gtgtatacct acgacgaatt caaagacccc gagcaccata   1320
gggccgcttt caacaataac gataagctca tcaacgccat caaggcccag tatgacgagt   1380
tcgacaactt cctcgataac cccagactcg gctatttcgg ccaggccttt ttcagcaagg   1440
agggcagaaa ttacatcatc aattacggca acgaatgcta tgacattctg gccctcctga   1500
gcggactgag gcactggtg gtccataaca acgaagaaga gtccaggatc tccaggacct   1560
ggctctacaa cctcgataag aacctcgaca acgaatacat ctccaccctc aactacctct   1620
acgacaggat caccaatgag ctgaccaact ccttctccaa gaactccgcc gccaacgtga   1680
actatattgc cgaaactctg ggaatcaacc ctgccgaatt cgccgaacaa tatttcagat   1740
tcagcattat gaaagagcag aaaaaacctcg gattcaatat caccaagctc agggaagtga   1800
tgctggacag gaaggatatg tccgagatca ggaaaaatca taaggtgttc gactccatca   1860
ggaccaaggt ctacaccatg atggactttg tgatttatag gtattacatc gaagaggatg   1920
ccaaggtggc tgccgccaat aagtccctcc ccgataatga gaagtccctg agcgagaagg   1980
atatctttgt gattaacctg aggggctcct tcaacgacga ccagaaggat gccctctact   2040
acgatgaagc taatagaatt tggagaaagc tcgaaaatat catgcacaac atcaaggaat   2100
ttagggaaa caagacaaga gagtataaga agaaggacgc ccctagactg cccagaatcc   2160
tgcccgctgg ccgtgatgtt tccgccttca gcaaactcat gtatgccctg accatgttcc   2220
tggatggcaa ggagatcaac gacctcctga caccacctgat taataaattc gataacatcc   2280
agagcttcct gaaggtgatg cctctcatcg gagtcaacgc taagttcgtg gaggaatacg   2340
ccttttttcaa agactccgcc aagatcgccg atgagctgag gctgatcaag tccttcgcta   2400
gaatgggaga acctattgcc gatgccagga gggccatgta tatcgacgcc atccgtatttt   2460
taggaaccaa cctgtcctat gatgagctca aggcctccgc cgacaccttt ccctggacg   2520
agaacgaaa caagctcaag aaaggcaagc acggcatgag aaatttcatt attaataacg   2580
tgatcagcaa taaaaggttc cactacctga tcagatacgg tgatcctgcc cacctccatg   2640
agatcgccaa aaacgaggcc gtggtgaagt tcgtgctcgg caggatcgct gacatccaga   2700
aaaaacaggg ccagaacggc aagaaccaga tcgacaggta ctacgaaact tgtatcggaa   2760
aggataaggg caagagcgtg agcgaaaagg tggacgctct cacaaagatc atcaccggaa   2820
tgaactacga ccaattcgac aagaaaagga gcgtcattga ggacaccggc agggaaaacg   2880
ccgagaggga gaagtttaaa aagatcatca gcctgtacct caccgtgatc taccacatcc   2940
tcaagaatat tgtcaatatc aacgccaggt acgtcatcgg attccattgc gtcgagcgtg   3000
atgctcaact gtacaaggag aaaggctacg acatcaatct caagaaactg gaagagaagg   3060
gattcagctc cgtcaccaag ctctgcgctg gcattgatga aactgcccc gataagagaa   3120
aggacgtgga aaaggagatg gctgaaagag ccaaggagag cattgacagc ctcgagagcg   3180
ccaaccccaa gctgtatgcc aattacatca aatacagcg cgagaagaaa gccgaggagt   3240
tcaccaggca gattaacagg gagaaggcca aaaccgccct gaacgcctac ctgaggaaca   3300
ccaagtggaa tgtgatcatc agggaggacc tcctgagaat tgacaacaag acatgtaccc   3360
tgttcagaaa caaggccgtc cacctggaag tggccaggta tgtccacgcc tatatcaacg   3420
acattgccga ggtcaattcc tacttccaac tgtaccatta catcatgcag agaattatca   3480
tgaatgagag gtacgagaaa agcagcggaa aggtgtccga gtacttcgac gctgtgaatg   3540
acgagaagaa gtacaacgat aggctcctga aactgctgtg tgtgcctttc ggctactgta   3600
tcccccaggtt taagaacctg agcatcgagg ccctgttcga taggaacgag gccgccaagt   3660
tcgacaagga gaaaaagaag gtgtccggca attccggatc cggacctaag aaaaagagga   3720
aggtggcggc cgcttaccca tacgatgttc cagattacgc ttgaggtacc ctagagctcg   3780
ctgatcagcc tcgactgtgc cttctagttg ccagccatct gttgtttgcc cctccccgt   3840
gccttccttg accctggaag gtgccactcc cactgtcctt tcctaataaa atgaggaaat   3900
tgcatcgcat tgtctgagta ggtgtcattc tattctgggg ggtggggtgg ggcaggacag   3960
caagggggag gattgggaag agaatagcag gcatgctggg gagggggcct atttcccatg   4020
attccttcat atttgcatat acgatacaag gctgttagag agataattgg aattaatttg   4080
actgtaaaca caaagatatt agtacaaaat acgtgacgta gaaagtaata atttcttggg   4140
tagtttgcag ttttaaaatt atgttttaaa atggactatc atatgcttac cgtaacttga   4200
aagtatttcg atttcttggc tttatatatc ttgtggaaag gacgaaacac cgcaagtaaa   4260
cccctaccaa ctggtcgggg tttgaaacgg gtcttcggga agaccctcaag taaacccccta   4320
ccaactggtc ggggtttgaa acttttttttc ccgggaatgg ccgcaggaac ccctagtgat   4380
ggagttggcc actccctctc tgcgcgctcg ctcgctcact gaggccgggc gaccaaaggt   4440
cgcccgacgc ccgggctttg cccgggcggc ctcagtgagc gagcgagcgc gcagctgcct   4500
gcagggggcgc ctgatgcggt attttctcct tacgcatctg tgcggtattt cacaccgcat   4560
acgtcaaagc aaccatagta cgcgccctgt agcggcgcat aacgcgggt gggtgtggtg   4620
gttacgcgca gcgtgaccgc tacacttgcc agcgccctag cgcccgctcc tttcgctttc   4680
ttcccttcct ttctcgccac gttcgccggc tttccccgtc aagctctaaa tcggggggctc   4740
cctttagggt tccgatttag tgctttacgg cacctcgacc ccaaaaaact tgatttgggt   4800
gatggttcac gtagtgggcc atcgccctga tagacggttt ttcgcccttt gacgttggag   4860
tccacgttct ttaatagtgg actcttgttc caaactggaa caacactcaa ccctatctcg   4920
```

```
ggctattctt ttgatttata agggattttg ccgatttcgg cctattggtt aaaaaatgag   4980
ctgatttaac aaaaatttaa cgcgaatttt aacaaaatat taacgtttac aattttatgg   5040
tgcactctca gtacaatctg ctctgatgcc gcatagttaa gccagccccg acacccgcca   5100
acacccgctg acgcgccctg acgggcttgt ctgctcccgg catccgctta cagacaagct   5160
gtgaccgtct ccgggagctg catgtgtcag aggttttcac cgtcatcacc gaaacgcgcg   5220
agacgaaagg gcctcgtgat acgcctattt ttataggtta atgtcatgat aataatggtt   5280
tcttagacgt caggtggcac ttttcgggga aatgtgcgcg gaaccccctat ttgtttattt   5340
ttctaaatac attcaaatat gtatccgctc atgagacaat aaccctgata aatgcttcaa   5400
taatattgaa aaaggaagag tatgagtatt caacatttcc gtgtcgccct tattcccttt   5460
tttgcggcat tttgccttcc tgtttttgct cacccagaaa cgctggtgaa agtaaaagat   5520
gctgaagatc agttgggtgc acgagtgggt tacatcgaac tggatctcaa cagcggtaag   5580
atccttgaga gttttcgccc cgaagaacgt tttccaatga tgagcacttt taaagttctg   5640
ctatgtggcg cggtattatc ccgtattgac gccgggcaag agcaactcgg tcgccgcata   5700
cactattctc agaatgactt ggttgagtac tcaccagtca cagaaaagca tcttacggat   5760
ggcatgacag taagagaatt atgcagtgct gccataacca tgagtgataa cactgcggcc   5820
aacttacttc tgacaacgat cggaggaccg aaggagctaa ccgctttttt gcacaacatg   5880
ggggatcatg taactcgcct tgatcgttgg gaaccggagc tgaatgaagc cataccaaac   5940
gacgagcgtg acaccacgat gcctgtagca atggcaacaa cgttgcgcaa actattaact   6000
ggcgaactac ttactctagc ttcccggcaa caattaatag actggatgga ggcggataaa   6060
gttgcaggac cacttctgcg ctcggccctt ccggctggct ggtttattgc tgataaatct   6120
ggagccggtg agcgtggaag ccgcggtatc attgcagcac tggggccaga tggtaagccc   6180
tcccgtatcg tagttatcta cacgacgggg agtcaggcaa ctatggatga acgaaataga   6240
cagatcgctg agataggtgc ctcactgatt aagcattggt aactgtcaga ccaagtttac   6300
tcatatatac tttagattga tttaaaactt cattttttaat ttaaaaggat ctaggtgaag   6360
atccttttttg ataatctcat gaccaaaatc ccttaacgtg agttttcgtt ccactgagcg   6420
tcagaccccg tagaaaagat caaaggatct cttgagatcc tttttttctt gcgcgtaatc   6480
tgctgcttgc aaacaaaaaa accaccgcta ccagcggtgg tttgtttgcc ggatcaagag   6540
ctaccaactc tttttccgaa ggtaactggc ttcagcagag cgcagatacc aaatactgtc   6600
cttctagtgt agccgtagtt aggccaccac ttcaagaact ctgtagcacc gcctacatac   6660
ctcgctctgc taatcctgtt accagtggct gctgccagtg gcgataagtc gtgtcttacc   6720
gggttggact caagacgata gttaccggat aaggcgcagc ggtcgggctg aacggggggt   6780
tcgtgcacac agcccagctt ggagcgaacg acctacaccg aactgagata cctacagcgt   6840
gagctatgag aaagcgccac gcttcccgaa gggagaaagg cggacaggta ccggtaagc   6900
ggcagggtcg gaacaggaga gcgcacgagg gagcttccag ggggaaacgc ctggtatctt   6960
tatagtcctg tcgggtttcg ccacctctga cttgagcgtc gatttttgtg atgctcgtca   7020
ggggggcgga gcctatggaa aaacgccagc aacgcggcct ttttacggtt cctggccttt   7080
tgctggcctt ttgctcacat gt                                           7102
```

```
SEQ ID NO: 41            moltype = DNA  length = 9363
FEATURE                  Location/Qualifiers
source                   1..9363
                         mol_type = other DNA
                         organism = synthetic construct
SEQUENCE: 41
gtcgacggat cgggagatct cccgatcccc tatggtgcac tctcagtaca atctgctctg   60
atgccgcata gttaagccag tatctgctcc ctgcttgtgt gttggaggtc gctgagtagt   120
gcgcgagcaa aatttaagct acaacaaggc aaggcttgac cgacaattgc atgaagaatc   180
tgcttagggt taggcgtttt gcgctgcttc gcgatgtacg ggccagatat acgcgttgac   240
attgattatt gactagttat taatagtaat caattacggg gtcattagtt catagcccat   300
atatggagtt ccgcgttaca taacttacgg taaatggccc gcctggctga ccgcccaacg   360
acccccgccc attgacgtca ataatgacgt atgttcccat agtaacgcca atagggactt   420
tccattgacg tcaatgggtg gagtatttac ggtaaactgc ccacttggca gtacatcaag   480
tgtatcatat gccaagtacg ccccctattg acgtcaatga cggtaaatgg cccgcctggc   540
attatgccca gtacatgacc ttatgggact ttcctacttg gcagtacatc tacgtattag   600
tcatcgctat taccatggtg atgcggtttt ggcagtacat caatgggcgt ggatagcggt   660
ttgactcacg gggatttcca agtctccacc ccattgacgt caatgggagt ttgttttggc   720
accaaaatca acgggacttt ccaaaatgtc gtaacaactc cgccccattg acgcaaatgg   780
gcggtaggcg tgtacggtgg gaggtctata taccagatct gagcctggga gctctctggc   840
taactaggga acccactgct taagcctcaa taaagcttgc cttgagtgct tcaagtagtg   900
tgtgcccgtc tgttgtgtga ctctggtaac tagagatccc tcagaccctt ttagtcagtg   960
tggaaaatct ctagcagtgg cgcccgaaca gggacttgaa agcgaaaggg aaaccagagg   1020
agctctctcg acgcaggact cggcttgctg aagcgcgcac ggcaagaggc gaggggcggc   1080
gactggtgag tacgccaaaa attttgacta gcggaggcta aggagagaga tgggtgcg    1140
agagcgtcag tattaagcgg gggagaatta gatcgcgatg ggaaaaaatt cggttaaggc   1200
caggggggaaa gaaaaaatat aaataaacat atagtatggg caagcaggga gctagaacga   1260
ttcgcagtta atcctggcct gttagaaaca tcagaaggct gtagacaaat actgggacag   1320
ctacaaccat cccttcagac aggatcagaa gaacttagat cattatataa tacagtagca   1380
accctctatt gtgtgcatca aaggatagag ataaaagaca ccaaggaagc tttagacaag   1440
atagaggaag agcaaaacaa agtaagacc accgcacagc aagcggccgg ccgcgctgat   1500
cttcagacct ggaggaggag atatgaggga caattggaga agtgaattat ataaatataa   1560
agtagtaaaa attgaaccat taggagtagc acccaccaag gcaaagagaa gagtggtgca   1620
gagagaaaaa agagcagtgg aataggagc tttgttcctt gggttcttgg gagcagcagg   1680
aagcactatg ggcgcagcgt caatgacgct gacggtacag gccagacaat tattgtctgg   1740
tatagtgcag cagcagaaca atttgctgag ggctattgcg gcgcaacagc atctgttgca   1800
actcacagtc tggggcatca agcagctcca ggcaagaatc ctggctgtgg aaagatacct   1860
aaaggatcaa cagctcctgg ggatttgggg ttgctctgga aaactcattt gcaccactgc   1920
tgtgccttgg aatgctagtt ggagtaataa atctctggaa cagatttgga tcacacgac    1980
ctggatggag tgggacagag aaattaacaa ttacacaagc ttaatacact ccttaattga   2040
agaatcgcaa aaccagcaag aaaagaatga acaagaatta ttggaattag ataaatgggc   2100
```

```
aagtttgtgg aattggttta acataacaaa ttggctgtgg tatataaaat tattcataat  2160
gatagtagga ggcttggtag gtttaagaat agttttttgct gtactttcta tagtgaatag  2220
agttaggcag ggatattcac cattatcgtt tcagacccac ctcccaaccc cgaggggacc  2280
cgacaggccc gaaggaatag aagaagaagg tggagagaga gacagagaca gatccattcg  2340
attagtgaac ggatcggcac tgcgtgcgcc aattctgcag acaaatggca gtattcatcc  2400
acaattttaa aagaaaaggg gggattgggg ggtacagtgc aggggaaaga atagtgagaca  2460
taatagcaac agacatacaa actaaagaat tacaaaaaca aattacaaaa attcaaaatt  2520
ttcgggttta ttacagggac agcagagatc cagtttggtt agtaccgggc ccgctctagc  2580
gtcgaggagg ttggcccatt gcatacgttg tatccatatc ataatatgta catttatatt  2640
ggctcatgtc caacattacc gccatgttga cattgattat tgactagtta ttaatagtaa  2700
tcaattacgg ggtcattagt tcatagccca tatatggagt tccgcgttac ataacttacg  2760
gtaaatggcc cgcctggctg accgcccaac gaccccgcc cattgacgtc aataatgacg  2820
tatgttccca tagtaacgcc aatagggact ttccattgac gtcaatgggt ggagtattta  2880
cggtaaactg cccacttggc agtacatcaa gtgtatcata tgccaagtac gccccctatt  2940
gacgtcaatg acggtaaatg gcccgcctgg cattatgccc agtacatgac cttatgggac  3000
tttcctactt ggcagtacat ctacgtatta gtcatcgcta ttaccatggt gatgcggttt  3060
tggcagtaca tcaatgggcg tggatagcgg tttgactcac ggggatttcc aagtctccac  3120
cccattgacg tcaatgggag tttgttttgg caccaaaatc aacgggactt tccaaaatgt  3180
cgtaacaact ccgccccatt gacgcaaatg ggcggtaggc gtgtacggtg ggaggtctat  3240
ataagcagag ctcgtttagt gaaccgtcag atcgcctgga gacgccatcc acgctgtttt  3300
gacctccata gaagacaccg ggaccgatcc agcctccgcg gccccgaatt cgccaccatg  3360
gccagcgagt tcaagaagaa gctcttctgg agggcagtgg tggccgagtt cctggccacg  3420
accctctttg tcttcatcag catcggttct gccctgggct tcaaataccc ggtggggaac  3480
aaccagacgg cggtccagga caacgtgaag gtgtcgctgg ccttcgggct gagcatcgcc  3540
acgctggcgc agagtgtggg ccacatcagc ggcgcccacc tcaacccggc tgtcacactg  3600
gggctgctgc tcagctgcca gatcagcatc ttccgtgccc tcatgtacat catcgcccag  3660
tgcgtggggg ccatcgtcgc caccgccatc ctctcaggca tcacctcctc cctgactggg  3720
aactcgcttg gccgcaatga cctggctgat ggtgtgaact cgggccaggg cctgggcatc  3780
gagatcatcg ggaccctcca gctggtgcta tgcgtgctgg ctactaccga ccggaggcgc  3840
cgtgaccttg gtggctcagc ccccccttgcc atcggcctct ctgtagccct tggacacctc  3900
ctggctattg actacactgg ctgtgggatt aaccctgctc ggtcctttgg ctccgcggtg  3960
atcacacaca acttcagcaa ccactggatt ttctgggtgg ggccattcat cggggggagcc  4020
ctggctgtac tcatctacga cttcatcctg gccccacgca gcagtgacct cacagaccgc  4080
gtgaaggtgt ggaccagcgg ccaggtggag gagtatgacc tggatgccga cgacatcaac  4140
tccagggtgg agatgaagcc caaatacccca tacgatgttc cagattacgc tggatccgct  4200
agcggcagtg gagagggcag aggaagtctg ctaacatgcg gtgacgtcga ggagaatcct  4260
ggcccagtga gcaagggcga ggagctgttc accggggtgg tgcccatcct ggtcgagctg  4320
gacggcgacg taaacggcca caagttcagc gtgtccggcg agggcgaggg cgatgccacc  4380
tacggcaagc tgaccctgaa gttcatctgc accaccggca agctgcccgt gccctggccc  4440
accctcgtga ccaccctgac ctacggcgtg cagtgcttca gccgctaccc cgaccacatg  4500
aagcagcacg acttcttcaa gtccgccatg cccgaaggct acgtccagga gcgcaccatc  4560
ttcttcaagg acgacggcaa ctacaagacc cgcgccgagg tgaagttcga gggcgacacc  4620
ctggtgaacc gcatcgagct gaagggcatc gacttcaagg aggacggcaa catcctgggg  4680
cacaagctgg agtacaacta caacagccac aacgtctata tcatggccga caagcagaag  4740
aacggcatca aggtgaactt caagatccgc cacaacatcg aggacggcag cgtgcagctc  4800
gccgaccact accagcagaa cacccccatc ggcgacggcc ccgtgctgct gcccgacaac  4860
cactacctga gcacccagtc cgccctgagc aaagacccca acgagaagcg cgatcacatg  4920
gtcctgctgg agttcgtgac cgccgccggg atcactctcg gcatggacga gctgtacaag  4980
taaggatcct aggcggccgc gcatgccctg caggtgatct atcgatcggc cggcccctct  5040
ccctcccccc cccctaacg ttactggccg aagccgcttg gaataaggcc ggtgtgcgtt  5100
tgtctatatg ttattttcca ccatattgcc gtcttttggc aatgtgaggg cccggaaacc  5160
tggccctgtc ttcttgacga gcattcctag gggtctttcc cctctcgcca aaggaatgca  5220
aggtctgttg aatgtcgtga aggaagcagt tcctctggaa gcttcttgaa gacaaacaac  5280
gtctgtagcg accctttgca ggcagcggaa ccccccacct ggcgacaggt gcctctgcgg  5340
ccaaaagcca cgtgtataag atacacctgc aaaggcggca caacccccagt gccacgttgt  5400
gagttggata gttgtggaaa gagtcaaatg gctctcctca agcgtattca acaaggggct  5460
gaaggatgcc cagaaggtac cccattgtat gggatctgat ctggggcctc ggtacacatg  5520
ctttacatgt gtttagtcga ggttaaaaaa acgtctaggc cccccgaacc acggggacgt  5580
ggttttcctt tgaaaaacac gatgataata tggccacaac cgggccggat atcacgcgtg  5640
atctgatcag cacgtgttga caattaatca tcggcatagt atatcggcat agtataatac  5700
gacaaggtga ggaactaaac catggccaag cctttgtctc aagaagaatc caccctcatt  5760
gaaagagcaa cggctacaat caacagcatc cccatctctg aagactacag cgtcgccagc  5820
gcagctctct ctagcgacgg ccgcatcttc actggtgtca atgtatatca tttttactggg  5880
ggaccttgtg cagaactcgt ggtgctgggc actgctgctgc ctcggcggac tggcaacctg  5940
acttgtatcg tcgcgatcgg aaatgagaac aggggcatct tgagccctg cggacggtgc  6000
cgacaggtgc ttctcgatct gcatcctggg atcaaagcca tagtgaagga cagtgatgga  6060
cagccgacgg cagttgggat tcgtgaattg ctgccctctg gttatgtgtg gagggctaa  6120
gcaatgcata catgtgttta aacctcgact taattaagtc gagggtcgac ggtatcgata  6180
agctcgcttc acgagatcat gtttaagggt tccggttctca ctaggtacaa ttcgatatca  6240
agcttatcga taatcaacct ctggattaca aaatttgtga agattgact ggtattctta  6300
actatgttgc tccttttacg ctatgtggat acgctgcttt aatgcctttg tatcatgcta  6360
ttgcttcccg tatggctttc attttctcct ccttgtaaa atcctggttg ctgtctcttt  6420
atgaggagtt gtgtgcccgtt gtcaggcaac gtggcgtggt gtgcactgtg tttgctgacg  6480
caacccccac tggttggggc attgccacca cctgtcagct cctttccggg actttcgctt  6540
tccccctccc tattgccacg gcggaactca tcgccgcctg ccttgcccgc tgctggacag  6600
gggctcggct gttgggcact gacaattccg tggtgttgtc ggggaaatca tcgtcctttc  6660
cttggctgct cgcctgtgtt gccacctgga ttctgcgcgg gacgtccttc tgctacgtcc  6720
cttcggccct caatccagcg gaccttcctt cccgcggcct gctgccggct ctgcggcctc  6780
ttccgcgtct tcgccttcgc cctcagacga gtcggatctc cctttgggcc gcctccccgc  6840
```

-continued

```
atcgataccg tcgacctcga tcgagaccta gaaaaacatg gagcaatcac aagtagcaat    6900
acagcagcta ccaatgctga ttgtgcctgg ctagaagcac aagaggagga ggaggtgggt    6960
tttccagtca cacctcaggt acctttaaga ccaatgactt acaaggcagc tgtagatctt    7020
agccactttt taaaagaaaa gggggactg gaagggctaa ttcactccca acgaagacaa    7080
gatatccttg atctgtggat ctaccacaca caaggctact tccctgattg gcagaactac    7140
acaccagggc cagggatcag atatccactg acctttggat ggtgctacaa gctagtacca    7200
gttgagcaag agaaggtaga agaagccaat gaaggagaga cacccgctt gttacaccct    7260
gtgagcctgc atgggatgga tgacccggag agagaagtat tagagtggag gtttgacagc    7320
cgcctagcat ttcatcacat ggcccgagag ctgcatccgg actgtactgg gtctctctgg    7380
ttagaccaga tctgagcctg ggagctctct ggctaactag ggaacccact gcttaagcct    7440
caataaagct tgccttgagt gcttcaagta gtgtgtgccc gtctgttgtg tgactctggt    7500
aactagagat ccctcagacc cttttagtca gtgtggaaaa tctctagcag catgtgagca    7560
aaaggccagc aaaaggccag gaaccgtaaa aaggccgcgt tgctggcgtt tttccatagg    7620
ctccgcccc ctgacgagca tcacaaaaat cgacgctcaa gtcagaggtg gcgaaacccg    7680
acaggactat aaagatacca ggcgtttccc cctggaagct ccctcgtgcg ctctcctgtt    7740
ccgaccctgc cgcttaccgg atacctgtcc gcctttctcc cttcgggaag cgtggcgctt    7800
tctcatagct cacgctgtag gtatctcagt tcggtgtagg tcgttcgctc caagctgggc    7860
tgtgtgcacg aacccccgt tcagcccgac cgctgcgcct tatccggtaa ctatcgtctt    7920
gagtccaacc cggtaagaca cgacttatcg ccactggcag cagccactgg taacaggatt    7980
agcagagcga ggtatgtagg cggtgctaca gagttcttga agtggtggcc taactacggc    8040
tacactagaa gaacagtatt tggtatctgc gctctgctga agccagttac cttcggaaaa    8100
agagttggta gctcttgatc cggcaaacaa accaccgctg gtagcggtgg tttttttgtt    8160
tgcaagcagc agattacgcg cagaaaaaaa ggatctcaag aagatccttt gatcttttct    8220
acggggtctg acgctcagtg gaacgaaaac tcacgttaag ggattttggt catgagatta    8280
tcaaaaagga tcttcaccta gatccttta aattaaaaat gaagttttaa atcaatctaa    8340
agtatatatg agtaaacttg gtctgacagt taccaatgct taatcagtga ggcacctatc    8400
tcagcgatct gtctatttcg ttcatccata gttgcctgac tccccgtcgt gtagataact    8460
acgatacggg agggcttacc atctggcccc agtgctgcaa tgataccgcg agacccacgc    8520
tcaccggctc cagatttatc agcaataaac cagccagccg gaagggccga gcgcagaagt    8580
ggtcctgcaa ctttatccgc ctccatccag tctattaatt gttgccggga agctagagta    8640
agtagttcgc cagttaatag tttgcgcaac gttgttgcca ttgctacagg catcgtggtg    8700
tcacgctcgt cgtttggtat ggcttcattc agctccggtt cccaacgatc aaggcgagtt    8760
acatgatccc ccatgttgtg caaaaaagcg gttagctcct tcggtcctcc gatcgttgtc    8820
agaagtaagt tggccgcagt gttatcactc atggttatgg cagcactgca taattctctt    8880
actgtcatgc catccgtaag atgcttttct gtgactggtg agtactcaac caagtcattc    8940
tgagaatagt gtatgcggcg accgagttgc tcttgcccgg cgtcaatacg ggataatacc    9000
gcgccacata gcagaacttt aaaagtgctc atcattggaa aacgttcttc ggggcgaaaa    9060
ctctcaagga tcttaccgct gttgagatcc agttcgatgt aacccactcg tgcacccaac    9120
tgatcttcag catcttttac tttcaccagc gtttctggtg gacgcaaaaac aggaaggcaa    9180
aatgccgcaa aaaagggaat aagggcgaca cggaaatgtt gaatactcat actcttcctt    9240
tttcaatatt attgaagcat ttatcagggt tattgtctca tgagcggata catatttgaa    9300
tgtatttaga aaaataaaca aataggggtt ccgcgcacat ttccccgaaa agtgccacct    9360
gac                                                                 9363
```

```
SEQ ID NO: 42            moltype = RNA   length = 20
FEATURE                  Location/Qualifiers
source                   1..20
                         mol_type = other RNA
                         organism = synthetic construct
SEQUENCE: 42
gaagacaaag agggtcgtgg                                                 20

SEQ ID NO: 43            moltype = RNA   length = 30
FEATURE                  Location/Qualifiers
source                   1..30
                         mol_type = other RNA
                         organism = synthetic construct
SEQUENCE: 43
gtggttggag aactggatgt agatgggctg                                      30

SEQ ID NO: 44            moltype = DNA   length = 34
FEATURE                  Location/Qualifiers
source                   1..34
                         mol_type = other DNA
                         organism = synthetic construct
SEQUENCE: 44
caccgtggtt ggagaactgg atgtagatgg gctg                                 34

SEQ ID NO: 45            moltype = DNA   length = 34
FEATURE                  Location/Qualifiers
source                   1..34
                         mol_type = other DNA
                         organism = synthetic construct
SEQUENCE: 45
caaccagccc atctacatcc agttctccaa ccac                                 34

SEQ ID NO: 46            moltype = DNA   length = 34
FEATURE                  Location/Qualifiers
source                   1..34
```

-continued

```
                          mol_type = other DNA
                          organism = synthetic construct
SEQUENCE: 46
aaacgtggtt ggagaactgg atgtagatgg gctg                                    34

SEQ ID NO: 47          moltype = DNA   length = 34
FEATURE                Location/Qualifiers
source                 1..34
                       mol_type = other DNA
                       organism = synthetic construct
SEQUENCE: 47
aaaacagccc atctacatcc agttctccaa ccac                                    34

SEQ ID NO: 48          moltype = DNA   length = 34
FEATURE                Location/Qualifiers
source                 1..34
                       mol_type = other DNA
                       organism = synthetic construct
SEQUENCE: 48
cttgcagccc atctacatcc agttctccaa ccac                                    34

SEQ ID NO: 49          moltype = DNA   length = 24
FEATURE                Location/Qualifiers
source                 1..24
                       mol_type = other DNA
                       organism = synthetic construct
SEQUENCE: 49
caccgaagac aaagagggtc gtgg                                               24

SEQ ID NO: 50          moltype = DNA   length = 24
FEATURE                Location/Qualifiers
source                 1..24
                       mol_type = other DNA
                       organism = synthetic construct
SEQUENCE: 50
caacccacga ccctctttgt cttc                                               24

SEQ ID NO: 51          moltype = DNA   length = 24
FEATURE                Location/Qualifiers
source                 1..24
                       mol_type = other DNA
                       organism = synthetic construct
SEQUENCE: 51
aaacgaagac aaagagggtc gtgg                                               24

SEQ ID NO: 52          moltype = DNA   length = 24
FEATURE                Location/Qualifiers
source                 1..24
                       mol_type = other DNA
                       organism = synthetic construct
SEQUENCE: 52
aaaaccacga ccctctttgt cttc                                               24

SEQ ID NO: 53          moltype = DNA   length = 24
FEATURE                Location/Qualifiers
source                 1..24
                       mol_type = other DNA
                       organism = synthetic construct
SEQUENCE: 53
cttgccacga ccctctttgt cttc                                               24

SEQ ID NO: 54          moltype = DNA   length = 22
FEATURE                Location/Qualifiers
source                 1..22
                       mol_type = other DNA
                       organism = synthetic construct
SEQUENCE: 54
attgtcccag atatagccgt tg                                                 22

SEQ ID NO: 55          moltype = DNA   length = 20
FEATURE                Location/Qualifiers
source                 1..20
                       mol_type = other DNA
                       organism = synthetic construct
SEQUENCE: 55
gctgtcattt ccgtttgctg                                                    20

SEQ ID NO: 56          moltype = DNA   length = 20
FEATURE                Location/Qualifiers
```

```
source                  1..20
                        mol_type = other DNA
                        organism = synthetic construct
SEQUENCE: 56
gctcttctgg agggcagtgg                                                          20

SEQ ID NO: 57           moltype = DNA   length = 21
FEATURE                 Location/Qualifiers
source                  1..21
                        mol_type = other DNA
                        organism = synthetic construct
SEQUENCE: 57
cagtgtgaca gccgggttga g                                                        21

SEQ ID NO: 58           moltype = DNA   length = 20
FEATURE                 Location/Qualifiers
source                  1..20
                        mol_type = other DNA
                        organism = synthetic construct
SEQUENCE: 58
ccatggggaa ggtgaaggtc                                                          20

SEQ ID NO: 59           moltype = DNA   length = 21
FEATURE                 Location/Qualifiers
source                  1..21
                        mol_type = other DNA
                        organism = synthetic construct
SEQUENCE: 59
gaagggtca ttgatggcaa c                                                         21

SEQ ID NO: 60           moltype = AA   length = 1188
FEATURE                 Location/Qualifiers
source                  1..1188
                        mol_type = protein
                        organism = synthetic construct
SEQUENCE: 60
MKEQKKFSLQ GVRHVCGSYF NMALNNYCRT LNGVFIKCKI KFALKEDDFP RSLSSLRKIF  60
SSGPIMPQTE KKVAKMIASV DTAMKLKQQL FKHFPMLGPI MDKTISCMNH HKGSSVADAP  120
LDLCMNAILN FGECLYHCRN FYTHFKPYNS PEDLKLQYDI QHIIALNLGT LFDVSRRIGK  180
KREGLTPEEL EFLTGKNRFN QVGKKFLERN DWYLKIEKPS DMKDYDKTIL SDFGMVYLCS  240
IFLAKNYALR LFDESKLFNK ETIRNLFSEE QVRFLKEMLV IYRIRTPRGK QLDSHDSKQA  300
LAMDMLNELR KCPRPLYDVL SEEYKKRTFY VPVEHENEKT EEYVKMLRSD DRFPYFTLRY  360
IDDMEKFSRI RFQIRLGSYR FKFYDKMNID GTPRIRSLQK EINGFGRLSD MENKRKREWK  420
DMFQATEEID YEDQFGDYQT GVTQFVEDTA DTKPYVTNHR AAYNVHSNHI GLIWNDADSI  480
ILQDDNKLFF PDLKIDENGK ADIYQPSPKA SLSVFDFPAM VFYMYLREKT EATKEFPSAE  540
QLIINKYDHL VRFFKDISDG RFGPSENKNA FSKKLKEEYD LKTGEIPEKL LHWLSSESEE  600
DPSEKYAKKL EEEIKLRRER VQRRLEKFNQ DLREIRKKDS VPYGKKGHVN IRHSQLAKYL  660
MRSIMEWQPT RNDGKNKLTG QNFNVMTAFL ATLGYTSQVK DLRDLFSRAN MLEGPNAHPF  720
LKKVLNNNSI KDIQGFYRTY LVEELNQIED KQRRIAKAKN VKDTVRQFPF AHFNRMRYQK  780
RDEDYYRNLA KRYLNIGDNE KDKAVILLPD GMFTSYIYDL IMKLPENNEK MRINLASDVA  840
HCNSSFLISR FFENIRNDYA QPFYREERTY ELFSILNNKV VRNTLQPLFI SPHDINIQLT  900
EKEKDGKGRL ILQKIDHFCK SITQKGNFNN VEEAKEATSR KLKHLITDCK NNERDIRRYK  960
TQDMVIYLMA RDILKDIIPD SEKDKYAKDR KLLLKDVCEE GFLRQAVKME YEYSIEEKGK  1020
RTRTVKITHP NMSLKNYGEF HRLLNDERLK SLLQQLANMD EIDYTDLMGE FADYDQKRSE  1080
IFRLAQSIEK HLYEQNEQGL NDEKSDLFYH TRYNGKKIPR RNSFSSLLEL IGEEESQMTE  1140
TDKKQTISIR NAFGHNTYKV SLAEMNATEL PNVAKTILKK MEELRNKL                1188

SEQ ID NO: 61           moltype = DNA   length = 3567
FEATURE                 Location/Qualifiers
source                  1..3567
                        mol_type = other DNA
                        organism = synthetic construct
SEQUENCE: 61
atgaaagaac aaaaaaaatt ttctctccaa ggcgtaagac acgtctgtgg tagttatttc  60
aacatggctc tcaacaatta ttgtcgaacg ttgaatggag tattcatcaa atgtaaaatt  120
aaattcgcat tgaaagagga tgattttcca cgatcgttat caagtttgag gaaaattttc  180
tcttctgggc ctattatgcc tcaaacagaa aaaaaagtgg caaagatgat tgcttctgtt  240
gataccgcca tgaagttaaa acagcagtta ttcaaacact ttcccatgtt aggtcccatt  300
atggataaaa ccatcagttg catgaaccac cataaaggct cttctgttgc cgacgctcct  360
cttgaccttt gcatgaacgc aattcttaac ttcggcgaat gcctttacca ttgtaggaat  420
ttctatcgc atttcaaacc ttacaacagt ccagaagacc tgaaactaca atatgacatc  480
caacacatta ttgccttgaa tcttggcacc ttattcgatg tcagccggag aatcgggaaa  540
aaacgcgaag gtctgacacc ggaagagttg gaattcctta caggtaaaaa taggtttaac  600
caagtcggga aaaaattcct tgagcgtaac gactggtatt tgaaaataga gaaaccatcc  660
gacatgaaag attatgacaa gaccatattg tcagacttcg gcatggtgta cctttgctcc  720
atctttcttg ccaaaaacta cgccctccgc ctttttgatg agtcaaaatt attcaacaaa  780
gaaacaataa ggaatttatt ctctgaagaa caggttcgat ccttaaggga gatgcttgtt  840
atctatcgca tcaggacacc acgagggaag caactagaca gtcacgacag caaacaagct  900
ttggccatgg atatgctcaa cgaactccgc aaatgcccaa gacctcttta cgatgtgcta  960
```

```
tccgaagaat ataaaaagag gacattctat gtcccagtgg agcatgaaaa tgaaaagaca   1020
gaagaatatg tcaagatgct ccgttcggat gacagattcc cttatttcac attgaggtat   1080
attgacgaca tggagaagtt cagcagaatt cgttttcaaa tacgactcgg ttcctatcgc   1140
ttcaagttct acgacaagat gaacattgac ggtaccccac gtatcagaag tctgcaaaaa   1200
gaaatcaatg gtttcggacg tctatccgac atggaaaaca agaggaaaag ggaatggaaa   1260
gacatgttcc aagccaccga agagatagat tacgaggatc aatttggaga ctatcagaca   1320
gggGtgaccc aatttgtaga agacacggct gatacaaagc cctatgttac caaccatcga   1380
gcagcataca atgttcacag taatcatatt ggattgattt ggaatgacgc tgatagtata   1440
atactacaag atgacaataa gttgtttttc cctgacttga agattgacga gaatggaaag   1500
gcagatattt atcaaccttc cccaaaggct tcactcagcg tgttcgattt tccagccatg   1560
gtgtttttaca tgtacctgcg agagaagacc gaagcaacaa aagaattccc ttcagccgaa   1620
caactcatca tcaacaaata tgaccatttg gttcgattct ttaaagatat ttccgatggc   1680
agatttggac catcagaaaa caagaacgct tttagcaaaa agctcaagga agaatatgat   1740
ttgaaaaccg gggaaatacc ggaaaagctc ctgcactggc tttcctctga gtcagaagaa   1800
gacccttccg aaaaatatgc gaagaagctt gaagaagaaa tcaaactgcg cagagaacgt   1860
gttcaacgta gattggaaaa attcaaccaa gaccttagag agataagaaa gaaagattcc   1920
gttccatatg ggaaaaaagg tcatgtgaat atccgccaca gccaattagc caaatacctta   1980
atgaggtcta tcatggagtg gcaacccaca agaaatgatg gaaagaacaa actgactggc   2040
caaaacttca atgtgatgac cgctttcctt gccactttag gatatacctc acaagtgaag   2100
gatttacggg atttattctc tcgtgccaac atgttggaag gtcccaatgc acacccottc   2160
ttgaagaaag tgttgaacaa taactcgatt aaagatatac agggttttta ccggacatat   2220
ctggtagaag aacttaacca aatagaagac aagcaaagaa ggatcgccaa agctaaaaac   2280
gtcaaagata cggtacgcca attcccgttt gctcattta accgtatgag gtaccagaaa   2340
cgagatgaag attattacag gaatttggca aagagatatc tgaatatagg cgacaatgaa   2400
aaggacaagg ctgtcatttt gttgcccgac ggcatgttca ctagttacat ctacgacctc   2460
attatgaaac tccctgaaaa caatgagaag atgcgaatca acttagccag cgatgtagcc   2520
cattgcaatt cctccttctt aatcagccgc ttttttgaaa atattagaaa cgactatgct   2580
caacctttct atcgtgagga aagaacgtat gaactgttta gcatcctaaa taacaaaaaa   2640
gtaagaaata ctcttcaacc cttatttatt agtccccatg atatcaatat ccagcttacg   2700
gagaaagaaa aggatggtaa aggacggctt atcttacaaa agataagatca tttttgcaaa   2760
tctatcacac aaaaagggaa cttcaacaat gtggaagaag ccaaagaagc cacttctcgc   2820
aaattgaaac atctcattac cgattgcaag aacaacgaac gggatatccg ccgatataag   2880
actcaagaca tggtgattta cttgatggcc cgcgacattc ttaaagacat catccccgac   2940
agcgaaaaag acaaatatgc aaaagaccgc aaattattgc aaagatagt atgcgaagaa   3000
ggcttcttac gtcaagccgt caagatggag tatgagtatt ctattgagga aaaagggaaa   3060
aggaccagaa ccgttaaaat cacccatcct aatatgtctt tgaagaacta tggtgagttt   3120
caccgtttac tcaacgatga acgccttaaa tcattgttac aacagttggc taatatggat   3180
gagatcgact atacggattt gatgggggaa tttgctgatt acgaccaaaa acgttcagaa   3240
atcttccgcc tagcgcaatc catagaagaa catctttacg acgagaacga gcaagggctt   3300
aacgatgaaa agagcgacct cttttatcat actagataca atggcaaaaa gataccacgc   3360
cgaaacagtt tcagttcact gctggaattg ataggagaag aagagtccca aatgaccgaa   3420
acagataaga agcaaactat cagcatccga aatgcctttg ggcacaacac ttataaagtg   3480
tctctcgcag agatgaatgc tactgaactt cccaatgtgg caaaaaccat tctcaagaaa   3540
atggaagaac tgagaaacaa gctctaa                                       3567

SEQ ID NO: 62          moltype = RNA  length = 36
FEATURE                Location/Qualifiers
source                 1..36
                       mol_type = other RNA
                       organism = synthetic construct
SEQUENCE: 62
gttgtagaag cctatcgtta ggataggtat gacaac                             36

SEQ ID NO: 63          moltype = AA  length = 1335
FEATURE                Location/Qualifiers
source                 1..1335
                       mol_type = protein
                       organism = synthetic construct
SEQUENCE: 63
MEKHHSQPRK AQFPFSISEK SVMGGYFNIA RLNFYKTIVT IFAQVGVKGE YPEDKIDRVL   60
DALYKNIAGK DNELSKEQAQ WKRLKQLKGE QITKLQRLLF NHFPVLGPIM ASEASYKIYK   120
SELNAKEAED AVQNDKEELK KIKKSNVINN EQLMRGVGID DCLNVLATMA ACLTDCRNYY   180
SHYIPYNSIE DQKKQYKRQA QIARWLDKVI VASRRIDKQR NSLTTNEMEF LTGIDHYFQQ   240
DKKDDTGKLI RDEKGRTLKE FVEYPDYYFR IKGERQLVDI AGKTLNEEQA QNALTDFGIV   300
FFCTLFLQKT YAKMMQEELK LYENGPYRGD VKGKENDDAK KNTILREMLS IYRIRVPRGK   360
RLDSKDDATT LSMDMLNELR KCPMPLYDVL GKDGQRFFED EVQHPNEQTP EKVKRLRATD   420
RFPHLALRYI DLHDKTFTRI RFQVQLGNFR FKFYNKKTID GAEEVRSIQK EINGYGRLQE   480
IEAKRLETYA PLFQKSELVS TKLEHEDLNL DLVQFTEDHA DSKPYITNHR ATYNIHNNRI   540
GMYWEASQNV KEYKVFSSDG MYLPTLNTID GKAPISMPAP KASLSIYELP AMLFYQYLLD   600
NNNVKKNEYD APQDILINKH DALVKFFEAV RGGELIPALS KDELSRKLES EYDLKISEVP   660
NKLVDYLIGK EDNGKRLYDY ATHEVLLRLR RSLRRFEHFE EDRKMIGSKD NKYGKKGFVD   720
VRHGRLAQYL AESIMDWRKP LNGEKDKLTG LNYSKMQAAL ATFGGKTTFD KLNTLFKEAG   780
LYDNRPGSHP FLQSTMQKAP QNIEMLYLAY LEAETDKLKK FVVIKNLNNL SEKELKEYKD   840
LVTFTVKEKR TYSDGRTKMV MVDKVAVNII GNTNFANLPF IHHQRARFAQ RNAEYYKSLA   900
GRYLSVDGKS ATIQLPDGIF TKHILKLLKE KYATHEALQL HLTDDDMNHN AAYLISSFFE   960
TVLNDCSQPY YRTFHYENNE KKTSKFAHIY DLFNILNNVK EANAYKPYPM TTDDINSRLT   1020
KKATNRDGLF VIRKDDNGED YLVKQITLDI ENHLKKMEDA VEAKIKFKNL YGYNADKARK   1080
NGAEEREKML RKLTHCISDV KNNERAIRRY KTQDMVLFLL AKSTLSTILA QQNGVASEEL   1140
FRLKNVCNNN FLSQTVRFEF PIKVNEMTIK VVQENMALKN YGEFYRFIND DRLMSLLTQL   1200
```

-continued

```
KDVTEISYAD LTGELATYDL RRSQVFRLMQ ELEKIAFEQH TKELTNIDNS MFFKDGDMNN  1260
VPRRNNFKAL INLFDSIDSH QLTKDDCERL VEIRNAFCHN TYRINIDDLQ EKLPTIAIQI  1320
VGKIENLLKG ADMKK                                                   1335

SEQ ID NO: 64              moltype = RNA   length = 36
FEATURE                    Location/Qualifiers
source                     1..36
                           mol_type = other RNA
                           organism = synthetic construct
SEQUENCE: 64
gttttcatac ctatccaaac gataggcttc taaaac                             36

SEQ ID NO: 65              moltype = AA   length = 1124
FEATURE                    Location/Qualifiers
source                     1..1124
                           mol_type = protein
                           organism = synthetic construct
SEQUENCE: 65
MEDDKKTTGS ISYELKDKHF WAAFLNLARH NVYITINHIN KLLEIREIDN DEKVLDIKTL  60
WQKGNKDLNQ KARLRELMTK HFPFLETAIY TKNKEDKKEV KQEKQAEAQS LESLKDCLFL  120
FLDKLQEARN YYSHYKYSEF SKEPEFEEGL LEKMYNIFGN NIQLVINDYQ HNKDINPDED  180
FKHLDRKGQF KYSFADNEGN ITESGLLFFV SLFLEKKDAI WMQQKLNGFK DNLENKKKMT  240
HEVFCRSRIL MPKLRLESTQ TQDWILLDML NELIRCPKSL YERLQGDDRE KFKVPFDPAD  300
EDYNAEQEPF KNTLIRHQDR FPYFVLRYFD YNEIFKNLRF QIDLGTYHFS IYKKLIGGQK  360
EDRHLTHKLY GFERIQEFAK QNRPDEWKAI VKDLDTYETS NKRYISETTP HYHLENQKIG  420
IRFRNGNKEI WPSLKTNDEN NEKSKYKLDK QYQAEAFLSV HELLPMMFYY LLLKKEKPNN  480
DEINASIVEG FIKREIRNIF KLYDAFANGE INNIDDLEKY CADKGIPKRH LPKQMVAILY  540
DEHKDMVKEA KRKQKEMVKD TKKLLATLEK QTQKEKEDDG RNVKLLKSGE IARWLVNDMM  600
RFQPVQKDNE GKPLNNSKAN STEYQMLQRS LALYNNEEKP TRYFRQVNLI ESNNPHPFLK  660
WTKWEECNNI LTFYYSYLTK KIEFLNKLKP EDWKKNQYFL KLKEPKTNRE TLVQGWKNGF  720
NLPRGIFTEP IREWFKRHQN NSKEYEKVEA LDRVGLVTKV IPLFFKEEYF KDKEENFKED  780
TQKEINDCVQ PFYNFPYNVG NIHKPKEKDF LHREERIELW DKKKDKFKGY KEKIKSKKLT  840
EKDKEEFRSY LEFQSWNKFE RELRLVRNQD IVTWLLCKEL IDKLKIDELN IEELKKLRLN  900
NIDTDTAKKE KNNILNRVMP MELPVTVYEI DDSHKIVKDK PLHTIYIKEA ETKLLKQGNF  960
KALVKDRRLN GLFSFVKTNS EAESKRNPIS KLRVEYELGE YQEARIEIIQ DMLALEEKLI  1020
NKYKDLPTNK FSEMLNSWLE GKDEADKARF QNDVDFLIAV RNAFSHNQYP MHNKIEFANI  1080
KPFSLYTANN SEEKGLGIAN QLKDKTKETT DKIKKIEKPI ETKE                   1124

SEQ ID NO: 66              moltype = RNA   length = 37
FEATURE                    Location/Qualifiers
source                     1..37
                           mol_type = other RNA
                           organism = synthetic construct
SEQUENCE: 66
gttgttttta cctttcaaac agaaggcaga tacaaca                            37

SEQ ID NO: 67              moltype = DNA   length = 7679
FEATURE                    Location/Qualifiers
source                     1..7679
                           mol_type = other DNA
                           organism = synthetic construct
SEQUENCE: 67
cctgcaggca gctgcgcgct cgctcgctca ctgaggccgc ccgggcgtcg ggcgaccttt  60
ggtcgcccgg cctcagtgag cgagcgagcg cgcagagagg gagtggccaa ctccatcact  120
aggggttcct gcggcctcta gactcgaggc gttgacattg attattgact agttattaat  180
agtaatcaat tacggggtca ttagttcata gcccatatat ggagttccgc gttacataac  240
ttacggtaaa tggcccgcct ggctgaccgc ccaacgaccc ccgcccattg acgtcaataa  300
tgacgtatgt tcccatagta acgccaatag ggactttcca ttgacgtcaa tgggtggagt  360
atttacggta aactgcccac ttggcagtac atcaagtgta tcatatgcca agtacgcccc  420
ctattgacgt caatgacggt aaatggcccg cctggcatta tgcccagtac atgaccttat  480
gggactttcc tacttggcag tacatctacg tattagtcat cgctattacc atggtgatgc  540
ggttttggca gtacatcaat gggcgtggat agcggtttga ctcacgggga tttccaagtc  600
tccaccccat tgacgtcaat gggagtttgt tttggcacca aaatcaacgg gactttccaa  660
aatgtcgtaa caactccgcc ccattgacgc aaatgggcgg taggcgtgta cggtgggagg  720
tctatataag cagagctctc tggctaacta ccggtgccac catgccggca gctaagaaaa  780
agaaactgga tggcagcgtc gacatgaagg agcagaagaa gttcagcctg cagggcgtga  840
gacacgtgtg cggcagctac ttcaacatgg ccctgaacaa ctactgcaga accctgaacg  900
gcgtgttcat caagtgcaag atcaagttcg ccctgaagga ggacgacttc cccagaagcc  960
tgagcgcct gagaaagatc ttcagcagcg gcccccatgcc gcccagacc gagaagagga  1020
tggccaagat gatcgccagc gtggacaccg ccatgaagct gaagcagcag ctgttcaagc  1080
acttccccat gctgggcccc atcatggaca agaccatcag ctgcatgaac caccacaagg  1140
gcagcagcgt ggccgacgcc cccctggacc tgtgcatgaa cgccatcctg aacttcggcg  1200
agtgcctgta ccactgcaga aacttctaca cccacttcaa gccctacaac agcccgagg  1260
acctgaacgc gcagtacgac atccagcaca tcatcgccct gaacctgggc accctgttcg  1320
acgtgagcag aagaatcggc aagaagagag agggcctgac ccccgaggag ctggagttcc  1380
tgaccggcaa gaacagattc aaccaggtgg gcaagaagtt cctggagaga aacgactggt  1440
acttgaagat cgagaagccc agcgacatga aggactacga caagaccatc ctgagcgact  1500
tcggcatggt gtacctgtgc agcatcctcc tggccaagaa ctacgccctg agactgttcg  1560
acgagagcaa gctgttcaac aaggagacaa tcagaaacct gttcagcgag gagcaggtga  1620
```

-continued

```
gattcctgaa ggagatgctg gtgatctaca gaatcagaac ccccagaggc aagcagctgg  1680
acagccacga cagcaagcag gccctggcca tggacatgct gaacgagctg agaaagtgcc  1740
ccagacccct gtacgacgtg ctgagcgagg agtacaagaa gagaaccttc tacgtgcccg  1800
tggagcacga gaacgagaaa accgaggagt acgtgaagat gctgagaagc gacgacagat  1860
tcccctactt caccctgaga tacatcgacg acatggagaa gttcagcaga atcagattcc  1920
agatcagact gggcagctac agattcaagt tctacgacaa gatgaacatc gacggccaccc  1980
ccagaatcag aagcctgcag aaggagatca acggcttcgg cagactgagc gacatggaga  2040
acaagagaaa gagagagtgg aaggacatgt tccaggccac cgaggagatc gactacgagg  2100
accagttcgg cgactaccag accggcgtga cccagttcgt ggaggacacc gccgacacca  2160
agccctacgt gaccaaccac agagccgcct acaacgtgcc cagcaaccac atcggcctga  2220
tctggaacga cgccgacagc atcatcctgc aggacgacaa caagctgttc ttccccgacc  2280
tgaagatcga cgagaacggc aaggccgaca tctaccagcc cagccccaag gccagcctga  2340
gcgtgttcga cttccccgcc atggtgttct acatgtacct gagagagaaa accgaggcca  2400
ccaaggagtt ccccagcgcc gagcagctga tcatcaacaa gtacgaccac ctggtgagat  2460
tcttcaagga catcagcgac ggcagattcg gccccagcga gaacaagaac gccttcagca  2520
agaagctgaa ggaggagtac gacctgaaaa ccggcgagat ccccgagaag ctgctgcact  2580
ggctgagcag cgagagcgag gaggacccca gcgagaagta cgccaagaag ctggaggagg  2640
agatcaagct gagaagagag agagtgcaga gaagattgga gaagttcaac caggacctga  2700
gagagatcag aaagaaggac agcgtgccct acggcaagaa gggccacgtg aacatcagac  2760
acagccagct ggccaagtac ctgatgagaa gcatcatgga gtggcagccc accagaaacg  2820
acggcaagaa caagctgacc ggccagaact tcaacgtgat gaccgccttc ctggccaccc  2880
tgggctacac cagccaggtg aaggacctga gagacttgtt cagcagagcc aacatgctga  2940
agggccccaa cgcccacccc ttcctgaaga aggtgctgaa caacaacagc atcaaggaca  3000
tccagggctt ctacagaacc tacctggtgg aggagctgaa ccagatcgag gacaagcaga  3060
gaagaatcgc caaggccaag aacgtgaagg acaccgtgag acagttcccc ttcgcccact  3120
tcaacagaat gagataccag aagagagacg aggactacta cagaaacctg gccaagagat  3180
acctgaacat cggcgacaac gagaaggaca aggccgtgat cctgctgccc gacggccatgt  3240
tcaccagcta catctacgac ctgatcatga agctgcccga gaacaacgag aagatgagaa  3300
tcaacctggc cagcgacgtg gcccactgca acagcagctt cctgatcagc agattcttcg  3360
agaacatcag aaacgactac gcccagccct tctacagaga ggagagaacc tacgagctgt  3420
tcagcatcct gaacaacaag aaggtgagaa acaccctgca gccccttgttc atcagccccc  3480
acgacatcaa catccagctg accgagaagg agaaggacgg caagggcaga ctgatcctgc  3540
agaagatcga ccacttctgc aagagcatca cccagaaggg caacttcaac aacgtggagg  3600
aggccaagga ggccaccaac agaaagctga agcacctgat caccgactgc aagaacaacg  3660
agagagacat cagaagatac aagacccagg acatggtgat ctacctgatg gccagagaca  3720
tcctgaagga catcatcccc gacagcgaga aggacaagta cgccaaggac agaaagctgc  3780
tgctgaagga cgtgtgcgag gagggcttcc tgagacaggc cgtgaagatg gagtacgagt  3840
acagcatcga ggagaagggc aagagaacca gaaccgtgaa gatcacccac cccaacatga  3900
gcctgaagaa ctacggcgag ttccacagac tgctgaacga cgagaagactg aagagcctgc  3960
tgcagcagct ggccaacatg gacgagatcg actacaccga cctgatgggc gagttcgccg  4020
actacgacca gaagagaagc gagatcttca gactggccca gagcatcgag aagcacctgt  4080
acgagcagaa cgagcagggc ctgaacgacg agaagagcga cctgttctac cacaccagat  4140
acaacgagaa gaagatcccc agaagaaaca gcttcagcag cctgctggag ctgatcggcg  4200
aggaggagag ccagatgacc gagacagaca agaagcagac catcagcatc agaaacgcct  4260
tcggccacaa cacctacaag gtgagcctgg ccgagatgaa cgccaccgag ctgcccaacg  4320
tggccaagac catcctgaag aagatggagg agctgagaaa caagctgaca ggcggcggcc  4380
ccggcggcgg cgccgccgcc ggcagcggca gcctaagaa aaaacgaaaa gttggcagcg  4440
gaagcaaaag gccggcggcc acgaaaaagg ccggccaggc aaaaaagaaa aagctcgagt  4500
acccatacga tgttccagat tacgcttgag aattccccctt gagcatctga cttctggcta  4560
ataaaggaaa tttattttca ttgcaatagt gtgttggaat ttttttgtgtc tctcaggtac  4620
cgaggggccta tttcccatga ttccttcata tttgcatata cgatacaagg ctgttaggaga  4680
gataattgga attaatttga ctgtaaacac aaagatatta gtacaaaata cgtgacgtag  4740
aaagtaataa tttcttgggt agtttgcagt tttaaaatta tgttttaaaa tggactatca  4800
tatgcttacc gtaacttgaa agtatttcga tttcttggct ttatatatct tgtggaaagg  4860
acgaaacacc ggagaccacg gcaggtctca gttgtagaag cctatcgtta ggataggtat  4920
gacaactttt tttgcggccg caggaacccc tagtgatgga gttggccact ccctctctgc  4980
gcgctcgctc gctcactgag gccgggcgac caaaggtcgc ccgacgcccg ggctttgccc  5040
gggcggcctc agtgagcgag cgagcgcgca gctgcctgca ggggcgcctg atgcggtatt  5100
ttctccttac gcatctgtgc ggtatttcac accgcatacg tcaaagcaac catagtacgc  5160
gccctgtagc ggcgcattaa gcgcggcggg tgtggtggtt acgcgcagcg tgaccgctac  5220
acttgccagc gccttagcgc ccgctccttt cgctttcttc ccttcctttc tcgccacgtt  5280
cgccggcttt ccccgtcaag ctctaaatcg ggggctccct ttagggttcc gatttagtgc  5340
tttacggcac ctcgacccca aaaaacttga tttgggtgat ggttcacgta gtgggccatc  5400
gccctgatag acggtttttc gccctttgac gttggagtcc acgttctttta atagtggact  5460
cttgttccaa actggaacaa cactcaactc tatctcgggc tattcttttg atttataagg  5520
gattttgccg atttcggtct attggttaaa aaatgagctg atttaacaaa aatttaacgc  5580
gaattttaac aaaatattaa cgtttacaat tttatggtgc actctcagta caatctgctc  5640
tgatgccgca tagttaagcc agccccgaca cccgccaaca cccgctgacg cgccctgacg  5700
ggcttgtctg ctcccggcat ccgcttacag acaagctgtg accgtctccg ggagctgcat  5760
gtgtcagagg ttttcaccgt catcaccgaa acgcgcgaga cgaaagggcc tcgtgatacg  5820
cctatttttta taggttaatg tcatgataat aatggtttct tagacgtcag gtggcacttt  5880
tcggggaaat gtgcgcggaa cccctatttg tttatttttc taaatacatt caaatatgta  5940
tccgctcatg agacaataac cctgataaat gcttcaataa tattgaaaaa ggaagagtat  6000
gagtattcaa catttccgtg tcgcccttat tcccttttttt gcggcatttt gccttcctgt  6060
ttttgctcac ccagaaacgc tggtgaaagt aaaagatgct gaagatcagt tgggtgcacg  6120
agtgggttac atcgaactgg atctcaacag cggtaagatc cttgagagtt ttcgccccga  6180
agaacgtttt ccaatgatga gcactttttaa agttctgcta tgtggcgcgg tattatcccg  6240
tattgacgcc gggcaagagc aactcggtcg ccgcatacac tattctcaga atgacttggt  6300
tgagtactca ccagtcacag aaaagcatct tacggatggc atgacagtaa gagaattatg  6360
```

```
cagtgctgcc ataaccatga gtgataacac tgcggccaac ttacttctga caacgatcgg   6420
aggaccgaag gagctaaccg cttttttgca caacatgggg gatcatgtaa ctcgccttga   6480
tcgttgggaa ccggagctga atgaagccat accaaacgac gagcgtgaca ccacgatgcc   6540
tgtagcaatg gcaacaacgt tgcgcaaact attaactggc gaactactta ctctagcttc   6600
ccggcaacaa ttaatagact ggatggaggc ggataaagtt gcaggaccac ttctgcgctc   6660
ggcccttccg gctggctggt ttattgctga taaatctgga gccggtgagc gtggaagccg   6720
cggtatcatt gcagcactgg ggccagatgg taagccctcc cgtatcgtag ttatctacac   6780
gacggggagt caggcaacta tggatgaacg aaatagacag atcgctgaga taggtgcctc   6840
actgattaag cattggtaac tgtcagacca agtttactca tatatacttt agattgattt   6900
aaaacttcat ttttaattta aaaggatcta ggtgaagatc ctttttgata atctcatgac   6960
caaaatccct taacgtgagt tttcgttcca ctgagcgtca gaccccgtag aaaagatcaa   7020
aggatcttct tgagatcctt ttttttctgcg cgtaatctgc tgcttgcaaa caaaaaaacc   7080
accgctacca gcggtggttt gtttgccgga tcaagagcta ccaactcttt ttccgaaggt   7140
aactggcttc agcagagcgc agataccaaa tactgttctt ctagtgtagc cgtagttagg   7200
ccaccacttc aagaactctg tagcaccgcc tacatacctc gctctgctaa tcctgttacc   7260
agtggctgct gccagtggcg ataagtcgtg tcttaccggg ttggactcaa gacgatagtt   7320
accggataag gcgcagcggt cgggctgaac ggggggttcg tgcacacagc ccagcttgga   7380
gcgaacgacc tacaccgaac tgagatacct acagcgtgag ctatgagaaa gcgccacgct   7440
tcccgaaggg agaaaggcgg acaggtatcc ggtaagcggc agggtcggaa caggagagcg   7500
cacgagggag cttccagggg gaaacgcctg gtatctttat agtcctgtcg ggtttcgcca   7560
cctctgactt gagcgtcgat ttttgtgatg ctcgtcaggg gggcggagcc tatggaaaaa   7620
cgccagcaac gcggcctttt tacggttcct ggccttttgc tggccttttg ctcacatgt    7679
```

```
SEQ ID NO: 68            moltype = DNA   length = 26
FEATURE                  Location/Qualifiers
source                   1..26
                         mol_type = other DNA
                         organism = synthetic construct
SEQUENCE: 68
agggcagaac cgatgctgat gaagac                                        26

SEQ ID NO: 69            moltype = DNA   length = 31
FEATURE                  Location/Qualifiers
source                   1..31
                         mol_type = other DNA
                         organism = synthetic construct
SEQUENCE: 69
caccgagggc agaaccgatg ctgatgaaga c                                  31

SEQ ID NO: 70            moltype = DNA   length = 31
FEATURE                  Location/Qualifiers
source                   1..31
                         mol_type = other DNA
                         organism = synthetic construct
SEQUENCE: 70
caacgtcttc atcagcatcg gttctgccct c                                  31

SEQ ID NO: 71            moltype = DNA   length = 30
FEATURE                  Location/Qualifiers
source                   1..30
                         mol_type = other DNA
                         organism = synthetic construct
SEQUENCE: 71
aaacagggca gaaccgatgc tgatgaagac                                    30

SEQ ID NO: 72            moltype = DNA   length = 30
FEATURE                  Location/Qualifiers
source                   1..30
                         mol_type = other DNA
                         organism = synthetic construct
SEQUENCE: 72
cttggtcttc atcagcatcg gttctgccct                                    30

SEQ ID NO: 73            moltype = DNA   length = 21
FEATURE                  Location/Qualifiers
source                   1..21
                         mol_type = other DNA
                         organism = synthetic construct
SEQUENCE: 73
gcccatctac atccagttct c                                             21

SEQ ID NO: 74            moltype = DNA   length = 21
FEATURE                  Location/Qualifiers
source                   1..21
                         mol_type = other DNA
                         organism = synthetic construct
SEQUENCE: 74
cagcccatct acatccagtt c                                             21
```

```
SEQ ID NO: 75            moltype = DNA   length = 58
FEATURE                  Location/Qualifiers
source                   1..58
                         mol_type = other DNA
                         organism = synthetic construct
SEQUENCE: 75
caccgcccat ctacatccag ttctcctcga ggagaactgg atgtagatgg gctttttt       58

SEQ ID NO: 76            moltype = DNA   length = 58
FEATURE                  Location/Qualifiers
source                   1..58
                         mol_type = other DNA
                         organism = synthetic construct
SEQUENCE: 76
ggccaaaaaa gcccatctac atccagttct cctcgaggag aactggatgt agatgggc       58

SEQ ID NO: 77            moltype = DNA   length = 58
FEATURE                  Location/Qualifiers
source                   1..58
                         mol_type = other DNA
                         organism = synthetic construct
SEQUENCE: 77
cacccagccc atctacatcc agttcctcga ggaactggat gtagatgggc tgtttttt       58

SEQ ID NO: 78            moltype = DNA   length = 58
FEATURE                  Location/Qualifiers
source                   1..58
                         mol_type = other DNA
                         organism = synthetic construct
SEQUENCE: 78
ggccaaaaaa cagcccatct acatccagtt cctcgaggaa ctggatgtag atgggctg       58

SEQ ID NO: 79            moltype = DNA   length = 4828
FEATURE                  Location/Qualifiers
source                   1..4828
                         mol_type = other DNA
                         organism = synthetic construct
SEQUENCE: 79
cctgcaggca gctgcgcgct cgctcgctca ctgaggccgc ccgggcgtcg ggcgaccttt       60
ggtcgcccgg cctcagtgag cgagcgagcg cgcagagagg gagtggccaa ctccatcact      120
aggggttcct gcggcctcta gactcgaggc gttgacattg attattgact agttattaat      180
agtaatcaat tacggggtca ttagttcata gcccatatat ggagttccgc gttacataac      240
ttacggtaaa tggcccgcct ggctgaccgc ccaacgaccc ccgcccattg acgtcaataa      300
tgacgtatgt tcccatagta acgccaatag ggactttcca ttgacgtcaa tgggtggagt      360
atttacggta aactgcccac ttggcagtac atcaagtgta tcatatgcca gtacgcccc       420
ctattgacgt caatgacggt aaatggcccg cctggcatta tgcccagtac atgaccttat      480
gggactttcc tacttggcag tacatctacg tattagtcat cgctattacc atggtgatgc      540
ggttttggca gtacatcaat gggcgtggat agcggtttga ctcacgggga tttccaagtc      600
tccaccccat tgacgtcaat gggagtttgt tttggcacca aaatcaacgg gactttccaa      660
aatgtcgtaa caactccgcc ccattgacgc aaatgggcgg taggcgtgta cggtgggagg      720
tctatataag cagagctctc tggctaacta ccggtgccac catggtgagc aagggcgagg      780
agctgttcac cggggtggtg cccatcctgg tcgagctgga cggcgacgta aacggccaca      840
agttcagcgt gtccggcgag ggcgagggcg atgccaccta cggcaagctg accctgaagt      900
tcatctgcac caccggcaag ctgccccgtgc cctggcccac cctcgtgacc accctgacct      960
acggcgtgca gtgcttcagc cgctaccccg accacatgaa gcagcacgac ttcttcaagt     1020
ccgccatgcc cgaaggctac gtccaggagc gcaccatctt cttcaaggac gacggcaact     1080
acaagacccg cgccgaggtg aagttcgagg gcgacaccct ggtgaaccgc atcgagctga     1140
agggcatcga cttcaaggag gacggcaaca tcctgggggca caagctggag tacaactaca     1200
acagccacaa cgtctatatc atggccgaca agcagaagaa cggcatcaag gtgaacttca     1260
agatccgcca caacatcgag gacggcagcg tgcagctcgc cgaccactac cagcagaaca     1320
cccccatcgg cgacggcccc gtgctgctgc ccgacaacca ctacctgagc acccagtccg     1380
ccctgagcaa agaccccaac gagaagcgcg atcacatggt cctgctggag ttcgtgaccg     1440
ccgccgggat cactctcggc atggacgagc tgtacaagta aagcggccga attcctagag     1500
ctcgctgatc agcctcgact gtgccttcta gttgccagcc atctgttgtt tgcccctcc      1560
ccgtgccttc cttgaccctg gaaggtgcca ctcccactgt cctttcctaa taaaatgagg     1620
aaattgcatc gcattgtctg agtaggtgtc attctattct gggggggtgg gtggggcagg     1680
acagcaaggg ggaggattgg gaagagaata gcaggcatgc tggggaggta ccgagggcct     1740
atttcccatg attccttcat atttgcatat acgatacaag gctgttagag agataattg      1800
aattaatttg actgtaaaca caaagatatt agtacaaaat acgtgacgta gaaagtaata     1860
atttcttggg tagtttgcag ttttaaaatt atgttttaaa atggactatc atatgcttac     1920
cgtaacttga agtatttcg atttcttggc tttatatatc ttgtggaaag gacgaaacac     1980
cggagaccac ggcaggtctc agttttagta ctctggaaac agaatctact aaaacaaggc     2040
aaaatgccgt gtttatctcg tcaacttgtt ggcgagattt ttgcggccgc aggaacccct     2100
agtgatggag ttggccactc cctctctgcg cgctcgctcg ctcactgagg ccgggcgacc     2160
aaaggtcgcc cgacgcccgg gctttgcccg gcggcctca gtgagcgagc gagcgcgcag     2220
ctgcctgcag gggcgcctga tgcggtattt tctccttacg catctgtgcg gtatttcaca     2280
ccgcatacgc caaagcaacc atagtacgcg ccctgtagcg gcgcattaag cgcggcgggt     2340
gtggtggtta cgcgcagcgt gaccgctaca cttgccagcg ccctagcgcc cgctcctttc     2400
gctttcttcc cttcctttct cgccacgttc gccggctttc ccgtcaagc tctaaatcgg     2460
```

```
gggctcccctt tagggttccg atttagtgct ttacggcacc tcgaccccaa aaaacttgat   2520
ttgggtgatg gttcacgtag tgggccatcg ccctgataga cggttttttcg cccctttgacg  2580
ttggagtcca cgttctttaa tagtggactc ttgttccaaa ctggaacaac actcaaccct    2640
atctcgggct attcttttga tttataaggg attttgccga tttcggccta ttggttaaaa    2700
aatgagctga tttaacaaaa atttaacgcg aattttaaca aaatattaac gtttacaatt    2760
ttatggtgca ctctcagtac aatctgctct gatgccgcat agttaagcca gccccgacac    2820
ccgccaacac ccgctgacgc gccctgacgg gcttgtctgc tcccggcatc cgcttacaga    2880
caagctgtga ccgtctccgg gagctgcatg tgtcagaggt tttcaccgtc atcaccgaaa    2940
cgcgcgagac gaaagggcct cgtgatacgc ctatttttat aggttaatgt catgataata    3000
atggtttctt agacgtcagg tggcacttttt cggggaaatg tgcgcggaac ccctatttgt    3060
ttatttttct aaatacattc aaatatgtat ccgctcatga gacaataacc ctgataaatg    3120
cttcaataat attgaaaaag gaagagtatg agtattcaac atttccgtgt cgcccttatt    3180
cccttttttg cggcattttg ccttcctgtt tttgctcacc cagaaacgct ggtgaaagta    3240
aaagatgctg aagatcagtt gggtgcacga gtgggttaca tcgaactgga tctcaacagc    3300
ggtaagatcc ttgagagttt tcgccccgaa gaacgttttc caatgatgag cacttttaaa    3360
gttctgctat gtggcgcggt attatcccgt attgacgccg ggcaagagca actcggtcgc    3420
cgcatacact attctcagaa tgacttggtt gagtactcac cagtcacaga aaagcatctt    3480
acggatggca tgacagtaag agaattatgc agtgctgcca taaccatgag tgataacact    3540
gcggccaact tacttctgac aacgatcgga ggaccgaagg agctaaccgc ttttttgcac    3600
aacatggggg atcatgtaac tcgccttgat cgttgggaac cggagctgaa tgaagccata    3660
ccaaacgacg agcgtgacac cacgatgcct gtagcaatgg caacaacgtt gcgcaaacta    3720
ttaactggcg aactacttac tctagcttcc cggcaacaat taatagactg gatggaggcg    3780
gataaagttg caggaccact tctgcgctcg gcccttccgg ctggctggtt tattgctgat    3840
aaatctggag ccggtgagcg tggaagccgc ggtatcattg cagcactggg gccagatggt    3900
aagccctccc gtatcgtagt tatctacacg acggggagtc aggcaactat ggatgaacga    3960
aatagacaga tcgctgagat aggtgcctca ctgattaagc attggtaact gtcagaccaa    4020
gtttactcat atatacttta gattgattta aaacttcatt tttaatttaa aaggatctag    4080
gtgaagatcc tttttgataa tctcatgacc aaaatccctt aacgtgagtt ttcgttccac    4140
tgagcgtcag accccgtaga aaagatcaaa ggatcttctt gagatccttt ttttctgcgc    4200
gtaatctgct gcttgcaaac aaaaaaacca ccgctaccag cggtggtttg tttgccggat    4260
caagagctac caactctttt tccgaaggta actggcttca gcagagcgca gataccaaat    4320
actgtccttc tagtgtagcc gtagttaggc caccacttca agaactctgt agcaccgcct    4380
acatacctcg ctctgctaat cctgttacca gtggctgctg ccagtggcga taagtcgtgt    4440
cttaccgggt tggactcaag acgatagtta ccggataagg cgcagcggtc gggctgaacg    4500
gggggttcgt gcacacagcc cagcttggag cgaacgacct acaccgaact gagataccta    4560
cagcgtgagc tatgagaaag cgccacgctt cccgaaggga gaaaggcgga caggtatccg    4620
gtaagcggca gggtcggaac aggagagcgc acgagggagc ttccaggggg aaacgcctgg    4680
tatctttata gtcctgtcgg gtttcgccac ctctgacttg agcgtcgatt tttgtgatgc    4740
tcgtcagggg gcggagcct atggaaaaac gccagcaacg cggccttttt acggttcctg    4800
gccttttgct ggccttttgc tcacatgt                                        4828
```

SEQ ID NO: 80          moltype = RNA   length = 66
FEATURE                Location/Qualifiers
source                 1..66
                       mol_type = other RNA
                       organism = synthetic construct
SEQUENCE: 80
gtggttggag aactggatgt agatgggctg gttgtagatg acctcgtttt ggaggggaaa   60
cacaac                                                                66

SEQ ID NO: 81          moltype = RNA   length = 66
FEATURE                Location/Qualifiers
source                 1..66
                       mol_type = other RNA
                       organism = synthetic construct
SEQUENCE: 81
gtggttggag aactggatgt agatgggctg gttgtagaag ccgttcattc gggacggtat   60
gacaac                                                                66

SEQ ID NO: 82          moltype = RNA   length = 66
FEATURE                Location/Qualifiers
source                 1..66
                       mol_type = other RNA
                       organism = synthetic construct
SEQUENCE: 82
gtggttggag aactggatgt agatgggctg gttgtagaag cctatcgtta ggataggtat   60
gacaac                                                                66

SEQ ID NO: 83          moltype = DNA   length = 9067
FEATURE                Location/Qualifiers
source                 1..9067
                       mol_type = other DNA
                       organism = synthetic construct
SEQUENCE: 83
tggcgaatgg gacgcgccct gtagcggcgc attaagcgcg gcgggtgtgg tggttacgcg   60
cagcgtgacc gctacacttg ccagcgccct agcgcccgct cctttcgctt tcttcccttc   120
ctttctcgcc acgttcgccg gctttccccg tcaagctcta aatcggggc tcccctttagg   180
gttccgattt agtgctttac ggcacctcga ccccaaaaaa cttgattagg gtgatggttc   240
acgtagtggg ccatcgccct gatagacggt ttttcgccct ttgacgttgg agtccacgtt   300
```

-continued

```
ctttaatagt ggactcttgt tccaaactgg aacaacactc aaccctatct cggtctattc   360
tttttgattta taagggattt tgccgatttc ggcctattgg ttaaaaaatg agctgattta   420
acaaaaattt aacgcgaatt ttaacaaaat attaacgttt acaatttcag gtggcacttt   480
tcggggaaat gtgcgcggaa cccctatttg tttatttttc taaatacatt caaatatgta   540
tccgctcatg aattaattct tagaaaaact catcgagcat caaatgaaac tgcaatttat   600
tcatatcagg attatcaata ccatattttt gaaaaagccg tttctgtaat gaaggagaaa   660
actcaccgag gcagttccat aggatggcaa gatcctggta tcggtctgcg attccgactc   720
gtccaacatc aatacaacct attaatttcc cctcgtcaaa aataaggtta tcaagtgaga   780
aatcaccatg agtgacgact gaatccggtg agaatggcaa aagtttatgc atttctttcc   840
agacttgttc aacaggccag ccattacgct cgtcatcaaa atcactcgca tcaaccaaac   900
cgttattcat tcgtgattgc gcctgagcga gacgaaatac gcgatcgctg ttaaaaggac   960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatcctttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccaggggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcggacg cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccacgca aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga ctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgg   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
```

-continued

```
ttttgtttaa ctttaagaag gagatatacc atgggcagca gccatcatca tcatcatcac   5100
agcagcggcc tggtgccgcg cggcagccat atggctagca tgactggtgg acagcaaatg   5160
ggtcgcggat ccccggcagc taagaaaaag aaactggatg gcagcgtcga catgaaggag   5220
cagaagaagt tcagcctgca gggcgtgaga cacgtgtgcg gcagctactt caacatggcc   5280
ctgaacaact actgcagaac cctgaacggc gtgttcatca agtgcaagat caagttcgcc   5340
ctgaaggagg acgacttccc cagaagcctg agcagcctga gaaagatctt cagcagcggc   5400
cccatcatgc cccagaccga gaagaaggtg gccaagatga tcgccagcgt ggacaccgcc   5460
atgaagctga agcagcagct gttcaagcac ttccccatgc tgggccccat catggacaag   5520
accatcagct gcatgaacca ccacaagggc agcagcgtgg ccgacgcccc cctggacctg   5580
tgcatgaacg ccatcctgaa cttcggcgag tgcctgtacc actgcagaaa cttctacacc   5640
cacttcaagc cctacaacag ccccgaggac ctgaagctgc agtacgacat ccagcacatc   5700
atcgccctga acctgggcac cctgttcgac gtgagcagaa gaatcggcaa gaagagagag   5760
ggcctgaccc ccgaggagct ggagttcctg accggcaaga acagattcaa ccaggtgggc   5820
aagaagttcc tggagagaaa cgactggtac ttgaagatcg agaagcccag cgacatgaag   5880
gactacgaca agaccatcct gagcgacttc ggcatggtgt acctgtgcag catcttcctg   5940
gccaagaact acgccctgag actgttcgac gagagcaagc tgttcaacaa ggagacaatc   6000
agaaacctgt tcagcgagga gcaggtgaga ttcctgaagg agatgctggt gatctacaga   6060
atcagaaccc ccagaggcaa gcagctgaac agccacgaca gcaagcaggc cctggccatg   6120
gacatgctga acgagctgag aaagtgcccc agacccctgt acgacgtgct gagcgaggag   6180
tacaagaaga gaaccttcta cgtgcccgtg gagcacgaga acgagaaaac cgaggagtac   6240
gtgaagatgc tgagaagcga cgacagattc ccctacttca ccctgagata catcgacgac   6300
atggaagagt tcagcagaat cagattccag atcagactgg gcagctacag attcaagttc   6360
tacgacaaga tgaacatcga cggcacccc agaatcagaa gcctgcagaa ggagatcaac   6420
ggcttcggca gactgagcga catggagaac aagagaaaga gagtggaa ggacatgttc   6480
caggccaccg aggagatcga ctacgaggac cagttcggcg actaccagac cggcgtgacc   6540
cagttcgtgg aggacaccgc cgaccacaag ccctacgtga ccaaccacag accgcctac   6600
aacgtgcaca gcaaccacat cggcctgatc tggaacgacg ccgacagcat catcctgcag   6660
gacgacaaca agctgttctt cccccgacctg aagatcgacg agaacggcaa ggccgacatc   6720
taccagccca gcccccaaggc cagcctgagc gtgttcgact tccccgccat ggtgttctac   6780
atgtacctga gagagaaaac cgaggccacc aaggagttcc ccagcgccga gcagctgatc   6840
atcaacaagt acgaccacct ggtgagattc ttcaaggaca tcagcgacgg cagattcggc   6900
cccagcgaga acaagaacgc cttcagcaag aagctgaagg aggagtacga cctgaaaacc   6960
ggcgagatcc ccgagaagct gctgcactgg ctgagcagcg agagcgagga ggaccccagc   7020
gagaagtacg ccaagaagct ggaggaggag atcaagctga gaagagagag agtgcagaga   7080
agattggaag agttcaacca ggacctgaga gagatcagaa agaaggacag cgtgccctac   7140
ggcaagaagg gccacgtgaa catcagacac agccagctgg ccaagtacct gatgagaagc   7200
atcatggagt ggcagcccac cagaaacgac ggcaagaaca agctgaccgg ccagaacttc   7260
aacgtgatga ccgccttcct ggccacccctg ggctacacca gccaggtgaa ggacctgaga   7320
gacttgttca gcagagccaa catgctggag ggcccaaacg cccaccccctt cctgaagaag   7380
gtgctgaaca acaacagcat caaggacatc cagggcttct acagaaccta cctggtggag   7440
gagctgaacc agatcgagga caagcagaga agaatcgcca aggccaagaa cgtgaaggac   7500
accgtgagac agttccccctt cgcccacttc aacagaatga gataccagaa gagagacgag   7560
gactactaca gaaacctggc caagagatac ctgaacatcg gcgacaacga gaaggacaag   7620
gccgtgatcc tgctgcccga cggcatgttc accagctaca tctacgacct gatcatgaag   7680
ctgcccgaga acaacgagaa gatgagaatc aacctggcca gcgacgtggc ccactgcaac   7740
agcagcttcc tgatcagcag attcttcgag aacatcagaa cgactacgc ccagcccttc   7800
tacagagagg agagaacctat cgagctgttc agcatcctga acaacagaag ggtgagaaac   7860
accctgcagc ccctgttcat cagcccccac gacatcaaca tccagctgac cgagaaggag   7920
aaggacggca agggcagact gatcctgcag aagatcgacc acttctgcaa gagcatcacc   7980
cagaagggca acttcaacaa cgtggaggag gccaaggagg ccaccagcag aaagctgaag   8040
cacctgatca ccgactgcaa gaacaacgag agagacatca gaatacaca gacccaggac   8100
atggtgatct acctgatggc cagagacatc ctgaaggaca tcatccccga cagcgagaag   8160
gacaagtacg ccaaggacag aaagctgctg ctgaaggacg tgtgcgagga gggcttcctg   8220
agacaggccg tgaagatgga gtacgagtac agcatcgagg agaagggcaa gagaaccaga   8280
accgtgaaga tcacccaccc caacatgagc ctgaagaact acggcgagtt ccacagactg   8340
ctgaacgacg agagactgaa gagcctgctg cagcagctgg ccaacatgca cgagatcgac   8400
tacaccgacc tgatgggcga gttcgccgac tacgaccaga gagaagcga gatcttcaga   8460
ctggcccaga gcatcgagaa gcacctgtac gagcagaacg agcagggcct gaacgacgag   8520
aagagccagagc tgtcctacca caccagatac aacggcaagga agatccccga aagaaacagc   8580
ttcagcagcc tgctggagct gatcggcgag gaggagagcc agatgaccga gacagacagc   8640
aagcagacca tcagcatcag aaacgccttc ggccacaaca cctacaaggt gagcctggcc   8700
gagatgaacg ccaccgagct gcccaacgtg gccaagacca tcctgaagaa gatggaggag   8760
ctgagaaaca agctgacagg cggcggcccc ggcggcggcg ccgccgccgg cagcggcagc   8820
cctaagaaaa aacgaaaagt tggcacggga agcaaaaggc gaaaaggcc ggaaaaggcc   8880
ggccaggcaa aaaagaaaaa gtaactcgag caccaccacc accaccactg agatccggct   8940
gctaacaaag cccgaaagga agctgagttg gctgctgcca ccgctgagca ataactagca   9000
taaccccttg gggcctctaa acgggtcttg aggggttttt tgctgaaagg aggaactata   9060
tccggat                                                              9067
```

SEQ ID NO: 84          moltype = AA   length = 10
FEATURE                Location/Qualifiers
source                 1..10
                       mol_type = protein
                       organism = synthetic construct
VARIANT                9
                       note = X is S or T.
SEQUENCE: 84
LXXXRNXYXH                                                             10

-continued

```
SEQ ID NO: 85           moltype = AA   length = 12
FEATURE                 Location/Qualifiers
source                  1..12
                        mol_type = protein
                        organism = synthetic construct
VARIANT                 7
                        note = X is V or I.

SEQUENCE: 85
RXXXKXXNGF GR                                                    12

SEQ ID NO: 86           moltype = AA   length = 19
FEATURE                 Location/Qualifiers
source                  1..19
                        mol_type = protein
                        organism = synthetic construct
VARIANT                 3
                        note = X is I or V.
VARIANT                 12
                        note = X is I or V.

SEQUENCE: 86
PYXTXXXXY XXXXNXIGL                                              19

SEQ ID NO: 87           moltype = AA   length = 15
FEATURE                 Location/Qualifiers
source                  1..15
                        mol_type = protein
                        organism = synthetic construct
VARIANT                 3
                        note = X is A or C.
VARIANT                 9
                        note = X is E or D.
VARIANT                 10
                        note = X is L or F.

SEQUENCE: 87
PXXXLSXXXX PAXXF                                                 15

SEQ ID NO: 88           moltype = AA   length = 13
FEATURE                 Location/Qualifiers
source                  1..13
                        mol_type = protein
                        organism = synthetic construct
VARIANT                 2
                        note = X is D, R or K.
VARIANT                 7
                        note = X is D or S.
VARIANT                 8
                        note = X is M or I.
VARIANT                 9
                        note = X is M or V.
VARIANT                 11
                        note = X is F or W.

SEQUENCE: 88
AXXLXXXXX XQP                                                    13

SEQ ID NO: 89           moltype = AA   length = 6
FEATURE                 Location/Qualifiers
source                  1..6
                        mol_type = protein
                        organism = synthetic construct

SEQUENCE: 89
KLTXXN                                                           6

SEQ ID NO: 90           moltype = AA   length = 12
FEATURE                 Location/Qualifiers
source                  1..12
                        mol_type = protein
                        organism = synthetic construct
VARIANT                 7
                        note = X is L or M.

SEQUENCE: 90
IXLPXGXFXX XI                                                    12

SEQ ID NO: 91           moltype = AA   length = 13
FEATURE                 Location/Qualifiers
source                  1..13
                        mol_type = protein
                        organism = synthetic construct
VARIANT                 1
                        note = X is D or N.
```

-continued

```
VARIANT                  2
                         note = X is T or N.
VARIANT                  6
                         note = X is I or L.
VARIANT                  7
                         note = X is K or R.
VARIANT                  8
                         note = X is V or R.
VARIANT                  10
                         note = X is K or R.
SEQUENCE: 91
XXEXXXXYX XQD                                                13

SEQ ID NO: 92            moltype = AA  length = 9
FEATURE                  Location/Qualifiers
source                   1..9
                         mol_type = protein
                         organism = synthetic construct
VARIANT                  3
                         note = X is S or A.
VARIANT                  4
                         note = X is F or A.
SEQUENCE: 92
RNXXXHXXY                                                    9

SEQ ID NO: 93            moltype = AA  length = 10
FEATURE                  Location/Qualifiers
source                   1..10
                         mol_type = protein
                         organism = synthetic construct
VARIANT                  2
                         note = X is R, V or Y.
VARIANT                  3
                         note = X is E, Y or H.
VARIANT                  4
                         note = X is L, Y or C.
VARIANT                  7
                         note = X is V, F or M.
VARIANT                  9
                         note = X is S or T.
SEQUENCE: 93
LXXXRNXYXH                                                   10

SEQ ID NO: 94            moltype = AA  length = 12
FEATURE                  Location/Qualifiers
source                   1..12
                         mol_type = protein
                         organism = synthetic construct
VARIANT                  2
                         note = X is S or T.
VARIANT                  3
                         note = X is I, V or L.
VARIANT                  4
                         note = X is S or Q.
VARIANT                  6
                         note = X is N, A or E.
VARIANT                  7
                         note = X is V or I.
SEQUENCE: 94
RXXXKXXNGF GR                                                12

SEQ ID NO: 95            moltype = AA  length = 19
FEATURE                  Location/Qualifiers
source                   1..19
                         mol_type = protein
                         organism = synthetic construct
VARIANT                  3
                         note = X is I or V.
VARIANT                  5
                         note = X is D or N.
VARIANT                  6
                         note = X is H or W.
VARIANT                  7
                         note = X is H or R.
VARIANT                  8
                         note = X is A or T.
VARIANT                  9
                         note = X is K, A or T.
VARIANT                  11
```

```
                                    note = X is L or N.
VARIANT                             12
                                    note = X is I or V.
VARIANT                             13
                                    note = X is H or S.
VARIANT                             14
                                    note = X is N, S or A.
VARIANT                             15
                                    note = X is R or H.
SEQUENCE: 95
PYXTXXXXXY XXXXNXIGL                                                               19

SEQ ID NO: 96                       moltype = AA  length = 20
FEATURE                             Location/Qualifiers
source                              1..20
                                    mol_type = protein
                                    organism = synthetic construct
VARIANT                             2
                                    note = X isT, M or K.
VARIANT                             3
                                    note = X is A or C.
VARIANT                             4
                                    note = X is W, Y or S.
VARIANT                             7
                                    note = X is I or V.
VARIANT                             8
                                    note = X is F or Y.
VARIANT                             9
                                    note = X is E or D.
VARIANT                             10
                                    note = X is L or F.
VARIANT                             13
                                    note = X is L or M.
VARIANT                             14
                                    note = X is A, L or V.
VARIANT                             16
                                    note = X is L or Y.
VARIANT                             17
                                    note = X is L, C or M.
VARIANT                             18
                                    note = X is H or Y.
VARIANT                             19
                                    note = X is L or I.
VARIANT                             20
                                    note = X is Y or R.
SEQUENCE: 96
PXXXLSXXXX PAXXFXXXXX                                                              20

SEQ ID NO: 97                       moltype = AA  length = 13
FEATURE                             Location/Qualifiers
source                              1..13
                                    mol_type = protein
                                    organism = synthetic construct
VARIANT                             2
                                    note = X is D, R or K.
VARIANT                             3
                                    note = X is F or Y.
VARIANT                             5
                                    note = X is A or M.
VARIANT                             6
                                    note = X is H, T or R.
VARIANT                             7
                                    note = X is D or S.
VARIANT                             8
                                    note = X is M or I.
VARIANT                             9
                                    note = X is M or V.
VARIANT                             10
                                    note = X is F, R or E.
VARIANT                             11
                                    note = X is F or W.
SEQUENCE: 97
AXXLXXXXXX XQP                                                                     13

SEQ ID NO: 98                       moltype = AA  length = 9
FEATURE                             Location/Qualifiers
source                              1..9
                                    mol_type = protein
                                    organism = synthetic construct
```

-continued

```
VARIANT               1
                      note = X is C or G.
VARIANT               2
                      note = X is N, G or K.
VARIANT               3
                      note = X is N or D.
VARIANT               7
                      note = X is G or S.
VARIANT               8
                      note = X is L, A or Q.
SEQUENCE: 98
XXXKLTXXN                                                                               9

SEQ ID NO: 99         moltype = AA  length = 14
FEATURE               Location/Qualifiers
source                1..14
                      mol_type = protein
                      organism = synthetic construct
VARIANT               1
                      note = X is K or A.
VARIANT               2
                      note = X is S, P or V.
VARIANT               4
                      note = X is E, L or M.
VARIANT               7
                      note = X is R or D.
VARIANT               9
                      note = X is L or M.
VARIANT               11
                      note = X is E or T.
VARIANT               12
                      note = X is S or T.
VARIANT               13
                      note = X is Y or H.
SEQUENCE: 99
XXIXLPXGXF XXXI                                                                        14

SEQ ID NO: 100        moltype = AA  length = 19
FEATURE               Location/Qualifiers
source                1..19
                      mol_type = protein
                      organism = synthetic construct
VARIANT               1
                      note = X is L or I.
VARIANT               5
                      note = X is Y, W or F.
VARIANT               12
                      note = X is D or Q.
VARIANT               16
                      note = X is P or T.
VARIANT               19
                      note = X is D or R.
SEQUENCE: 100
XIXXXFXXXX XXXXQXFYX                                                                   19

SEQ ID NO: 101        moltype = AA  length = 13
FEATURE               Location/Qualifiers
source                1..13
                      mol_type = protein
                      organism = synthetic construct
VARIANT               1
                      note = X is D or N.
VARIANT               2
                      note = X is T or N.
VARIANT               4
                      note = X is K, T or R.
VARIANT               5
                      note = X is E or D.
VARIANT               6
                      note = X is I or L.
VARIANT               7
                      note = X is K or R.
VARIANT               8
                      note = X is V or R.
VARIANT               10
                      note = X is K or R.
VARIANT               11
                      note = X is I, L or T.
SEQUENCE: 101
```

-continued

```
XXEXXXXXYX XQD                                                          13

SEQ ID NO: 102          moltype = AA   length = 10
FEATURE                 Location/Qualifiers
source                  1..10
                        mol_type = protein
                        organism = synthetic construct
VARIANT                 3
                        note = X is S or A.
VARIANT                 4
                        note = X is F or A.
VARIANT                 5
                        note = X is A or G.
VARIANT                 7
                        note = X is N or L.
VARIANT                 8
                        note = X is S, R or T.
VARIANT                 10
                        note = X is P or K.
SEQUENCE: 102
RNXXXHXXYX                                                              10

SEQ ID NO: 103          moltype = DNA   length = 18
FEATURE                 Location/Qualifiers
source                  1..18
                        mol_type = other DNA
                        organism = synthetic construct
SEQUENCE: 103
gggtcttcga gaagacct                                                     18

SEQ ID NO: 104          moltype = DNA   length = 24
FEATURE                 Location/Qualifiers
source                  1..24
                        mol_type = other DNA
                        organism = synthetic construct
SEQUENCE: 104
gatcaacatt aaatgtgagc gagt                                              24

SEQ ID NO: 105          moltype = DNA   length = 7690
FEATURE                 Location/Qualifiers
source                  1..7690
                        mol_type = other DNA
                        organism = synthetic construct
SEQUENCE: 105
cctgcaggca gctgcgcgct cgctcgctca ctgaggccgc ccgggcgtcg ggcgaccttt       60
ggtcgcccgg cctcagtgag cgagcgagcg cgcagagagg gagtggccaa ctccatcact      120
aggggttcct gcggcctcta gactcgaggc gttgacattg attattgact agttattaat      180
agtaatcaat tacggggtca ttagttcata gcccatatat ggagttccgc gttacataac      240
ttacggtaaa tggcccgcct ggctgaccgc ccaacgaccc ccgcccattg acgtcaataa      300
tgacgtatgt tcccatagta acgccaatag ggactttcca ttgacgtcaa tgggtggagt      360
atttacggta aactgcccac ttggcagtac atcaagtgta tcatatgcca agtacgcccc      420
ctattgacgt caatgacggt aaatggcccg cctggcatta tgcccagtac atgaccttat      480
gggactttcc tacttggcag tacatctacg tattagtcat cgctattacc atggtgatgc      540
ggttttggca gtacatcaat gggcgtggat agcggtttga ctcacgggga tttccaagtc      600
tccaccccat tgacgtcaat gggagtttgt tttggcacca aaatcaacgg gactttccaa      660
aatgtcgtaa caactccgcc ccattgacgc aaatgggcgg taggcgtgta cggtgggagg      720
tctatataag cagagctctc tggctaacta ccggtgccac catgccggca gctaagaaaa      780
agaaactgga tggcagcgtc gacatgaagg agcagaagaa gttcagcctg cagggcgtga      840
gacacgtgtg cggcagctac ttcaacatgg ccctgaacaa ctactgcaga accctgaacg      900
gcgtgttcat caagtgcaag atcaagttcg ccctgaagga ggacgacttc cccagaagcc      960
tgagcagcct gagaaagatc ttcagcagcg gccccatcat gccccagacc gagaagaagg     1020
tggccaagat gatcgccagc gtggacaccg ccatgaagct gaagcagcag ctgttcaagc     1080
acttccccat gctgggcccc atcatggaca agaccatcag ctgcatgaac caccacaagg     1140
gcagcagcgt ggccgacgcc ccctggacc tgtgcatgaa cgccatcctg aacttcggcg     1200
agtgcctgta ccactgcaga aacttctaca cccacttcaa gccctacaac agccccgagg     1260
acctgaagct gcagtacgac atccagcaca tcatcgccct gaacctgggc accctgttcg     1320
acgtgagcag aagaatcggc aagaagagag agggcctgac ccccgaggag ctggagttcc     1380
tgaccggcaa gaacagattc aaccaggtgg gcaagaagt cctggagaga aacgactggt     1440
acttgaagat cgagaagccc agcgacatga aggactacga caagaccatc ctgagcgact     1500
tcggcatggt gtacctgtgc agcatcttcc tggccaagaa ctacgccctg agactgttcg     1560
acgagagcaa gctgttcaac aaggagacaa tcagaaacct gttcagcgag gagcaggtga     1620
gattcctgaa ggagatgctg gtgatctaca atcagaac ccccagaggc aagcagctgg     1680
acagccacga cagcaagcag gccctggcca tggacatgct gaacgagctg agaaagtgcc     1740
ccagacccct gtacgacgtg ctgagcgagg agtacaagga gagaacctc tacgtgcccg     1800
tggagcacga gaacgagaaa accgaggagt acgtgaagat gctgagaagc gacgacgagt     1860
tcccctactt caccctgaga tacatgacg acatggagaa gttcagcaga atcagattcc     1920
agatcagact gggcagctac agattcaagt ctacgacaa gatgaacatc gacggcacc     1980
ccagaatcag aagcctgcag aaggagatca cggcttcgg cagactgagc gacatggaga     2040
acaagagaaa gagagagtgg aaggacatgt tccaggccac cgaggagatc gactacgagg     2100
```

-continued

```
accagttcgg cgactaccag accggcgtga cccagttcgt ggaggacacc gccgacacca   2160
agccctacgt gaccaaccac agagccgcct acaacgtgca cagcaaccac atcggcctga   2220
tctggaacga cgccgacagc atcatcctgc aggacgacaa caagctgttc ttccccgacc   2280
tgaagatcga cgagaacggc aaggccgaca tctaccagcc cagccccaag gccagcctga   2340
gcgtgttcga cttccccgcc atggtgttct acatgtacct gagagagaaa accgaggcca   2400
ccaaggagtt ccccagcgcc gagcagctga tcatcaacaa gtacgaccac ctggtgagat   2460
tcttcaagga catcagcgac ggcagattcg gccccagcga gaacaagaac gccttcagca   2520
agaagctgaa ggaggagtac gacctgaaaa ccggcgagat ccccgagaag ctgctgcact   2580
ggctgagcag cgagagcgag gaggacccca gcgagaagta cgccaagaag ctggaggagg   2640
agatcaagct gagaagagag agagtgcaga gaagattgga gaagttcaac caggacctga   2700
gagagatcag aaagaaggac agcgtgccct acggcaagaa gggccacgtg aacatcagac   2760
acagccagct ggccaagtac ctgatgagaa gcatcatgg gtggcagccc accagaaacg   2820
acggcaagaa caagctgacc ggccagaact tcaacgtgat gaccgccttc ctggccaccc   2880
tgggctacac cagccaggtg aaggacctga gagacttgtt cagcagagcc aacatgctgg   2940
agggccccaa cgcccacccc ttcctgaaga aggtgctgaa caacaacagc atcaaggaca   3000
tccagggctt ctacagaacc tacctggtgg aggagctgaa ccagatcgag gacaagcaga   3060
gaagaatcgc caaggccaag aacgtgaagg acaccgtgag acagttcccc ttcgcccact   3120
tcaacagaat gagataccag aagagagacg aggactacta cagaaacctg gccaagagat   3180
acctgaacat cggcgacaac gagaaggaca aggccgtgat cctgctgccc gacggcatgt   3240
tcaccagcta catctacgac ctgatcatga agctgcccga gaacaacgag aagatgagaa   3300
tcaacctggc cagcgacgtg gcccactgca acagcagctt cctgatcagc agattcttcg   3360
agaacatcag aaacgactac gcccagcccct tctacagaga ggagagaacc tacgagctgt   3420
tcagcatcct gaacaacaag aaggtgagaa acaccctgca gccctgttc atcagcccc   3480
acgacatcaa catccagctg accgagaagg agaaggacgg caagggcaga ctgatcctgc   3540
agaagatcga ccacttctgc aagagcatca cccagaaggg caacttcaac aacgtggagg   3600
aggccaagga ggccaccagc agaaagctga agcacctgat caccgactgc aagaacaacg   3660
agagagacat cagaagatac aagacccagg acatggtgat ctacctgatg gccagagaca   3720
tcctgaagga catcatcccc gacagcgaga aggacaagta cgccaaggac agaaagctgc   3780
tgctgaagga cgtgtgcgag gagggcttcc tgagacaggc cgtgaagatg gagtacgagt   3840
acagcatcga ggagaagggc aagagaacca gaaccgtgaa gatcacccac cccaacatga   3900
gcctgaagaa ctacggcgag ttccacagac tgctgaacga cgagagactg aagagcctgc   3960
tgcagcagct ggccaacatg gacgagatcg actacaccga cctgatgggc gagttcgccg   4020
actacgacca gaagagaagc gagatcttca gactggccca gagcatcgag aagcacctgt   4080
acgagcagga cgagcagggc ctgaacgacg agaagagcga cctgttctac cacaccagat   4140
acaacggcaa gaagatcccc agaagaaaca gcttcagcag cctgctggag ctgatcggca   4200
aggaggagag ccagatgacc gagacagaca agaagcagac catcagcatc agaaacgcct   4260
tcggccacaa cacctacaag gtgagcctgg ccgagatgaa cgccaccgag ctgcccaacg   4320
tggccaagac catcctgaag aagatggagg agctgagaaa caagctgaca ggcggcggcc   4380
ccggcggcgg cgccgccgcc ggcagcggca gccctaagaa aaaacgaaaa gttggcagcg   4440
gaagcaaaag gccggcggcc acgaaaaagg ccggccagc aaaaaagaaa aagctcgagt   4500
acccatacga tgttccagat tacgcttgag aattcccctt gagcatctga cttctggcta   4560
ataaaggaaa tttattttca ttgcaatagt gtgttggaat ttttttgtgtc tctcaggtac   4620
cgagggccta tttcccatga ttccttcata tttgcatata cgatacaagg ctgttagaga   4680
gataattgga attaatttga ctgtaaacac aaagatatta gtacaaaata cgtgacgtag   4740
aaagtaataa tttcttgggt agtttgcagt tttaaaatta tgttttaaaa tggactatca   4800
tatgcttacc gtaacttgaa agtatttcga tttcttggct ttatatatct tgtggaaagg   4860
acgaaacacc gtgccgttct tctgcttgtc ggccatgata tgtttgtagaa gcctatcgtt   4920
aggataggta tgacaacttt ttttgcggcc gcaggaaccc ctagtgatgg agttggccac   4980
tccctctctg cgcgctcgct cgctcactga ggccgggcga ccaaaggtcg cccgacgccc   5040
gggctttgcc cgggcggcct cagtgagcga gcgagcgcgc agctgcctgc aggggcgcct   5100
gatgcggtat tttctcctta cgcatctgtg cggtatttca caccgcatac gtcaaagcaa   5160
ccatagtacg cgccctgtag cggcgcatta gcgcggcgg gtgtggtggt tacgcgcagc   5220
gtgaccgcta cacttgccag cgccttagc cccgctcctt tcgctttctt cccttccttt   5280
ctcgccacgt tcgccggctt tccccgtcaa gctctaaatc gggggctccc tttagggttc   5340
cgatttagtg ctttacggca cctcgacccc aaaaaacttg atttgggtga tggttcacgt   5400
agtgggccat cgccctgata cgggtttttt cgccctttga cgttggagtc cacgttcttt   5460
aatagtggac tcttgttcca aactggaaca acactcaact ctatctcggg ctattctttt   5520
gatttataag ggattttgcc gatttcggtc tattggttaa aaaatgagct gatttaacaa   5580
aaatttaacg cgaatttaa caaaatatta acgtttacaa ttttatggtg cactctcagt   5640
acaatctgct ctgatgccgc atagttaagc cagccccgac acccgccaac acccgctgac   5700
gcgccctgac gggcttgtct gctcccggca tccgcttaca gacaagctgt gaccgtctcc   5760
gggagctgca tgtgtcagag gttttcaccg tcatcaccga aacgcgcgag acgaaagggc   5820
ctcgtgatac gcctattttt ataggttaat gtcatgataa taatggtttc ttagacgtca   5880
ggtggcactt ttcggggaaa tgtgcgcgga acccctattt gtttattttt ctaaatacat   5940
tcaaatatgt atccgctcat gagacaataa ccctgataaa tgcttcaata atattgaaaa   6000
aggaagagta tgagtattca acatttccgt gtcgccctta ttcccttttt tgcggcattt   6060
tgccttcctg tttttgctca cccagaaacg ctggtgaaag taaaagatgc tgaagatcag   6120
ttgggtgcac gagtgggtta catcgaactg gatctcaaca gcggtaagat ccttgagagt   6180
tttcgccccg aagaacgttt tccaatgatg agcacttttt aagttctgct atgtggcgcg   6240
gtattatccc gtattgacgc cgggcaagag caactcggtc gccgcataca ctattctcag   6300
aatgacttgg ttgagtactc accagtcaca gaaaagcatc ttacgatgg catgacagta   6360
agagaattat gcagtgctgc cataaccatg agtgataaca ctgcggccaa cttacttctg   6420
acaacgatcg aggaccgaa ggagctaacc gcttttttgc acaacatggg ggatcatgta   6480
actcgccttg atcgttggga accggagctg aatgaagcca taccaaacga cgagcgtgac   6540
accacgatgc ctgtagcaat ggcaacaacg ttgcgcaaac tattaactgg cgaactactt   6600
actctagctt cccggcaaca attaatagac tggatggagg cggataaagt tgcaggacca   6660
cttctgcgct cggcccttcc ggctggctgg tttattgctg ataaatctgg agccggtgag   6720
cgtggaagcc gcggtatcat tgcagcactg gggccagatg gtaagccctc ccgtatcgta   6780
gttatctaca cgacggggag tcaggcaact atggatgaac gaaatagaca gatcgctgag   6840
```

-continued

```
ataggtgcct cactgattaa gcattggtaa ctgtcagacc aagtttactc atatatactt   6900
tagattgatt taaaacttca tttttaattt aaaaggatct aggtgaagat cctttttgat   6960
aatctcatga ccaaaatccc ttaacgtgag ttttcgttcc actgagcgtc agaccccgta   7020
gaaaagatca aaggatcttc ttgagatcct ttttttctgc gcgtaatctg ctgcttgcaa   7080
acaaaaaaac caccgctacc agcggtggtt tgtttgccgg atcaagagct accaactctt   7140
tttccgaagg taactggctt cagcagagcg cagataccaa atactgttct tctagtgtag   7200
ccgtagttag gccaccactt caagaactct gtagcaccgc ctacatacct cgctctgcta   7260
atcctgttac cagtggctgc tgccagtggc gataagtcgt gtcttaccgg gttggactca   7320
agacgatagt taccggataa ggcgcagcgg tcgggctgaa cggggggttc gtgcacacag   7380
cccagcttgg agcgaacgac ctacaccgaa ctgagatacc tacagcgtga gctatgagaa   7440
agcgccacgc ttcccgaagg gagaaaggcg gacaggtatc cggtaagcgg cagggtcgga   7500
acaggagagc gcacgaggga gcttccaggg ggaaacgcct ggtatcttta tagtcctgtc   7560
gggtttcgcc acctctgact tgagcgtcga tttttgtgat gctcgtcagg ggggcggagc   7620
ctatggaaaa acgccagcaa cgcggccttt ttacggttcc tggccttttg ctggcctttt   7680
gctcacatgt                                                           7690
```

ISOLATED CAS13 PROTEIN AND USE THEREOF

CROSS-REFERENCE TO RELATED APPLICATIONS

This application is a continuation application of PCT/CN2022/129825, filed on Nov. 4, 2022, which claims priorities from Chinese patent application CN2021113061499, filed on Nov. 5, 2021 and Chinese patent application CN2022105188261, filed on May 13, 2022, the entire contents of which are hereby incorporated by reference.

REFERENCE TO SEQUENCE LISTING

The instant application contains a Sequence Listing as an XML file entitled "P244114862US-SEQ.xml" created on Apr. 30, 2024 and having a size of 288,853 bytes. The Sequence Listing is incorporated herein by reference.

TECHNICAL FIELD

The present invention relates to the technical field of gene editing, and in particular to an isolated Cas13 protein and use thereof.

BACKGROUND

CRISPR-Cas13 is an RNA targeting and editing system based on a bacterial immune system, which can protect the bacterial from virus attack. This system is basically similar to a CRISPR-Cas9 system, but different from a DNA-targeting CRISPR-Cas9 system in that the Cas13 protein can cleaves an RNA in a targeting manner.

The CRISPR-Cas13 is of type VI in a second major type of a CRISPR-Cas system. It contains a single effector protein Cas13. When assembled with a CRISPR RNA (e.g. crRNA), it can form an RNA-targeting effector complex guided by the crRNA. Many Cas13 proteins have two different types of ribonuclease activities. One type is pretreatment of a pre-crRNA to form a type VI mature interference complex, which an RNase is responsible for; and the other type of RNase activity is provided by two higher eukaryotes and prokaryotes nucleotide-binding (HEPN) domains. The HEPN domains can help to cleave an RNA, such as an ssRNA, and when there is a folding structure in the target RNA, Cas13 generally prefers cleavage in a non-base-paired ssRNA region.

Currently, CRISPR-Cas13 can be divided into several subtypes (A, B, C and D) according to phylogeny.

The art has been always devoted to finding a novel Cas13 protein. Up to now, thousands of Cas13 proteins have been found, but not many of them are active. For example, most of the Cas13 proteins have not been reported as having an RNA targeting or modifying activity. It has been pointed out in the literature that once activated by target recognition, Cas13 will cleave the RNA indiscriminately and induce dormancy or death of a cell.

It is still a difficult problem to develop a Cas13 protein having an RNA targeting/modification activity.

CONTENT OF THE PRESENT INVENTION

In view of the above, it is necessary to provide an isolated Cas13 protein having activities of binding to, targeting and/or modifying a target RNA, aiming at the aforementioned problems.

The present invention discloses an isolated Cas13 protein, wherein the amino acid sequence of the Cas13 protein comprises a sequence having ≥50% sequence identity with the sequence as shown in any one of SEQ ID NO: 1-SEQ ID NO: 7, and SEQ ID NO: 60.

The aforementioned Cas13 protein is obtained by the inventor after repeated screening and attempts among many proteins, which has activities such as capable of forming a complex with a gRNA, forming a complex with a gRNA and binding to a target nucleic acid, being guided to a target nucleic acid by a gRNA, and/or targeting or modifying a target nucleic acid.

It can be understood that the amino acid sequence of the aforementioned Cas13 protein can also include a sequence having ≥50%, ≥60%, ≥70%, ≥75%, ≥80%, ≥85%, ≥90%, ≥92%, ≥95%, ≥96%, ≥97%, ≥98%, ≥99%, ≥99.5% or 100% sequence identity with the sequence as shown in any one of SEQ ID NO: 1-SEQ ID NO: 7 and SEQ ID NO: 60. That is, the amino acid sequence shown in the aforementioned sequence is only a part of the sequence of the Cas13 protein, and the Cas13 protein may further include other functional or non-functional domains. The amino acid sequence of the aforementioned Cas13 protein can also be a sequence having ≥50%, ≥60%, ≥70%, ≥75%, ≥80%, ≥85%, ≥90%, ≥92%, ≥95%, ≥96%, ≥97%, ≥98%, ≥99%, ≥99.5% or 100% sequence identity with the sequence as shown in any one of SEQ ID NO: 1-SEQ ID NO: 7 and SEQ ID NO: 60. That is, the protein composed of the amino acid sequence shown in the aforementioned sequence is the Cas13 protein.

In some embodiments, the Cas13 protein can form a complex with a gRNA.

In some embodiments, the Cas13 protein can be guided to a target nucleic acid by a gRNA. It can be understood that, after the Cas13 protein is guided to the target nucleic acid by the gRNA, optionally, the target nucleic acid may be or may not be targeted or modified. For example, in some cases, after the Cas13 protein is guided to the target nucleic acid by the gRNA, the target nucleic acid may not be targeted and modified (e.g., the target nucleic acid is not cleaved), and those skilled in the art can only use its ability of recognizing the target nucleic acid, for example to enable the target nucleic acid to be bound but not cleaved. In some cases, after the Cas13 protein is guided to the target nucleic acid by the gRNA, the target nucleic acid can be targeted or modified (e.g., the target nucleic acid is cleaved). For example, a target mRNA is cleaved and thus a translation level is reduced.

In some embodiments, the Cas13 protein can be guided to the target nucleic acid by the gRNA, and target or modify the target nucleic acid.

It can be understood that, when the Cas13 protein targets the target nucleic acid, one or more of the following activities can be produced: cleaving one or more target nucleic acids, visualizing or detecting one or more target nucleic acids, labeling one or more target nucleic acids, transporting one or more target nucleic acids, masking one or more target nucleic acids, binding to one or more target nucleic acids, increasing a transcription and/or translation level of a gene corresponding to a target nucleic acid, and reducing the transcription and/or translation level of the gene corresponding to the target nucleic acid.

In some embodiments, the targeting the target nucleic acid is cleaving the target nucleic acid or binding to the target nucleic acid.

In some embodiments, the targeting the target nucleic acid is binding to the target nucleic acid. The binding can be binding caused by base complementary pairing between a gRNA guide sequence and the target sequence.

In some embodiments, the targeting the target nucleic acid is cleaving the target nucleic acid.

In some embodiments, the target nucleic acid is an RNA. In some embodiments, the RNA is optionally selected from an mRNA, a miRNA, an rRNA, a tRNA, a snRNA and a structural RNA. The Cas13 protein can be guided to the target nucleic acid by the gRNA, and then the target nucleic acid can optionally be cleaved or not.

In some embodiments, the target nucleic acid is an mRNA. In some cases, when the target nucleic acid is an mRNA, the Cas13 protein can be guided to the target nucleic acid by the gRNA, and then the target nucleic acid can optionally be cleaved or not.

In some embodiments, the target nucleic acid is a PTBP1 (polypyrimidine tract binding protein 1) mRNA, an AQp1 (aquaporin 1) mRNA, a VEGFA (vascular endothelial growth factor A) mRNA, a VEGFR1 (vascular endothelial growth factor receptor 1) mRNA, or a VEGFR2 (vascular endothelial growth factor receptor-2) mRNA.

In some embodiments, the target nucleic acid is the PTBP1 (polypyrimidine tract binding protein 1) mRNA or the AQp1 (aquaporin 1) mRNA. That is, it is also used for knocking down the level of the AQp1 mRNA, thereby reducing the generation of aqueous humor, lowering a intraocular pressure, and treating a disease such as glaucoma; or it can be used for knocking down the level of the PTBP1 mRNA, thereby realizing the transdifferentiation of a brain astrocyte into a neuron, so as to treat a disease such as Parkinson's disease. In some embodiments, the target nucleic acid is the VEGFA mRNA, the VEGFR1 mRNA or the VEGFR2 mRNA, which can be used for treating age-related macular degeneration (AMD) by knocking down the mRNA level.

It should be understood that in the previous development, people have found that many gene/protein regulatory targets are related to human and animal/plant diseases, animal and plant traits, etc. A CRISPR system established based on the present invention is feasible for the binding, targeting or modifying of such targets.

In some embodiments, the Cas13 protein is derived from the same kingdom, phylum, class, order, family, genus or species as a protein including the amino acid sequence as shown in any one of SEQ ID NO: 1-SEQ ID NO: 7 and SEQ ID NO: 60.

Herein, the protein including the sequence of SEQ ID NO: 1 is accordingly Cas13 m.1, the protein including the sequence of SEQ ID NO: 2 is accordingly Cas13 m.2, the protein including the sequence of SEQ ID NO: 3 is accordingly Cas13 m.3, the protein including the sequence of SEQ ID NO: 4 is accordingly Cas13 m.4, the protein including the sequence of SEQ ID NO: 5 is accordingly Cas13 m.5, the protein including the sequence of SEQ ID NO: 6 is accordingly CasRfg.1, the protein including the sequence of SEQ ID NO: 7 is accordingly CasRfg.2, and the protein including the sequence of SEQ ID NO: 60 is accordingly Cas13 m.6.

In some embodiments, the Cas13m. 1 protein is derived from *Cytophagales bacterium; the Cas*13 m.2 protein is derived from a bacterium including a genome numbered CNA0011077 in CNGB database; the Cas13 m.3 protein is derived from *Bacteroidetes bacterium*; the Cas13 m.4 protein is derived from a bacterium including a genome numbered CNA0007373 in CNGB database; the Cas13 m.5 protein is derived from *Bacteroidetes bacterium*; the Cas13 m.6 protein is derived from *Prevotellaceae bacterium*; the CasRfg.1 protein is derived from a bacterium including a genome numbered GCA_003940745.1 in a NCBI database; and the CasRfg.2 protein is derived from a bacterium including a genome numbered CNA0009477 in the CNGB database.

In some embodiments, the Cas13 protein is derived from:
1) a sewage metagenome, *Cytophagales bacterium*, or *Bacteroidetes bacterium*;
2) a species with a genome having an ANI value ≥95% with a genome numbered GCA_003940745.1, GCA_013298125.1, GCA_902762805.1 or GCA_013298545.1 in NCBI database or a genome numbered CNA0011077, CNA0007373 or CNA0009477 in the CNGB database;
3) a species with a genome having an ANI value ≥95% with a genome of a sewage WW isolate, a bin5.concoct.b16b17b19.071, RUG10805 or bin17.concoct.ball.095 isolate.

Average nucleotide identity (ANI) is an index to evaluate the similarity of all orthologous protein coding genes between two genomes at a nucleic acid level. For bacteria/archaebacteria, a threshold ANI=95% is generally used as a basis for judging whether they are of the same species (Richter M, Rosselló-Móra R. Shifting the genomic gold standard for the prokaryotic species definition. Proc Natl Acad Sci USA. 2009 Nov. 10; 106(45):19126-31). Therefore, the present invention is defined by the aforementioned threshold, and it is considered that each species having an ANI value ≥95% with the aforementioned genome is of the same species, in which the Cas13 protein has homology and function similarity with the protein claimed by the present invention, and thus belongs to the scope of the present invention.

In some embodiments, the isolated Cas13 protein is derived from a species with a genome having an ANI value ≥95% with a genome numbered GCA_003940745.1, GCA_013298125.1, GCA_902762805.1 or GCA_013298545.1 in NCBI database or a genome numbered CNA0011077, CNA0007373 or CNA0009477 in CNGB database.

In some embodiments, the isolated Cas13 protein is derived from a species with a genome having an ANI value ≥95% with a genome numbered GCA_013298125.1, GCA_902762805.1 or GCA_013298545.1 in NCBI database or a genome numbered CNA0011077, CNA0007373 or CNA0009477 in CNGB database.

In some embodiments, the isolated Cas13 protein is derived from a bacterium including a genome numbered GCA_003940745.1, GCA_013298125.1, GCA_902762805.1 or GCA_013298545.1 in NCBI database or a genome numbered CNA0011077, CNA0007373 or CNA0009477 in CNGB database.

In some embodiments, the isolated Cas13 protein is derived from the isolate strain of sewage WW, bin5.concoct.b16b17b19.071, RUG10805 or bin17.concoct.ball.095.

The present invention further discloses an isolated Cas13 protein, including amino acid sequences as shown in the following motifs 1-15:

```
motif 1:
                                      (SEQ ID NO: 84)
L-x(3)-R-N-x-Y-[ST]-H motif 2:
                                      (SEQ ID NO: 85)
R-x(3)-K-x-[VI]-N-G-F-G-R
```

-continued

```
motif 3:
                                    (SEQ ID NO: 86)
P-Y-[IV]-T-x(5)-Y-x-[IV]-x(2)-N-x-I-G-L motif 4:
P-x-L-x(2)-D-x(3)-[NK]

motif 5:
                                    (SEQ ID NO: 87)
P-x-[AC]-x-L-S-x(2)-[ED]-[LF]-P-A-x(2)-F motif 6:
[LI]-P-x-K-L motif 7:
[KT]-x-[AL]-x(2)-[KVE]-[IL]

motif 8:
                                    (SEQ ID NO: 88)
A-[DRK]-x-L-x(2)-[DS]-[MI]-[MV]-x-[FW]-Q-P motif 9:
                                    (SEQ ID NO: 89)
K-L-T-x(2)-N motif 10:
F-x-[HR]-[AF]-x(5)-[QR]

motif 11:
                                    (SEQ ID NO: 90)
I-x-L-P-x-G-[LM]-F-x(3)-I motif 12:
[LI]-I-x(2)-[YWF]-F motif 13:
I-x(3)-I motif 14:
                                    (SEQ ID NO: 91)
[DN]-[TN]-E-x(2)-[IL]-[KR]-[VR]-Y-[KR]-x-Q-D motif 15:
                                    (SEQ ID NO: 92)
R-N-[SA]-[FA]-x-H-x(2)-Y
``` wherein A, F, C, U, D, N, E, Q, G, H, L, I, K, O, M, P, R, S, T, V, W, Y are standard amino acid codes, "x" is any amino acid, a numbers in a bracket after x represent multiple consecutive x's, the content in "[ ]" is an optional amino acid code, and "-" is a separator.

In some embodiments, the Cas13 protein includes the motifs 1-15 from the N-terminal to the C-terminal sequentially.

In some embodiments, the motif 1 is selected from the motif 16, the motif 2 is selected from the motif 17, the motif 3 is selected from the motif 18, the motif 4 is selected from the motif 19, the motif 5 is selected from the motif 20, the motif 6 is selected from the motif 21, the motif 7 is selected from the motif 22, the motif 8 is selected from the motif 23, the motif 9 is selected from the motif 24, the motif 10 is selected from the motif 25, the motif 11 is selected from the motif 26, the motif 12 is selected from the motif 27, the motif 13 is selected from the motif 28, the motif 14 is selected from the motif 29, and the motif 15 is selected from the motif 30.

The amino acid sequences as shown in the motifs 16-30 are as follows:

```
motif 16:
                                    (SEQ ID NO: 93)
L-[RVY]-[EYH]-[LYC]-R-N-[VFM]-Y-[ST]-H
```

-continued

```
motif 17:
                                    (SEQ ID NO: 94)
R-[ST]-[IVL]-[SQ]-K-[NAE]-[VI]-N-G-F-G-R motif 18:
                                    (SEQ ID NO: 95)
P-Y-[IV]-T-[DN]-[HW]-[HR]-[AT]-[KAT]-Y-[LN]-[IV]-
[HS]-[NSA]-N-[RH]-I-G-L motif 19:
P-[END]-L-[TKD]-[PIT]-D-[GKE]-[AGN]-[RDG]-[NK]

motif 20:
                                    (SEQ ID NO: 96)
P-[TMK]-[AC]-[WYS]-L-S-[IV]-[FY]-[ED]-[LF]-P-A-

[LM]-[ALV]-F-[LY]-[LCM]-[HY]-[LI]-[YR]

motif 21:
[SNG]-[QE]-[LI]-P-[RED]-K-L motif 22:
[KT]-[WHK]-[AL]-[AQE]-[SQE]-[KVE]-[IL]

motif 23:
                                    (SEQ ID NO: 97)
A-[DRK]-[FY]-L-[AM]-[HTR]-[DS]-[MI]-[MV]-[FRE]-

[FW]-Q-P motif 24:
                                    (SEQ ID NO: 98)
[CG]-[NGK]-[ND]-K-L-T-[GS]-[LAQ]-N motif 25:
F-[ALV]-[HR]-[AF]-[NS]-[QSR]-[NSM]-[KR]-[WY]-[QR]

motif 26:
                                    (SEQ ID NO: 99)
[KA]-[SPV]-I-[ELM]-L-P-[RD]-G-[LM]-F-[ET]-[ST]-
[YH]-I motif 27:
                                    (SEQ ID NO: 100)
[LI]-I-x(2)-[YWF]-F-x(5)-[DQ]-x(2)-Q-[PT]-F-Y-[DR]

motif 28:
I-[RAL]-[KQ]-[KD]-I motif 29:
                                    (SEQ ID NO: 101)
[DN]-[TN]-E-[KTR]-[ED]-[IL]-[KR]-[VR]-Y-[KR]-

[ILT]-Q-D motif 30:
                                    (SEQ ID NO: 102)
R-N-[SA]-[FA]-[AG]-H-[NL]-[SRT]-Y-[PK]
```

In some embodiments, the amino acid sequence of the Cas13 protein includes a sequence having ≥50%, ≥60%, ≥70%, ≥75%, ≥80%, ≥85%, ≥90%, ≥92%, ≥95%, ≥96%, ≥97%, ≥98%, ≥99%, ≥99.5% or 100% sequence identity with the sequence as shown in any one of SEQ ID NO: 2, SEQ ID NO: 3, and SEQ ID NO: 60. Further, in some embodiments, any amino acid residue in the amino acid sequence of the Cas13 protein, except the amino acids identified by the motifs 1-15, is subjected to conservative amino acid replacement on the basis of a wild-type sequence, and the wild-type sequence includes the sequence as shown in any one of SEQ ID NO: 2, SEQ ID NO: 3 and SEQ ID NO: 60. In some embodiments, the amino acid sequence of the Cas13 protein includes a sequence as shown in any one of SEQ ID NO: 2, SEQ ID NO: 3 and SEQ ID NO: 60.

In some embodiments, one or more amino acid residues (e.g., a catalytic residue) in the amino acid sequence of the Cas13 protein can be mutated, so that the Cas13 protein completely or partially loses its nuclease activity under the guidance of a gRNA. For example, an RxxxxH motif of a HEPN (higher eukaryotes and pro-karyotes nucleotide) domain of an RNase is mutated to inactivate the HEPN domain. Although such a changed protein reduces or loses the nuclease activity and does not cleave the target nucleic acid, it can still approach and bind to the target nucleic acid. For example, it can be fused with other domains for single base conversion, translation activation or translation suppression of the target nucleic acid.

In some embodiments, the nuclease activity can be reduced by mutation or modification, such as reduced by at least 10%, at least 20%, at least 30%, at least 40%, at least 50%, at least 60%, at least 70%, at least 80%, at least 90%, at least 95%, at least 97% or 100% compared with that of a wild-type Cas13 protein.

In some embodiments, the Cas13 protein can form a complex with a gRNA.

In some embodiments, the Cas13 protein can be guided to a target nucleic acid by a gRNA.

In some embodiments, the Cas13 protein is derived from the same kingdom, phylum, class, order, family, genus or species as a protein including the sequence as shown in any one of SEQ ID NO: 1-SEQ ID NO: 7 and SEQ ID NO: 60.

In some embodiments, the Cas13 protein is unnatural.

The Cas13 protein of the present invention can be modified, for example, linked to a modifying moiety (e.g. another polypeptide, oligopeptide or other molecules). Generally, the modification of the protein will not adversely affect a desired activity (e.g., an activity of binding to a gRNA, an endonuclease activity, an activity of binding to a specific site of a target nucleic acid under the guidance of a gRNA, and an activity of binding to a specific site of a target nucleic acid under the guidance of a gRNA and cleaving the target nucleic acid) of the protein. Therefore, the present invention is further intended to include such a modified protein. For example, the Cas13 protein of the present invention can be functionally linked (by chemical coupling, covalent linkage, gene fusion, non-covalent linkage or other means) to one or more modifying moieties.

The present invention discloses a conjugate including the aforementioned Cas13 protein and a modifying moiety (i.e. a heterologous functional part) for modifying the Cas13 protein.

In some embodiments, the modifying moiety of the conjugate is selected from another polypeptide, an oligopeptide, a detectable label, a pharmaceutical agent, other molecules, and any combination thereof.

In some embodiments, the modifying moiety is selected from: a localization tag for providing subcellular localization, a tag for facilitating tracking, separation or purification, a translation activation domain, a translation suppression domain, a nuclease domain, a deaminase domain, a methylase domain, a demethylase domain, and a regulatory splicing domain (e.g., for regulating RNA splicing).

In some embodiments, the localization tag for providing subcellular localization is selected from a nuclear localization signal (NLS) and a nuclear export signal (NES) sequence. Non-limiting examples of the NLS include, but are not limited to, NLS sequences derived from the following: a NLS sequence derived from a SV40 virus large T antigen; a NLS sequence derived from a nucleoplasmin; a c-myc NLS sequence; a hRNPA1 M9 NLS sequence; a NLS sequence of a IBB domain of an importin-α; a NLS sequence of a myoma T protein; a NLS sequence of human p 53; a NLS sequence of mouse c-abl IV; a NLS sequence of an influenza virus NS1; a NLS sequence of a hepatitis virus delta antigen; a NLS sequence of a mouse Mx1 protein; a NLS sequence of a human poly(ADP-ribose) polymerase; and a NLS sequence of a steroid hormone receptor (human) glucocorticoid.

In some embodiments, the conjugate includes one or more nuclear localization signals (NLSs). In some embodiments, the conjugate includes one or more nuclear export signals (NESs). In some embodiments, the conjugate includes 1, 2, 3, 4, 5, 6, 7, 8, 9, 10 or more nuclear localization signals.

In some embodiments, the nuclear output signal includes at least four hydrophobic residues.

In some embodiments, the tag for facilitating tracking, separation or purification is selected from an epitope tag, a fluorescent protein (e.g., a green fluorescent protein (GFP), YFP, RFP, CFP, mCherry, tdTomato, etc.), a HIS tag (e.g., a 6×His tag), a hemagglutinin (HA) tag, a FLAG tag, a glutathione S-transferase (GST) tag, and a maltose-binding protein (MBP) tag;

In some embodiments, the translation activation domain is selected from domains of eIF4E and other translation initiation factors, a yeast poly(A)-binding protein, and GLD2.

In some embodiments, the translation suppression domain is selected from: a Pumilio protein, a deaminase (e.g., a deaminase CAF1), and an Argonaute protein.

In some embodiments, the nuclease domain is selected from: FOK I, a PIN endonuclease domain, a NYN domain, a SMR domain from SOT1, and an RNase domain from staphylococcal nuclease.

In some embodiments, the deaminase domain is derived from cytidine deaminase or adenosine deaminase.

In some embodiments, the deaminase domain is selected from: a PPR (pentatricopeptide repeat) protein, an ADAR family protein, and an APOBEC family protein.

In some embodiments, the methylase domain is derived from an m6A methyltransferase.

In some embodiments, the demethylase domain is derived from an RNA demethylase ALKBH5.

In some embodiments, the regulatory splicing domain is selected from: SRSF1, hnRNP A1 and RBM4.

In some embodiments, the conjugate includes the aforementioned Cas13 protein, and one or more modifying moieties. In some embodiments, the conjugate consists of the aforementioned Cas13 protein, and one or more modifying moieties. In some embodiments, the conjugate consists of the aforementioned Cas13 protein, one or more modifying moieties, and a linker for connecting the Cas13 protein and the modifying moieties. In some cases, the multiple modifying moieties may be the same or different.

In some embodiments, the conjugate includes or does not include the linker for connecting the Cas13 protein and the modifying moieties.

In some embodiments, the conjugate includes a Cas13 protein, a modifying moiety, and a linker for connecting the Cas13 protein and the modifying moiety.

In some embodiments, the conjugate consists of a Cas13 protein, a modifying moiety, and a linker for connecting the Cas13 protein and the modifying moiety.

In some embodiments, the conjugate does not include the linker for connecting the Cas13 protein and the modifying moiety. In some embodiments, the conjugate is formed by directly connecting the Cas13 protein and the modifying moiety, including directly connecting via a covalent bond.

In some embodiments, the linker may be an amino acid, an amino acid sequence, or other chemical groups. In some embodiments, the linker may be an amino acid, an amino acid derivative, or PEG (polyethylene glycol).

In some embodiments, the linker is a linear polypeptide formed by connecting one or more amino acid residues through peptide bonds, wherein the amino acid residues may be natural or unnatural, and for example may be modified.

Examples of the linker include a linker containing one or more (e.g., 1, 2, 3, 4 or 5) amino acids (e.g., Glu or Ser) or amino acid derivatives (e.g., Ahx, β-Ala, GABA or Ava), or PEG, etc.

It is also within the scope of the present invention to adopt the same structure as the modifying moiety as the linker. Non-limiting examples, for example, a subcellular localization signal (e.g., NLS or NES), a tag (e.g., a HA tag, a Flag tag), etc. as the linker, are also within the scope of the present invention.

In some embodiments, the conjugate can interact with a gRNA.

In some embodiments, the conjugate can form a complex with a gRNA.

In some embodiments, the conjugate can form a complex with a gRNA, and the complex binds to a target nucleic acid.

In some embodiments, the conjugate can be guided to a target nucleic acid by a gRNA.

In some embodiments, the conjugate can be guided to a target nucleic acid by a gRNA, and target or modify the target nucleic acid. It can be understood that after the conjugate is guided to the target nucleic acid by the gRNA, optionally, the target nucleic acid may be or may not be targeted or modified. For example, in some cases, after the conjugate is guided to the target nucleic acid by the gRNA, the target nucleic acid may not be targeted and modified (e.g., the target nucleic acid is not cleaved), and those skilled in the art can only use its ability of binding to the target nucleic acid. In some cases, after the conjugate is guided to the target nucleic acid by the gRNA, the target nucleic acid can be targeted or modified. For example, a target mRNA is cleaved and thus a translation level is reduced.

In some embodiments, the modifying moiety may be connected to an amino terminal of, the vicinity of the amino terminal of, a carboxyl terminal, and/or the vicinity of the carboxyl terminal of the Cas13 protein. In some embodiments, the modifying moiety is connected to the amino terminal and/or carboxyl terminal of the Cas13 protein. In some embodiments, the modifying moiety is connected to the vicinity of the amino terminal or the vicinity of the carboxyl terminal of the Cas13 protein. In some embodiments, when the modifying moiety is within about 1, 2, 3, 4, 5, 10, 15, 20, 25, 30, 40, 50 or more amino acids from the amino terminal or carboxyl terminal along the polypeptide chain, the modifying moiety is considered to be in the vicinity of the amino terminal or carboxyl terminal.

In some embodiments, the conjugate includes one or more nuclear localization signals and/or nuclear export signals with sufficient intensity to drive the conjugate to accumulate in a detectable amount in and/or outside the nucleus of a eukaryotic cell. Detection of the accumulated amount of the Cas13 protein or conjugate in a specific part of the cell can be performed by any suitable technique.

In some embodiments, the conjugate is unnatural.

The present invention further discloses a gRNA which can form a complex with the aforementioned Cas13 protein or the aforementioned conjugate.

It can be understood that the aforementioned gRNA can guide the aforementioned Cas13 protein or conjugate to a target nucleic acid. In some embodiments, the Cas13 protein or conjugate can be guided to the target nucleic acid by the gRNA, and target or modify the target nucleic acid. In some embodiments, the complex is guided to the target nucleic acid by the gRNA, and then the complex targets or modifies the target nucleic acid. In some embodiments, the targeting the target nucleic acid is cleaving the target nucleic acid or binding to the target nucleic acid.

In some embodiments, the gRNA includes a guide sequence which can be complementary to a target nucleic acid, and a direct repeat sequence which can interact with the Cas13 protein or the conjugate.

In some embodiments, the guide sequence can be complementary (completely or partially complementary) to the target nucleic acid, and the direct repeat sequence can interact with the Cas13 protein or the conjugate.

In some embodiments, when the gRNA is used in combination with the Cas13m protein (Cas13 m.1-Cas13 m.6) of the present invention, a protein having ≥50% sequence identity with the Cas13m protein, or a conjugate containing the same, the direct repeat sequence of the gRNA is located at the 3' terminal of the guide sequence.

In some embodiments, when the gRNA is used in combination with the CasRfg.1 or CasRfg.2 protein of the present invention, a protein having ≥50% sequence identity with the CasRfg.1 or CasRfg.2, or the conjugate containing the same, the direct repeat sequence of the gRNA is located at the 5' terminal of the guide sequence.

In some embodiments, the gRNA includes a guide sequence and a direct repeat sequence, wherein a secondary structure of the direct repeat sequence includes a complementary paired first stem, a non-complementary bulge structure, a complementary paired second stem and a non-complementary loop structure which are connected in sequence.

Further, in some embodiments, the gRNA is characterized in that: a. the first stem consists of 4-7 base pairs; b. one of the sequences of the non-complementary bulge structure is 2-6 nucleotides in length; c. the second stem consists of 4-7 base pairs; and/or d. the non-complementary loop structure (excluding the pair of bases that are complementary paired at the junction between the loop and the stem) has a sequence length of 5-8 nucleotides.

In some embodiments, one of the sequences of the first stem is selected from: GUUG, GUUGU, GUUGUA and GUUGUUA.

In some embodiments, the gRNA incudes a guide sequence and a direct repeat sequence, wherein the direct repeat sequence is selected from a sequence having ≥90% sequence identity, or a sequence having ≥95% sequence identity with the sequence as shown in any one of SEQ ID NO: 15-SEQ ID NO: 21 and SEQ ID NO: 62.

In some embodiments, the direct repeat sequence is selected from any one of SEQ ID NO: 15-SEQ ID NO: 21 and SEQ ID NO: 62.

In some embodiments, the gRNA includes a guide sequence and a direct repeat sequence, wherein the guide sequence is ≥10 nt (10 nucleotides), ≥11 nt, ≥12 nt, ≥13 nt, ≥14 nt, ≥15 nt, ≥16 nt, ≥17 nt, ≥18 nt, ≥19 nt, ≥20 nt, ≥21 nt, ≥22 nt, ≥23 nt, ≥24 nt, ≥25 nt, ≥26 nt, ≥27 nt, ≥28 nt, ≥29 nt, ≥30 nt, ≥31 nt, ≥32 nt, ≥33 nt, ≥34 nt, ≥35 nt, ≥40 nt, ≥50 nt or ≥60 nt in length.

In some embodiments, the gRNA includes a guide sequence and a direct repeat sequence, wherein the guide sequence is ≤10 nt (10 nucleotides), ≤11 nt, ≤12 nt, ≤13 nt, ≤14 nt, ≤15 nt, ≤16 nt, ≤17 nt, ≤18 nt, ≤19 nt, ≤20 nt, ≤21 nt, ≤22 nt, ≤23 nt, ≤24 nt, ≤25 nt, ≤26 nt, ≤27 nt, ≤28 nt, ≤29 nt, ≤30 nt, ≤31 nt, ≤32 nt, ≤33 nt, ≤34 nt, ≤35 nt, ≤40 nt, ≤50 nt or ≤60 nt in length.

In some embodiments, the gRNA includes a guide sequence and a direct repeat sequence, wherein the guide sequence ranges from 10 nt-60 nt, 10 nt-50 nt, 10 nt-40 nt, 12 nt-35 nt, 15 nt-35 nt, 15 nt-30 nt, 20 nt-35 nt, 20 nt-30 nt, 25 nt-35 nt or 25 nt-30 nt in length.

In some embodiments, the gRNA includes a guide sequence and a direct repeat sequence, wherein the direct repeat sequence is ≥10 nt, ≥15 nt, ≥20 nt, ≥25 nt, ≥30 nt, ≥35 nt, ≥40 nt, ≥ 45 nt, ≥50 nt, ≥60 nt, ≥70 nt, ≥80 nt, ≥90 nt, ≥100 nt, ≥150 nt, ≥200 nt or ≥300 nt in length.

In some embodiments, the gRNA includes a guide sequence and a direct repeat sequence, wherein the direct repeat sequence is ≤10 nt, ≤15 nt, ≤20 nt, ≤25 nt, ≤30 nt, ≤35 nt, ≤40 nt, ≤45 nt, ≤50 nt, ≤60 nt, ≤70 nt, ≤80 nt, ≤90 nt, ≤100 nt, ≤150 nt, ≤200 nt or ≤300 nt in length.

In some embodiments, the gRNA includes a guide sequence and a direct repeat sequence, wherein the direct repeat sequence ranges from 10 nt-300 nt, 10 nt-200 nt, 10 nt-100 nt, 15 nt-80 nt, 15 nt-50 nt, 15 nt-40 nt, 15 nt-35 nt, or 20 nt-40 nt in length.

In some embodiments, the direct repeat sequence is located at the 3' terminal of the guide sequence. In some embodiments, the direct repeat sequence is located at the 5' terminal of the guide sequence.

In some embodiments, the target nucleic acid is PTBP1 (polypyrimidine tract binding protein 1) mRNA, AQp1 (aquaporin 1) mRNA, VEGFA mRNA, VEGFR1 mRNA or VEGFR2 mRNA.

In some embodiments, the target nucleic acid is PTBP1 mRNA or AQp1 mRNA. In some embodiments, the target nucleic acid is VEGFA mRNA, VEGFR1 mRNA or VEGFR2 mRNA.

The present invention further discloses a composition including:

1) the aforementioned Cas13 protein, the aforementioned conjugate, a nucleic acid encoding the aforementioned Cas13 protein, or a nucleic acid encoding the afore-mentioned conjugate;
and 2) the aforementioned gRNA or a nucleic acid encoding the gRNA.

In some embodiments, the gRNA includes a guide sequence which can be complementary to a target nucleic acid, and the target nucleic acid is the PTBP1 mRNA or the AQp1 mRNA.

In some embodiments, the nucleic acid is a DNA. In some embodiments, the nucleic acid is an RNA.

The present invention also discloses a nucleic acid, including:

1) a nucleotide sequence encoding the aforementioned Cas13 protein, or a nucleotide sequence encoding the aforementioned conjugate;
and/or 2) a nucleotide sequence encoding the aforementioned gRNA.

In some embodiments, the nucleotide sequence is used for expression in a prokaryotic or eukaryotic cell.

In some embodiments, the nucleic acid is a DNA. In some embodiments, the nucleic acid is an RNA.

The present invention further discloses a vector, includ-ing:

1) a nucleotide sequence encoding the aforementioned Cas13 protein, or a nucleotide sequence encoding the aforementioned conjugate;
and/or 2) a nucleotide sequence encoding the aforementioned gRNA.

In some embodiments, the nucleotide sequence encoding the Cas13 protein is one or more, and the nucleotide sequence encoding the conjugate is one or more.

In some embodiments, the vector includes a regulatory element.

In some embodiments, the regulatory element can regu-late the expression of the nucleotide sequence.

In some embodiments, the regulatory element is a pro-moter and/or enhancer. In some embodiments, the regulatory element is a promoter.

In some embodiments, the vector is selected from a cloning vector and an expression vector. In some embodi-ments, the vector is a plasmid or viral vector.

In some embodiments, the vector can express the Cas13 protein or conjugate of the present invention in a cell. In some embodiments, the vector can express the Cas13 pro-tein or conjugate of the present invention in a eukaryotic cell. In some embodiments, the vector can express the Cas13 protein or conjugate of the present invention in a human cell.

In some embodiment, the vector is an unnatural vector.

The present invention further discloses a delivery com-position, including a delivery vector and at least one selected from: the aforementioned Cas13 protein, conjugate, gRNA, composition, nucleic acid and vector.

In some embodiments, the delivery vector is at least one selected from of a delivery particle, a delivery vesicle and a virus vector.

The present invention further discloses a cell, including at least one of the aforementioned Cas13 protein, conjugate, gRNA, composition, nucleic acid and vector.

In some embodiments, the cell is a eukaryotic cell.

In some embodiments, the target nucleic acid is derived from an animal cell, a plant cell or a microbial cell.

In some embodiments, an animal or plant cannot be produced from the cell.

In some embodiments, an animal or plant cannot be produced from the eukaryotic cell.

In some embodiments, the eukaryotic cell includes a stem cell and a stem cell line. In some embodiments, the stem cell is not an embryonic stem cell, and the stem cell line is not an embryonic stem cell line.

In some embodiments, for the cells including the Cas13 protein, conjugate, gRNA, complex, isolated nucleic acid, vector, composition and delivery composition of the present invention, the target nucleic acid in these cells has been targeted or modified.

The present invention further discloses a method of targeting or modifying a target nucleic acid, including delivering at least one selected from: the aforementioned Cas13 protein, conjugate, gRNA, composition, nucleic acid, vector and cell. In some embodiments, the delivery takes place ex vivo, in vitro or in vivo. In some embodiments, the method of targeting or modifying the target nucleic acid is used for modifying a cell, a cell line or an organism by changing the target nucleic acid. In some embodiments, the target nucleic acid is derived from an animal cell, a plant cell or a microbial cell.

In some embodiments, the target nucleic acid is PTBP1 (polypyrimidine tract binding protein 1) mRNA, AQp1 (aquaporin 1) mRNA, VEGFA mRNA, VEGFR1 mRNA or VEGFR2 mRNA.

In some embodiments, the target nucleic acid is PTBP1 (polypyrimidine tract binding protein 1) mRNA or AQp1 (aquaporin 1) mRNA. In some embodiments, the target nucleic acid is VEGFA mRNA, VEGFR1 mRNA or VEGFR2 mRNA.

In some embodiments, the method of targeting or modifying the target nucleic acid does not include a method for diagnosing and treating a disease.

In some embodiments, the method of targeting or modifying the target nucleic acid includes a method for diagnosing and treating a disease.

The present invention further discloses use of the aforementioned Cas13 protein, conjugate, gRNA, composition, nucleic acid or vector cell in preparation of a medicament for diagnosing, preventing or treating a disease in a subject. In some embodiments, the subject is a human individual.

The present invention further discloses a method for administrating the Cas13 protein, conjugate, gRNA, composition, nucleic acid or vector cell to a subject in an effective amount to diagnose, prevent or treat a disease.

The present invention further discloses a method for detecting a nucleic acid, including the step of allowing the following a and b to form a complex, and binding the complex to a target nucleic acid to be tested:

a. the aforementioned Cas13 protein or the aforementioned conjugate, b. the aforementioned gRNA.

In some embodiments, the method includes allowing the aforementioned conjugate to form a complex with the gRNA, and binding the complex with the target nucleic acid, wherein the conjugate contains a detectable label, in which a signal change is caused by the binding, cleavage or modification of the complex to the target nucleic acid, and the content of the target nucleic acid in a sample to be tested is analyzed by observing the signal change of the detectable label. Further, the detectable label includes a fluorescent group, a color-developing agent, a developer or a radioisotope.

Compared with the prior art, the present invention has the following beneficial effects.

The isolated Cas13 protein of the present invention is a novel Cas13 enzyme, which can be used in a CRISPR/Cas system. Also, as verified by experiments, the Cas13 protein of the present invention can have good editing efficiency for both an exogenous reporter gene and an endogenous gene when exerting its Cas13 nuclease activity.

BRIEF DESCRIPTION OF THE DRAWINGS

FIG. 3A and FIG. 3B are schematic cluster analysis diagrams of the Cas13 protein of Example 1 and other subtypes of Cas13 protein, wherein FIG. 3A is a schematic cluster analysis diagram of Cas13 m.1-Cas13 m.5, and FIG. 3B is a schematic cluster analysis diagram of Cas13 m.1-Cas13 m.6.

14

Figure 8:
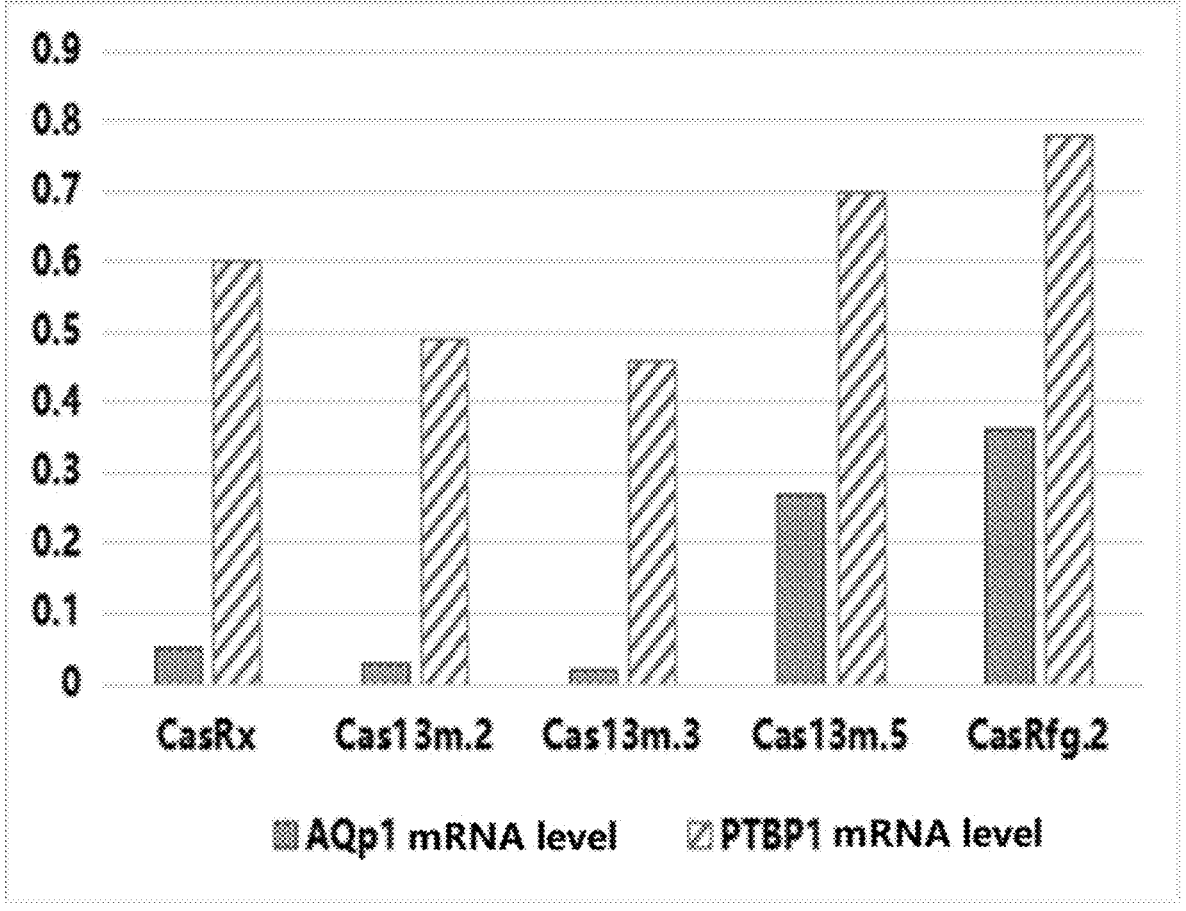

FIG. 8 is a schematic diagram of mRNA changes of endogenous target genes AQp1 and PTBP1 as detected by qPCR in Example 5.

Figure 9A:
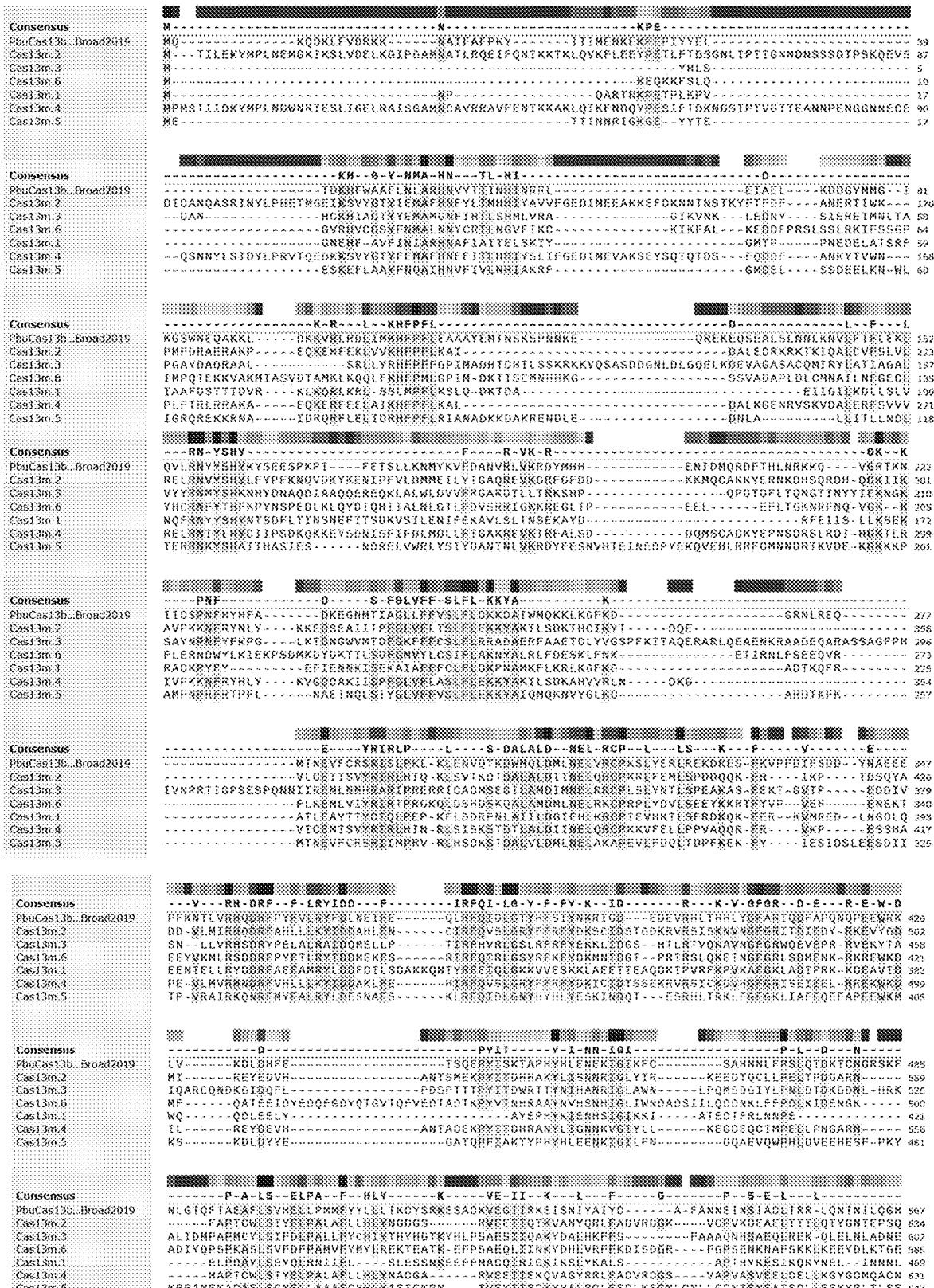

FIGS. 9A, 9B and 9C are schematic screenshot diagrams of multi-sequence alignment between a Cas13m protein and PbuCas13b in Example 9. The sequences in FIGS. 9A, 9B and 9C are as shown in SEQ ID NOs: 6, 2, 3, 60, 1, 4 and 5 in order.

Figure 10:
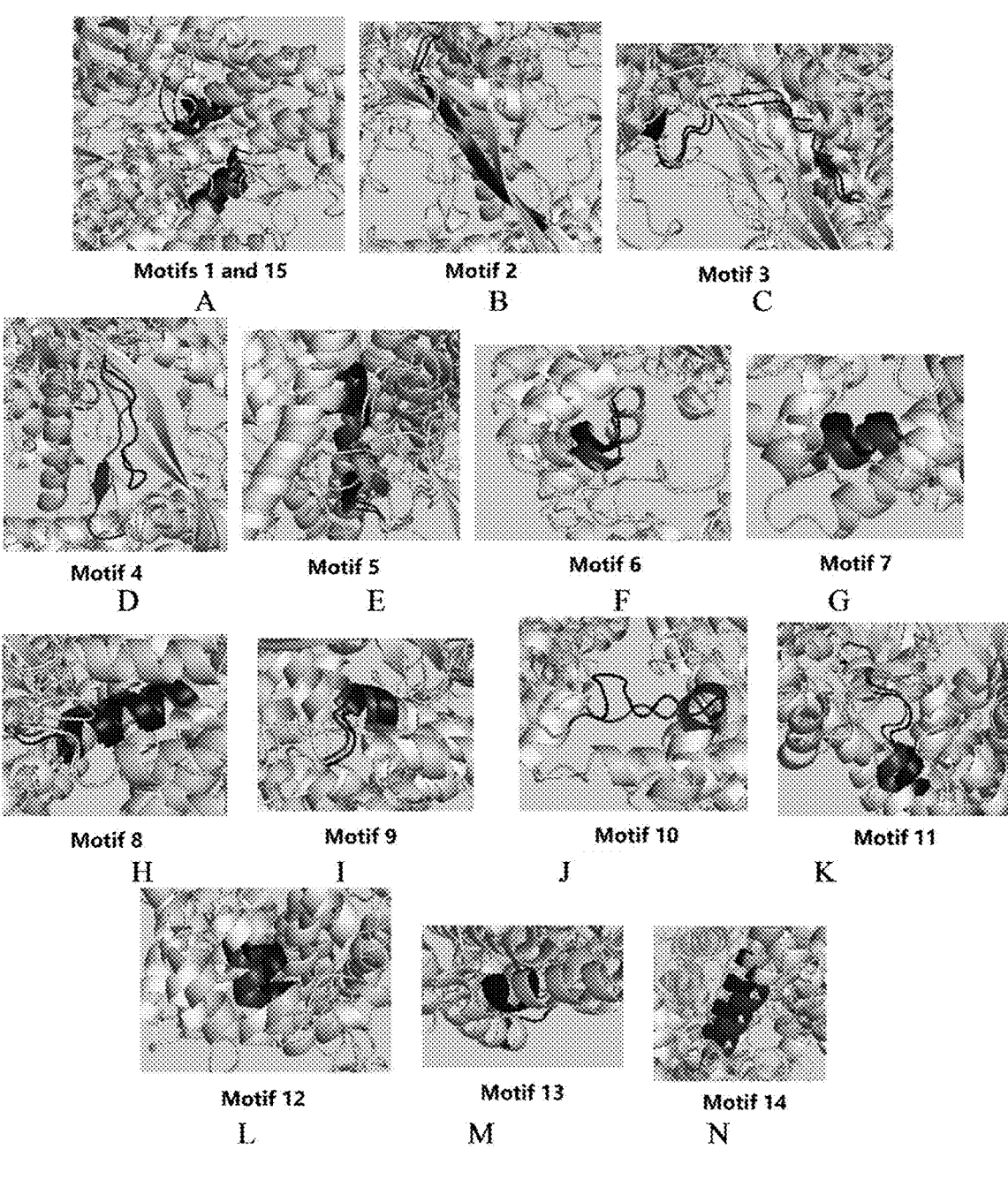

FIG. 10 is a superposition diagram of Example 9, wherein A-N respectively show the overlapping of motifs 1-15 of Cas13 m.6 and corresponding sequences of PbuCas13b after superposition between Cas13 m.6 and PbuCas13b.

Figure 11:
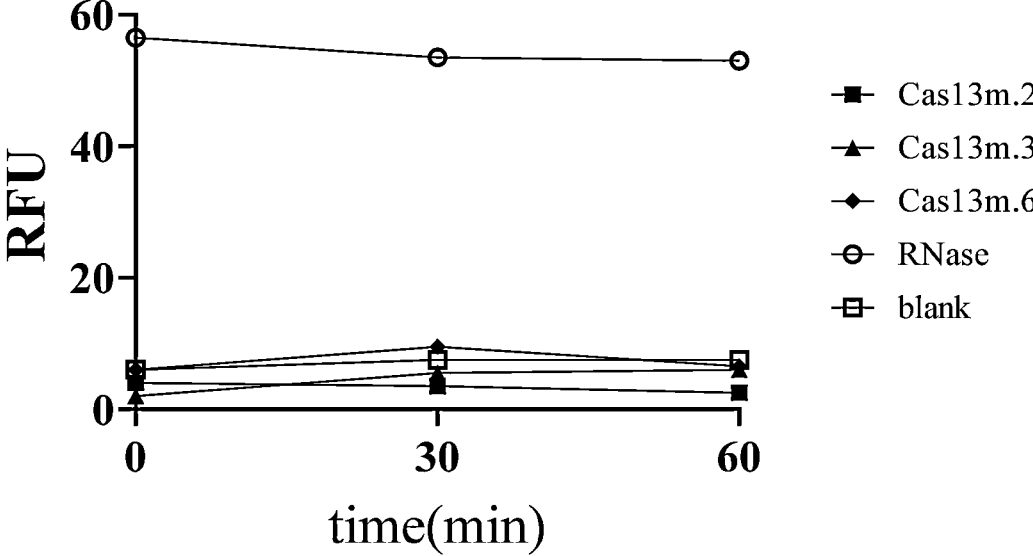

FIG. 11 shows a result of a collateral cleavage effect assay in Example 11.

DETAILED DESCRIPTION OF THE
PREFERRED EMBODIMENTS

In order to facilitate the understanding of the present invention, the present invention will be more fully described below with reference to relevant drawings. A preferred embodiment of the present invention is shown in the accompanying drawings. However, the present invention can be implemented in many different forms, and is not limited to the examples described herein. On the contrary, these examples are provided for a more thorough and comprehensive understanding of the present invention.

Unless otherwise defined, all technical and scientific terms used herein have the same meanings as those commonly understood by those skilled in the art to which the present invention pertains to. Herein, the terminology used in this specification of the present invention is only for the purpose of describing specific examples, and is not intended to limit the present invention. As used herein, the term "and/or" includes any and all combinations of one or more related listed items.

As used herein, a protein or polypeptide referred to as a "Cas13 protein" or having a "Cas enzyme activity" or "Cas endonuclease activity" refers to a CRISPR associated (Cas) polypeptide or protein encoded by a CRISPR associated (Cas) gene. The Cas13 protein or polypeptide can be guided to a target sequence in a target nucleic acid when being complexed or functionally combined with one or more guide RNAs (gRNAs). Under the guidance of the gRNA, the Cas endonuclease recognizes, targets or modifies a specific target site (a target sequence or a nucleotide sequence near the target sequence) in a target nucleic acid, for example a target site in an RNA (e.g. A coding RNA, e.g. mRNA) molecule.

As used herein, the term "HEPN domain" has the meaning generally recognized in the art. The HEPN domain has been proved to be an RNase domain, and has the ability to bind to and cleave a target RNA molecule. The target RNA can be any suitable form of RNA, including but not limited to a coding RNA and a non-coding RNA. The previously discovered CRISPR, class 2, type VI effector proteins all contain two HEPN domains, including, for example, Cas13a, Cas13b, Cas13c, Cas13d, Cas13e and Cas13f, and each of their HEPN domains has a conserved RxxxxH motif, which is the characteristic of the HEPN domain.

As used herein, the terms "gRNA" and "guide RNA" are used interchangeably, and they have the meanings commonly understood by those skilled in the art. The gRNA generally refers to a RNA molecule (or a collective name of a group of RNA molecules) that can bind to a Cas13 protein and facilitate to guide/target the Cas13 protein to a specific position (target sequence) within a target nucleic acid/target polynucleotide (e.g., a DNA or mRNA molecule). The gRNA contains a guide sequence and a direct repeat (DR) sequence. The gRNA may contain one or more modifications (e.g., base modification, scaffold modification, modification of an internucleoside bond, etc.) to provide the same function as an unmodified gRNA, or to provide a new or enhanced feature (e.g., improved stability) to the gRNA.

As used herein, the terms "guide sequence" and "targeting domain" are used interchangeably, and refer to a continuous nucleotide sequence in a gRNA, which is partially or completely complementary to the target sequence in the target nucleic acid, and can hybridize with the target sequence in the target nucleic acid through base pairing promoted by the Cas13 protein. Complete complementarity between the guide sequence of the present invention and the target sequence is not necessary, as long as there is sufficient complementarity to cause hybridization and promote the formation of a CRISPR/Cas complex.

A suitable direct repeat (DR) sequence can be found from a CRISPR locus structure of a procaryotic organism (e.g., a bacterium and an archaebacterium) through experimental screening. The size of the direct repeat sequence is usually within tens of bp, and partial fragments of it are reverse complementary to each other, which means that a secondary structure, such as a stem-loop structure (often called a hairpin structure), is formed inside the RNA molecule, while other fragments are embodied as unstructured. The direct repeat sequence is a constant part of a gRNA molecule, which contains a strong secondary structure, which facilitates the interaction between the Cas13 protein and the gRNA molecule.

As used herein, a term "target nucleic acid", "target RNA" or "target polynucleotide" refers to a polynucleotide containing a target sequence, and are often used interchangeably herein. The target nucleic acid can include any polynucleotide, such as a DNA (target DNA) or an RNA (target RNA). The "target nucleic acid" refers to a nucleic acid to be targeted or modified by the Cas13 protein as guided by the gRNA. The term "target nucleic acid" can be any polynucleotide endogenous or exogenous to a cell (e.g., a eukaryotic cell). For example, the "target nucleic acid" may be a polynucleotide existed in a eukaryotic cell, or a sequence (or a part thereof) encoding a gene product (e.g., protein) or a non-coding sequence (or a part thereof). In some cases, the "target nucleic acid" can include one or more disease-associated genes and polynucleotides, as well as genes and polynucleotides related to biochemical pathways of signaling. The "disease-associated" gene or polynucleotide refers to any gene or polynucleotide that produces a transcription or translation product at an abnormal level or in an abnormal form in a cell derived from a tissue affected by the disease, as compared with that of a non-disease control tissue or cell. In some cases, the target nucleic acid is a coding RNA. In some cases, the target nucleic acid is a non-coding RNA. In some cases, the target nucleic acid includes an mRNA, a miRNA, an rRNA, a tRNA, a snRNA, and a structural RNA. In some cases, the target nucleic acid is an mRNA. In some cases, the target nucleic acid is the whole mRNA molecule. In some cases, the target nucleic acid is a DNA. In some cases, the target nucleic acid is a whole chromosome DNA molecule. As used herein, the "target RNA", "target nucleic acid" and "target" mean a specific sequence or a reverse complementary sequence thereof that is desired to be bound, targeted or modified by using a CRISPR system.

As used herein, the term "target sequence" refers to a small stretch of sequence in a target nucleic acid molecule, which can be complementary (completely or partially complementary) to the guide sequence of the gRNA molecule. The length of the target sequence is often tens of bp, and for example, it can be about 10 bp, about 20 bp, about 30 bp, about 40 bp, about 50 bp or about 60 bp.

As used herein, the term "targeting" is defined to include one or more of the following: cleaving one or more target nucleic acids, visualizing or detecting one or more target nucleic acids, labeling one or more target nucleic acids, transporting one or more target nucleic acids, masking one or more target nucleic acids, binding to one or more target nucleic acids, increasing a transcription and/or translation level of a gene corresponding to a target sequence, and reducing the transcription and/or translation level of the gene corresponding to the target sequence.

As used herein, the term "modification" is defined to include one or more of the following: base substitution of a nucleic acid, a base deletion of nucleic acid, base insertion of nucleic acid, methylation of nucleic acid, demethylation of nucleic acid, and deamination of nucleic acid.

As used herein, the term "cleavage/cleaving" refers to allowing a covalent bond (e.g., a covalent phosphodiester bond) in a ribosyl phosphodiester backbone of a polynucleotide to be broken, including but not limited to: allowing a single-stranded polynucleotide to be broken, allowing either single strand of a double-stranded polynucleotide containing two complementary single strands to be broken, and allowing both single strands of the double-stranded polynucleotide containing two complementary single strands to be broken.

For example, as can be understood by those skilled in the art that, the Cas13 protein or conjugate of the present invention can be fused or associated with one or more heterologous functional moieties (e.g., by a fusion protein, a linker peptide, etc.). For example, a Cas13 mutant completely or partially losing a nuclease activity is partially fused with a heterologous functional moiety. These functional domains can have various activities, such as a methylase activity, a demethylase activity, a deaminase activity, a translation activation activity, a translation suppression activity, an RNA cleavage activity, a nucleic acid binding activity, a base editing activity, and a switching activity (e.g., light induction). The heterologous functional moiety may include, but is not limited to, a localization signal (e.g., a nuclear localization signal NLS and a nuclear export signal NES), a label or a detection label (e.g., a fluorescent dye such as FITC or DAPI), a targeting moiety, an antigenic determinant tag (e.g., Hismyc, V5, FLAG, HA, VSV-G, Trx, etc.), a deaminase or deamination domain (e.g., ADAR1, ADAR2, APOBEC, AID or TAD), a methylase, a demethylase, a ssRNA cleavage active domain, a dsRNA cleavage active domain, a DNA or RNA ligase, or any combination of the above.

For example, the Cas13 protein of the present invention can be fused with a deaminase, combined with a gRNA, and then used for targeting a target RNA, so as to realize single-base editing of the target RNA molecule.

For example, the heterologous functional moiety may be a detectable label. When a CRISPR-CAS complex contacts or binds to the target nucleic acid, the conjugate containing the Cas13 nuclease cleaves or modifies the target nucleic acid, and the presence of the target nucleic acid in the sample to be tested is analyzed by observing the presence of the detectable label. The detectable label is for example a fluorescent group, a color-developing agent, a developer or a radioisotope.

A method for measuring the binding of the Cas13 protein or conjugate to the target nucleic acid is known in the art, including but not limited to a chromatin immunoprecipitation assay, a gel mobility change assay, a reporter gene assay, and a microplate capture and detection assay. Similarly, a method for measuring cleavage or modification of the target nucleic acid is known in the art, including an in vitro or in vivo cleavage assay.

As used herein, the terms "complex" and "CRISPR/Cas complex" are used interchangeably. The term "complex" refers to a ribonucleoprotein complex formed by the binding of the gRNA and the Cas13 protein. The ribonucleoprotein complex can recognize (and sometimes further cleave or modify) a target sequence complementary to the guide sequence of the gRNA or a target nucleic acid in which the target sequence is located.

As used herein, the term "unnatural" means "modified", which means that artificial means is involved. When a nucleic acid molecule or polypeptide is referred, the term means that the nucleic acid molecule or the polypeptide is at least substantially free of at least one other component that is naturally associated with them in nature and associated with them when found. Furthermore, this term can indicate that a nucleic acid molecule or polypeptide has a sequence that is not existed in nature.

As used herein, the term "conjugate" refers to a modified Cas13 protein. The conjugate includes a Cas13 protein part and a modifying moiety. The modifying moiety can be a protein or polypeptide (or any functional fragment of them), an oligopeptide and other small molecules (including but not limited to a sugar molecule). The conjugate can be a fusion protein.

As used herein, the term "sequence identity (identity or percent identity)" is used for referring to the matching of sequences between two polypeptides or two nucleic acids. When a certain position in two sequences to be compared is occupied by the same base or amino acid monomer subunit (for example, a certain position of each of two DNA molecules is occupied by adenine, or a certain position of each of two polypeptides is occupied by lysine), then each molecule is identical at the position. Percent sequence identity between two sequences is a function of the number of matching positions shared by the two sequences divided by the number of positions to be compared×100%. For example, if 6 of 10 positions of two sequences are matched, then the two sequences have a sequence identity of 60%. Generally, two sequences are compared when they are aligned to produce the maximum sequence identity. Such alignment can be made by using published and commercially-available alignment algorithms and programs, such as but not limited to Clustal Ω, MAFFT, Probcons, T-Coffee, Probalign, BLAST, which can be reasonably selected and used by those skilled in the art. Those skilled in the art can determine the appropriate parameters for aligning sequences, including, for example, any algorithm needed to achieve preferred alignment or optimal alignment for the whole length of the compared sequences, and any algorithm needed to achieve preferred alignment or optimal alignment for the local parts of the compared sequences.

The sequence identity is related to sequence similarity. Identity or similarity comparison can be made by visual comparison (naked eyes), and more generally by means of a sequence comparison program. These computer programs can calculate the percentage (%) of identity or similarity among two or more sequences, and can also calculate the sequence identity shared by two or more amino acid or nucleic acid sequences.

The terms "polypeptide", "peptide" and "protein" are used interchangeably herein, and refer to a polymer having amino acids of any length. The polymer may be linear or branched, it may contain modified amino acids, and it may be interrupted by non-amino acids. These terms also cover amino acid polymers that have been modified; and these modifications are, for example, disulfide bond formation, glycosylation, lipidation, acetylation, phosphorylation or any other manipulation, such as conjugation with a labeling component. As used herein, the term "amino acid" includes natural and/or unnatural or synthetic amino acids, including glycine and D and L optical isomers, as well as amino acid analogs and peptide mimics.

As used herein, the term "domain" or "protein domain" refers to a part of a protein sequence that can be existed and function independently of the rest of the protein chain.

As used herein, the term "vector" refers to a nucleic acid carrier into which a polynucleotide can be inserted. When a vector can enable a protein encoded by the inserted polynucleotide to be expressed, the vector is called an expression vector. The vector can enter a host cell by manners of transformation, transduction or transfection, so that a genetic material element carried by the vector can be expressed in the host cell. The vector is well known to those skilled in the art, and includes but is not limited to: a plasmid; a cosmid; a phagemid; an artificial chromosome, such as a yeast artificial chromosome (YAC) or a bacterial artificial chromosome (BAC); a phage such as phage λ, and an animal virus. An animal virus that can be used as a vector includes, but is not limited to, a retrovirus (including a lentivirus), an adenovirus, an adeno-associated virus, a herpes virus (e.g., a herpes simplex virus), a poxvirus, a baculovirus, a papillomavirus, a papovavirus (such as SV40). A vector can contain a variety of elements for controlling expression, including but not limited to: a promoter sequence, a transcription initiation sequence, an enhancer sequence, a selection element, and a reporter gene. Additionally, the vector may also contain a replication origin. The vector includes, but is not limited to, a single-stranded, double-stranded or partially double-stranded nucleic acid molecule; a nucleic acid molecule containing one or more free ends or not containing a free end (e.g., a circular nucleic acid molecule); a nucleic acid molecule containing a DNA, an RNA or both; and other kinds of polynucleotides known in the art. Certain vectors can autonomously replicate in a host cell into which they are introduced. Other vectors are integrated into the genome of the host cell after being introduced into the host cell, and thus replicate along with the host genome. Furthermore, certain vectors can guide the expression of genes to which they are operably linked. Such a vector is referred to herein as an "expression vector". The vector used in a eukaryotic cell and producing expression in the eukaryotic cell can be called a "eukaryotic expression vector" here. A common expression vector used in a recombinant DNA technology is often in a form of plasmid.

A vector can be introduced into a host cell and thus produces a transcript, protein, or peptide, including the protein, conjugate, isolated nucleic acid, complex, composition, and the like as described herein.

The recombinant expression vector can contain the nucleic acid of the present invention in a form suitable for expressing the nucleic acid in a host cell, which means that the recombinant expression vector contains one or more regulatory elements, which can be selected based on the host cell used for expression and operably linked to a nucleic acid sequence to be expressed.

As used herein, the term "operably linked" is intended to mean that a Cas protein coding sequence or gRNA coding sequence in the vector is linked to one or more regulatory elements in a way that allows the nucleotide sequence to be expressed (e.g., to be expressed in an in vitro transcription/ translation system or in a host cell when the vector is introduced into the host cell). For example, in the vector, a promoter 1 is placed upstream of a coding sequence of the Cas13 protein. When the vector is introduced into a host cell, the transcription of a Cas13 gene can be started under the drive of the promoter 1.

As used herein, the term "regulatory element" is intended to include a promoter, an enhancer, an internal ribosome entry site (IRES), and other expression control elements (e.g., a transcription termination signal, such as a polyadenylation signal and a poly U sequence). The regulatory element includes those that guide nucleotide sequences to be expressed continuously in many types of host cells, and those that guide nucleotide sequences to be expressed only in certain host cells (e.g., a tissue-specific regulatory sequence). A tissue-specific promoter can guide the expression mainly in a desired tissue of interest, such as muscle, a neuron, bone, skin, blood, a specific organ (e.g., liver, pancreas), or a specific cell type (e.g., a lymphocyte). The regulatory element can also guide expression in a time-dependent manner, such as a cell cycle-dependent or developmental stage-dependent manner, which may or may not be tissue-specific or cell-type specific. In some embodiments, the vector includes one or more pol III promoters (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or a combination thereof. Examples of the pol III promoter include, but are not limited to, U6 and H1 promoters. Examples of the pol II promoter include, but are not limited to, a retrovirus Rous sarcoma virus (RSV) LTR promoter (optionally with an RSV enhancer), a cytomegalovirus (CMV) promoter (optionally with a CMV enhancer), a SV40 promoter, a dihydrofolate reductase promoter, a β-actin promoter, a phosphoglycerokinase (PGK) promoter, and an EF1α promoter. The term "regulatory element" also encompasses an enhancer element, such as WPRE, a CMV enhancer, a SV40 enhancer, and an intron sequence between exons 2 and 3 of a rabbit beta-globulin. Those skilled in the art will understand that the design of an expression vector may depend on factors such as the selection of a host cell to be transformed and a desired expression level. The vector can be introduced into the host cell to express the Cas13 protein, conjugate or CRISPR complex of the present invention.

As used herein, the term "promoter" has a meaning well-known to those skilled in the art, which refers to a stretch of non-coding nucleotide sequence located upstream of a gene and capable of initiating the expression of a downstream gene. A constitutive promoter is such a nucleotide sequence that, when operably linked to a polynucleotide encoding or defining a gene product, leads to the production of the gene product in a cell under most or all physiological conditions of the cell. An inducible promoter is such a nucleotide sequence that, when operably linked to a polynucleotide encoding or defining a gene product, leads to the production of the gene product in a cell basically only when an inducer corresponding to the promoter is existed in the cell. A tissue-specific promoter is such a nucleotide sequence that, when operably linked to a polynucleotide encoding or defining a gene product, leads to the production of the gene product in a cell basically only when the cell is a cell of the tissue type corresponding to the promoter.

As used herein, the term "host cell" refers to a cell that can be used for introducing a vector, including but not limited to a prokaryotic cell such as *Escherichia coli* or *Bacillus*

*subtilis*, a fungal cell such as a yeast cell or *Aspergillus*, or an animal cell such as a fibroblast, a CHO cell, a COS cell, a NSO cell, a HeLa cell, a BHK cell, a HEK 293 cell or other human cell.

As used herein, the term "expression" or "expressing" refers to a process of transcription from a DNA template into a polynucleotide (such as transcription into an mRNA or other RNA transcripts) and/or a process by which the transcribed mRNA is subsequently translated into a peptide, polypeptide or protein. The transcript and encoded polypeptide can be collectively referred to as a "gene product" or a "gene expression product". As used herein, "expression" of a gene or nucleic acid encompasses not only cell gene expression, but also transcription and translation of one or more nucleic acids in a cloning system or under any other context.

As used herein, the term "linker" refers to a group that connects a protein with a modifying moiety. The group may be an amino acid, an amino acid sequence, or other chemical groups. For example, it may an amino acid (e.g., Glu or Ser), an amino acid derivative, and PEG (polyethylene glycol). In some cases, the "linker" refers to a linear polypeptide formed by connecting one or more amino acid residues through peptide bonds, wherein the amino acid residues may be natural or unnatural, and for example may be modified. The linker of the present invention can be an artificially-synthesized amino acid sequence or a naturally occurring polypeptide sequence, such as a polypeptide with a hinge region function. Such a linker polypeptide is well known in the art. Such a linker may be newly discovered or well known in the art, and examples of it include but are not limited to a linker containing one or more (e.g., 1, 2, 3, 4 or 5) amino acids (e.g., Glu or Ser) or amino acid derivatives (e.g., Ahx, β-Ala, GABA or Ava), or PEG, etc.

The gRNA of the present invention may contain one or more modifications (e.g., base modification, scaffold modification, etc.) to provide the same function as an unmodified gRNA, or to provide a new or enhanced feature (e.g., improved stability) to the gRNA. Examples of a suitable gRNA containing the modifications include a gRNA containing a modified scaffold or an unnatural internucleoside bond. The gRNA modification includes, for example, a phosphorothioate modification, a 2'-O-methyl modification, a 2'-O-methoxyethyl (MOE) modification, a 2'-deoxy modification, a phosphorothioate internucleotide linkage, a phosphonoacetate (PACE) internucleotide linkage, a phosphorothioate (thioPACE) internucleotide linkage, a locked nucleic acid (LNA) or a cyclohexenyl substituted furanose ring.

The furanose ring of or the furanose ring and internucleotide bond of the gRNA of the present invention can be substituted by a non-furanose group. One such nucleic acid (which has been shown to have excellent hybridization properties) is called a peptide nucleic acid (PNA). In the PNA, a sugar scaffold of the polynucleotide is replaced by an amide-containing scaffold. The furanose ring in the gRNA molecule can also be substituted by a cyclohexenyl ring, and thus is called a cyclohexenyl nucleic acid (CeNA). Another modification includes a locked nucleic acid (LNA), in which a 2'-hydroxyl group is connected to the 4'-carbon atom of a sugar ring to form a 2'-C, 4'-C-oxymethylene bond, thereby forming a bicyclic sugar moiety.

The gRNA of the present invention may also include base modification or substitution. The gRNA of the present invention may contain an unmodified or natural base (e.g., purine bases adenine A and guanine G and pyrimidine bases thymine T, cytosine C and uracil U). The gRNA of the present invention may contain a modified base, including, for example, other synthetic and natural bases such as 5-methylcytosine, 5-hydroxymethylcytosine, xanthine, hypoxanthine, 2-aminoadenine, other derivatives of adenine and guanine, 5-uracil (pseudouracil), 4-thiouracil, other derivatives of cytosine, other derivatives of uracil, and derivatives of thymine.

The modification can be at any position in the molecular structure of the gRNA.

The 5' or 3' terminal of the gRNA may have an additional nucleotide connected to the guide sequence. A non-limiting example is that for example 2 additional guanine nucleotides may be contained at the 5' terminal to improve targeting specificity.

As used herein, the terms "delivering particle", "delivering particle system" and "particle" are used interchangeably. The particle is used for delivering the Cas13 protein, conjugate, gRNA, complex, nucleic acid, composition, etc. of the present invention. It is known that several types of particle delivery systems and/or formulations can be used in different ranges of biomedical applications. Generally speaking, the particle is defined as a small object of which the transport and characteristics are expressed as a whole unit. The particle is further classified according to its diameter. The size of a coarse particle is between 2,500-10,000 nanometers. The size of a fine particle is between 100-2,500 nanometers. The size of an ultrafine particle or a nanoparticle is generally between 1-100 nanometers. Many different conventional techniques can be used for particle characterization (including, for example, characterization of morphology, dimensions, etc.).

The particle delivery system within the scope of the present invention can be provided in any form, including but not limited to: a liposome (including, for example, an immunoliposome), a virion (including, for example, an artificial virion), an extracellular vesicle (including, for example, an exosome, a microvesicle and an apoptotic body), a particle (e.g., a nanoparticle), a microbubble, gene gun, electroporation, sonoporation, calcium phosphate-mediated transfection, cationic transfection, dendritic transfection, heat shock transfection, nuclear transfection, magnetic transfection, lipid transfection, puncture transfection, optical transfection, nucleic acid uptake enhanced by a proprietary agent, and microinjection.

As used herein, the term "exosome" refers to an endogenous nanovesicle that transports certain substances (including but not limited to an RNA and a protein).

As used herein, the term "liposome" is a spherical vesicle structure, which is composed of a single-layer or multi-layer lipid bilayer surrounding an internal aqueous compartment and a relatively impermeable external lipophilic phospholipid bilayer. The liposomes have attracted considerable attention as a drug delivery vectors, because they are biocompatible and non-toxic, can deliver hydrophilic and lipophilic drug molecules, protect their contents from being degraded by plasma enzymes, and transport across a biofilm and a blood-brain barrier. The liposome can be made from several different types of lipids; however, a phospholipid is most commonly used to produce the liposome as the drug carrier. Several other additives can be added into the liposome to modify its structure and characteristics. The liposome can be used for delivery or administration according to the present invention.

The cell of the present invention includes, but is not limited to, a prokaryotic cell such as an *Escherichia coli* cell, and an eukaryotic cell such as a yeast cell, an insect cell, a plant cell and an animal cell (such as a mammalian cell, for example a mouse cell, a human cell, etc., for example a human stem cell, a human stem cell line, such as a human hematopoietic stem cell, a hematopoietic progenitor cell, etc.).

The term eukaryotic cell includes, but is not limited to, a host cell, a cell line and a cell progeny, for example. In some embodiments, the host cell, cell line and cell progeny may be optionally selected from in vitro, ex vivo or in vivo.

The terms "drug", "medicament", "therapeutic agent" or "agent capable of being used for treatment" are used interchangeably, and refer to a molecule or compound that imparts some beneficial effect when administered to a subject. The beneficial effect includes the realization of diagnostic determination; improving a disease, a symptom, a disorder, or a pathological condition; reducing or preventing the onset of a disease, a symptom, a disorder or a pathological condition; and generally conflicting against a disease, a symptom, a disorder or a pathological condition.

As used herein, the term "subject" includes, but is not limited to, various animals, such as mammals, such as bovine, equine, ovine, porcine, canine, feline, rabbit, rodent (e.g., mouse or rat), non-human primate (e.g., macaque or cynomolgus macaques) or human. In certain embodiments, the subject (e.g., human) suffers from a condition (e.g., a condition caused by a disease-associated gene defect).

The term "effective amount" or "therapeutically effective amount" refers to the amount of a medicament sufficient to achieve a beneficial or desired result. The therapeutically effective amount can be changed depending on one or more of the subject and disease condition to be treated, the body weight and age of the subject, the severity of the disease condition, the mode of administration, etc., and can be easily determined by those of ordinary skills in the art. This term is also applicable to providing a dosage for providing an image for detection by any of the imaging methods described here. The specific dosage may vary depending on one or more of the following: the specific medicament as selected, the administration regimen as followed, whether the medicament is administered in combination with other compounds, the dosing time, the tissue to be imaged, and a physical delivery system carrying the medicament.

As used herein, the term a process of "administering . . . " to an individual can take place in vitro, ex vivo or in vivo.

As used herein, the term "Conserved Substitution" refers to the substitution (i.e. substitution) between amino acid molecules with similar traits. The traits include, but are not limited to, the ionic property, hydrophobicity and molecular weight of the molecule. Therefore, the substitution can be, for example, (1) substitution among aromatic amino acids (Phe, Trp, Tyr), (2) substitution among nonpolar aliphatic amino acids (Gly, Ala, Val, Leu, Met, Ile, Pro), (3) substitution among uncharged polar amino acids (Ser, Thr, Cys, Asn, Gln), (4) substitution among basic amino acids (Lys, Arg, His), or (5) substitution among acidic amino acids (Asp, Glu).

Example 1: Screening of Cas13 Protein

The Cas13 protein of the present invention was obtain by the following method:
1. Annotation for CRISPR and Gene
The (about millions of) proteins of a whole genome was predicted from the microbial genomes of NCBI Gebank and CNGB databases by a software, and then a CRISPR array on the genome was predicted by a CRISPRCasFinder software. The default parameter settings were used for initial screening.

2. Preliminary Screening of Protein

Taking protein sequence similarity of 95% as the standard, we used clustering to remove redundant proteins, remove proteins having a sequence identity of 100% with other proteins and a self-coverage of 100%, and meanwhile filtered out proteins less than 800 aa (amino acids) or greater than 1400 aa, so as to avoid the interference of too long or too short proteins and get hundreds of thousands of proteins.

3. Acquisition of CRISPR-Associated Protein

The protein sequences within 10 kb upstream and downstream of the CRISPR Array were compared with a known Cas13, and the alignment results with an evalue greater than 1*e$^{-5}$ were filtered out.

Then by comparing with the NR library of NCBI and the patent library of EBI, the Cas13 protein having a sequence identity ≥95% and a self-coverage ≥90% was filtered out, and then about 100 candidate proteins were obtained via selection by the inventor.

Upon verified by the experiment, the Cas13 proteins of the present invention Cas13 m.1 (SEQ ID NO: 1), Cas13 m.2 (SEQ ID NO: 2), Cas13 m.3 (SEQ ID NO: 3), Cas13 m.4 (SEQ ID NO: 4), Cas13 m.5 (SEQ ID NO: 5), Cas13 m.6 (SEQ ID NO: 60), CasRfg.1 (SEQ ID NO: 6), and CasRfg.2 (SEQ ID NO: 7) were obtained finally.

The amino acid sequence of the aforementioned Cas13 protein was as shown in Table 1 below.

TABLE 1

| Amino acid sequence of Cas13 protein | |
| --- | --- |
| Name | Amino acid sequence |
| Cas13m.1 (1025 aa) | MNPQARTRKPETPLKPVGNEHFAVFINIARHNAFIAITELSKIYGMTPPNEDELATSRFI AAFDSTTIDVRKLKQRLKRLSSLMPFLKSLQDKTDAEIIGILKDLLSLVNQFRNYYSH YNTSDFLTINSNEFITSDKVSILENIFEKAVLSLTNSEKAYDRFEIISLLKSEKRADKPYF YEFIENNKISEKAIAFFFCLFLDKPNAMKFLKRLKGFKGADTKQFRATLEAYTTYCIQ LPEPKFLSDRPNLAIILDGIEHLKRCPIEVHKTLSFRDKQKFERKVMREDLNGDLQEE NIELLRYDDRFAEFAMRYLDDFDILSDAKKQNTYRFEIQLGKKVVESKKLAEETTEA QDKIPVRFKPVKAFGKLADIPRKKDEAVIDWQQDLEELYAYEPHYKIENHSIGIKKIAT EDTFRLNNPEELPDAYLSEYQLRNIIFLSLESSNKEEFFMACQIRIGKIKSLYKALSAPT HYKESIKQKYNELINNNLLPKPLVKYLTHSLDELPTYKSKAIKKLKFWQDETENLLA EVKRHNEKSEKARKENKFFKSFLKSGQIATWLIKDIQHFLPLQGKLSVLKYNALQAK LAIYNSEELKEMLTDFQVYDTPKGTDRNMPEKGGGHQFIKTVFDKNPQKLPPHWLH FYNDYLNAKKQWIEDKIKFLTAMPDTEAEIMKQQPLFYFLDLGSNYEEGEKIVYFRE NSPAYIAKYCEELLKKPVDLPIALSYDLVANMRTGLEKAKSVTDFIDDKYQSEPPYYH LPRQYDLFKAFGDKPSEKLFATDKKPLHEVYGEYKAKKTDPRTIKKIKGFLDQEQRIR YLKVCDKLLVKILEKYLAKETELKNVQLTDAQGKLILDKVLETEFEMPPYGFKVRLK DYGRYRRFVKDRRLVSMQDYLNQSVFTPDTLITELNLYEKQRSEFLKIVLEFEKRLLS ASDTLNINLADQQTTLGEDKIRDYITHNYLLEVALRNNFISENEARAMLWFRNGALH NQLPDLQKLVGLIDTEEQKTQRYFLKGMEMYKKGIEKIS (SEQ ID NO: 1) |
| Cas13m.2 (1192 aa) | MTILEKYMPLNEMGKIKSLVDELKGIPGAMNATLRQEIFQNIKKTKLQVKFLEEYPET LFTDSGNLIPIIGNNDNSSSGTPSKQEVSDIDANQASRINYLPHETMGEIKSVYGTYIE MAFHNFYLTMHHIYAVVFGEDIMEEAKKEFDKNNTNSTKYFTFDFANERTIWKPMF DRAERAKPEQKEHFEKLVVKHPPFLKAIDALEDRKRKTKIQALCVFSLVLRELRNVY SHYLFYPFKNQVDKYKENIPFVLDMMEILYTGAQREVKGRFGFDDKKMQCAKKYE RNKDHSQRDHQGKIIKAVPKKNFRYNLYKKEDSEAIITPFGLVFLTSLFLEKKYAKILS DKTHCIKYTDQEVLCEIISVYRIRLHIQKLSVTKDTDALALDIINELQRCPKRLFEMLS PDDQQKFRIKPTDSQYADDVLMIRHQDRFAHLLLKYIDDAHLFNCIRFQVSLGRYFFR FYDKSCIDSTGDKRVRSISKNVNGFGRITDIEDYRKEVYGDMIREYEDVHANTSMEK PYITDHHAKYLISNNRIGLYIRKEEDTQCLLPELTPDGARNFAPTCWLSIYELPALAFL LHLYNGDGSRVEEIIQTKVANYQRLFADVRDGKVCPVKDEAELTTILQTYGNIEPSQL PRKLLDYLLKKEICAQDLFNTWAQSKIQRMIAQTDSLLQHLEKDLQAVSDLKQNKFG KKAFVAIKPGHIADFLAHDMMFFQPSMKDCNNKLTGLNFRILQSSMAVYDGNFDELS RIMRSAHIIGNANDACCNPIVMAVCRKHKGFSNIIRFYQAYLKERKAYLQQCANERH YDSLSFLHASQNKWRERTQAYYRSLAAKYLAENYDGVDTTKSIELPRGLFETYIRQE LSEIGSTKSMAGDATKNTSYLIYGYFRQVMSDDAQTFYDTRRCYQLFDVLYRKSPRD NHSYYSTAQIREMLMRSHSKSIRKDIDNYISQTTAAERTKEKERCDALLRKIKDTETE LKVYKIQDILLFLIAKRLLLDRKVENDSAVQMNAINQIRLRNIADGNTLSQKIPISISIK SRKGDPKIIQQDDLKLKNYSQFYSIISDRRLPSLLDLINSRVIKRTDIEDELSNYDKSHP HVLKSVFEFEKHYFDTHPIPSDTAYMALPDTGEMLKESNLTAEKQKEVRKIRNSFAHL SYPSRNITGAASTELPKKAEIISKNLIEHLSNAEIK (SEQ ID NO: 2) |
| Cas13m.3 (1272 aa) | MYHLSDANHGKHIAGTYYEMAMGNFIHTLSHMLVRAGIKVNKLEDNYSIEREIMNL TAPGAYDAQRAALSRLLYRHFPFFGPIMADHTDHILSSKRKKVQSASDDGNLDLGQE LKDEVAGASACQMIRYLATIAGALVYYRNMYSHKNHYDNAQDIAAQQEREQKLAL WLDVVFRGARDILLTRKSHPQPDTDFLTQNGTINYYIEKNGKSAYNPNFYFKPGLKT DNGWVMTDFGKFFFCSLFLRRADAERFAAETDLYVGSPFKITAQERARLQEAENKR AADEQARASSAGFPHIVNPRTIGPSESPQNNIIREMLNMHRARIPRERRIDADMSEGIL AMDIMNELRRCPLSLYNTLSPEAKASFEKTGVTPEGGIVSNLLVRHSDRYPELALRAI DQMELLPTIRFHVRLGSLRFRFYEKKLIDGSHTLRTVQKAVNGFGRWQEVEPRRVEK YTAIQARCQNDKGIDQFLPDSPTTTPYITDWRTTYNIHANRIGLAWNLPQMSDGIYLP NLDTDKGDNLHRKALIDMPAPMCYLSIFDLPALLFYCHIYTHYHGTKYHLPSAESIIQ AKYDALHKFFSFAAAQNHSAEQLREKQLELNLADNEIPDKLRCMMQTKPFFKNGRQ QLSPLGYPIMKNWIGVAEQRKHAAQVLRDVANEAADRLASFEKKHQRVVVGGRDN RYGRRGHADIRHGSLARYLATSMVRWQPALDQPGGDKLTSANHRALAGFLSEYGLH GSNINKLRNVLKEAGLIEGSHPHPFLAHVLESAPANIEALYVAYLKHEQSHATALKNK FTDRNGIVQPSEVPAFVRFNSSRWRNDSATTARRYLQTPPAPGSSDSAEHNAPIMLPD GLFTTHIMTLLNKVLGQNDRVPEEDYLRHDLPRIASIINPNGKTYGAAYIIRAWFDQV ENQDVQPFYDLPRFYREISLLAPRRKPNQELIRDYFSEEQIAQKIQTVPKKQRSEKVG HTIDTEKDIRRYRLQDITLYLTLLDMLTLMLSRNEAERTDRQMKSSTAERVSNMRLVD |

TABLE 1-continued

| Amino acid sequence of Cas13 protein | |
| --- | --- |

| Name | Amino acid sequence |
| --- | --- |

FDHSFDFDLLGSTSGEAAYSYLHQRSGITISMPALSLRSYGSIFRVLADSRFETLMDAL
NRQGVTHVNFGDITSELALYDTLRSHFLLQAHNVEQDAFSAKRGVLENHTSPFFYRS
GNLQLDDQGNITNPSTDAIRNHYGELIKILDRYSLKIDKKTKDGKSQDILLRDLMAEL
<u>RNAAAHNRYPKADFFFRQFDHFLNTCKPTDSNLTAPNYIRTVLEFLKSIVDNNFTPLL</u>
<u>HEESPENESKSE</u> (SEQ ID NO: 3)

Cas13m.4      MPMSTIIDKYMPLNDWNRIESLIGELRAISGAMNCAVRRAVFENIKKAKLQIKFNDQ
(1183 aa)     YPESIFTDKNGSIPIVGTTEANNPENGGNNECEQSNNYLSIDYLPRVTQEDKKSVYGT
              YFEMAFHNFFITLHHIYSLIFGEDIMEVAKSEYSQTQTDSFQDDFANKYTVWNPLFTR
              LRRAKAEQKERFEELAIKHFPFLKALDALKGENRVSKVDALERFSVVVRELRNIYLH
              YCIIPSDKQKKEYSDNISFIFDLMDLLFTGAKREVKTRFALSDDQMSCADKYEPNSDR
              SLRDIHGKTLRIVPKKNFRYHLYKVGDDAKIISPFGLVFLASLFLEKKYAKILSDKAHV
              VRLNDKGVICEMISVYRIRLHINRLSISKSTDTLALDIINELQRCPKKVFELLPPVAQQR
              FRVKPESSHAPEVLMVRHNDRFVHLLLKYIDDAKLFEHIRFQVSLGRYFFRFYDKICI
              DTSSEKRVRSICKDVHGFGRISEIEELRREKWKDILREYDEVHANTADEKPYITDHRA
              NYLIGNNKVGIYLLKEGDEQCIMPELLPNGARNHAPTCWLSTYELPALAFLLHLYNA
              DGARVEEIIEKQVAGYRRLFADVRDGSVAPVASVEELDELLKGYGDMQACNLPRKM
              LDYLLMKDVNAHDLFRKWAEAELQQMIEQTDRLSQRIDDDIKAAANMRQNKFGKK
              SFVAVKPGKIADFLAHDMMLFQPCTEDNSNKLTGLNFRILQSVMAVYNGDFDELSRV
              LRNAHIIGNATDEMCNPIVMAVCHKSMEFGNIVDFYKAYLRERRIYLERCLRHGDFE
              SLGFLHASQIRWQERSKEYYRALAARYLVDEYGGTESAKAIELPRGLFEPYIRKELSE
              MNAMKSLACNSDYNVSYLIYGYFKRVMSDDAQPFYDEKKCYRLFNVLYRKSPHDS
              PVYRNTAEIRDMLMQNSPNSIRKDIESYLSNTIIADRAKEKERCTALLREMKKCETEL
              KRYKIQDMLLFLIAKRILSDLPAAHDSAVQMQAISRIHLKDITDGNTLSEKISLSVKVV
              SKNGYIKKLTQHNLKLKNYSQFYAILSDRRLPSLLDLVRSNYINRNDIEAELDNYDKV
              HPEVMKAIIGLEKKHFEKHGFDDSGIVPDLSSILAETTMPADKQYEVRKI<u>RNSFAHSH</u>
              <u>YPGYHVANAGITELPKKAETIFNTLKSSLSDE</u> (SEQ ID NO: 4)

Cas13m.5      METTINNRIGKGEYYTEESKEFLAAYFNQAIHNVFIVLNHIAKRFGMDELSSDEELKN
(1190 aa)     WLIGRQEKKRNAIDRQRFLELIDRHFPFLRIANADKKDAKRENDLEDNLALLITLLN
              DLTER<u>RNKYSHA</u>ITHASIESNDRELVWRLYSIYDANINLVKRDYFESNVHTEINEDPY
              EKQVEH<u>LRRF</u>CMNNDRTKVDEKGKKKPAMPNPRFRTPFLNAETNQLSIYGLVFFVSL
              FLEKKYAIQMQKNVYGLKDARDTKFKMTNEVFCRSRIIMPRVRLHSDKSTDALVLD
              MLNELAKAPEVLFDQLTDPFKEKFYIESIDSLEESDIITPVRAIRKQNRFMYFALRYLD
              ESNAFSKLRFQIDLGNYHYHLYESKINDQTESRHLTRKLFGFGKLIAFEQEFAPEEWK
              MKSKDLDYYEGATQPFIAKTYPHYHLEENKIGILFNGQAEVQWPHLDVEEHESFPKY
              KRRANEKADAFLSGNELLAAAFCHHLYASIGKPNTVEKIIRDKYHALRQLFSDLKSG
              NLQNLLGDNTSNEAISQLLFEKYRLTLSEVPVRLHAFLSGQEQADTKAIARGKLELM
              AQQNKKRIERFDAMKKAVVKVGKAQYRTLRSGDIGDWLVRDFMRFQPIGYKRNQA
              GKQEPDLKSKANPKKYQLIQKSLALYEQKNNLLGLFKSCNLLSSENEHPFLNEVVQ
              SMPATWQDFYERYLHARSRFLEKCIEKGIKKNSYQACYSFLKIKPQLKDKEKLYQGW
              DAQMNLPTNMFIDAIHDWFRQTHHESLRTWFTQQEKPHQLIGLIRKYIELAHTDQIQ
              GFYDMFPLRYDFYKKEFPNGLVLHERINKQKQIWEAQLIQTKKRLEDAASKLKKVK
              QQVESLPDQELRFRNETEAMVYFTKLFDSSIVKNAILKLORDQKALRVNTIGEKIIKIY
              TAKYDAIHQEVRDFKSMLTTEKMIRRVKAEDCVTLFMLTDLMNQSQITIGQEQRTIK
              LSDIQPMGETQIQGILDAVQVLEQKLDFFSSDEQGKISQVKLGEWTIFSTDTKVKKQG
              NFKQLLKDRRLNNLAHYILPDIAGGAIRVRRNLLEMELDQYDRNRIPIIKLMYELEYA
              IYKVDPFSVELKYKKFSQCLREYAQKAVLNVEQVEHLNVLIAIRNAIMHNQYPNRDH
              LKAIVPFTVSEYAPVQEGLTIARQLLACAQVSVNIILSTISKF<u>E</u> (SEQ ID NO: 5)

Cas13m.6      MKEQKKFSLQGVRHVCGSYFNMALNNYCRTLNGVFIKCKIKFALKEDDFPRSLSSLR
(1188aa)      KIFSSGPIMPQTEKKVAKMIASVDTAMKLKQQLFKHFPMLGPIMDKTISCMNHHKGS
              SVADAPLDLCMNAILNFGECLYHC<u>RNFYTH</u>FKPYNSPEDLKLQYDIQHIIALNLGTLF
              DVSRRIGKKREGLTPEELEFLTGK<u>NRFNQ</u>VGKKFLERNDWYLKIEKPSDMKDYDKTI
              LSDFGMVYLCSIFLAKNYALRLFDESKLFNKETIRNLFSEEQVRFLKEMLVIYRIRTPR
              GKQLDSHDSKQALAMDMLNELRKCPRPLYDVLSEEYKKRTFYVPVEHENEKTEEY
              VKMLRSDDRFPYFTLRYIDDMEKFSRIRFQIRLGSYRFKFYDKMNIDGTPRIRSLQKEI
              NGFGRLSDMENKRKREWKDMFQATEEIDYEDQFGDYQTGVTQFVEDTADTKPYVT
              NHRAAYNVHSNHIGLIWNDADSIILQDDNKLFFPDLKIDENGKADIYQPSPKASLSVF
              DFPAMVFYMYLREKTEATKEFPSAEQLIINKYDHLVRFFKDISDGRFGPSENKNAFSK
              KLKEEYDLKTGEIPEKLLHWLSSESEEDPSEKYAKKLEEEIKLRRERVQRRLEKFNQD
              LREIRKKDSVPYGKKGHVNIRHSQLAKYLMRSIMEWQPTRNDGKNKLTGQNFNVM
              TAFLATLGYTSQVKDLRDLFSRANMLEGPNAHPFLKKVLNNNSIKDIQGFYRTYLVE
              ELNQIEDKQRRIAKAKNVKDTVRQFPFAHFNRMRYQKRDEDYYRNLAKRYLNIGDN
              EKDKAVILLPDGMFTSYIYDLIMKLPENNEKMRINLASDVAHCNSSFLISRFFENIRND
              YAQPFYREERTYELFSILNNKKVRNTLQPLFISPHDINIQLTEKEKDGKGRLILQKIDHF
              CKSITQKGNFNNVEEAKEATSRKLKHLITDCKNNERDIRRYKTQDMVIYLMARDILK
              DIIPDSEKDKYAKDRKLLLKDVCEEGFLRQAVKMEYEYSIEEKGKRTRTVKITHPNM
              SLKNYGEFHRLLNDERLKSLLQQLANMDEIDYTDLMGEFADYDQKRSEIFRLAQSIE
              KHLYEQNEQGLNDEKSDLFYHTRYNGKKIPRRNSFSSLLELIGEESQMTETDKKQTI
              SIR<u>NAFGHN</u>TYKVSLAEMNATELPNVAKTILKKMEELRNKL (SEQ ID NO: 60)

CasRfg.1      MKEKIKNKSSIIRIIMSNYDDKGLKEFKVLYNKQGGVDTFTCKTDIVDGTIIFLEIEKH
(1158 aa)     LRDFGDDFSWDISSDGKSVEITKLINGKETRKYKVSIKNSSTKDKKNLVELEVEDLKE
              SAIDRRRTKSSTKRVLLSKDVMERYAEIAFSKKERWEEIDSQKIYKVKRFLDYRSNML
              IYFQFINDFLTKGIPDELDKNGEIKQLELWKLIDDDETISDKNLNQVSKNLYTYISQEIK

TABLE 1-continued

Amino acid sequence of Cas13 protein

| Name | Amino acid sequence |
|---|---|
| | DSQTRAENNREKNKEKEHFKEFYAFNDISEESIREDVKKFIYLYANLRHNLMHYNYS<br>FFENLFEGKDLVIEKTKSLLSSTLDLNIFKELSNIVELREENKTNYLDDETTIRVLGKE<br>KKAKTLHKIYSILCSRKNGFNKFINSFFSTDGIEEEFLKSEIKKDFLERLNWVEKSLIEK<br>INNPPSDTKLKYKNDKTIENMTKEKEEKLELISLLNPQVSDYKTENFTPYYWDIHQSP<br>SYKKLYNDRKVLVSELSKLIAIGINSDTKKRITDLNAELLKIKIKMEKITKLNSKIRLQ<br>YKLQMAFGFIYANYSKVYKEKRVLNINGFVQNFDPTKLNKEKELESRLIYLKAPYNI<br>FEDNKSLDFNMKIVENIPVSEKSIFRIKPENNLSKFYILSYLLLPVELRGDFLGYVKHH<br>YYGIKNVDFEEIPDIKEDKPNENSDSFFHNLRLFEKNSKKFELIKYRLVEFGNLKDHLP<br>RIYEKFGIKPDVLEYIENSGNKDSKLFDRNILLPIMKYYQHIFKLLNDIEVHALLRFSE<br>KDSISLDESIKECSKGKFLNFGKLLFLSRYGLEAKKDNKFKDIFNRENGLSITKDDAK<br>TERKKYFEIFETRNKIAHLNYKQLFHDLLFDSNININKELEGIIQETKTIGLNAQTLGY<br>NFLNDFYMRKEMFISNQKKSSMTLINNPLSKDKDTKEIGLLKLYGLSKSQPKDLILAK<br>YKELMNLIEKTEDSILKKKDFLPVKEVSITVKKSTPNKKGIMVELPEILQIKDLNEMD<br>LLAYASNIRGKLHKDSSDLFGIYKKLTIKELKKKLINLFIKGEKRYLNLELVNKTGYM<br>AIYESTGLYPKSYEILNHEISFSEISMKNWYEHDFKPIFQIDGSLPNNTDYKNGVFIYTS<br>PYEFRDKELMKKQRTVHKRDIEKTFYNENDMDYTGIYNQKIKALY (SEQ ID NO: 6) |
| CasRfg.2<br>(931 aa) | MMGNKKSVAKANGLKSTFVLGENTAYMTSFGRGNAAQPEKHIRDATVTDIQHTFRA<br>KTDGGRTVHIEGRVGASDVLLPDAANQLHAKDAVEQMYFGKAFSDNIHIQIAYNIM<br>DIKKIFGVYANIIVHTVNNLCCDGDKQDDFLGMFKTQNRYQVAAWAHKIVSLHLVK<br>NELRGGGFFMDQEVWRAHVRTDFKSLNLAVNAFMKKYPQKYPYWSVKIVSDFIVQ<br>EMGIKNKVILEKAAESYAEFETVAKRLEKSAYYFSDIFAGKDGKFDEQKAFDLLRVL<br>GMMRQEAFHEKNSSASWLYNLDAEADEDIKAALRTVVDTKVNGINTNFAKQNKVN<br>LLVLQEIYPQKSKADLVREYYDFSVRKAFKNLGFSVKTLRETMCAFDAASVITDKQY<br>DTVRGKLYSLFDFVIYNYCLENEAVCNAFVEELRANLDPENKTALYQTLAEKVWAEI<br>GDIVLQRILPQMHAKKIQERSKETDAETVEMQGYVQAPKDLSLFSKAVYCISMFLDG<br>KEINSFLSALINKFENISSLCAVLAYNGLEPEFVAPFTFFADSQAIAEDLRYIKSIARMSK<br>GKKATKDSPVTVKEMQYFDAAAVLGETDTEKVKAAFHLGDKSASTADKAFRNFVV<br>NNVINSNRFVYVVRFINPKNAREIMQNRALIAFVLKDIPQSQLVRYCGTAGIACNADE<br>PNTEAMVNALADMLLQVRFDAFSNVQQKVKADSAEAVQKEKYKAIIGLYLTVLYLL<br>VKTLVKINMNYAIAFGILERDCQIMNQKHGKNPKRDRDAFYMREQQNKQYVYNAR<br>AITELFIENGWLNKRVQKSVENNAALYSDEAFYKYRNLVAHLNVISALPKYAKNITK<br>VKSLFDVYHYILFLSLCEDKYSNLPEAVTKSLCKNGKTMLENAREYQTVCKDFLYGL<br>NTPFAYNAARYINLSNREKFLAGFGK (SEQ ID NO: 7) |

In the aforementioned sequence, two RxxxxH (x represents any amino acid residue) motifs in each Cas13 protein were underlined. In the sequences of some Cas13 proteins (such as Cas13 m.1, Cas13 m.3), there were many sequences that satisfied the form of RxxxxH. However, by utilizing an online MAFFT v7.487 program (an E-INS-i algorithm, while others being default parameter settings), the amino acid sequences of the 5 proteins Cas13 m.1-Cas13 m.5 or the 6 proteins Cas13 m.1-Cas13 m.6 were aligned in multiple sequences, and the positions corresponding to the RxxxxH motifs of other proteins were identified as the RxxxxH motifs of the catalytic activity centers of the Cas13 m.1 and Cas13 m.3 proteins, which were also underlined in the aforementioned table. The alignment result also showed that the 6 proteins, Cas13m. 1-Cas13 m.6, contained RNxYxH and RNxxxH motifs from the N-terminal to the C-terminal sequentially, and X was independently selected from naturally occurring amino acid residues.

Additionally, the CasRfg.1 and CasRfg.2 proteins contained a RxxxxH motif and a RNxxxH motif from the N-terminal to the C-terminal sequentially.

The genomic sequence sources of the aforementioned Cas13 proteins were shown in Table 2 below.

TABLE 2

Source of genome sequence of Cas13 protein

| Protein | Database | Genome No, | The position of corresponding coding sequence in the genome | Annotations on the source of species in the database |
|---|---|---|---|---|
| Cas13m.1 | NCBI Genbank | GCA_013298125.1 | JAAFJP010000015.1:94576:97653:+ | Species name: *Cytophagales bacterium* (CFB group bacteria) Isolate: bin5.concoct.b16b17b19.071 |
| Cas13m.2 | CNGB | CNA0011077 | LW1-s151260_scaffolds_8411:1555:5133:+ | Species name: metagenome |
| Cas13m.3 | NCBI Genbank | GCA_902762805.1 | CACWPQ010000015.1:53195:57013:+ | Name of species: uncultured *Bacteroidetes bacterium* (CFB group) Isolate: RUG10805 |
| Cas13m.4 | CNGB | CNA0007373 | Boar-s10_scaffolds_11462:11216:14767:+ | Species name: metagenome |
| Cas13m.5 | NCBI Genbank | GCA_013298545.1 | JAAFIA010000070.1:913:4485:− | Name of species: *Bacteroidetes bacterium* (CFB group) Isolate: bin17.concoct.ball.095 |
| Cas13m.6 | NCBI Genbank | GCA_902779095.1 | GCA_902779095.1:CACZAB010000017.1:58800:62366:+ | Name of species: uncultured *Prevotellaceae bacterium* (CFB group) |

TABLE 2-continued

Source of genome sequence of Cas13 protein

| Protein | Database | Genome No, | The position of corresponding coding sequence in the genome | Annotations on the source of species in the database |
|---|---|---|---|---|
| CasRfg.1 | NCBI Genbank | GCA_003940745.1 | RRZU011077219.1:5441:8917:+ | Name of species: wastewater metagenome (metagenomes) Isolate: WW |
| CasRfg.2 | CNGB | CNA0009477 | F4286_scaffolds_12067:485:3280:+ | Species name: metagenome |

Note:
NCBI National Center for Biotechnology Information; and CNGB China National GeneBank.

The natural (wild type) DNA coding sequence of the aforementioned Cas13 protein was as follows:
the wild-type DNA coding sequence of the Cas13 protein Cas13m. 1 as shown in SEQ ID NO: 8;
the wild-type DNA coding sequence of the Cas13 protein Cas13 m.2 as shown in SEQ ID NO: 9;
the wild-type DNA coding sequence of the Cas13 protein Cas13 m.3 as shown in SEQ ID NO: 10;
the wild-type DNA coding sequence of the Cas13 protein Cas13 m.4 as shown in SEQ ID NO: 11;
the wild-type DNA coding sequence of the Cas13 protein Cas13 m.5 as shown in SEQ ID NO: 12;
the wild-type DNA coding sequence of the Cas13 protein Cas13 m.6 as shown in SEQ ID NO: 61;
the wild-type DNA coding sequence of the Cas13 protein CasRfg.1 as shown in SEQ ID NO: 13;
the wild-type DNA coding sequence of the Cas13 protein CasRfg.2 as shown in SEQ ID NO: 14.

Figure 1:
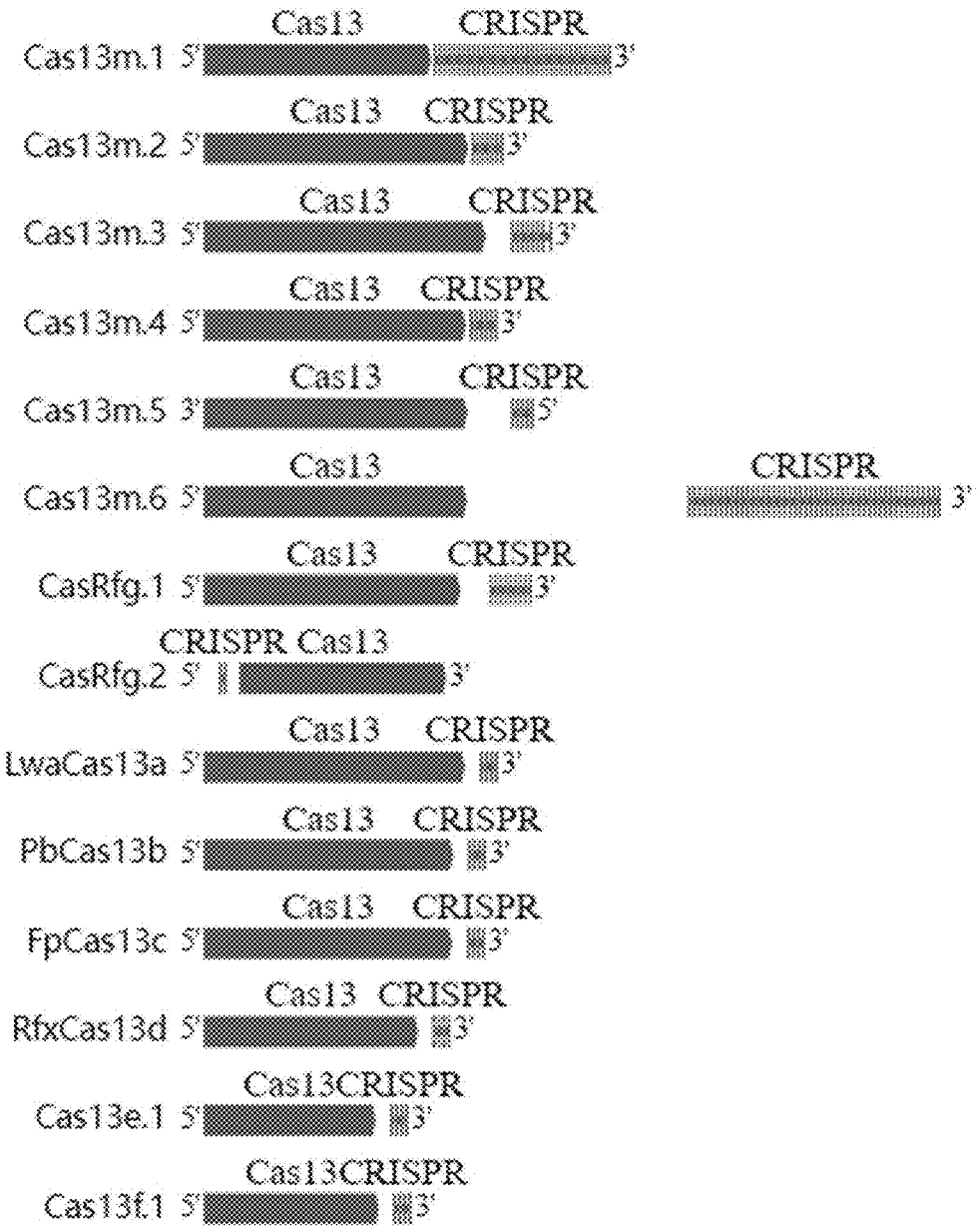
FIG. 1 is a schematic diagram for comparison of a locus structure between the Cas13 protein of Example 1 and various published subtypes of Cas13.

The locus structure of the aforementioned Cas13 protein was shown in FIG. 1, and in FIG. 1 the locus structure of the Cas13 protein of the present invention was compared with those of various published subtypes of Cas13, wherein CRISPR represented the CRISPR Array (a DNA sequence containing a corresponding DR sequence), and Cas13e.1 and Cas13f.1 were derived from the Chinese patent with the publication number of CN112410377A. It could be seen from the figure that the locus structures of Cas13 m.1-Cas13 m.5 had basically the same characteristics, and the locus structures of Cas13 m.1-Cas13 m.6 had basically the same characteristics.

Table 3 below listed the corresponding direct repeat (DR) sequences of the aforementioned Cas13 proteins:

tion. Two RxxxxH motifs of Cas13 m.1, Cas13 m.2, Cas13 m.3, Cas13 m.4, Cas13 m.5 and Cas13 m.6 proteins were obviously spaced far apart, which was basically spaced more than 920 aa apart except that of Cas13m. 1. Two RxxxxH motifs of Cas13 m.2 were spaced 923 aa apart, two RxxxxH motifs of Cas13 m.3 were even spaced 1,061 aa apart, two RxxxxH motifs of Cas13 m.5 were spaced 1,011 aa apart, and two RxxxxH motifs of Cas13 m.6 were spaced 1,011 aa apart.

On-line MAFFT version 7(E-INS-i algorithm) was utilized to construct phylogenetic trees for the newly discovered Cas13 protein (Cas13m. 1-Cas13 m.5 or Cas13m. 1-Cas13 m.6) of the present invention and the previously discovered various Cas13 subtypes (Cas13a, Cas13b, Cas13c, Cas13d, Cas13e and Cas13f), wherein partial protein sequences were published in NCBI, and Cas13e and Cas13f were available from the patent with the publication number of CN112410377A. The results showed that the Cas13m. 1-Cas13 m.5 or Cas13 m.1-Cas13 m.6 proteins of the present invention were clustered into groups on the phylogenetic tree, and other Cas13a/b/c/d/e/f subtypes were also clustered to be distributed in groups individually. The details were as shown in A and B in FIGS. 3A and 3B.

Figures 4, 5:
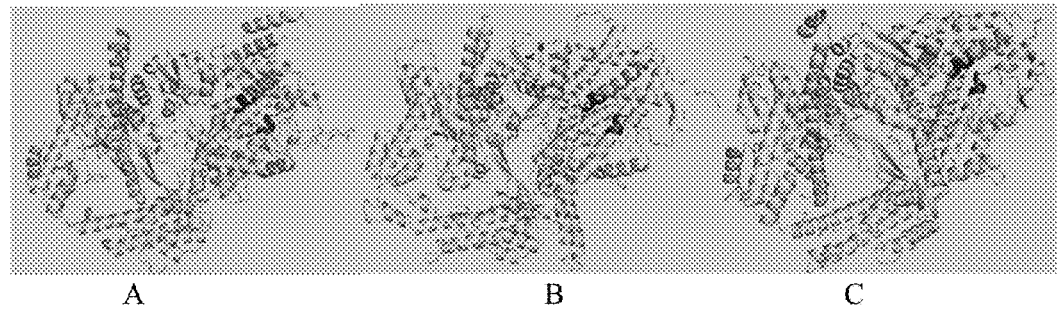
FIG. 4 is a schematic diagram of RNA secondary structure analysis of a corresponding direct repeat sequence of the Cas13 protein of Example 1 by RNAfold.
FIG. 5 shows three-dimensional predicted structures of Cas13 m.2, Cas13 m.3 and Cas13 m.6 proteins in Example 1.

The RNA secondary structures of the corresponding direct repeat sequences of Cas13 m.1-Cas13 m.6, CasRfg.1 and CasRfg.2 proteins of the present invention were predicted by RNAfold. It was as shown in FIG. 4. It could be seen from the figure that the DR sequences corresponding to Cas13 m.1-Cas13 m.6 had conserved secondary structures.

We used RNAfold to further analyze the RNA secondary structure of the aforementioned direct repeat sequences. As shown in FIG. 4, the corresponding direct repeat sequences

TABLE 3

The corresponding direct repeat (DR) sequences of the Cas13 proteins

| Cas13 protein | Corresponding direct repeat sequence | Sequence number |
|---|---|---|
| Cas13m.1 | GUUGUUACAGCCCUUAGUUUGUAGGGUAAUGACAAC | SEQ ID NO: 15 |
| Cas13m.2 | GUUGUAGAUGACCUCGUUUUGGAGGGGAAACACAAC | SEQ ID NO: 16 |
| Cas13m.3 | GUUGUAGAAGCCGUUCAUUCGGGACGGUAUGACAAC | SEQ ID NO: 17 |
| Cas13m.4 | GUUGUAAAUACCCACGUUUUGGUGGGCUAAUACAAC | SEQ ID NO: 18 |
| Cas13m.5 | GUUGUGUGUGCCUUUCAAAUUGAAGGCGUUCCCAAC | SEQ ID NO: 19 |
| Cas13m.6 | GUUGUAGAAGCCUAUCGUUAGGAUAGGUAUGACAAC | SEQ ID NO: 62 |
| CasRfg.1 | AUGACUAUACCAGCAAUGGCUGGAUUAAAAC | SEQ ID NO: 20 |
| CasRfg.2 | GGUUUUACACCCGUGUAAAACUACACAGUUCUAAAAC | SEQ ID NO: 21 |

Figure 2:
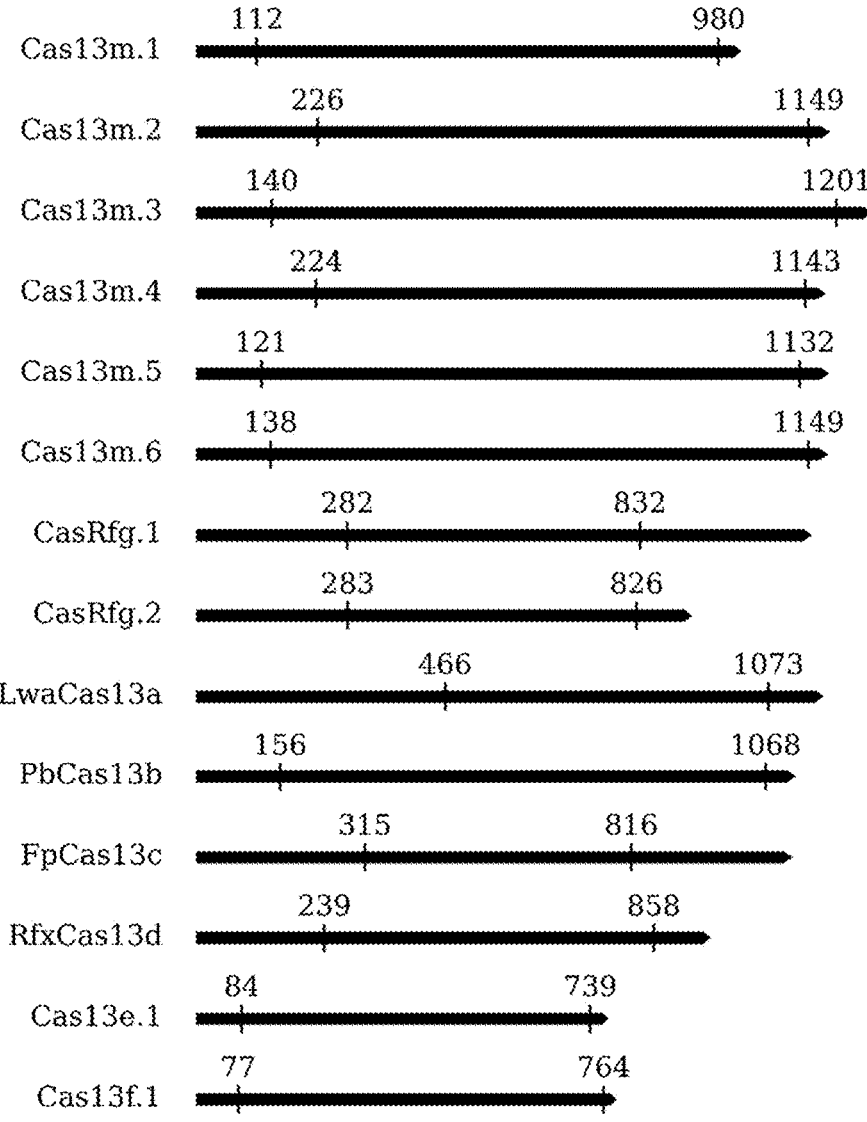
FIG. 2 shows the position of an RxxxxH motif in an amino acid chain, for the Cas13 protein of Example 1 and other subtypes of Cas13 protein.

FIG. 2 showed the position of the RxxxxH motif of each Cas13 protein in the amino acid chain in the present invenof Cas13 m.1, Cas13 m.2, Cas13 m.3, Cas13 m.4 and Cas13 m.5 had the following characteristics: obviously, they all had a conserved secondary structure, wherein A was a schematic diagram of the conserved secondary structure, including a complementary paired first stem (stem 1), a non-complementary bulge structure (bulge), a complementary paired second stem (stem 2), and a non-complementary loop structure (loop structure), the stem 1 and the stem 2 respectively contained complementary paired bases; and B-F were the secondary structures of the corresponding direct repeat sequences of Cas13 m.1, Cas13 m.2, Cas13 m.3, Cas13 m.4 and Cas13 m.5 respectively, wherein the stem 1 contained 4 base pairs (5'-GUUG-3'), 5 base pairs (5'-GUUGU-3'), 6 base pairs (5'-GUUGUA-3') or 7 base pairs (5'-GUUGUUA-3'). The direct repeat sequence of Cas13 m.6 also had the common structural characteristics as above. G and H were the secondary structures of the direct repeat sequences corresponding to CasRfg. 1 and CasRfg.2, respectively.

The three-dimensional structures of the Cas13m proteins were predicted by using the protein structure database program AlphaFold v2.0, as shown in FIG. 5, wherein A, B and C were Cas13 m.2, Cas13 m.3 and Cas13 m.6, respectively. Although two RxxxxH motifs (dark marks) were spaced far apart in the amino acid chain, they were very close in spatial location.

Figure 6:
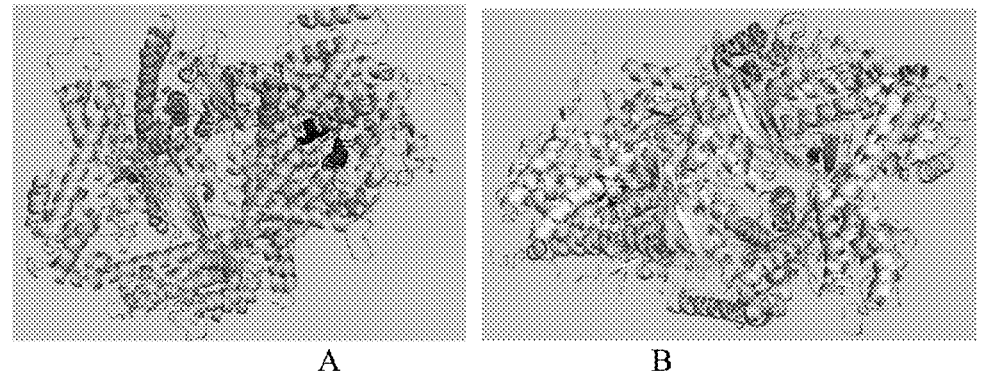
FIG. 6 is a schematic diagram of superposition of the Cas13 protein of Example 1.

Then, the proteins were superimposed by PyMOL V2.5.1, and the results were as shown in FIG. 6, wherein A was the superimposition result of Cas13 m.2 and Cas13 m.3, and B was the superimposition result of Cas13 m.3 and Cas13 m.6. The results showed that Cas13 m.2 and Cas13 m.3 had the similar three-dimensional structure (RMSD=2.402), and Cas13 m.3 and Cas13 m.6 had the similar three-dimensional structure (RMSD=2.368).

Figure 3A:
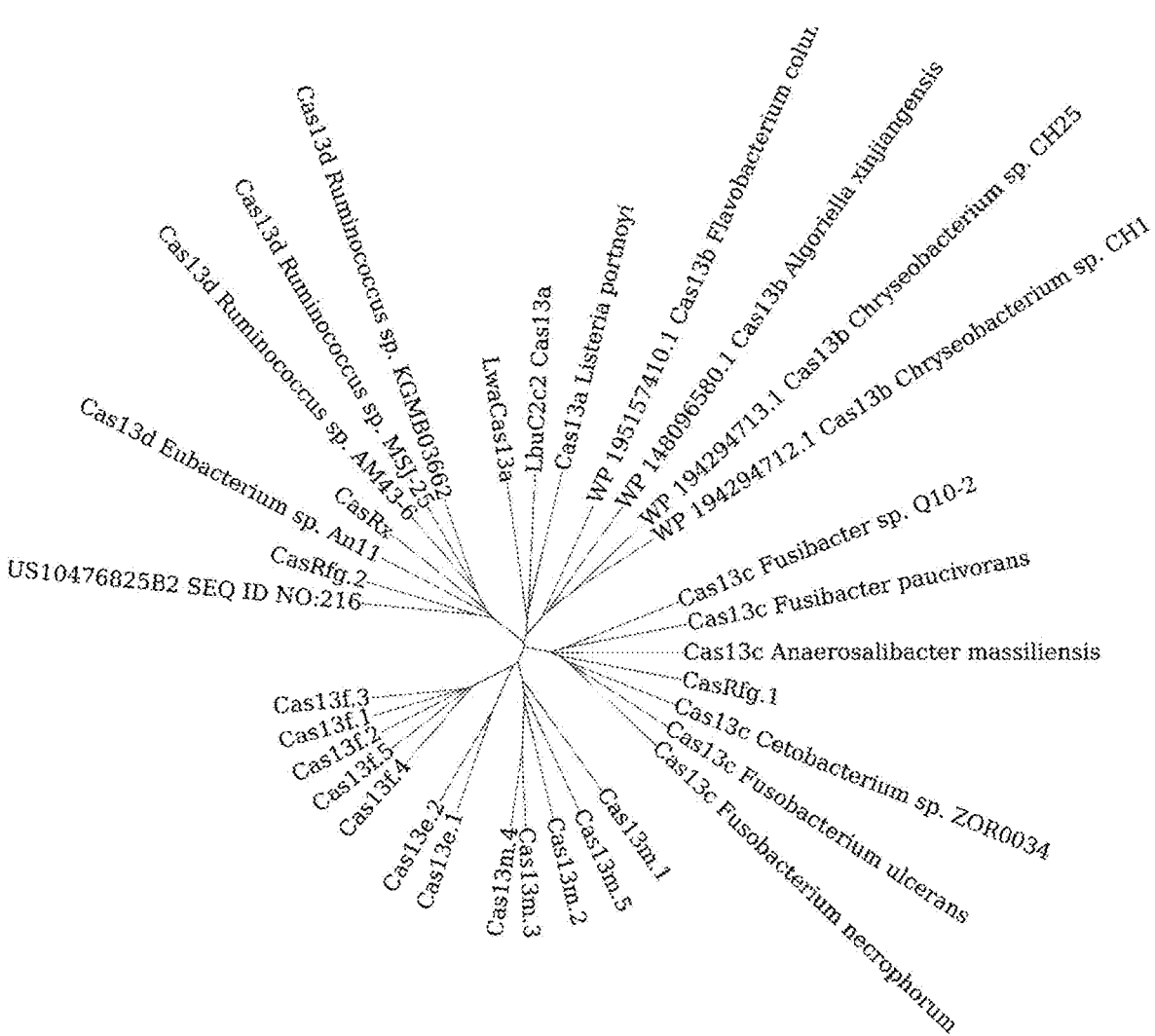
Figure 3B:
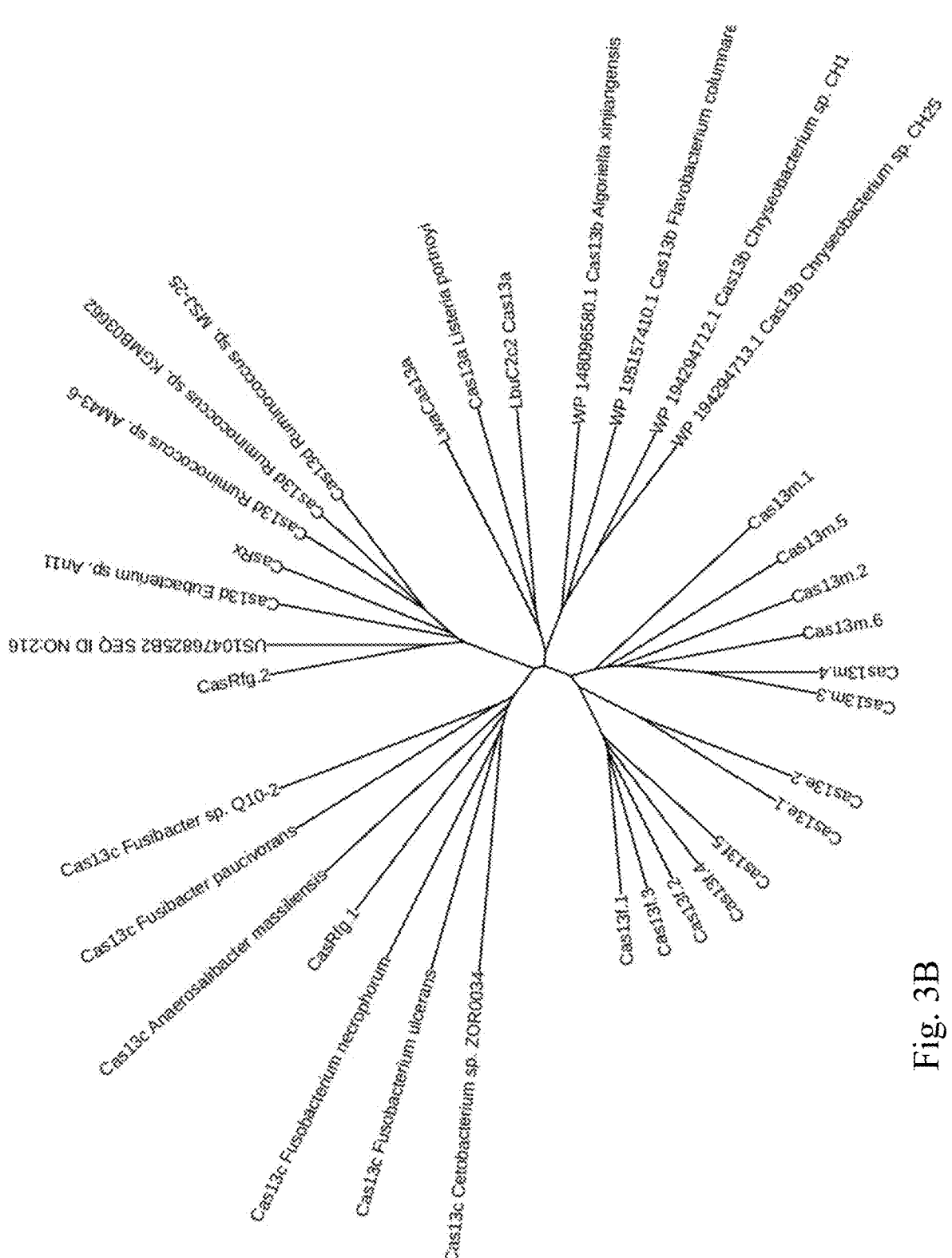

By alignment of the CasRfg. 1 protein with the Cas13 protein included in NCBI by BLASTp, it was found that the evalue value for alignment with Cas13c was the lowest compared with those of other Cas13 subtypes; and as combined with the phylogenetic tree analysis in FIGS. 3A-3B, CasRfg. 1 was classified as a Cas13c subtype. By alignment of the CasRfg.2 protein with the Cas13 protein included in NCBI by BLASTp, it was found that the evalue value for alignment with Cas13d was the lowest compared with those of other Cas13 subtypes; and as combined with the phylogenetic tree analysis in FIGS. 3A-3B, CasRfg.2 was classified as a Cas13d subtype.

Example 2: Preparation, Separation and Purification of Cas13 Protein (1) Construction of Vector
  1. a pET28a vector plasmid was taken, cleaved by double enzyme digestion via BamHI and XhoI, and subjected to agarose gel electrophoresis. A linearized vector was recovered by cutting the gel, an artificially synthesized DNA fragment containing the coding sequence of a recombinant protein (including the protein sequence and nuclear localization sequence of Example 1) was inserted into the cloning area of the vector pET28a by homologous recombination, and the vector was transformed into Stb13 competent by a reaction solution, coated onto an LB plate with kanamycin sulfate resistance, and incubated overnight at 37° C., and clones were picked for sequencing and identification.

The constructed recombinant vectors were named Cas13 m.1-pET28a, Cas13 m.2-pET28a, Cas13 m.3-pET28a, Cas13 m.4-pET28a, Cas13 m.5-pET28a, CasRfg. 1-pET28a and CasRfg.2-pET28a, respectively.

The recombinant vectors were respectively used for expressing a Cas13m. 1 recombinant protein (with the sequence of SEQ ID NO: 22), a Cas13 m.2 recombinant protein (with the sequence of SEQ ID NO: 23), a Cas13 m.3 recombinant protein (with the sequence of SEQ ID NO: 24)), a Cas13 m.4 recombinant protein (with the sequence of SEQ ID NO: 25), a Cas13 m.5 recombinant protein (with the sequence of SEQ ID NO: 26), a CasRfg. 1 recombinant protein (with the sequence of SEQ ID NO: 27), and a CasRfg.2 recombinant protein (with the sequence of SEQ ID NO: 28).

The architecture of the recombinant Cas13 series proteins was His tag-NLS-Cas13-SV40 NLS-nucleoplasmin NLS.
  2. Positive clones with correct sequences were incubated overnight, subjected to plasmid extraction, then transformed into an expression strain Rosetta (DE3), coated onto an LB plate with kanamycin sulfate resistance, and incubated overnight at 37° C.

(2) Protein Expression
  1. Monoclones were picked and plated into an LB culture solution containing 5 ml of kanamycin sulfate resistance, and incubated overnight at 37° C.
  2. They were transferred into 500 ml of an LB culture solution with kanamycin sulfate resistance at the ratio of 1:100, cultured at 220 rpm at 37° C. until the OD value was 0.6, added with IPTG to a final concentration of 0.2 mM, and induced at 16° C. for 24 h.
  3. Collection of bacteria by centrifuging: the bacteria were rinsed with 15 ml PBS, then centrifuged for collection, added with a lysis buffer for ultrasonic crushing, and centrifuged at 10,000 g for 30 min to obtain a supernatant containing the recombinant protein, and the supernatant was filtered through a 0.45 μm filter membrane before purification on a column.

(3) Protein Purification
The architecture of the recombinant Cas13 series proteins contained a NLS sequence, and the aforementioned recombinant Cas13 series proteins were purified by IMAC (Ni Sepharose 6 Fast Flow, CYTIVA) with 6 His at the N-terminal as a purification tag. Upon SDS-PAGE electrophoresis, it could be seen that a band of various purified recombinant proteins was presented in the interval of 100-250 kDa.

Example 3: Preparation, Separation and Purification of Cas13 m.6

A recombinant vector Cas13 m.6-pET28a (with the sequence of SEQ ID NO: 83) was constructed by employing the same method as that of the aforementioned Example 2, and transformed into an expression strain BL21-CodonPlus (DE3)-RIPL. Subsequently, a Cas13 m.6 recombinant protein (with an architecture of His tag-NLS-Cas13-SV40 NLS-nucleoplasmin NLS) was expressed and purified by the same method as above. Upon SDS-PAGE electrophoresis, it could be seen that a band of the finally purified recombinant Cas13 m.6 protein was presented in the interval of 100-250 kDa.

Example 4: Editing Activity on an Exogenous Gene in a Cell

1. Synthesizing of an EGFP-Targeting Vector to be Verified
    EGFP (enhanced green fluorescent protein) was used as an exogenous reporter gene, and its nucleic acid sequence (720 bp) was as shown in SEQ ID NO: 29.
    The sequence of an EGFP-targeting spacer was tgccgttcttctgcttgtcggccatgatat (SEQ ID NO: 30).
    The sequence of the exogenous EGFP expression vector was as shown in SEQ ID NO: 31, the sequence of the Cas13 m.2 verification vector was as shown in SEQ ID NO: 32, the sequence of the Cas13 m.3 verification vector was as shown in SEQ ID NO: 33, the sequence of the Cas13 m.5 verification vector was as shown in SEQ ID NO: 34, and the sequence of the CasRfg.2 verification vector was as shown in SEQ ID NO: 35.

The Cas13m. 1 verification vector and the Cas13 m.4 verification vector both had the same nucleotide backbone sequence as that of the Cas13 m.3 verification vector, except that the coding sequence of Cas13 protein and the coding sequence of DR sequence had been replaced accordingly. The CasRfg.1 verification vector had the same nucleotide backbone sequence as that of the CasRfg.2 verification temperature for 5 minutes. Note: it was continued to perform step c within 25 minutes;
   c. after incubation for 5 minutes, the diluted DNA was combined with the diluted Lipofectamine 2000. They were gently mixed and incubated at room temperature for 20 minutes (the solution might be cloudy visually). The complex was stabilized at room temperature for 6 hours.

The complex was added into the 293T cells and mixed, and detected by a flow cytometer after 48 h.

3. Detection of the Down-Regulation Effect of Cas13 Protein on EGFP Expression by Flow Cytometer The description of cells and plasmids as used was as shown in Table 4 below:

TABLE 4

| | | | |
|---|---|---|---|
| Grouping of transfected cells | | | |
| Groups | Transfected with the EGFP vector | Transfected with the EGFP-targeting Cas13 verification vector | Description |
| 293T | / | / | Cell control |
| EGFP | * | / | Control transfected with EGFP only |
| CasRfg.1 | * | * | Verification vector |
| Cas13m.1 | * | * | Verification vector |
| Cas13m.2 | * | * | Verification vector |
| Cas13m.3 | * | * | Verification vector |
| Cas13m.4 | * | * | Verification vector |
| Cas13m.5 | * | * | Verification vector |
| CasRfg.2 | * | * | Verification vector |

Note:
* represented containing related items, and/represented there was no related items.

vector, except that the coding sequence of Cas13 protein and the coding sequence of DR sequence had been replaced accordingly.

The aforementioned verification vector contained a codon-optimized coding sequence of Cas13 protein, which could express a Cas13 protein linked with NLS, and could also express a gRNA which could target EGFP and contained the corresponding DR sequence of Cas13. The guide sequence of the gRNA corresponded to the aforementioned spacer sequence (SEQ ID NO: 30).

All the aforementioned vectors were synthesized by a reagent company by a conventional method.

2. Transfection of a 293T Cell with the Vector to be Verified

A plasmid expressing the exogenous gene EGFP (referred to as EGFP for short) was transfected into a 293T cell in a 24-well plate with the aforementioned various plasmids as verification vectors at a ratio of 1:2 (300 ng:600 ng) respectively.

The transfection method was as follows:

The 293T cells were digested by trypsin (0.25% of Trypsin, EDTA, Thermo, 11058021), counted, and plated into a 24-well plates at $2 \times 10^5$ cells according to 500 µL per well.

For each transfected sample, the complex was prepared according to the following steps:
   a. each well of the 24-well plate into which the cells were added, were added with 50 µL of serum-free Opti-MEM I (Thermo, 25200056) reduced serum medium for dilution of the aforementioned plasmid DNA, and mixed gently; and
   b. it was gently mixed with Lipofectamine 2000 (Thermo, 11668019) before use, and then 1.8 µL of the Lipofectamine 2000 was diluted in each well, i.e., in 50 µL of the Opti-MEM I medium. It was incubated at room The 293T cells obtained after 48 h of transfection in the aforementioned step 2 were digested with trypsin (0.25% of Trypsin, EDTA, Thermo, 11058021), and centrifuged at 300 g for 5 min, the supernatant was discarded, and the cells in each well were resuspended with 500 µL of PBS. The EGFP fluorescent expression was detected by a flow cytometer, wherein the cell debris were removed by FCS-A and SSC-A gating, and then detection was conducted by the flow cytometer.

The Mean-FITC-A results of the FITC channel were collected and recorded, and the downregulation amplitude was calculated according to the following calculation formula:

$$\text{downregulation amplitude (\%)} = (a - x) \div a \times 100,$$

wherein the GFP fluorescence of the EGFP group was a, and the GFP fluorescence of other groups was x.

The blank control group did not participate in the comparison.

Figure 7:
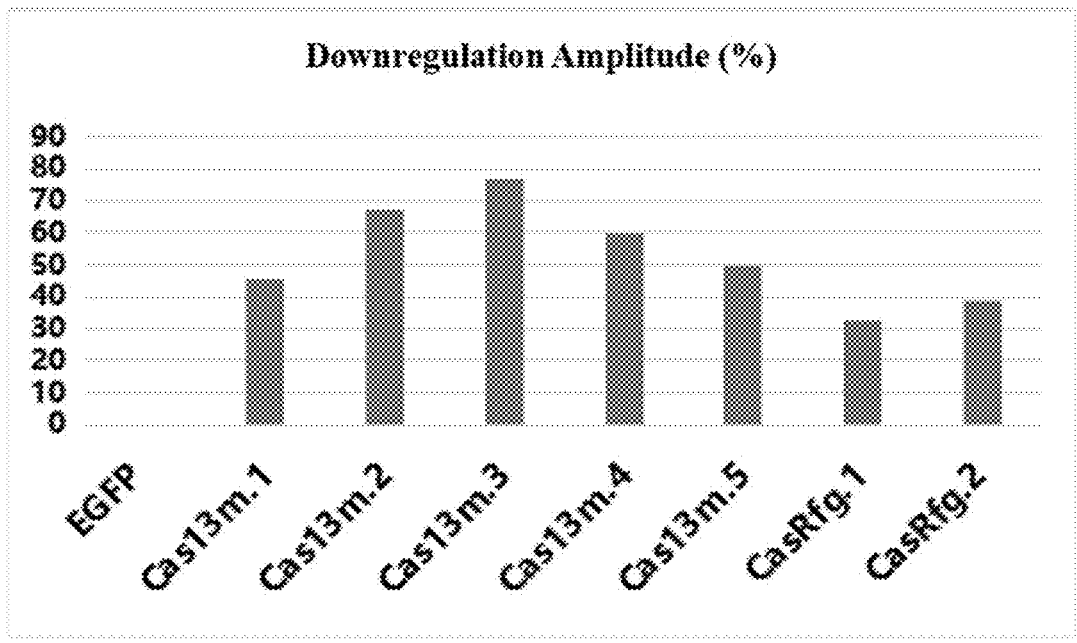
FIG. 7 shows a result of GFP fluorescence as detected by a flow cytometer in Example 4.

The experiment of this example was conducted in triplicate. The downregulation amplitude results were as shown in Table 5 below and FIG. 7, and the result data was the average of three tests.

TABLE 5

| | |
|---|---|
| Results of GFP fluorescence as detected by a flow cytometer | |
| Groups | Downregulation amplitude (%) |
| EGFP | 0.00 |
| Cas13m.1 | 46 |

TABLE 5-continued

| Results of GFP fluorescence as detected by a flow cytometer | |
| --- | --- |
| Groups | Downregulation amplitude (%) |
| Cas13m.2 | 67.31 |
| Cas13m.3 | 76.82 |
| Cas13m.4 | 59.73 |
| Cas13m.5 | 50.08 |
| CasRfg.1 | 33 |
| CasRfg.2 | 39.19 |

Note:
according to the average of three tests, the GFP fluorescence intensity of the 293T group was 1,073.55, and the GFP fluorescence intensity of the EGFP group was 8,052,219.55.

It could be seen from the table that the aforementioned Cas13 protein could significantly down-regulate the expression of EGFP, which proved that it could effectively reduce the mRNA level and exert its editing activity in eukaryotic cells under the guidance of the gRNA. Cas13 m.2 and Cas13 m.3 down-regulated the expression of EGFP at the largest amplitude.

Example 5: Verification of Endogenous Gene Editing Efficiency

1. Construction of an Editing Vector Targeting Endogenous Genes AQp1 and PTBP1

The codon-optimized Cas13 m.2, Cas13 m.3, Cas13 m.5, CasRfg.2, and CasRx (one of Cas13d) expression vectors carrying an universal gRNA scaffold expression cassette were respectively synthesized in a reagent company, which were Cas13 m.2-BsaI (with the sequence as shown in SEQ ID NO: 36). Cas13 m.3-BsaI (with the sequence as shown in SEQ ID NO: 37), Cas13 m.5-Bsa (with the sequence as shown in SEQ ID NO: 38), CasRfg.2-BsaI (with the sequence as shown in SEQ ID NO: 39) and CasRx-BpiI (with the sequence as shown in SEQ ID NO: 40).

The endogenous sites selected in the experiment were AQp1 and PTBP1, wherein AQp1 was verified by using a 293T cell line (293T-AQp1 cells) with high expression of AQp1, and PTBP1 was verified by using a 293T cell line.

A method for constructing the 293T cell line with high expression of AQp1: a vector Lv-AQp1-T2a-GFP with overexpression of the AQP1 gene and the EGFP gene was constructed with the sequence as shown in SEQ ID NO: 41. AQp1 and EGFP were spaced apart by a 2A peptide. The Lv-AQp1-T2a-GFP plasmid was packaged into a lentivirus and transduced into 293T cells to form a cell line stably overexpressing the AQp1 gene.

The guide sequence of an AQp1-targeting gRNA was selected as

```
                                    (SEQ ID NO: 42)
          GAAGACAAAGAGGGUCGUGG
```

The guide sequence of an PTBP1-targeting gRNA was selected as:

```
                                    (SEQ ID NO: 43)
     GUGGUUGGAGAACUGGAUGUAGAUGGGCUG
```

A target site-targeted fragment was obtained by using a primer annealing manner, and the primers of it were as follows:

```
PTBP1-targeting group:
Cas13m.2 group:
                                    (SEQ ID NO: 44)
F:      CACCGTGGTTGGAGAACTGGATGTAGATGGGCTG (SEQ ID NO: 45)
R:      CAACCAGCCCATCTACATCCAGTTCTCCAACCAC Cas13m.3 group:
                                    (SEQ ID NO: 44)
F:      CACCGTGGTTGGAGAACTGGATGTAGATGGGCTG (SEQ ID NO: 45)
R:      CAACCAGCCCATCTACATCCAGTTCTCCAACCAC Cas13m.5 group:
                                    (SEQ ID NO: 44)
F:      CACCGTGGTTGGAGAACTGGATGTAGATGGGCTG (SEQ ID NO: 45)
R:      CAACCAGCCCATCTACATCCAGTTCTCCAACCAC CasRfg.2 Group:
                                    (SEQ ID NO: 46)
F:      AAACGTGGTTGGAGAACTGGATGTAGATGGGCTG (SEQ ID NO: 47)
R:      AAAACAGCCCATCTACATCCAGTTCTCCAACCAC CasRx group:
                                    (SEQ ID NO: 46)
F:      AAACGTGGTTGGAGAACTGGATGTAGATGGGCTG (SEQ ID NO: 48)
R:      CTTGCAGCCCATCTACATCCAGTTCTCCAACCAC AQp1-targeting group:
Cas13m.2 group:
                                    (SEQ ID NO: 49)
F:      CACCGAAGACAAAGAGGGTCGTGG (SEQ ID NO: 50)
R:      CAACCCACGACCCTCTTTGTCTTC Cas13m.3 group:
                                    (SEQ ID NO: 49)
F:      CACCGAAGACAAAGAGGGTCGTGG (SEQ ID NO: 50)
R:      CAACCCACGACCCTCTTTGTCTTC Cas13m.5 group:
                                    (SEQ ID NO: 49)
F:      CACCGAAGACAAAGAGGGTCGTGG (SEQ ID NO: 50)
R:      CAACCCACGACCCTCTTTGTCTTC CasRfg.2 Group:
                                    (SEQ ID NO: 51)
F:      AAACGAAGACAAAGAGGGTCGTGG (SEQ ID NO: 52)
R:      AAAACCACGACCCTCTTTGTCTTC CasRx group:
                                    (SEQ ID NO: 51)
F:      AAACGAAGACAAAGAGGGTCGTGG (SEQ ID NO: 53)
R:      CTTGCCACGACCCTCTTTGTCTTC
```

The primer annealing reaction system was as follows: it was incubated in a PCR instrument at 95° C. for 5 minutes, then immediately taken out and incubated on ice for 5 minutes, so that the primers were annealed to each other to form a double-stranded DNA with sticky ends:

US 12,698,492 B2

37

| | |
|---|---|
| Oligo-F (10 µM) | 2 µl |
| Oligo-R (10 µM) | 2 µl |
| 2 µl of 10× endonuclease reaction buffer | 2 µl |
| Deionized water | up to 20 µl |

After the synthesized Cas13m-BsaI and CasRfg-BsaI plasmids were digested with a BsaI endonuclease, the annealed products and the backbones purified and recovered after the digestion were subjected to T4 linkage respectively. After the transformation into *Escherichia coli*, the positive clones were selected and the verification vector plasmids targeting the endogenous gene mRNA were extracted for cell experiment verification. After the synthesized CasRx-BpiI plasmid was digested with a BsaI endonuclease, the annealed products and the backbones purified and recovered after the digestion were subjected to T4 linkage. After the transformation into *Escherichia coli*, the positive clones were selected and the verification vector plasmids targeting the endogenous gene mRNA were extracted for cell experiment verification.

2. Transfection of 293T Cells and 293T-AQp1 Cells with the Vector to be Verified 293T-AQp1 cells were transfected with the AQp1-targeting plasmids (verification vector plasmids targeting the endogenous gene mRNA) of Cas13 m.2, Cas13 m.3, Cas13 m.5, CasRfg.2 and CasRx obtained in the previous step at 800 ng in a 24-well plate. The negative control group was transfected with the CasRx-BpiI plasmid.

The 293T cells were transfected with the PTBP1-targeting plasmids of Cas13 m.2, Cas13 m.3, Cas13 m.5, CasRfg.2 and CasRx at 800 ng in a 24-well plate. The negative control group was transfected with the CasRx-BpiI plasmid.

The transfection method was as follows:
1) The cells were digested by trypsin (0.25% of Trypsin, EDTA, Thermo, 11058021), counted, and plated into a 24-well plates at 2×10⁵ cells according to 500 µL per well.
2) For each transfected sample, the complex was prepared according to the following steps:
a. each well of the 24-well plate into which the cells were added, were added with 50 µL of serum-free Opti-MEM I (Thermo, 25200056) reduced serum medium for dilution of the aforementioned plasmid DNA, and mixed gently;
b. it was gently mixed with Lipofectamine 2000 (Thermo, 11668019) before use, and then 1.8 µL the Lipofectamine 2000 was diluted in each well, i.e., in 50 µL of the Opti-MEM I medium. It was incubated at room temperature for 5 minutes. Note: it was continued to perform step c within 25 minutes;
c. after incubation for 5 minutes, the diluted DNA was combined with the diluted Lipofectamine 2000. They were gently mixed and incubated at room temperature for 20 minutes (the solution might be cloudy visually). Note: the complex was stabilized at room temperature for 6 hours.

The complex was added into the cells and mixed, and then detected with a QuantStudio™ 5 Real-Time PCR System, 96-well after 72 h.

3. Detection of the mRNA Changes of the Target Gene by qPCR
1) Experimental Method
At 72 h after transfection, the cells were subjected to RNA extraction with a SteadyPure Universal RNA Extraction Kit AG21017 kit, and the mRNA concentration was detected with an ultramicro spectrophotometer. The mRNA product was reverse transcribed by using an Evo M-MLV Mix Kit with gDNA Clean for qPCR AG11728 reverse transcription kit, and the reverse transcribed product was detected by using a SYBR Green Premix Pro Taq HS qPCR Kit (Low Rox Plus) AG11720 qPCR kit.

Primers used in the qPCR were as follows:

```
detection of PTBP1:
                                    (SEQ ID NO: 54)
ATTGTCCCAGATATAGCCGTTG (SEQ ID NO: 55)
GCTGTCATTTCCGTTTGCTG detection of AQp1:
                                    (SEQ ID NO: 56)
GCTCTTCTGGAGGGCAGTGG (SEQ ID NO: 57)
CAGTGTGACAGCCGGGTTGAG detection of internal reference GAPDH:
                                    (SEQ ID NO: 58)
CCATGGGGAAGGTGAAGGTC (SEQ ID NO: 59)
GAAGGGGTCATTGATGGCAAC
```

A reaction system was configured according to the instructions of the SYBR Green Premix Pro Taq HS qPCR Kit (Low Rox Plus) AG11720, and detected by using a QuantStudio™ 5 Real-Time PCR System, 96-well.
2) Calculation Method
In this experiment, the change of the target RNA was calculated by using a relative quantitative method, namely a 2-ΔΔCt method. The calculation method of it was as follows:

$$\Delta Ct = Ct(AQp1) - Ct(GAPDH) \text{ or } Ct(PTBP1) - Ct(GAPDH);$$

ΔΔCt=ΔCt (a sample to be verified, such as the Cas13 m.2 group)–ΔCt (a negative control group);

$$2 - \Delta\Delta Ct = 2^{\wedge}(-\Delta\Delta Ct).$$

The experiment of this example was conducted in triplicate, and the relative mRNA expression levels of AQp1 and PTBP1 calculated according to the aforementioned calculation manner, were as shown in Table 6 below and FIG. 8, and the result data was the average of three tests:

TABLE 6

Relative expression levels of target mRNA as calculated by 2-ΔΔCt method

| Groups | AQp1 mRNA level | PTBP1 mRNA level |
|---|---|---|
| Negative Control | 1.00 | 1.00 |
| CasRx | 0.05 | 0.60 |
| Cas13m.2 | 0.03 | 0.49 |
| Cas13m.3 | 0.02 | 0.46 |
| Cas13m.5 | 0.27 | 0.70 |
| CasRfg.2 | 0.36 | 0.78 |

The qPCR results showed that all of Cas13 m.2, Cas13 m.3, Cas13 m.5 and CasRfg.2 had the effect of down-regulating the expression of AQp1 and PTBP1. Cas13 m.2 and Cas13 m.3 down-regulated the expression of the genes AQp1 and PTBP1 with better effects than that of CasRx, and had good editing activities. Cas13 m.5 and CasRfg.2 also had significant editing activities.

Example 6: Connection Order of DR Sequence and Guide Sequence

The influence of the connection order of the DR sequence and the guide sequence in a gRNA molecule on the editing efficiency was verified.

1. Construction of an Editing Vector Targeting the Endogenous Gene AQp1

The endogenous site selected in this experiment was AQp1, and AQp1 was verified by using the 293T cell line with high expression of AQp1 of the previous example.

The guide sequence of an AQp1-targeting gRNA was

GAAGACAAAGAGGGUCGUGG (SEQ ID NO: 42)

The verification vectors as used were as follows

| Serial Number | gRNA structure (5'-3') |
| --- | --- |
| Cas13m.2 | Guide sequence-direct repeat sequence |
| Cas13m.3 | Guide sequence-direct repeat sequence |
| Cas13m.5 | Guide sequence-direct repeat sequence |
| CasRfg.2 | Direct repeat sequence-guide sequence |
| Cas13m.2-r | Direct repeat sequence-guide sequence |
| Cas13m.3-r | Direct repeat sequence-guide sequence |
| Cas13m.5-r | Direct repeat sequence-guide sequence |
| CasRfg.2-r | Guide sequence-direct repeat sequence |

The verification vectors targeting the endogenous gene AQp1 mRNA of Cas13 m.2, Cas13 m.3, Cas13 m.5 and CasRfg.2 had been constructed in the experimental example 5, and the verification vectors targeting the endogenous gene AQp1 mRNA of Cas13 m.2-r, Cas13 m.3-r, Cas13 m.5-r, and CasRfg.2-r with adjusted gRNA structures (the positions of the guide sequence and the direct repeat sequence were reversed) (other sequences except the gRNA coding sequence were the same as those of the verification vectors of Cas13 m.2, Cas13 m.3, Cas13 m.5 and CasRfg.2) were synthesized in a reagent company.

2. Transfection of 293T Cells and 293T-AQp1 Cells with the Vector to be Verified 293T-AQp1 cells were transfected with the verification vectors targeting the endogenous gene AQp1 mRNA of Cas13 m.2, Cas13 m.3, Cas13 m.5, CasRfg.2, Cas13 m.2-r, Cas13 m.3-r, Cas13 m.5-r, and CasRfg.2-r, and a control plasmid (which was the same as the verification vector plasmid targeting the endogenous gene AQp1 mRNA of CasRx in the aforementioned Example 5) at 800 ng in a 24-well plate. The negative control group was transfected with the CasRx-BpiI plasmid in the aforementioned Example 5.

The transfection method was as follows:

1. The cells were digested by trypsin (0.25% of Trypsin, EDTA, Thermo, 11058021), counted, and plated into a 24-well plates at $2 \times 10^5$ cells according to 500 µLper well.

2. For each transfected sample, the complex was prepared according to the following steps:

a. each well of the 24-well plate into which the cells were added, were added with 50 µL of serum-free Opti- MEM I (Thermo, 25200056) reduced serum medium for dilution of the aforementioned plasmid DNA, and mixed gently;

b. it was gently mixed with Lipofectamine 2000 (Thermo, 11668019) before use, and then 1.8 µL of the Lipofectamine 2000 was diluted in each well, i.e., in 50 µLof the Opti-MEM I medium. It was incubated at room temperature for 5 minutes. Note: it was continued to perform step c within 25 minutes;

c. after incubation for 5 minutes, the diluted DNA was combined with the diluted Lipofectamine 2000. They were gently mixed and incubated at room temperature for 20 minutes (the solution might be cloudy visually). Note: the complex was stabilized at room temperature for 6 hours.

The complex was added into the cells and mixed, and then detected with a QuantStudio™ 5 Real-Time PCR System, 96-well after 72 h.

3. Detection of the RNA Changes of the Target Gene by qPCR

At 72 h after transfection, the cells were subjected to RNA extraction with a SteadyPure Universal RNA Extraction Kit AG21017 kit, and the RNA concentration was detected with an ultramicro spectrophotometer. The RNA product was reverse transcribed by using an Evo M-MLV Mix Kit with gDNA Clean for qPCR AG11728 reverse transcription kit, and the reverse transcribed product was detected by using a SYBR Green Premix Pro Taq HS qPCR Kit (Low Rox Plus) AG11720 qPCR kit.

The primers used in the qPCR included the primer pair for detecting AQp1 as shown in SEQ ID NOs: 56-57 and the primer pair for detecting the internal reference GAPDH as shown in SEQ ID Nos: 58-59.

A reaction system was configured according to the instructions of the SYBR Green Premix Pro Taq HS qPCR Kit (Low Rox Plus) AG11720, and detected by using a QuantStudio™ 5 Real-Time PCR System, 96-well.

The qPCR results were as follows:

In this experiment, the relative expression level of the target RNA was calculated by using a relative quantitative method, namely a 2-ΔΔCt method. The calculation method of it was as follows:

$$\Delta Ct = Ct(AQp1) - Ct(GAPDH);$$

ΔΔCt=ΔCt (a sample to be verified, such as the Cas13 m.2 group)−ΔCt (a negative control group);

$$2 - \Delta\Delta Ct = 2^{\wedge}(-\Delta\Delta Ct).$$

The amount of AQp1 mRNA calculated according to the aforementioned calculation manner was as shown in Table 7 below:

TABLE 7

| Relative expression levels of target RNA as calculated by 2-ΔΔCt method | |
| --- | --- |
| Groups | AQp1 mRNA level |
| Negative Control | 1.00 |
| Cas13m.2 | 0.04 |
| Cas13m.3 | 0.04 |

TABLE 7-continued

| Relative expression levels of target RNA as calculated by 2-ΔΔCt method | |
| --- | --- |
| Groups | AQp1 mRNA level |
| Cas13m.5 | 0.36 |
| CasRfg.2 | 0.30 |
| Cas13m.2-r | 0.83 |
| Cas13m.3-r | 0.78 |
| Cas13m.5-r | 0.74 |
| CasRfg.2-r | 0.67 |

The qPCR results showed that the editing activities of Cas13 m.2-r, Cas13 m.3-r, Cas13 m.5-r and CasRfg.2-r were decreased obviously after changing the relative positions of the direct repeat sequence and the guide sequence.

Example 7: The Editing Activity of Cas13 m.6 on an Exogenous Gene in a Cell and the Activity Comparison Between the Cas13m and Published Proteins Unless otherwise specified, the experiment was conducted in this example by using the same method as that of Example 4.

1. Synthesizing of an EGFP-Targeting Vector to be Verified

An EGFP-targeting validation vector Cas13 m.6 was obtained by preparation, with the full-length sequence as shown in SEQ ID NO: 105 (7,690 bp).

After looking up in NCBI, it was searched that NCBI disclosed two Cas13 proteins, namely a C13-38 protein (GenBank: MBQ9236733.1) and a C13-40 protein (NCBI Reference Sequence: WP_025000926.1), and corresponding DR sequences thereof.

A comparison of gene editing activity was conducted by the inventor among Cas13m, C13-38 and C13-40.

The sequence of C13-38 was:

(SEQ ID NO: 63)

MEKHHSQPRKAQFPFSISEKSVMGGYFNIARLNFYKTIVTIFAQVGVKG

EYPEDKIDRVLDALYKNIAGKDNELSKEQAQWKRLKQLKGEQITKLQRL

LFNHFPVLGPIMASEASYKIYKSELNAKEAEDAVQNDKEELKKIKKSNV

INNEQLMRGVGIDDCLNVLATMAACLTDCRNYYSHYIPYNSIEDQKKQY

KRQAQIARWLDKVIVASRRIDKQRNSLTTNEMEFLTGIDHYFQQDKKDD

TGKLIRDEKGRTLKEFVEYPDYYFRIKGERQLVDIAGKTLNEEQAQNAL

TDFGIVFFCTLFLQKTYAKMMQEELKLYENGPYRGDVKGKENDDAKKNT

ILREMLSIYRIRVPRGKRLDSKDDATTLSMDMLNELRKCPMPLYDVLGK

DGQRFFEDEVQHPNEQTPEKVKRLRATDRFPHLALRYIDLHDKTFTRIR

FQVQLGNFRFKFYNKKTIDGAEEVRSIQKEINGYGRLQEIEAKRLETYA

PLFQKSELVSTKLEHEDLNLDLVQFTEDHADSKPYITNHRATYNIHNNR

IGMYWEASQNVKEYKVFSSDGMYLPTLNTIDGKAPISMPAPKASLSIYE

LPAMLFYQYLLDNNNVKKNEYDAPQDILINKHDALVKFFEAVRGGELIP

ALSKDELSRKLESEYDLKISEVPNKLVDYLIGKEDNGKRLYDYATHEVL

LRLRRSLRRFEHFEEDRKMIGSKDNKYGKKGFVDVRHGRLAQYLAESIM

DWRKPLNGEKDKLTGLNYSKMQAALATFGGKTTFDKLNTLFKEAGLYDN

RPGSHPFLQSTMQKAPQNIEMLYLAYLEAETDKLKKFVVIKNLNNLSEK

ELKEYKDLVTFTVKEKRTYSDGRTKMVMVDKVAVNIIGNTNFANLPFIH

HQRARFAQRNAEYYKSLAGRYLSVDGKSATIQLPDGIFTKHILKLLKEK

YATHEALQLHLTDDDMNHNAAYLISSFFETVLNDCSQPYYRTFHYENNE

KKTSKFAHIYDLFNILNNVKEANAYKPYPMTTDDINSRLTKKATNRDGL

FVIRKDDNGEDYLVKQITLDIENHLKKMEDAVEAKIKFKNLYGYNADKA

RKNGAEEREKMLRKLTHCISDVKNNERAIRRYKTQDMVLFLLAKSTLST

ILAQQNGVASEELFRLKNVCNNNFLSQTVRFEFPIKVNEMTIKVVQENM

ALKNYGEFYRFINDDRLMSLLTQLKDVTEISYADLTGELATYDLRRSQV

FRLMQELEKIAFEQHTKELTNIDNSMFFKDGDMNNVPRRNNFKALINLF

DSIDSHQLTKDDCERLVEIRNAFCHNTYRINIDDLQEKLPTIAIQIVGK

IENLLKGADMKK

The DR sequence corresponding to C13-38 was:

(SEQ ID NO: 64)

5'-GUUUUCAUACCUAUCCAAACGAUAGGCUUCUAAAAC-3'

The sequence of C13-40 was:

(SEQ ID NO: 65)

MEDDKKTTGSISYELKDKHFWAAFLNLARHNVYITINHINKLLEIREID

NDEKVLDIKTLWQKGNKDLNQKARLRELMTKHFPFLETAIYTKNKEDKK

EVKQEKQAEAQSLESLKDCLFLFLDKLQEARNYYSHYKYSEFSKEPEFE

EGLLEKMYNIFGNNIQLVINDYQHNKDINPDEDFKHLDRKGQFKYSFAD

NEGNITESGLLFFVSLFLEKKDAIWMQQKLNGFKDNLENKKKMTHEVFC

RSRILMPKLRLESTQTQDWILLDMLNELIRCPKSLYERLQGDDREKFKV

PFDPADEDYNAEQEPFKNTLIRHQDRFPYFVLRYFDYNEIFKNLRFQID

LGTYHFSIYKKLIGGQKEDRHLTHKLYGFERIQEFAKQNRPDEWKAIVK

DLDTYETSNKRYISETTPHYHLENQKIGIRFRNGNKEIWPSLKTNDENN

EKSKYKLDKQYQAEAFLSVHELLPMMFYYLLLKKEKPNNDEINASIVEG

FIKREIRNIFKLYDAFANGEINNIDDLEKYCADKGIPKRHLPKQMVAIL

YDEHKDMVKEAKRKQKEMVKDTKKLLATLEKQTQKEKEDDGRNVKLLKS

GEIARWLVNDMMRFQPVQKDNEGKPLNNSKANSTEYQMLQRSLALYNNE

EKPTRYFRQVNLIESNNPHPFLKWTKWEECNNILTFYYSYLTKKIEFLN

KLKPEDWKKNQYFLKLKEPKTNRETLVQGWKNGFNLPRGIFTEPIREWF

KRHQNNSKEYEKVEALDRVGLVTKVIPLFFKEEYFKDKEENFKEDTQKE

INDCVQPFYNFPYNVGNIHKPKEKDFLHREERIELWDKKKDKFKGYKEK

IKSKKLTEKDKEEFRSYLEFQSWNKFERELRLVRNQDIVTWLLCKELID

KLKIDELNIEELKKLRLNNIDTDTAKKEKNNILNRVMPMELPVTVYEID

DSHKIVKDKPLHTIYIKEAETKLLKQGNFKALVKDRRLNGLFSFVKTNS

EAESKRNPISKLRVEYELGEYQEARIEIIQDMLALEEKLINKYKDLPTN

KFSEMLNSWLEGKDEADKARFQNDVDFLIAVRNAFSHNQYPMHNKIEFA

NIKPFSLYTANNSEEKGLGIANQLKDKTKETTDKIKKIEKPIETKE

The DR sequence corresponding to C13-40 was:

(SEQ ID NO: 66)

5'-GUUGUUUUUACCUUUCAAACAGAAGGCAGAUACAACA-3'

C13-38 and C13-40 verification vectors were constructed according to the aforementioned method, and their nucleotide backbone sequences were the same as that of the Cas13 m.3 verification vector of Example 4, except that the coding sequence of Cas13 protein and the coding sequence of DR sequence had been replaced accordingly.

The aforementioned Cas13 m.6, C13-38 and C13-40 verification vectors all contained the coding sequence of Cas13 protein, which could express a Cas13 protein linked with NLS, and could also express the EGFP-targeting gRNA (the guide sequences of the gRNAs corresponding to C13-38 and C13-40 were both located at the 5' terminal of the DR sequence). The guide sequence of the gRNA corresponded to the aforementioned spacer sequence (SEQ ID NO: 30). All the aforementioned vectors were synthesized by a reagent company by a conventional method.

2. Transfection of a 293T Cell with the Vector to be Verified

The 293T cells were transfected with a plasmid expressing the exogenous gene EGFP and the Cas13 verification vector plasmids (the Cas13 m.6 verification vector, the C13-38 verification vector, the C13-40 verification vector, or other Cas13m verification vectors obtained by preparation in Example 4) at the ratio of 300 ng:600 ng.

The description of cells and plasmids as used was as shown in Table 8 below:

TABLE 8

Experimental Grouping

| Name | Transfected with the EGFP vector | Transfected with the EGFP-targeting Cas13 verification vector | Comments |
|---|---|---|---|
| 293T | | | Cell control |
| EGFP | * | | Control transfected with EGFP only |
| Cas13m.2 | * | * | Verification vector |
| Cas13m.3 | * | * | Verification vector |
| Cas13m.5 | * | * | Verification vector |
| Cas13m.6 | * | * | Verification vector |
| C13-38 | * | * | Verification vector |
| C13-40 | * | * | Verification vector |

Note:
* represented containing related items, and blank represented there was no related items 3. Detection of the Down-Regulation the Effect of Cas13 Protein on EGFP Expression by Flow Cytometer It was given that the GFP fluorescence of the EGFP group was a, and the GFP fluorescence of other groups was x.

$$\text{downregulation amplitude } \% = (a - x) \div a \times 100\%$$

The experiment of this example was conducted in triplicate. The result data was the average of three tests, and the result was as shown in Table 9 below.

TABLE 9

Results of GFP fluorescence as detected by a flow cytometer

| Groups | Downregulation amplitude (%) |
|---|---|
| EGFP | 0.00 |
| Cas13m.2 | 61.8 * # |
| Cas13m.3 | 67.2 * # |
| Cas13m.5 | 42.3 * # |

TABLE 9-continued

Results of GFP fluorescence as detected by a flow cytometer

| Groups | Downregulation amplitude (%) |
|---|---|
| Cas13m.6 | 65.5 * # |
| C13-38 | 4.2 |
| C13-40 | 2.9 |

Note:
* indicated a significant difference compared with the C13-38 group (p < 0.01),
indicated a significant difference compared with the C13-40 group (p < 0.01).

The results showed that the downregulation amplitude of EGFP of the Cas13 m.6 group was 65.5%. It indicated that the Cas13 m.6 protein could significantly down-regulate the expression of EGFP, which proved that it could effectively reduce the mRNA level and exert its editing activity in eukaryotic cells under the guidance of the gRNA.

Also, the results showed that the editing activities of Cas13 m.2, Cas13 m.3, Cas13 m.5 and Cas13 m.6 were significantly higher than those of C13-38 and C13-40.

Example 8: Validation of Endogenous Gene Editing Efficiency of Cas13 m.6

Unless otherwise specified, this example used the same method as that of Example 5.

1. Construction of an Editing Vector Targeting Endogenous Genes AQp1 and PTBP1

An expression vector Cas13 m.6-BsaI was constructed, and its sequence was as shown in SEQ ID NO: 77.

The endogenous sites selected in the experiment were AQp1 and PTBP1, wherein AQp1 was verified by using the aforementioned 293T cell line (293T-AQp1 cells) with high expression of AQp1, and PTBP1 was verified by using a 293T cell line.

The guide sequence of the AQp1-targeting gRNA was selected as:

```
                                        (SEQ ID NO: 68)
            AGGGCAGAACCGATGCTGATGAAGAC
```

The guide sequence targeting PTBP1 was selected as:

```
                                        (SEQ ID NO: 43)
         GUGGUUGGAGAACUGGAUGUAGAUGGGCUG
```

A target site-targeted fragment was obtained by using a primer annealing manner, and the primers of it were as follows:

```
PTBP1-targeting:
Cas13m.6 group:
                                        (SEQ ID NO: 44)
    caccGTGGTTGGAGAACTGGATGTAGATGGGCTG (SEQ ID NO: 45)
    caacCAGCCCATCTACATCCAGTTCTCCAACCAC CasRx group: SEQ ID NO: 46 and SEQ ID NO: 48

AQp1-targeting:
Cas13m.6 group:
                                        (SEQ ID NO: 69)
    CACCGagggcagaaccgatgctgatgaagac (SEQ ID NO: 70)
    CAACGtcttcatcagcatcggttctgccctc
```

-continued

CasRx group:

(SEQ ID NO: 71)

aaacagggcagaaccgatgctgatgaagac (SEQ ID NO: 72)

CTTGgtcttcatcagcateggttctgccct

A BsaI-digested Cas13 m.6-BsaI vector was linked with the annealing products by T4. The CasRx-BpiI plasmid was digested with BpiI, and linked with the annealing products by T4. The verification vectors targeting the endogenous genes AQp1 and PTBP1 were obtained.

2. Transfection of 293T Cells and 293T-AQp1 Cells with the Vector to be Verified The verification vector was transfected into the 293T cells and the 293T-AQp1 cells, respectively. The negative control group was transfected with the CasRx-BpiI plasmid.

3. Detection of the mRNA Changes of the Target Gene by qPCR

Detection was conducted by qPCR, and the mRNA levels of AQp1 and PTBP1 were calculated by the 2-$\Delta\Delta$Ct method. The experiment of this example was conducted in triplicate, and the result data was the average of three tests. The result was shown in Table 10 below.

TABLE 10

Relative expression level of target mRNA

| Groups | AQp1 mRNA level | PTBP1 mRNA level |
|---|---|---|
| Negative Control | 1.00 | 1.00 |
| CasRx | 0.03 | 0.59 |
| Cas13m.6 | 0.01 | 0.51 |

The qPCR results showed that Cas13 m.6 could significantly down-regulate the expression of AQp1 and PTBP1, of which the effect was slightly better than that of CasRx.

Example 9: Identification of Key Amino Acid Residues of Cas13m Protein

In an experiment of knocking down the expression of AQp1 and PTBP1, Cas13 m.2, Cas13 m.3 and Cas13 m.6 showed the highest level of knocking down, followed by Cas13 m.5. In the knock-down experiment of the exogenous EGFP, Cas13 m.2 and Cas13 m.3 showed a higher level of knock-down than those of Cas13 m.1, Cas13 m.4 and Cas13 m.5.

In the literature (Slaymaker, Ian M., et al. "High-resolution structure of Cas13b and biochemical characterization of RNA targeting and cleavage." *Cell reports* 26.13 (2019): 3741-3751.), the crystal structure of PbuCas13b was reported, and in this paper, the amino acid residues in the PbuCas13b protein interacting with a crRNA and the catalytic residues of the HEPN domain of the PbuCas13b protein were shown.

Considering that the Cas13m protein was closer to Cas13b on the evolutionary tree, the inventor had carried out multi-sequence alignment between the Cas13m protein in the file of the present application and PbuCas13b (online MAFFT v7.504, E-INS-i algorithm, and the others were default parameters). The results were as shown in FIG. 9A-FIG. 9C. The conserved motifs (motifs 1-15) of high-activity Cas13m proteins (Cas13 m.2, Cas13 m.3, Cas13 m.6) were identified at positions corresponding to the aforementioned key residues (amino acid residues interacting with the crRNA and the catalytic residues of the HEPN domain) of the PbuCas13b protein, and they were written in a commonly used Prosite form, as shown in Table 11 below. The motifs 1-15 appeared more frequently in Cas13 m.2, Cas13 m.3 and Cas13 m.6, and the motifs 16-30 were further definitions of the motifs 1-15.

TABLE 11

Results of multi-sequence alignment of conserved motifs

| The amino acid residues corresponding to PbuCas13b | Consensus motif of Cas13m.2, Cas13m.3 and Cas13m.6 | Consensus motif of Cas13m.2, Cas13m.3 and Cas13m.6 (further defined) |
|---|---|---|
| R156, H161 | Motif 1:<br>L-x(3)-R-N-x-Y-[ST]-H | Motif 16: L-[RVY]-[EYH]-[LYC]-R-N-[VFM]-Y-[ST]-H |
| Thr405,<br>His407 | Motif 2:<br>R-x(3)-K-x-[VI]-N-G-F-G-R | Motif 17:<br>R-[ST]-[IVL]-[SQ]-K-[NAE]-[VI]-N-G-F-G-R |
| His452,<br>Asn455,<br>Lys457 | Motif 3:<br>P-Y-[IV]-T-x(5)-Y-x-[IV]-x(2)-N-x-I-G-L | Motif 18: P-Y-[IV]-T-[DN]-[HW]-[HR]-[AT]-[KAT]-Y-[LN]-[IV]-[HS]-[NSA]-N-[RH]-I-G-L |
| Asn480,<br>Lys484,<br>Asn486 | Motif 4:<br>P-x-L-x(2)-D-x(3)-[NK] | Motif 19: P-[END]-L-[TKD]-[PIT]-D-[GKE]-[AGN]-[RDG]-[NK] |
| His500 | Motif 5:<br>P-x-[AC]-x-L-S-x(2)-[ED]-[LF]-P-A-x(2)-F | Motif 20: P-[TMK]-[AC]-[WYS]-L-S-[IV]-[FY]-[ED]-[LF]-P-A-[LM]-[ALV]-F-[LY]-[LCM]-[HY]-[LI]-[YR] |
| Gly566,<br>His567 | Motif 6:<br>[LI]-P-x-K-L | Motif 21:<br>[SNG]-[QE]-[LI]-P-[RED]-K-L |
| Lys590 | Motif 7:<br>[KT]-x-[AL]-x(2)-[KVE]-[IL] | Motif 22: [KT]-[WHK]-[AL]-[AQE]-[SQE]-[KVE]-[IL] |
| Arg638 | Motif 8:<br>A-[DRK]-x-L-x(2)-[DS]-[MI]-[MV]-x-[FW]-Q-P | Motif 23: A-[DRK]-[FY]-L-[AM]-[HTR]-[DS]-[MI]-[MV]-[FRE]-[FW]-Q-P |
| Asn652,<br>Asn653,<br>Lys655,<br>Ala656,<br>Ser658 | Motif 9:<br>K-L-T-x(2)-N | Motif 24: [CG]-[NGK]-[ND]-K-L-T-[GS]-[LAQ]-N |

TABLE 11-continued

| The amino acid residues corresponding to PbuCas13b | Consensus motif of Cas13m.2, Cas13m.3 and Cas13m.6 | Consensus motif of Cas13m.2, Cas13m.3 and Cas13m.6 (further defined) |
|---|---|---|
| Lys741 | Motif 10: F-x-[HR]-[AF]-x(5)-[QR] | Motif 25: F-[ALV]-[HR]-[AF]-[NS]-[QSR]-[NSM]-[KR]-[WY]-[QR] |
| Asn756, Ser757, Arg762 | Motif 11: I-x-L-P-x-G-[LM]-F-x(3)-I | Motif 26: [KA]-[SPV]-I-[ELM]-L-P-[RD]-G-[LM]-F-[ET]-[ST]-[YH]-I |
| Arg791, Val795, Ala796 | Motif 12: [LI]-I-x(2)-[YWF]-F | Motif 27: [LI]-I-x(2)-[YWF]-F-x(5)-[DQ]-x(2)-Q-[PT]-F-Y-[DR] |
| Trp842, Lys846 | Motif 13: I-x(3)-I | Motif 28: I-[RAL]-[KQ]-[KD]-I |
| Lys870, Lys871, Glu873, Arg874, Arg877 | Motif 14: [DN]-[TN]-E-x(2)-[IL]-[KR]-[VR]-Y-[KR]-x-Q-D | Motif 29: [DN]-[TN]-E-[KTR]-[ED]-[IL]-[KR]-[VR]-Y-[KR]-[ILT]-Q-D |
| R1068, H1073 | Motif 15: R-N-[SA]-[FA]-x-H-x(2)-Y | Motif 30: R-N-[SA]-[FA]-[AG]-H-[NL]-[SRT]-Y-[PK] |

The three-dimensional structures of the Cas13m protein and PbuCas13b were predicted by the program AlphaFold v2.0, and then the proteins were superimposed by PyMOL V2.5.1.

The result showed that the three-dimensional structure of the PbuCas13b protein predicted by AlphaFold was very similar to that of a protein in the crystal structure of a complex of PbuCas13b and the gRNA as reported in a literature (NDB: 6DTD) (RMSD=2.122), which indicated that the conformational difference of PbuCas13b before and after binding to the gRNA was not particularly big, that was, the comparison of the three-dimensional structure between Cas13m and the PbuCas13b protein was meaningful, and it was not necessary to strictly compare the Cas13-gRNA complexes of both of them.

The three-dimensional spatial locations of the motifs 1-15 of the Cas13m protein in the protein were very similar to those of the corresponding sequences of PbuCas13b. Taking Cas13 m.6 as an example, it was superimposed with PbuCas13b. A-N in FIG. 10 respectively showed the overlapping of the motifs 1-15 of Cas13 m.6 and the corresponding sequences of PbuCas13b.

It could be predicted that motifs 1-13 could enable the Cas13 m.2, Cas13 m.3 and Cas13 m.6 proteins to interact with their respective DR sequences, and the motifs 14 and 15 were catalytic activity centers. It could be understood by those skilled in the art that, the homologous protein or mutant of Cas13 m.2, Cas13 m.3 or Cas13 m.6 was also expected to show the target nucleic acid binding activity or endonuclease activity when it contains the motifs 1-15, especially when amino acid residues other than the motifs 1-15 were subjected to conservative amino acid replacement on the basis of a wild-type sequence. The aforementioned homologous protein or mutant might have a sequence identity ≥50% with the Cas13 m.2, Cas13 m.3 or Cas13 m.6 protein (e.g., a sequence identity ≥60%, ≥70%, ≥80%, ≥85%, ≥90%, ≥95%, ≥96%, ≥97%, ≥98%, ≥99% or ≥99.5%). The source of the aforementioned homologous protein could also be of the same kingdom, phylum, class, order, family, genus or species as the source of the Cas13 m.2, Cas13 m.3 or Cas13 m.6 protein.

Therefore, this paper provided a Cas13 protein having this consensus motif (a conjugate containing it, a nucleic acid encoding these proteins or conjugates, a vector containing these nucleic acids, and a method of using these proteins/nucleic acids).

Example 10: Off-Target Test

1. Construction of Control Vector

In this experiment, the PTBP1 gene was selected as the target gene for off-target verification.

The controls shRNA1 and shRNA2 respectively intercepted 21 nt from the head and tail of the target sequence used by Cas13 as the targets, specifically as follows:

```
ShRNA1 target site:
                            (SEQ ID NO: 73)
GCCCATCTACATCCAGTTCTC ShRNA2 target site:
                            (SEQ ID NO: 74)
CAGCCCATCTACATCCAGTTC
```

Primers used for constructing the control vector were as shown in the table 12 below:

TABLE 12

List of Primer sequence

| Primer name | Sequence | SEQ ID NO: |
|---|---|---|
| PTBP1-g3-shRNA-1F | caccGCCCATCTACATCCAGTTCTCCTCG AGGAGAACTGGATGTAGATGGGCTTTTTT | 75 |
| PTBP1-g3-shRNA-1R | ggccAAAAAAGCCCATCTACATCCAGTTC TCCTCGAGGAGAACTGGATGTAGATGGGC | 76 |
| PTBP1-g3-shRNA-2F | caccCAGCCCATCTACATCCAGTTCCTCG AGGAACTGGATGTAGATGGGCTGTTTTTT | 77 |
| PTBP1-g3-shRNA-2R | ggccAAAAAACAGCCCATCTACATCCAGT TCCTCGAGGAACTGGATGTAGATGGGCTG | 78 |

The aforementioned primers were respectively annealed according to shRNA1: PTBP1-g3-shRNA-1F/PTBP1-g3-shRNA-1R and shRNA2: PTBP1-g3-shRNA-2F/PTBP1-g3-shRNA-2R, so as to obtain annealed products.

The vector pAAV-CMV-EGFP was subjected to double enzyme digestion via BsaI and NotI to obtain a linearized backbone. The backbone was connected with the annealing products of shRNA1 and shRNA2, respectively, and then transformed into *Escherichia coli* to obtain the control vectors shRNA1 and shRNA2 (which could express shRNA1 and shRNA2 respectively under the drive by an U6 promoter).

The vector CasRx-blank was constructed by a conventional method. The CasRx-blank was obtained by replacing the coding sequence GGGTCTTCGAGAAGACCT (SEQ ID NO: 103) of the guide sequence of the gRNA with GATCAACATTAAATGTGAGCGAGT (SEQ ID NO: 104) (the coded gRNA could target the LacZ of *E. coli*.), on the basis of the aforementioned CasRx-BpiI plasmid. Moreover, the PTBP1-targeting plasmids of Cas13 m.2, Cas13 m.3, Cas13 m.5, CasRfg.2 and CasRx (named Cas13 m.2-PTBP1, Cas13 m.3-PTBP1, Cas13 m.5-PTBP1, CasRfg.2-PTBP1, and CasRx-PTBP1 respectively) constructed in Example 5 were also used.

The sequence of the backbone vector pAAV-CMV-EGFP was as shown in SEQ ID NO: 79.

2. Transfection of a 293T Cell with the Vector to be Verified

The 293T cells were transfected with the plasmid to be verified at 500 ng in a 24-well plate.

The transfection method was as follows:

1). The 293T cells were digested by trypsin (0.25% of Trypsin, EDTA, Thermo, 11058021), counted, and plated into a 24-well plates at $2 \times 10^5$ cells according to 500 µLper well.

2). For each transfected sample, the complex was prepared according to the following steps:

a. each well of the 24-well plate into which the cells were added, were added with 50 uL of serum-free Opti-MEM I (Thermo, 25200056) reduced serum medium for dilution of the aforementioned plasmid DNA, and mixed gently;

b. it was gently mixed with Lipofectamine 2000 (Thermo, 11668019) before use, and then 1.8 µL of the Lipofectamine 2000 was diluted in each well, i.e., in 50 µL of the Opti-MEM I medium. It was incubated at room temperature for 5 minutes. Note: it was continued to perform step c within 25 minutes;

c. after incubation for 5 minutes, the diluted DNA was combined with the diluted Lipofectamine 2000. They were gently mixed and incubated at room temperature for 20 minutes (the solution might be cloudy visually). Note: the complex was stabilized at room temperature for 6 hours.

At 72 h after transfection, the cells were subjected to RNA extraction with a SteadyPure Universal RNA Extraction Kit AG21017 kit, and the RNA concentration was detected with an ultramicro spectrophotometer. The extracted RNA was sent to a reagent company for RNA sequencing.

3. Off-Target Analysis

Samples were sequenced by PE150 bp RNA-Seq, and several fastq files obtained by sequencing were aligned with the reference genome of the target species by HISAT2 or STAR software, respectively, to obtain several BAM files after the alignment. The expression levels of the obtained transcripts and various genes were detected by kallisto, RSEM or HTSeq.

The variation analysis of expression levels among groups was conducted by using DESeq2, limma-voom and edger, and a gene satisfying p.adj<0.05, |log 2FoldChange|≥0.75 and basemean >2.5 was taken as the differential expression gene (DEG). The table below listed the number of DEGs in each experimental group compared with that of the CasRx-blank group:

TABLE 13

| Number of differentially expressed genes | | | |
|---|---|---|---|
| | up (number of up-regulated DEG) | down (number of down-regulated DEG) | up + down |
| CasRx_vs_CasRx-blank | 74 | 24 | 98 |
| Cas13m.5_vs_CasRx-blank | 8 | 10 | 18 |
| CasRfg.2_vs_CasRx-blank | 23 | 17 | 40 |
| Cas13m.2_vs_CasRx-blank | 13 | 18 | 31 |
| Cas13m.3_vs_CasRx-blank | 4 | 5 | 9 |
| shRNA1_vs_CasRx-blank | 12 | 37 | 49 |
| shRNA2_vs_CasRx-blank | 22 | 31 | 53 |

It could be seen from the data in the table that, compared with CasRx, shRNA1 and shRNA2, the number of potential off-target genes in Cas13 m.2, Cas13 m.3 and Cas13 m.5 was less, which had less influence on the gene expression profile of the cells. Therefore, this characteristic of Cas13 m.2, Cas13 m.3 and Cas13 m.5 would make them have better safety and lower toxicity when they were used in disease treatment.

Example 11: Assay of Collateral Cleavage Effect

1. Acquisition of gRNA

APTBP1-targeting gRNA was transcribed by using a T7 in vitro transcription kit T7 High Yield RNA Transcription Kit, Vazyme, TR101-01.

The sequence of the gRNA molecular obtained by transcription in vitro was as follows:

```
Cas13m.2-PTBP1:
                              (SEQ ID NO: 80)
5'-GUGGUUGGAGAACUGGAUGUAGAUGGGCUGGUUGUAGAUGACCUCGU

UUUGGAGGGGAAACACAAC-3'

Cas13m.3-PTBP1:
                              (SEQ ID NO: 81)
5'-GUGGUUGGAGAACUGGAUGUAGAUGGGCUGGUUGUAGAAGCCGUUCA

UUCGGGACGGUAUGACAAC-3'

Cas13m.6-PTBP1:
                              (SEQ ID NO: 82)
5'-GUGGUUGGAGAACUGGAUGUAGAUGGGCUGGUUGUAGAAGCCUAUCG

UUAGGAUAGGUAUGACAAC-3'
```

2. Detection of Collateral Cleavage Effect

RNaseAlert was a novel RNA substrate, one end of which was labeled with a fluorescent reporter molecule (fluorophor) and the other end was labeled with a quencher. The physical proximity of the quencher would suppress the fluorescence of the phosphor to an extremely low level. However, when the RNase was existed, the RNA substrate was cleaved, and the phosphor and the quencher were separated. When the phosphor was excited by a light at 490 nm, it would emit a green fluorescence signal at 520 nm.

When Cas13 had the collateral cleavage activity (i.e., the non-specific RNA cleaving activity activated by the target RNA), the RNaseAlert substrate would also be cleaved to emit a green fluorescent signal that could be detected.

The main experimental equipment and materials were as follows:

RNaseAlert®-1 Kit, IDT, 11-02-01-02

RNase Inhibitor, Murine, NEB, M0314L

Corning® 96-well all-black polystyrene microplate, Corning, 3915

Microplate reader, BioTek, SLXFA.

The following RNaseAlert collateral cleavage system was formulated:

| | |
|---|---|
| Cas13 protein (Cas13m) | 45 nM |
| gRNA | 22.5 nM |
| RNase Inhibitor | 2 μL |
| 293T cell RNA | 100 ng |
| RNaseAlert | 10 μL |
| 10X RNaseAlert ®-1 Buffer | 10 μL |
| RNase-free deionized water | up to 100 μl |

Note: the RNA group of the 293T cells were extracted according to the instructions of the SteadyPure Universal RNA Extraction Kit. The Cas13m recombinant protein purified in Example 2 was used. The Cas13 protein and the gRNA were not added in the reaction systems of the RNase group (a positive control group added with the RNase) and the blank group (a blank control group).

The reaction was carried out at 37° C. for 1 h, and the fluorescence at 520 nm was detected every 30 min by the microplate reader.

The detected effect was shown in Table 14 below and FIG. 11:

TABLE 14

Results of collateral cleavage tests

| RFU | 0 min | | | 30 min | | | 60 min | | |
|---|---|---|---|---|---|---|---|---|---|
| | 1 | 2 | mean | 1 | 2 | mean | 1 | 2 | mean |
| Cas13m.2 | 3 | 5 | 4 | 3 | 4 | 3.5 | 1 | 4 | 2.5 |
| Cas13m.3 | 2 | 2 | 2 | 4 | 7 | 5.5 | 7 | 5 | 6 |
| Cas13m.6 | 7 | 5 | 6 | 8 | 11 | 9.5 | 6 | 7 | 6.5 |

TABLE 14-continued

Results of collateral cleavage tests

| RFU | 0 min | | | 30 min | | | 60 min | | |
|---|---|---|---|---|---|---|---|---|---|
| | 1 | 2 | mean | 1 | 2 | mean | 1 | 2 | mean |
| RNase | 55 | 58 | 56.5 | 52 | 55 | 53.5 | 53 | 53 | 53 |
| blank | 5 | 7 | 6 | 5 | 10 | 7.5 | 8 | 7 | 7.5 |

The relative fluorescence intensity of each of Cas13 m.2, Cas13 m.3 and Cas13 m.6 was lower than 10, and the fluorescence intensity did not increase over time, and no collateral cleavage activity was observed.

The literature (Koonin, Eugene V., and Kira S. Makarova. "Evolutionary plasticity and functional versatility of CRISPR systems." PLOS biology 20.1 (2022): e3001481.) pointed out that Cas13, once activated by target recognition, would cleave the RNA indiscriminately and induce dormancy or death of the cell. The experimental results of this example showed that the characteristic that Cas13 m.2, Cas13 m.3 and Cas13 m.6 had no collateral cleavage activity, would make them have better safety and lower toxicity when they were used in disease treatment.

The technical features of the aforementioned examples can be arbitrarily combined. To simplify the description, we do not describe all possible combinations of the technical features in the aforementioned examples. However, as long as there is no contradiction in the combination of these technical features, it should be considered as the scope stated in this specification.

The examples described above are merely illustrative of several embodiments of the present invention, the description of them is more specific and detailed, but cannot be construed as limiting the scope of the present invention accordingly. It should be noted that, several variations and modifications can be made by those of ordinary skills in the art, under the premise of not departing from the concept of the present invention, and these variations and modifications all fall within the claimed scope of the present invention. Therefore, the claimed scope of the patent of the present invention shall be determined by the appended claims.

What is claimed is:

1. A non-naturally occurring conjugate comprising a Cas13 protein and a nuclear localization signal and/or a nuclear export signal;

wherein the Cas13 protein comprises the amino acid sequence of SEQ ID NO: 3;

wherein the Cas13 protein has Cas13 nuclease activity and can form a complex with a gRNA to bind to a target nucleic acid in a non-bacterial cell.

2. A composition comprising the conjugate of claim 1 and a gRNA capable of forming a complex with the conjugate.

* * * * *